US008273891B2

(12) United States Patent
Schumacher et al.

(10) Patent No.: US 8,273,891 B2
(45) Date of Patent: *Sep. 25, 2012

(54) INDAZOLES, BENZOTHIAZOLES, BENZOISOTHIAZOLES, BENZISOXAZOLES, PYRAZOLOPYRIDINES, ISOTHIAZOLOPYRIDINES, AND PREPARATION AND USES THEREOF

(75) Inventors: Richard Schumacher, Monroe, NY (US); Mihaela Diana Danca, Mendham, NJ (US); Jianguo Ma, Natick, MA (US); Brian Herbert, Stockholm, NJ (US); True Minh Nguyen, New York, NY (US); Wenge Xie, Mahwah, NJ (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 133 days.

This patent is subject to a terminal disclaimer.

(21) Appl. No.: 12/700,936

(22) Filed: Feb. 5, 2010

(65) Prior Publication Data

US 2010/0137288 A1    Jun. 3, 2010

Related U.S. Application Data

(63) Continuation of application No. 11/525,213, filed on Sep. 22, 2006.

(51) Int. Cl.
C07D 221/02 (2006.01)
C07D 217/00 (2006.01)

(52) U.S. Cl. ..................................... 546/143; 546/112
(58) Field of Classification Search .................. 546/143, 546/112
See application file for complete search history.

(56) References Cited

U.S. PATENT DOCUMENTS

| | | | |
|---|---|---|---|
| 4,310,227 A | 1/1982 | Zinchuk |
| 4,474,446 A | 10/1984 | Reynolds et al. |
| 4,605,652 A | 8/1986 | Welstead et al. |
| 4,775,668 A | 10/1988 | Jefson et al. |
| 4,789,673 A | 12/1988 | Donatsch et al. |
| 4,798,829 A | 1/1989 | King et al. |
| 4,845,092 A | 7/1989 | Sanger et al. |
| 4,886,808 A | 12/1989 | King et al. |
| 4,895,943 A | 1/1990 | Friedman et al. |
| 4,910,193 A | 3/1990 | Buchheit |
| 4,910,207 A | 3/1990 | Donatsch et al. |
| 4,937,247 A | 6/1990 | King et al. |
| 4,942,160 A | 7/1990 | Sanger et al. |
| 4,975,436 A | 12/1990 | Tyers |
| 4,985,424 A | 1/1991 | Van Wijingaarden et al. |
| 5,017,582 A | 5/1991 | Donatsch et al. |
| 5,034,398 A | 7/1991 | King et al. |
| 5,063,231 A | 11/1991 | Sanger et al. |
| 5,098,889 A | 3/1992 | Costall et al. |
| 5,098,909 A | 3/1992 | Williams |
| 5,192,770 A | 3/1993 | Clark et al. |
| 5,204,356 A | 4/1993 | Tyers |
| 5,223,625 A | 6/1993 | Van Wijingaarden et al. |
| 5,272,154 A | 12/1993 | Dixon et al. |
| 5,273,972 A | 12/1993 | Jagdmann et al. |
| 5,446,050 A | 8/1995 | Rosen |
| 5,543,426 A | 8/1996 | Dixon et al. |
| 5,561,149 A | 10/1996 | Azria et al. |
| 5,641,802 A | 6/1997 | Arcomone et al. |
| 5,679,673 A | 10/1997 | Bowen et al. |
| 5,714,496 A | 2/1998 | Brown et al. |
| 5,773,436 A | 6/1998 | Muller et al. |
| 5,985,866 A | 11/1999 | Muller et al. |
| 6,021,005 A | 2/2000 | Cathey, Jr. et al. |
| 6,115,556 A | 9/2000 | Reddington |
| 6,492,385 B2 | 12/2002 | Myers et al. |
| 6,500,840 B2 | 12/2002 | Myers et al. |
| 6,599,916 B2 | 7/2003 | Myers et al. |
| 6,624,173 B1 | 9/2003 | Crooks et al. |
| 6,780,861 B2 | 8/2004 | Nozulak et al. |
| 6,828,330 B2 | 12/2004 | Walker et al. |
| 6,849,620 B2 | 2/2005 | Walker et al. |
| 6,911,543 B2 | 6/2005 | Walker et al. |
| 7,001,900 B2 | 2/2006 | Jacobsen et al. |
| 7,001,902 B2 | 2/2006 | Gallet et al. |
| 7,354,930 B2 | 4/2008 | Flessner et al. |
| 7,396,833 B2 | 7/2008 | Xie et al. |
| 7,429,664 B2 * | 9/2008 | Xie et al. ..................... 546/112 |
| 7,625,924 B2 | 12/2009 | Nguyen et al. |
| 2002/0086871 A1 | 7/2002 | O'Neill et al. |
| 2002/0119972 A1 | 8/2002 | Leftheris et al. |

(Continued)

FOREIGN PATENT DOCUMENTS

CA    2 361 437    8/2000

(Continued)

OTHER PUBLICATIONS

Astles et al., Current Drug Targets—CNS Neurological Disorders, 2002, 1, pp. 337-348.
Bermudez et al., J. Med. Chem. 1990, 33, 1924-1929.
Flammia, D., "Lobeline: Structure-Affinity Investigation of Nicotinic Acetylcholinergic Receptor Binding", J. Med. Chem. (1999), 42:3726-2731.
Stevens, K. E.et al., "Selective $\alpha_7$-nicotinic agonists normalize inhibition of auditory response in DBA mice", Psychopharmacology (1998), 136:320-327.
Decker, M. et al., "Neuronal Nictotic Acetylcholine Receptors Novel Targets for CNS Therapeutic". pp. 1-14.

(Continued)

*Primary Examiner* — Andrew D Kosar
*Assistant Examiner* — Raymond Covington
(74) *Attorney, Agent, or Firm* — Millen, White, Zelano & Branigan, P.C.

(57) ABSTRACT

The present invention relates generally to the field of ligands for nicotinic acetylcholine receptors (nACh receptors), activation of nACh receptors, and the treatment of disease conditions associated with defective or malfunctioning nicotinic acetylcholine receptors, especially of the brain. Further, this invention relates to novel compounds (e.g., indazoles and benzothiazoles), which act as ligands for the $\alpha 7$ nACh receptor subtype, methods of preparing such compounds, compositions containing such compounds, and methods of use thereof.

39 Claims, No Drawings

U.S. PATENT DOCUMENTS

| | | | |
|---|---|---|---|
| 2003/0073707 A1 | 4/2003 | Walker et al. |
| 2003/0236270 A1 | 12/2003 | Jacobsen et al. |
| 2004/0002513 A1 | 1/2004 | Mazurov et al. |
| 2004/0132790 A1 | 7/2004 | Xie et al. |
| 2004/0138286 A1 | 7/2004 | Imazaki et al. |
| 2004/0224977 A1 | 11/2004 | Walker et al. |
| 2005/0182062 A1 | 8/2005 | Galli et al. |
| 2005/0209236 A1 | 9/2005 | Hendrix et al. |
| 2006/0014750 A1 | 1/2006 | O'Donnell et al. |
| 2006/0019984 A1 | 1/2006 | Groppi et al. |
| 2006/0160877 A1 | 7/2006 | Luithle et al. |
| 2007/0078147 A1 | 4/2007 | Schumacher et al. |

FOREIGN PATENT DOCUMENTS

| | | |
|---|---|---|
| DE | 101 56 719 A1 | 5/2003 |
| DE | 103 05 922 A1 | 3/2004 |
| EP | 0 013 138 A1 | 7/1980 |
| EP | 0 200 444 A2 | 11/1986 |
| EP | 0 214 772 A1 | 3/1987 |
| EP | 0 261 964 A2 | 3/1988 |
| EP | 0 279 512 A2 | 8/1988 |
| EP | 0 377 238 A1 | 7/1990 |
| EP | 0 498 466 A1 | 8/1992 |
| EP | 1 079 828 A1 | 3/2001 |
| EP | 1 217 001 A1 | 6/2002 |
| EP | 1 219 622 A2 | 7/2002 |
| EP | 1 235 826 A1 | 9/2002 |
| FR | 2 548 666 A1 | 1/1985 |
| GB | 2 125 398 A | 3/1984 |
| GB | 2 145 416 A | 3/1985 |
| JP | 2002 30084 | 1/2002 |
| WO | WO-84 00166 A1 | 1/1984 |
| WO | WO-85 01048 A1 | 3/1985 |
| WO | WO-90 14347 A1 | 11/1990 |
| WO | WO-91 09593 A2 | 7/1991 |
| WO | WO-92 12149 A1 | 7/1992 |
| WO | WO-93 08185 A1 | 4/1993 |
| WO | WO-94 14805 A1 | 7/1994 |
| WO | WO-97 30998 A1 | 8/1997 |
| WO | WO-99 56745 A1 | 11/1999 |
| WO | WO-00 45846 A1 | 8/2000 |
| WO | WO-00 58311 A1 | 10/2000 |
| WO | WO-01 029034 A1 | 4/2001 |
| WO | WO-01 58869 A2 | 8/2001 |
| WO | WO-01-90109 A1 | 11/2001 |
| WO | WO-01-92260 A1 | 12/2001 |
| WO | WO-02 17358 A2 | 2/2002 |
| WO | WO-02 36114 A1 | 5/2002 |
| WO | WO-02 085901 A1 | 10/2002 |
| WO | WO-02 096911 A1 | 12/2002 |
| WO | WO-02 100833 A1 | 12/2002 |
| WO | WO-02 100857 A1 | 12/2002 |
| WO | WO-02 100858 A2 | 12/2002 |
| WO | WO-03 022856 A1 | 3/2003 |
| WO | WO-03 029252 A1 | 4/2003 |
| WO | WO-03 037896 A1 | 5/2003 |
| WO | WO-03 042210 A1 | 5/2003 |
| WO | WO-03 051874 A1 | 6/2003 |
| WO | WO-03 070731 A2 | 8/2003 |
| WO | WO-03 072578 A1 | 9/2003 |
| WO | WO-03 078431 A1 | 9/2003 |
| WO | WO-03 080606 A1 | 10/2003 |
| WO | WO-03/094830 A2 | 11/2003 |
| WO | WO-03 101987 A1 | 11/2003 |
| WO | WO-2004 014864 A1 | 2/2004 |
| WO | WO-2004-014922 A1 | 2/2004 |
| WO | WO-2004 016616 A1 | 2/2004 |
| WO | WO-2004 016617 A1 | 2/2004 |
| WO | WO-2004 029050 A1 | 4/2004 |
| WO | WO-2004 033456 A2 | 4/2004 |
| WO | WO-2004029050 | 4/2004 |
| WO | WO-2004 052348 A2 | 6/2004 |
| WO | WO-2004 052461 A1 | 6/2004 |
| WO | WO-2005 012299 A1 | 2/2005 |

OTHER PUBLICATIONS

Evans, S. M. et al., "Probing the 5-HT$_3$ Receptor Site Using Novel
Holladay, M.W. et al., "Neuronal Nicotinic Acetylcholine Receptors as Targets for Drug Discovery", Journal of Medicinal Chemistry, vol. 40, No. 26 (1997), pp. 4169-4194.
Mazurov et al., Biorg. & Med. Chem. Lett, 2005, No. 15, pp. 2073-2077.
Nuhrich et al., Eur. J. Med. Chem., 1996, No. 31, pp. 957-964.
Azuma, R. et al. "Metabolism and Disposition of GTS-21, A Novel Drug for Alzheimer's Disease", Xenobiotica (1999), vol. 29, No. 7, pp. 747-762.
Azuma, R. et al., "The effect of repeat administration of GTS-21 on mixed-function oxidase activities in rat", Elsevier Science Ireland Ltd., Toxicology Letters 110 (1999) pp. 137-144. Indole-3-Glyoxylic Acid Derivatives", Med. Chem. Res. (1993) 3:386-406.
Search report for European Patent Application No. EP 05 75 5169 dated Apr. 3, 2008.
Austrian Search Report and Written Opinion for Application No. 200606539-5 mailed Oct. 3, 2008.
International Search Report and Written Opinion, dated Dec. 14, 2005, issued in PCT/US2005/010120.
International Partial Search Report and Invitation to Pay Additional Fees, issued Sep. 1, 2005 in PCT/US2005/010120.
Mitsubishi Pharma Corp., 1-Azabicycloalkane Compound and Pharmaceutical Use Thereof, Patent Abstracts of Japan, Publication No. 2002-030084, Date of Publication: Jan. 29, 2002.
International Search Report and the Written Opinion of the International Searching Authority, issued Mar. 1, 2007 in PCT/US2006/037142.
Office Action for U.S. Appl. No. 11/089,553 dated Sep. 13, 2007.
Office Action for U.S. Appl. No. 11/08,533 dated Nov. 30, 2007.
Office Action for U.S. Appl. No. 11/089,533 dated Jun. 5, 2008.
Office Action for U.S. Appl. No. 12/032,068 dated Oct. 30, 2008.
McGraw Hill Dictionary of Chemical Terms (1990) pp. 282.
Concise Encyclopedia Chemistry (1993) pp. 490.
Hawley's Condensed Chemical Dictionary (1993) pp. 594.

* cited by examiner

INDAZOLES, BENZOTHIAZOLES, BENZOISOTHIAZOLES, BENZISOXAZOLES, PYRAZOLOPYRIDINES, ISOTHIAZOLOPYRIDINES, AND PREPARATION AND USES THEREOF

This application is a continuation of application Ser. No. 11/525,213, filed Sep. 22, 2006. In addition, this application claims the benefit of U.S. Provisional Application Ser. No. 60/791,881, filed Apr. 14, 2006, and U.S. Provisional application Ser. No. 60/719,552, filed Sep. 23, 2005, the entire disclosure of which are hereby incorporated by reference.

This application is also related to U.S. patent application Ser. No. 11/089,533, filed Mar. 25, 2005 (which claims the benefit of U.S. Provisional Application Ser. No. 60/555,951, filed Mar. 25, 2004, and U.S. Provisional Application Ser. No. 60/616,033, filed Oct. 6, 2004) and U.S. patent application Ser. No. 10/669,645, filed Sep. 25, 2003 (which claims the benefit of U.S. Provisional Application Ser. No. 60/413,151, filed Sep. 25, 2002, and U.S. Provisional Application Ser. No. 60/448,469, filed Feb. 21, 2003) the entire disclosures of each of which are hereby incorporated by reference.

FIELD OF THE INVENTION

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds, which act as ligands for the α7 nAChR subtype, methods of preparing such compounds, compositions comprising such compounds, and methods of use thereof.

BACKGROUND OF THE INVENTION

There are two types of receptors for the neurotransmitter, acetylcholine: muscarinic receptors and nicotinic receptors, based on the selectivity of action of muscarine and nicotine, respectively. Muscarinic receptors are G-protein coupled receptors. Nicotinic receptors are members of the ligand-gated ion channel family. When activated, the conductance of ions across the nicotinic ion channels increases.

Nicotinic alpha-7 receptor protein forms a homo-pentameric channel in vitro that is highly permeable to a variety of cations (e.g., $Ca^{++}$). Each nicotinic alpha-7 receptor has four transmembrane domains, named M1, M2, M3, and M4. The M2 domain has been suggested to form the wall lining the channel. Sequence alignment shows that nicotinic alpha-7 is highly conserved during evolution. The M2 domain that lines the channel is identical in protein sequence from chicken to human. For discussions of the alpha-7 receptor, see, e.g., Revah et al. (1991), *Nature,* 353, 846-849; Galzi et al. (1992), *Nature* 359, 500-505; Fucile et al. (2000), *PNAS* 97(7), 3643-3648; Briggs et al. (1999), *Eur. J. Pharmacol.* 366 (2-3), 301-308; and Gopalakrishnan et al. (1995), *Eur. J. Pharmacol.* 290(3), 237-246.

The nicotinic alpha-7 receptor channel is expressed in various brain regions and is believed to be involved in many important biological processes in the central nervous system (CNS), including learning and memory. Nicotinic alpha-7 receptors are localized on both presynaptic and postsynaptic terminals and have been suggested to be involved in modulating synaptic transmission. It is therefore of interest to develop novel compounds, which act as ligands for the α7nACh receptor subtype, for the treatment of disease conditions associated with defective or malfunctioning nicotinic acetylcholine receptors.

SUMMARY OF THE INVENTION

This invention relates to novel compounds, which act as ligands for the α7 nACh receptor subtype, methods of preparing such compounds, compositions comprising such compounds, and methods of use thereof.

DETAILED DESCRIPTION OF THE INVENTION

The present invention includes compounds of Formulas I, II, III, or IV:

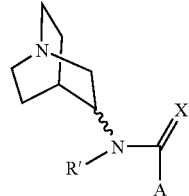

(I)

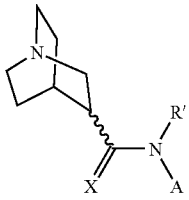

(II)

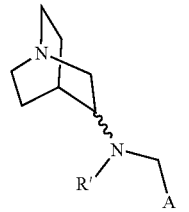

(III)

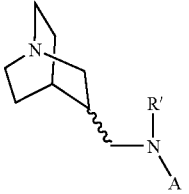

(IV)

wherein

A is

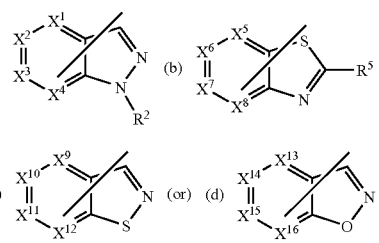

X is O or S;

$X^1$ to $X^4$ are each, independently, N, CH, $CR^1$, or C—, wherein C— represents the point of attachment of group A to the remainder of the structure of formulas (I), (II), (III) or (IV) (for example, $X^1$, $X^2$, $X^3$ and $X^4$ are each CH or $CR^1$, and group A is attached at the 3-position to the remainder of the structure of formulas (I), (II), (III) or (IV), $X^1$, $X^2$ and $X^3$ are each CH or $CR^1$, $X^4$ is N, and group A is attached at the 3-position to the remainder of the structure of formulas (I), (II), (III) or (IV), $X^1$, $X^2$ and $X^4$ are each CH or $CR^1$, $X^3$ is N, and group A is attached at the 3-position to the remainder of the structure of formulas (I), (II), (III) or (IV), or $X^1$, $X^3$ and $X^4$ are each CH or $CR^1$, $X^2$ is N, and group A is attached at the 3-position to the remainder of the structure of formulas (I), (II), (III) or (IV));

$X^5$ to $X^8$ are each, independently, N, CH, $CR^3$, or C—, wherein C— represents the point of attachment of group A to the remainder of the structure of formulas (I), (II), (III) or (IV) (for example, $X^5$, $X^6$, and $X^8$ are each CH or $CR^3$ and $X^7$ is C— whereby group A is attached at its 5-position to the remainder of the structure of formulas (I), (II), (III) or (IV), or $X^5$, $X^7$, and $X^8$ are each CH or $CR^3$ and $X^6$ is C— whereby group A is attached at its 6-position to the remainder of the structure of formulas (I), (II), (III) or (IV));

$X^9$ to $X^{12}$ are each, independently, N, CH, $CR^4$, or C—, wherein C— represents the point of attachment of group A to the remainder of the structure of formulas (I), (II), (III) or (IV) (for example, $X^9$, $X^{10}$, $X^{11}$ and $X^{12}$ are each CH or $CR^4$, and group A is attached at the 3-position to the remainder of the structure of formulas (I), (II), (III) or (IV), $X^9$, $X^{10}$ and $X^{11}$ are each CH or $CR^4$, $X^{12}$ is N, and group A is attached at the 3-position to the remainder of the structure of formulas (I), (II), (III) or (IV), or $X^9$, $X^{10}$ and $X^{12}$ are each CH or $CR^4$, $X^{11}$ A is N, and group A is attached at the 3-position to the remainder of the structure of formulas (I), (II), (III) or (IV), or $X^9$, $X^{11}$ and $X^{12}$ are each CH or $CR^4$, $X^{10}$ is N, and group A is attached at the 3-position to the remainder of the structure of formulas (I), (II), (III) or (IV));

$X^{13}$ to $X^{16}$ are each, independently, N, CH, CR, or C—, wherein C— represents the point of attachment of group A to the remainder of the structure of formulas (I), (II), (III) or (IV) (for example, $X^{13}$, $X^{14}$, $X^{15}$ and $X^{16}$ are each CH or CR, and group A is attached at the 3-position to the remainder of the structure of formulas (I), (II), (III) or (IV), $X^{13}$, $X^{14}$ and $X^{15}$ are each CH or CR, $X^{16}$ is N, and group A is attached at the 3-position to the remainder of the structure of formulas (I), (II), (III) or (IV), or $X^{13}$, $X^{14}$ and $X^{16}$ are each CH or CR, $X^{15}$ is N, and group A is attached at the 3-position to the remainder of the structure of formulas (I), (II), (III) or (IV), or $X^{13}$, $X^{15}$ and $X^{16}$ are each CH or CR, $X^{14}$ is N, and group A is attached at the 3-position to the remainder of the structure of formulas (I), (II), (III) or (IV));

R' is H, alkyl having 1 to 4 carbon atoms, halogenated alkyl having 1 to 4 carbon atoms, cycloalkyl having 3 to 7 carbon atoms, or cycloalkylalkyl having 4 to 7 carbon atoms;

R is H, F, Cl, Br, I, OH, CN, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—($C_{1-6}$-alkyl-O)$_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—, with the proviso that R is not $NH_2$; or R is of one of the following formulas

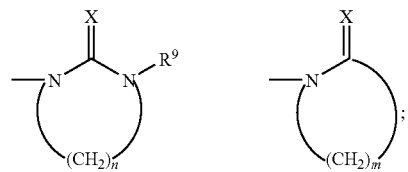

n is 2 to 4;
m is 3 to 5; or two R can together form a 5-membered fused ring structure containing at least one N atom;

$R^1$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—($C_{1-6}$-alkyl-O)$_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^1$ is of one of the following formulas

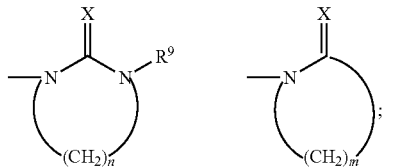

two $R^1$ can together form a 5-membered fused ring structure containing at least one N atom;

$R^2$ is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl- (e.g., $CH_2CH_2$—O—$CH_3$), Ar—$C_{1-4}$-alkyl-NH—CO—, or Het-NH—CO— (e.g., (1-azabicyclo[2.2.2]oct-3-yl)-NH—CO—);

$R^3$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—($C_{1-6}$alkyl-O)$_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^3$ is of one of the following formulas

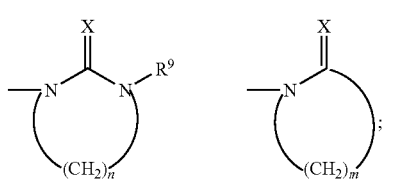

two $R^3$ can together form a 5-membered fused ring structure containing at least one N atom;

$R^4$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—($C_{1-6}$alkyl-O)$_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^4$ is of one of the following formulas two $R^4$ can together form a 5-membered fused ring structure containing at least one N atom;

$R^5$ is H, F, Cl, Br, I, OH, CN, nitro, $NH_2$, carboxy, $CONR^6R^7$, $NR^2COR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, or OHet;

$R^6$ and $R^7$ are each, independently, H, alkyl having 1 to 4 carbon atoms, alkoxyalkyl having 2 to 8 carbon atoms, cycloalkyl having 3 to 7 carbon atoms, or cycloalkylalkyl having 4 to 7 carbon atoms, or $R^6$ and $R^7$ together are an alkylene group containing 4-6 carbon atoms which forms a ring with the N atom (e.g., piperidinyl, pyrrolidinyl);

$R^8$ is H, alkyl having 1 to 4 carbon atoms, fluorinated alkyl having 1 to 4 carbon atoms (e.g., $CF_3$), alkenyl having 3 to 6 carbon atoms, alkynyl having 3 to 6 carbon atoms (e.g., propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 1 to 4 carbon atoms, fluorinated hydroxyalkyl having 1 to 4 carbon atoms, monoalkylamino having 1 to 4 carbon atoms, dialkylamino wherein each alkyl group independently has 1 to 4 carbon atoms, Ar, or Het;

$R^9$ is alkyl having 1 to 4 carbon atoms, Ar, Ar-alkyl wherein the alkyl portion has 1 to 4 carbon atoms, or Het;

$R^{10}$ is alkyl having 1 to 4 carbon atoms, fluorinated alkyl having 1 to 4 carbon atoms (e.g., $CF_3$), alkenyl having 3 to 6 carbon atoms, alkynyl having 3 to 6 carbon atoms (e.g., propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, $NR^6R^7$, $NR^2R^8$, Ar, or Het;

Ar is an aryl group having 6 to 10 carbon atoms which is unsubstituted or substituted one or more times by alkyl having 1 to 8 carbon atoms, alkoxy having 1 to 8 carbon atoms, halogen (F, Cl, Br, or I, preferably F or Cl), dialkylamino wherein the alkyl portions each have 1 to 8 carbon atoms, amino, cyano, hydroxyl, nitro, halogenated alkyl having 1 to 8 carbon atoms, halogenated alkoxy having 1 to 8 carbon atoms, hydroxyalkyl having 1 to 8 carbon atoms, hydroxyalkoxy having 2 to 8 carbon atoms, alkenyloxy having 3 to 8 carbon atoms, alkylthio having 1 to 8 carbon atoms, alkylsulphinyl having 1 to 8 carbon atoms, alkylsulphonyl having 1 to 8 carbon atoms, monoalkylamino having 1 to 8 carbon atoms, cycloalkylamino wherein the cycloalkyl group has 3 to 7 carbon atoms and is optionally substituted, aryloxy wherein the aryl portion has 6 to 10 carbon atoms (e.g., phenyl, naphthyl, biphenyl) and is optionally substituted, arylthio wherein the aryl portion has 6 to 10 carbon atoms (e.g., phenyl, naphthyl, biphenyl) and is optionally substituted, cycloalkyloxy wherein the cycloalkyl group has 3 to 7 carbon atoms and is optionally substituted, sulfo, sulfonylamino, acylamido (e.g., acetamido), acyloxy (e.g., acetoxy) or combinations thereof;

Het is a heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), aryl having 6 to 10 carbon atoms (e.g., phenyl, naphthyl, biphenyl) which is optionally substituted, alkyl having 1 to 8 carbon atoms, alkoxy having 1 to 8 carbon atoms, cycloalkyl having 3 to 7 carbon atoms, cycloalkylalkyl having 4 to 7 carbon atoms (e.g., cyclopropylmethyl), halogenated alkoxy having 1 to 8 carbon atoms (e.g., $OCHF_2$), cycloalkoxy having 3 to 7 carbon atoms, cycloalkylalkoxy having 4 to 7 carbon atoms (e.g., cyclopropylmethyloxy), alkoxyalkyl having 2 to 8 carbon atoms (e.g., $CH_3OCH_2$), alkyl(halogenated alkyl)amino wherein each alkyl group has 1 to 8 carbon atoms (e.g., methyl(trifluoromethyl)amino), di(halogenated alkyl)amino wherein each alkyl group has 1 to 8 carbon atoms, (halogenated alkyl)amino having 1 to 8 carbon atoms, cyano, halogenated alkyl having 1 to 8 carbon atoms (e.g., fluorinated alkyl, such as trifluoromethyl, trifluoroethyl), nitro, oxo, OH, alkoxycarbonylalkyl having 3 to 8 carbon atoms, amino, monoalkylamino having 1 to 8 carbon atoms, dialkylamino wherein each alkyl group has 1 to 8 carbon atoms, $SO_2R^{11}$, —$CXR^{11}$, piperidinylethyl or combinations thereof;

Carbo is a partially unsaturated carbocyclic group having 5 to 14 carbon atoms, which is unsubstituted or substituted one or more times by halogen, alkyl having 1 to 8 carbon atoms, alkoxy having 1 to 8 carbon atoms, hydroxy, nitro, cyano, oxo, or combinations thereof (e.g., indanyl, tetrahydronaphthenyl, etc.); and $R^{11}$ is alkyl having 1 to 4 carbon atoms, halogenated alkyl having 1 to 4 carbon atoms (e.g., $CF_3$), alkenyl having 3 to 6 carbon atoms, alkynyl having 3 to 6 carbon atoms (e.g., propynyl, pentenyl), wherein the alkyl, halogenated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, or Ar;

and pharmaceutically acceptable salts or solvates (e.g., hydrates) or N-oxides thereof, or solvates of pharmaceutically acceptable salts thereof, or pharmaceutically acceptable salts or solvates of N-oxides thereof.

According to a further compound and/or method aspect of the invention, the compound is selected from Formulas I, II, III, or IV:

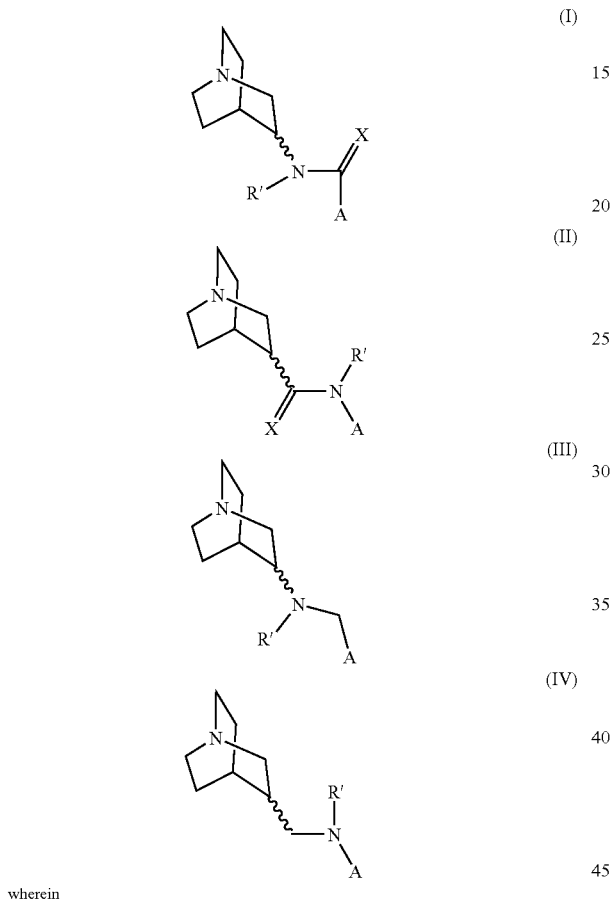

wherein

A is

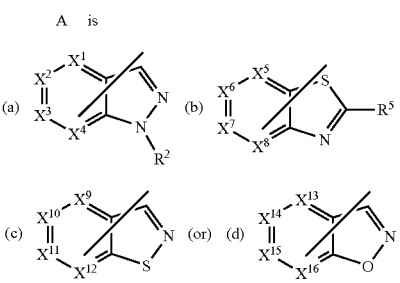

X is O or S;

$X^1$ to $X^4$ are each, independently, N, CH, $CR^1$, or C—, wherein C— represents the point of attachment of group A to the remainder of the structure of formulas (I), (II), (III) or (IV) (for example, $X^1$, $X^2$, $X^3$ and $X^4$ are each CH or $CR^1$, and group A is attached at the 3-position to the remainder of the structure of formulas (I), (II), (III) or (IV), $X^1$, $X^2$ and $X^3$ are each CH or $CR^1$, $X^4$ is N, and group A is attached at the 3-position to the remainder of the structure of formulas (I), (II), (III) or (IV), $X^1$, $X^2$ and $X^4$ are each CH or $CR^1$, $X^3$ is N, and group A is attached at the 3-position to the remainder of the structure of formulas (I), (II), (III) or (IV), or $X^1$, $X^3$ and $X^4$ are each CH or $CR^1$, $X^2$ is N, and group A is attached at the 3-position to the remainder of the structure of formulas (I), (II), (III) or (IV));

$X^5$ to $X^8$ are each, independently, N, CH, $CR^3$, or C—, wherein C— represents the point of attachment of group A to the remainder of the structure of formulas (I), (II), (III) or (IV) (for example, $X^5$, $X^6$, and $X^8$ are each CH or $CR^3$ and $X^7$ is C— whereby group A is attached at its 5-position to the remainder of the structure of formulas (I), (II), (III) or (IV), or $X^5$, $X^7$, and $X^8$ are each CH or $CR^3$ and $X^6$ is C— whereby group A is attached at its 6-position to the remainder of the structure of formulas (I), (II), (III) or (IV));

$X^9$ to $X^{12}$ are each, independently, N, CH, $CR^4$, or C—, wherein C— represents the point of attachment of group A to the remainder of the structure of formulas (I), (II), (III) or (IV) (for example, $X^9$, $X^{10}$, $X^{11}$ and $X^{12}$ are each CH or $CR^4$, and group A is attached at the 3-position to the remainder of the structure of formulas (I), (II), (III) or (IV), $X^9$, $X^{10}$ and $X^{11}$ are each CH or $CR^4$, $X^{12}$ is N, and group A is attached at the 3-position to the remainder of the structure of formulas (I), (II), (III) or (IV), or $X^9$, $X^{10}$ and $X^{12}$ are each CH or $CR^4$, $X^{11}$ is N, and group A is attached at the 3-position to the remainder of the structure of formulas (I), (II), (III) or (IV), or $X^9$, $X^{11}$ and $X^{12}$ are each CH or $CR^4$, $X^{10}$ is N, N and group A is attached at the 3-position to the remainder of the structure of formulas (I), (II), (III) or (IV));

$X^{13}$ to $X^{16}$ are each, independently, N, CH, CR, or C—, wherein C— represents the point of attachment of group A to the remainder of the structure of formulas (I), (II), (III) or (IV) (for example, $X^{13}$, $X^{14}$, $X^{15}$ and $X^{16}$ are each CH or CR, and group A is attached at the 3-position to the remainder of the structure of formulas (I), (II), (III) or (IV), $X^{13}$, $X^{14}$ and $X^{15}$ are each CH or CR, $X^{16}$ is N, and group A is attached at the 3-position to the remainder of the structure of formulas (I), (II), (III) or (IV), or $X^{13}$, $X^{14}$ and $X^{16}$ are each CH or CR, $X^{15}$ is N, and group A is attached at the 3-position to the remainder of the structure of formulas (I), (II), (III) or (IV), or $X^{13}$, $X^{15}$ and $X^{16}$ are each CH or CR, $X^{14}$ is N, and group A is attached at the 3-position to the remainder of the structure of formulas (I), (II), (III) or (IV));

R' is H, alkyl having 1 to 4 carbon atoms, halogenated alkyl having 1 to 4 carbon atoms, cycloalkyl having 3 to 7 carbon atoms, or cycloalkylalkyl having 4 to 7 carbon atoms;

R is H, F, Cl, Br, I, OH, CN, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—$(C_{1-6}$-alkyl-O$)_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—, with the proviso that R is not $NH_2$; or R is of one of the following formulas

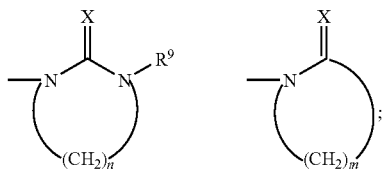

n is 2 to 4;

m is 3 to 5; or two R can together form a 5-membered fused ring structure containing at least one N atom;

$R^1$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—$(C_{1-6}$-alkyl-O$)_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^1$ is of one of the following formulas

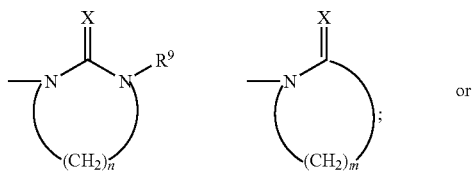

two $R^1$ can together form a 5-membered fused ring structure containing at least one N atom;

$R^2$ is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl- (e.g., $CH_2CH_2$—O—$CH_3$), Ar—$C_{1-4}$-alkyl-NH—CO—, or Het-NH—CO— (e.g., (1-azabicyclo[2.2.2]oct-3-yl)-NH—CO—);

$R^3$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—$(C_{1-6}$-alkyl-O$)_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, or —CO—$R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^3$ is of one of the following formulas

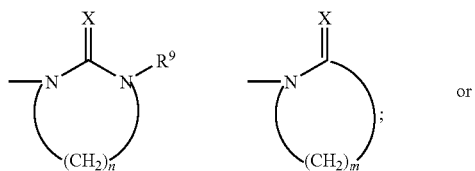

two $R^3$ can together form a 5-membered fused ring structure containing at least one N atom;

$R^4$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, $-O-(C_{1-6}\text{-alkyl-O})_{1-2}-C_{1-6}\text{-alkyl}$, $NR^2-C_{1-6}\text{-alkyl-}NR^6R^7$, $NR^2-C_{1-6}\text{-alkyl-}CONR^6R^7$, $NR^2-CO-C_{1-6}\text{-alkyl-Ar}$, $NR^2-C_{1-6}\text{-alkyl-CO-}O-R^2$, $NR^2-C_{1-6}\text{-alkyl-}NR^2(CO-O-R^2)$, $-C_{1-6}\text{-alkyl-}NR^2$, $-O-C_{1-6}\text{-alkyl-}NR^6R^7$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5-C\equiv C-$), cycloalkyl having 3 to 7 carbon atoms, cycloalkenyl having 5 to 8 carbon atoms which is unsubstituted or substituted by HCO—, $C_{1-6}$-alkoxy, $NR^6R^7$, $CO-NR^6R^7$, $C_{2-6}$-alkoxycarbonyl, or $-CO-R^{10}$, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^4$ is of one of the following formulas

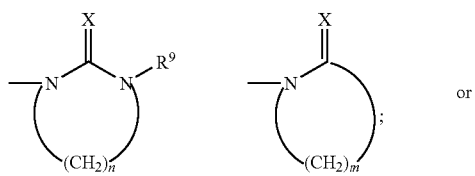

two $R^4$ can together form a 5-membered fused ring structure containing at least one N atom;

$R^5$ is H, F, Cl, Br, I, OH, CN, nitro, $NH_2$, carboxy, $CONR^6R^7$, $NR^2COR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, alkyl having 1 to 4 carbon atoms, fluorinated alkyl having 1 to 4 carbon atoms (e.g., $CF_3$), alkenyl having 2 to 6 carbon atoms, alkynyl having 2 to 6 carbon atoms (e.g., ethynyl, propynyl, pentenyl), wherein the alkyl, fluorinated alkyl, alkenyl, or alkynyl groups are in each case unsubstituted or substituted by Ar or Het (e.g., phenylacetylene $C_6H_5-C\equiv C-$), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), alkylthio having 1 to 4 carbon atoms (e.g., $SCH_3$), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms (e.g., 2,2,2-trifluoro-1-hydroxyl-1-(trifluoromethyl)ethyl), hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, or OHet;

$R^6$ and $R^7$ are each, independently, H, alkyl having 1 to 4 carbon atoms, alkoxyalkyl having 2 to 8 carbon atoms, cycloalkyl having 3 to 7 carbon atoms, or cycloalkylalkyl having 4 to 7 carbon atoms, or $R^6$ and $R^7$ together are an alkylene group containing 4-6 carbon atoms which forms a ring with the N atom (e.g., piperidinyl, pyrrolidinyl);

$R^8$ is H, alkyl having 1 to 4 carbon atoms, fluorinated alkyl having 1 to 4 carbon atoms (e.g., $CF_3$), alkenyl having 3 to 6 carbon atoms, alkynyl having 3 to 6 carbon atoms (e.g., propynyl, pentenyl), wherein the alkyl, fluorinated alkyl, alkenyl, or alkynyl groups are in each case unsubstituted or substituted by Ar or Het (e.g., phenylacetylene $C_6H_5-C\equiv C-$), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 1 to 4 carbon atoms, fluorinated hydroxyalkyl having 1 to 4 carbon atoms, monoalkylamino having 1 to 4 carbon atoms, dialkylamino wherein each alkyl group independently has 1 to 4 carbon atoms, Ar, or Het;

$R^9$ is alkyl having 1 to 4 carbon atoms, Ar, Ar-alkyl wherein the alkyl portion has 1 to 4 carbon atoms, or Het;

$R^{10}$ is alkyl having 1 to 4 carbon atoms, fluorinated alkyl having 1 to 4 carbon atoms (e.g., $CF_3$), alkenyl having 3 to 6 carbon atoms, alkynyl having 3 to 6 carbon atoms (e.g., propynyl, pentenyl), wherein the alkyl, fluorinated alkyl, alkenyl, or alkynyl groups are in each case unsubstituted or substituted by Ar or Het (e.g., phenylacetylene $C_6H_5-C\equiv C-$), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, $NR^6R^7$, $NR^2R^8$, Ar, or Het;

Ar is an aryl group having 6 to 10 carbon atoms which is unsubstituted or substituted one or more times by alkyl having 1 to 8 carbon atoms, alkoxy having 1 to 8 carbon atoms, halogen (F, Cl, Br, or I, preferably F or Cl), dialkylamino wherein the alkyl portions each have 1 to 8 carbon atoms, amino, cyano, hydroxyl, nitro, halogenated alkyl having 1 to 8 carbon atoms, halogenated alkoxy having 1 to 8 carbon atoms, hydroxyalkyl having 1 to 8 carbon atoms, hydroxyalkoxy having 2 to 8 carbon atoms, alkenyloxy having 3 to 8 carbon atoms, alkylthio having 1 to 8 carbon atoms, alkylsulphinyl having 1 to 8 carbon atoms, alkylsulphonyl having 1 to 8 carbon atoms, monoalkylamino having 1 to 8 carbon atoms, cycloalkylamino wherein the cycloalkyl group has 3 to 7 carbon atoms and is optionally substituted, aryloxy wherein the aryl portion has 6 to 10 carbon atoms (e.g., phenyl, naphthyl, biphenyl) and is optionally substituted, arylthio wherein the aryl portion has 6 to 10 carbon atoms (e.g., phenyl, naphthyl, biphenyl) and is optionally substituted, cycloalkyloxy wherein the cycloalkyl group has 3 to 7 carbon atoms and is optionally substituted, sulfo, sulfonylamino, acylamido (e.g., acetamido), acyloxy (e.g., acetoxy) or combinations thereof;

Het is a heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), aryl having 6 to 10 carbon atoms (e.g., phenyl, naphthyl, biphenyl) which is optionally substituted, alkyl having 1 to 8 carbon atoms, alkoxy having 1 to 8 carbon atoms, cycloalkyl having 3 to 7 carbon atoms, cycloalkylalkyl having 4 to 7 carbon atoms (e.g., cyclopropylmethyl), halogenated alkoxy having 1 to 8 carbon atoms (e.g., $OCHF_2$), cycloalkoxy having 3 to 7 carbon atoms, cycloalkylalkoxy having 4 to 7 carbon atoms (e.g., cyclopropylmethyloxy), alkoxyalkyl having 2 to 8 carbon atoms (e.g., $CH_3OCH_2$), alkyl(halogenated alkyl)amino wherein each alkyl group has 1 to 8 carbon atoms (e.g., methyl(trifluoromethyl)amino), di(halogenated alkyl)amino wherein each alkyl group has 1 to 8 carbon atoms, (halogenated alkyl)amino having 1 to 8 carbon atoms, cyano, halogenated alkyl having 1 to 8 carbon atoms (e.g., fluorinated alkyl, such as trifluoromethyl, trifluoroethyl), nitro, oxo, OH, alkoxycarbonylalkyl having 3 to 8 carbon atoms, amino, monoalkylamino having 1 to 8 carbon atoms, dialkylamino wherein each alkyl group has 1 to 8 carbon atoms, $SO_2R^{11}$, —$CXR^{11}$, piperidinylethyl or combinations thereof;

Carbo is a partially unsaturated carbocyclic group having 5 to 14 carbon atoms, which is unsubstituted or substituted one or more times by halogen, alkyl having 1 to 8 carbon atoms, alkoxy having 1 to 8 carbon atoms, hydroxy, nitro, cyano, oxo, or combinations thereof (e.g., indanyl, tetrahydronaphthenyl, etc.); and $R^{11}$ is alkyl having 1 to 4 carbon atoms, halogenated alkyl having 1 to 4 carbon atoms (e.g., $CF_3$), alkenyl having 3 to 6 carbon atoms, alkynyl having 3 to 6 carbon atoms (e.g., propynyl, pentenyl), wherein the alkyl, halogenated alkyl, alkenyl, or alkynyl groups are in each case unsubstituted or substituted by Ar or Het (e.g., phenylacetylene $C_6H_5$—C≡C—), cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, or Ar;

and pharmaceutically acceptable salts or solvates (e.g., hydrates) or N-oxides thereof, or solvates of pharmaceutically acceptable salts thereof, or pharmaceutically acceptable salts or solvates of N-oxides thereof;

with the proviso that the 1-azabicyclo group is in the form of a quaternary ammonium salt of the subformula:

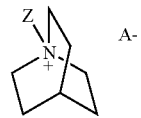

wherein Z is alkyl having 1 to 4 carbon atoms (e.g., methyl, ethyl, propyl), halogenated alkyl having 1 to 4 carbon atoms (e.g., chloromethyl, chloroethyl), cycloalkylalkyl having 4 to 7 carbon atoms (e.g., cyclopropylmethyl), or arylalkyl having 7 to 16 carbon atoms (e.g., benzyl), and anion A is, for example, iodide, bromide, chloride, triflate, tosylate, or mesylate.

According to a further compound and/or method aspect of the invention, the compound is selected from Formulas I-IV, wherein:

$R^2$ if present, is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl- (e.g., $CH_2CH_2$—O—$CH_3$), or Ar—$C_{1-4}$-alkyl-NH—CO—; and Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms which is optionally substituted, alkyl having 1 to 8 carbon atoms, alkoxy having 1 to 8 carbon atoms, cycloalkyl having 3 to 7 carbon atoms, halogenated alkoxy having 1 to 8 carbon atoms, cycloalkoxy having 3 to 7 carbon atoms, cycloalkylalkoxy having 4 to 7 carbon atoms, alkyl(halogenated alkyl)amino wherein each alkyl group has 1 to 8 C atoms, di(halogenated alkyl)amino wherein each alkyl group has 1 to 8 C atoms, (halogenated alkyl)amino having 1 to 8 carbon atoms, cyano, halogenated alkyl having 1 to 8 carbon atoms, nitro, oxo, OH, alkoxycarbonylalkyl having 3 to 8 carbon atoms, amino, monoalkylamino having 1 to 8 carbon atoms, dialkylamino wherein each alkyl group has 1 to 8 C atoms, $SO_2R^{11}$, —$CXR^{11}$, piperidinylethyl or combinations thereof.

In Formulas I-IV, the group A, for example, an indazolyl, benzothiazolyl, benzoisothiazolyl, benzisoxazolyl, pyrazolo[3,4-b]pyridinyl, pyrazolo[4,3-c]pyridinyl, or isothiazolo[5,4-b]pyridinyl group, can be attached to the remainder of the structure via any suitable attachment point.

In Formula I, when A is of subformula (a), e.g., an indazolyl group, it is preferably attached to the remainder of the compound via its 3, 4 or 7 position, particularly via the 3-position. When A is of subformula (b), e.g., a benzothiazolyl group, it is preferably attached to the remainder of the compound via its 4 or 7 position. When A is of subformula (c), e.g., a benzoisothiazolyl group, it is preferably attached to the remainder of the compound via its 3, 4 or 7 position, particularly via the 3-position. When A is of subformula (d), e.g., a benzisoxazolyl group, it is preferably attached to the remainder of the compound via its 3, 4 or 7 position, particularly via the 3-position.

Similarly, in Formula II, when A is of subformula (a), e.g., an indazolyl group, it is preferably attached to the remainder of the compound via its 3, 4 or 7 position, particularly via the 3-position. When A is of subformula (b), e.g., a benzothiazolyl group, it is preferably attached to the remainder of the compound via its 4 or 7 position. When A is of subformula (c), e.g., a benzoisothiazolyl group, it is preferably attached to the remainder of the compound via its 3, 4 or 7 position, particularly via the 3-position. When A is of subformula (d), e.g., a benzisoxazolyl group, it is preferably attached to the remainder of the compound via its 3, 4 or 7 position, particularly via the 3-position.

Also, in Formula III, when A is of subformula (a), e.g., an indazolyl group, it is preferably attached to the remainder of the compound via its 3, 4 or 7 position, particularly via the 3-position. When A is of subformula (b), e.g., a benzothiazolyl group, it is preferably attached to the remainder of the compound via its 4 or 7 position. When A is of subformula (c), e.g., a benzoisothiazolyl group, it is preferably attached to the remainder of the compound via its 3, 4 or 7 position, particularly via the 3-position. When A is of subformula (d), e.g., a benzisoxazolyl group, it is preferably attached to the remainder of the compound via its 3, 4 or 7 position, particularly via the 3-position.

Further, in Formula IV, when A is of subformula (a), e.g., an indazolyl group, it is preferably attached to the remainder of the compound via its 3, 4 or 7 position, particularly via the 3-position. When A is of subformula (b), e.g., a benzothiazolyl group, it is preferably attached to the remainder of the compound via its 4 or 7 position. When A is of subformula (c), e.g., a benzoisothiazolyl group, it is preferably attached to the remainder of the compound via its 3, 4 or 7 position, particularly via the 3-position. When A is of subformula (d), e.g., a benzisoxazolyl group, it is preferably attached to the remainder of the compound via its 3, 4 or 7 position, particularly via the 3-position.

The following subformulas illustrate some of the preferred attachments between the A groups, e.g., indazole, benzothiazole, benzoisothiazole, benzisoxazole, pyrazolo[3,4-b]pyridinyl, pyrazolo[3,4-c]pyridine, pyrazolo[4,3-c]pyridinyl, and isothiazolo[5,4-b]pyridinyl, and the remainder of the structure for Formula I. In each of the following subformulas, the R, $R^1$, $R^3$, and/or $R^4$ substituent is generally present 1, 2, or 3 times, preferably 1 or 2 times, more preferably once.

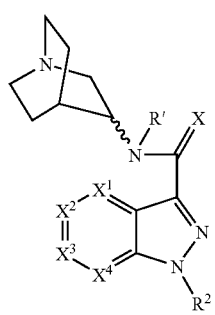

(Ia)

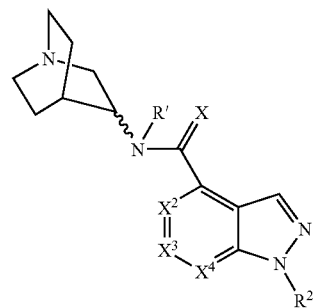

(Ib)

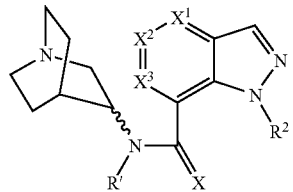

(Ie)

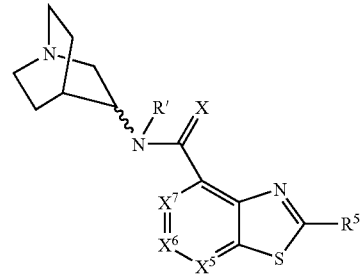

(If)

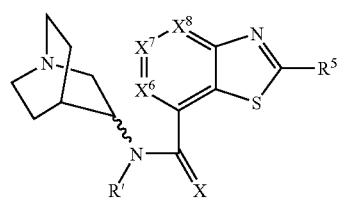

(Ii)

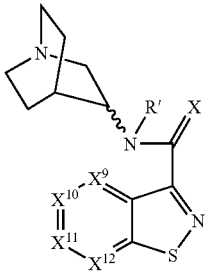

(Ij)

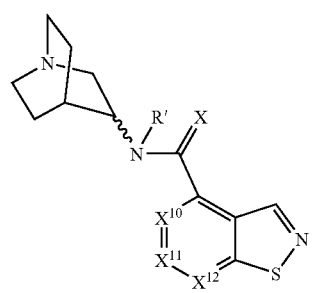

(Ik)

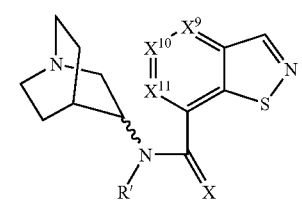
(Io)

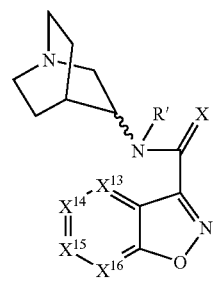
(Ip)

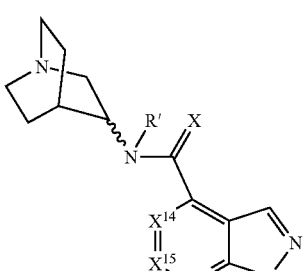
(Iq)

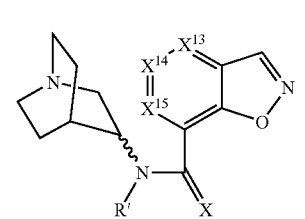
(It)

The following subformulas further illustrate some of the preferred attachments between the A groups, e.g., groups, e.g., indazole, benzothiazole, benzoisothiazole, benzisoxazole, pyrazolo[3,4-b]pyridinyl, pyrazolo[3,4-c]pyridine, pyrazolo[4,3-c]pyridinyl, and isothiazolo[5,4-b]pyridinyl, and the remainder of the structure for Formula II. In each of the following subformulas, the R, $R^1$, $R^3$, and/or $R^4$ substituent is generally present 1, 2, or 3 times, preferably 1 or 2 times, more preferably once.

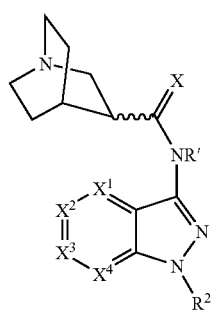
(IIa)

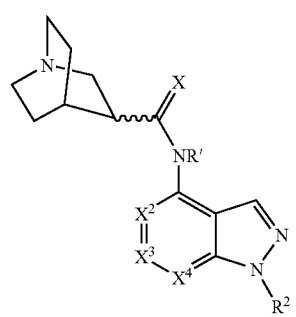
(IIb)

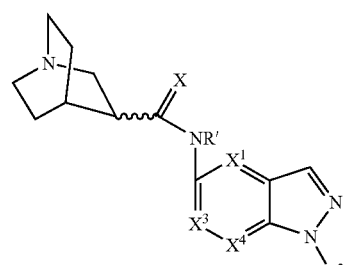
(IIc)

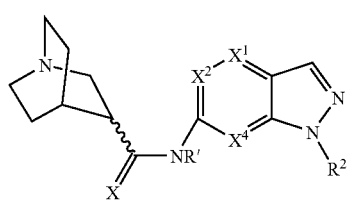
(IId)

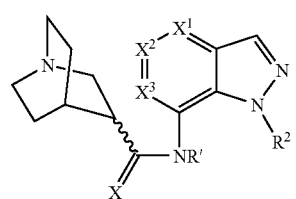
(IIe)

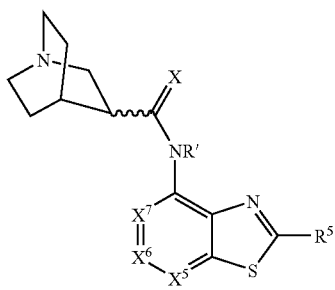
(IIf)

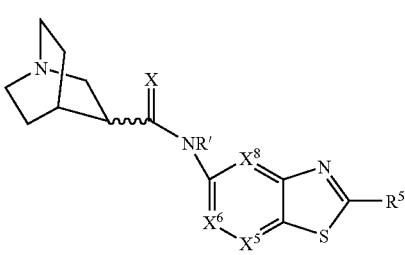
(IIg)

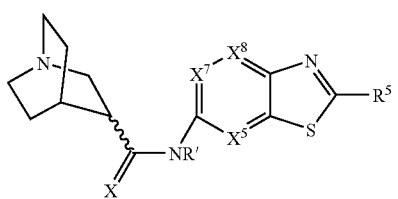 (IIh)

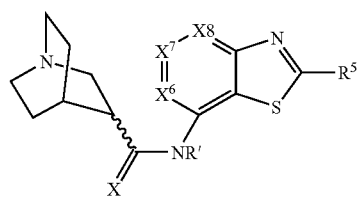 (IIi)

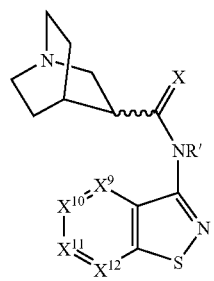 (IIj)

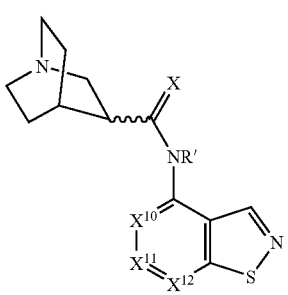 (IIk)

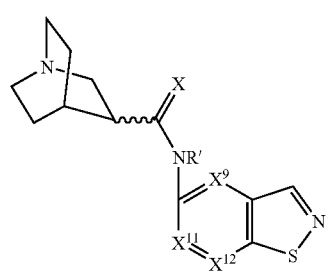 (IIm)

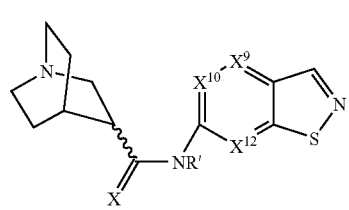 (IIn)

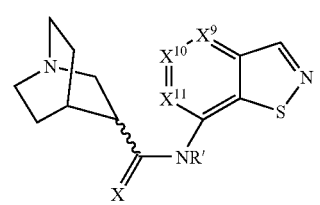 (IIo)

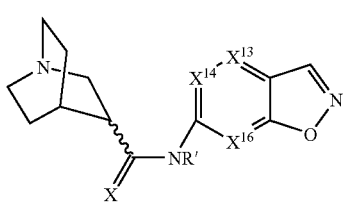 (IIs)

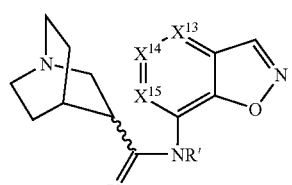 (IIt)

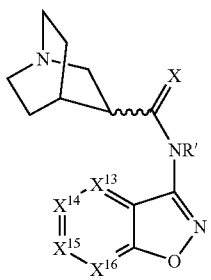 (IIp)

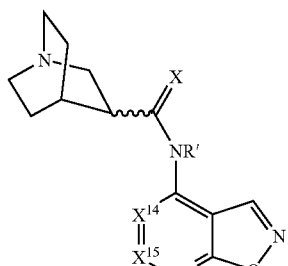 (IIq)

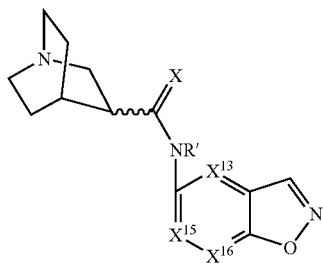 (IIr)

The following subformulas further illustrate some of the preferred attachments between the A groups, e.g., indazole, benzothiazole, benzoisothiazole, benzisoxazole, pyrazolo[3,4-b]pyridinyl, pyrazolo[3,4-c]pyridine, pyrazolo[4,3-c]pyridinyl, and isothiazolo[5,4-b]pyridinyl, and the remainder of the structure for Formula III. In each of the following subformulas, the R, $R^1$, $R^3$, and/or $R^4$ substituent is generally present 1, 2, or 3 times, preferably 1 or 2 times, more preferably once.

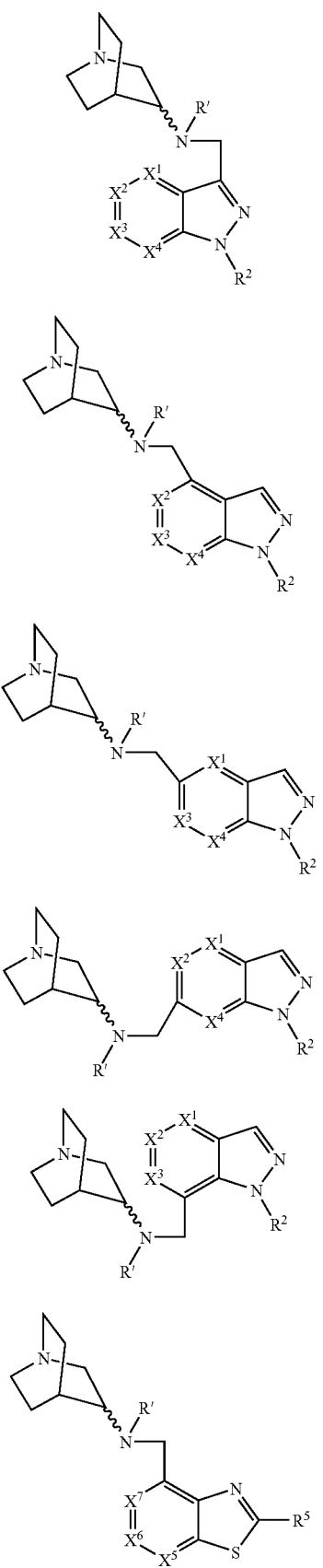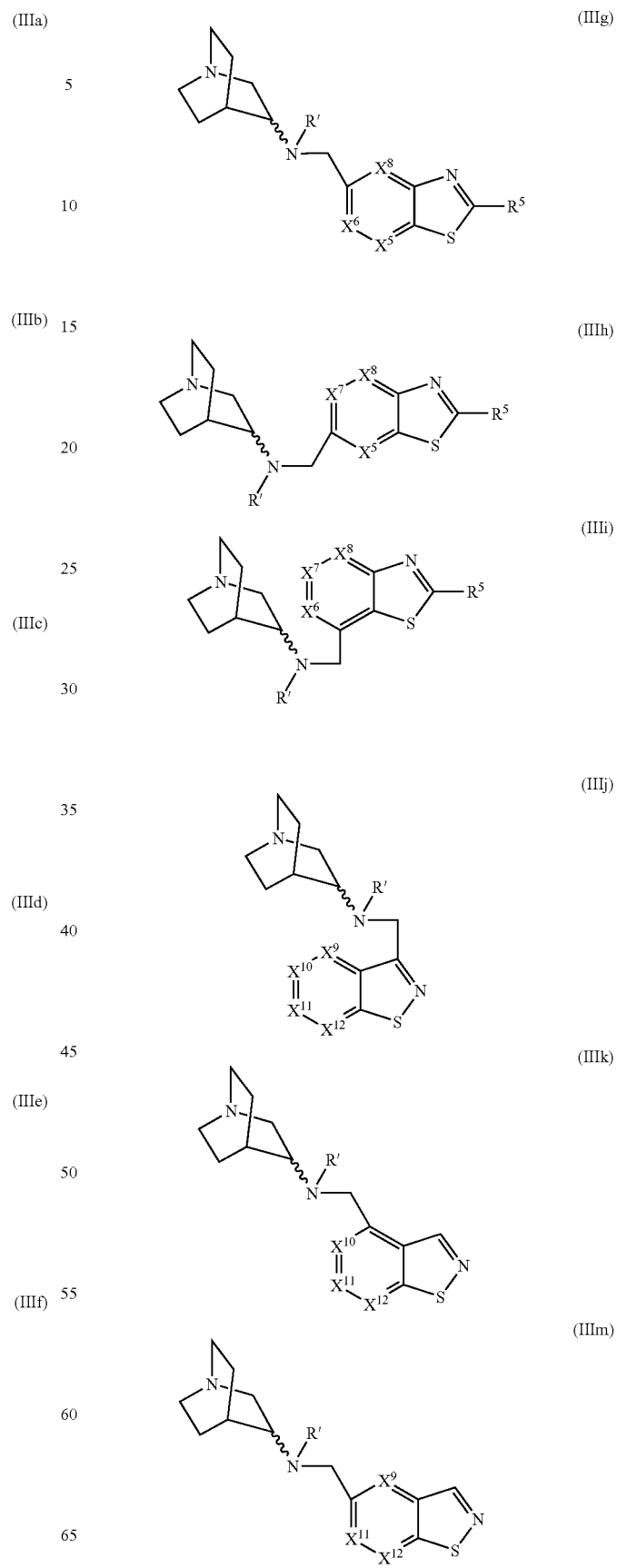

-continued

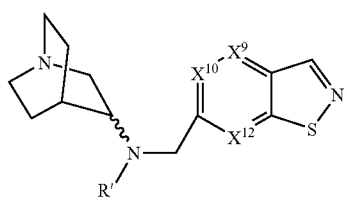
(IIIn)

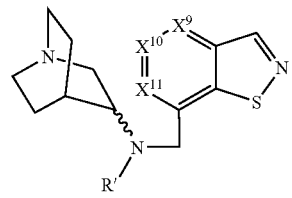
(IIIo)

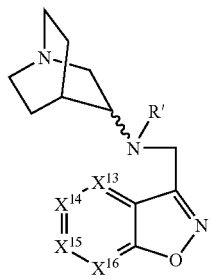
(IIIp)

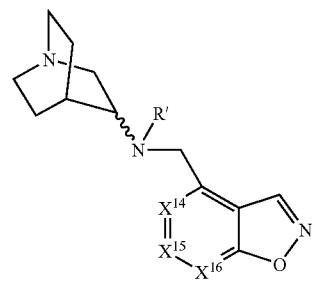
(IIIq)

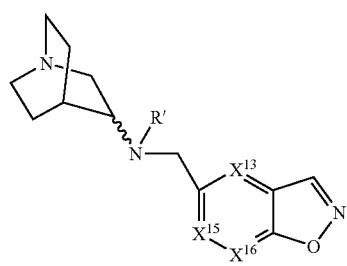
(IIIr)

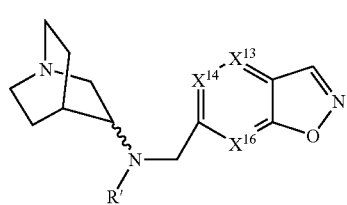
(IIIs)

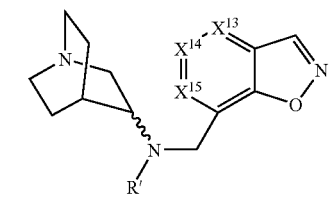
(IIIt)

The following subformulas further illustrate some of the preferred attachments between the A groups, e.g., indazole, benzothiazole, benzoisothiazole, benzisoxazole, pyrazolo[3,4-b]pyridinyl, pyrazolo[3,4-c]pyridine, pyrazolo[4,3-c]pyridinyl, and isothiazolo[5,4-b]pyridinyl, and the remainder of the structure for Formula IV. In each of the following subformulas, the R, $R^1$, $R^3$, and/or $R^4$ substituent is generally present 1, 2, or 3 times, preferably 1 or 2 times, more preferably once.

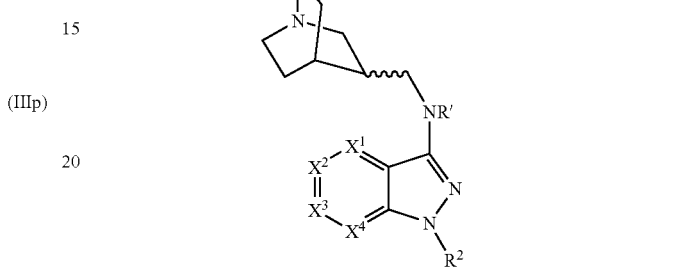
(IVa)

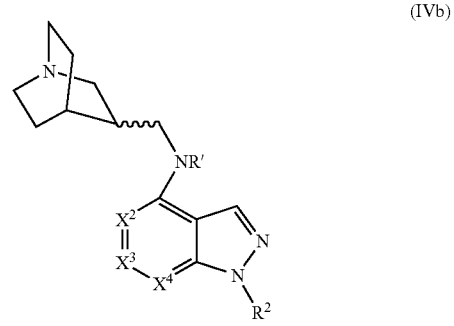
(IVb)

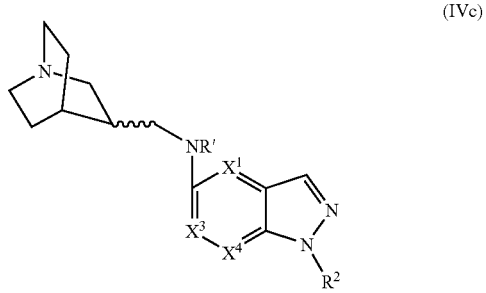
(IVc)

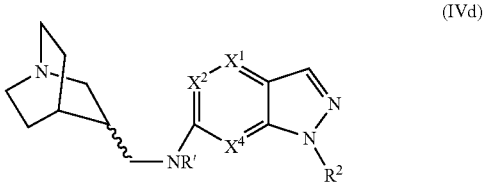
(IVd)

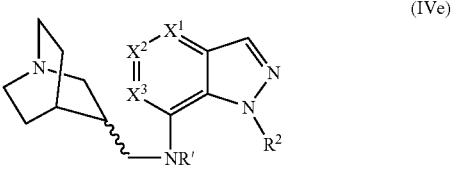
(IVe)

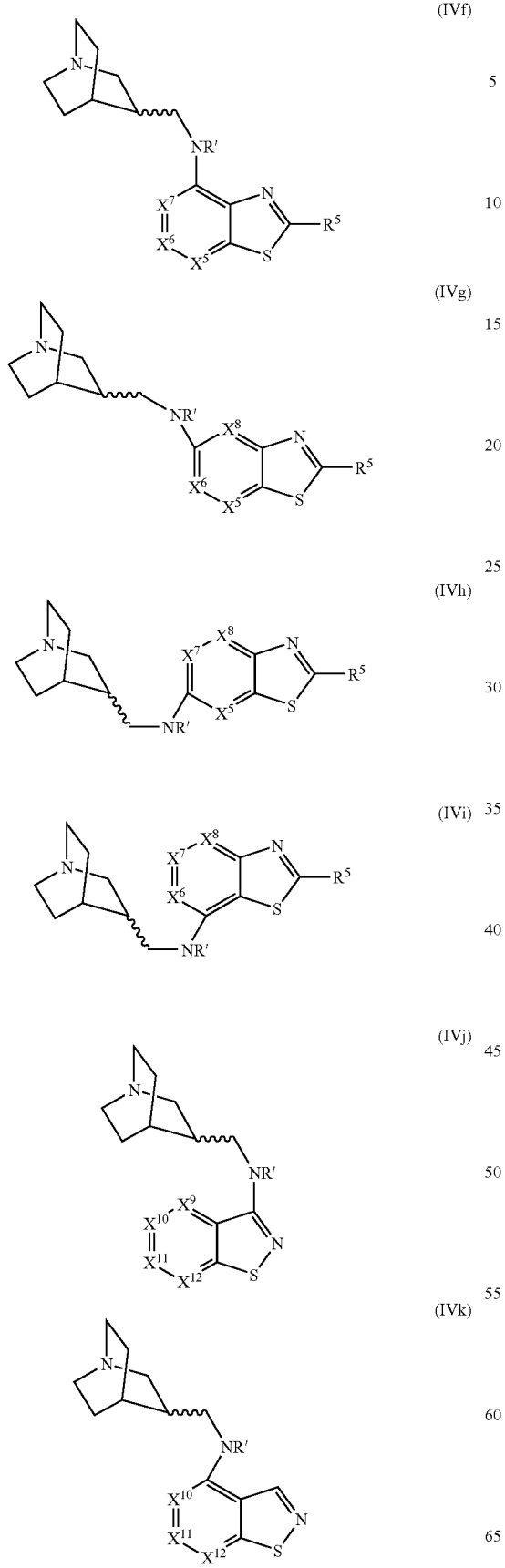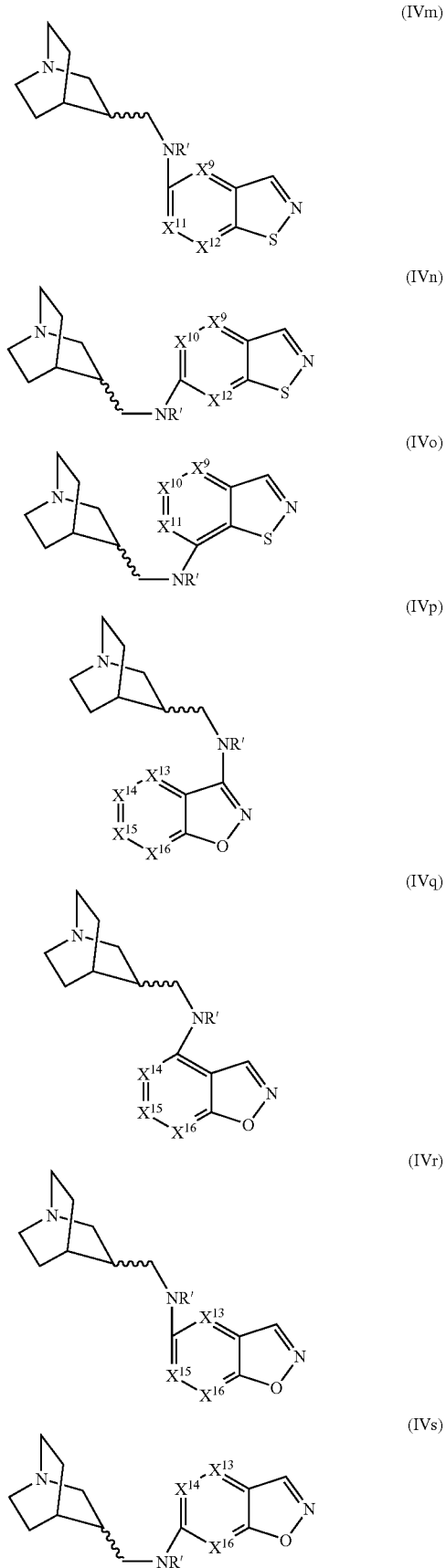

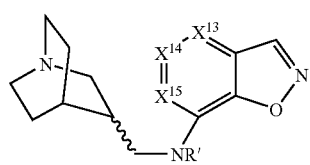
(IVt)

In all cases, X is preferably O.

In all cases, R' is preferably H, cyclopropylmethyl, or $CH_3$, particularly H.

Alkyl throughout means a straight-chain or branched-chain aliphatic hydrocarbon radical having 1 to 8 carbon atoms, preferably 1 to 4 carbon atoms. Suitable alkyl groups include but are not limited to methyl, ethyl, propyl, isopropyl, butyl, sec-butyl, and tert-butyl.

Alkenyl throughout means a straight-chain or branched-chain aliphatic hydrocarbon radical having preferably 2 to 6 carbon atoms. Suitable alkenyl groups include but are not limited to ethenyl, propenyl, butenyl, and pentenyl.

Alkynyl throughout means a straight-chain or branched-chain aliphatic hydrocarbon radical having preferably 2 to 6 carbon atoms. Suitable alkynyl groups include but are not limited to ethyne(ethynyl), propyne(propynyl), butyne(butynyl), etc.

Alkoxy means alkyl-O— groups in which the alkyl portion has 1 to 8 carbon atoms, preferably 1 to 4 carbon atoms. Suitable alkoxy groups include but are not limited to methoxy, ethoxy, propoxy, isopropoxy, isobutoxy, and sec-butoxy.

Alkoxyalkyl means alkyl-O-alkyl- groups in which each alkyl portion independently has 1 to 8 carbon atoms, preferably 1 to 4 carbon atoms. Suitable alkoxyalkyl groups include, but are not limited to, methoxymethyl, ethoxymethyl, and methoxyethyl.

Alkylthio means alkyl-S— groups in which the alkyl portion preferably has 1 to 4 carbon atoms. Suitable alkylthio groups include but are not limited to methylthio and ethylthio.

Cycloalkyl means a cyclic, bicyclic or tricyclic saturated hydrocarbon radical having 3 to 7 carbon atoms. Suitable cycloalkyl groups include but are not limited to cyclopropyl, cyclobutyl, cyclopentyl, and cyclohexyl. Other suitable cycloalkyl groups include but are not limited to spiropentyl, bicyclo[2.1.0]pentyl, and bicyclo[3.1.0]hexyl.

Cycloalkoxy means cycloalkyl-O- groups in which the cycloalkyl portion preferably is a cyclic, bicyclic or tricyclic saturated hydrocarbon radical having 3 to 7 carbon atoms.

Cycloalkylalkyl groups contain 4 to 7 carbon atoms. Suitable cycloalkylalkyl groups include but are not limited to, for example, cyclopropylmethyl, cyclopropylethyl, cyclobutylmethyl, and cyclopentylmethyl.

Cycloalkylalkoxy groups contain 4 to 7 carbon atoms. Suitable cycloalkylalkoxy groups include but are not limited to, for example, cyclopropylmethyloxy, cyclopropylethyloxy, cyclobutylmethyloxy, and cyclopentylmethyloxy.

Cycloalkyl and cycloalkylalkyl structures can be substituted by, for example, $C_{1-4}$-alkyl, $C_{1-4}$-alkoxy, hydroxyl, amino, monoalkylamino having 1 to 4 carbon atoms, and/or dialklyamino in which each alkyl group has 1 to 4 carbon atoms.

Aryl, as a group or substituent per se or as part of a group or substituent (e.g., Ar, OAr, Ar—$C_{1-6}$-alkyl-O—, or Ar—$C_{1-6}$-alkyl-Het-O—), refers to an aromatic carbocyclic radical having 6 to 10 carbon atoms, unless indicated otherwise. Suitable aryl groups include but are not limited to phenyl, napthyl and biphenyl. Substituted aryl groups include the above-described aryl groups which are substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and/or acyloxy (e.g., acetoxy).

Heterocyclic groups (e.g., the Het portions of Het, OHet, Het-$C_{1-6}$-alkyl-O—, Het-CO-Het-, and Het-$C_{1-6}$-alkyl-$NR^2$) refer to saturated, partially saturated and fully unsaturated heterocyclic groups having one, two or three rings and a total number of 5 to 10 ring atoms wherein at least one of the ring atoms is an N, O or S atom. Preferably, the heterocyclic group contains 1 to 3 hetero-ring atoms selected from N, O and S. Suitable saturated and partially saturated heterocyclic groups include, but are not limited to dihydropyranyl, tetrahydropyranyl, tetrahydrofuranyl, tetrahydrothienyl, pyrrolidinyl, piperidinyl, piperazinyl, morpholinyl, isoxazolinyl and the like. Suitable heteroaryl groups include but are not limited to furyl, thienyl, thiazolyl, oxazolyl, pyrrolyl, pyrazolyl, imidazolyl, pyridyl, pyrimidinyl, indolyl, quinolinyl, isoquinolinyl, naphthyridinyl and the like. Other examples of suitable heterocyclic groups are 2-furyl, 3-furyl, 2-quinolinyl, 1,3-benzodioxyl, 2-thienyl, 3-thienyl, 1,3-thiazoly-2-yl, 1,3-oxazol-2-yl, pyrrolidin-1-yl, 6-pyrrolidin-1-yl, piperidin-1-yl, 6-piperazin-1-yl, morpholin-4-yl, 2-benzofuranyl, 2-benzothiophenyl, 3-thienyl, 2,3-dihydro-5-benzofuranyl, 4-indoyl, 4-pyridyl, 3-quinolinyl, 4-quinolinyl, 1,4-benzodioxan-6-yl, 3-indoyl, 2-pyrrolyl, tetrahydro-2H-pyran-4-yl, 3,6-dihydro-2H-pyran-4-yl, 5-indolyl, 1,5-benzoxepin-8-yl, 3-pyridyl, 6-coumarinyl, 5-benzofuranyl, 2-isoimidazol-4-yl, 3-pyrazolyl, 3-carbazolyl, hexahydropyrrolo[1,2-a]pyrazin-2(1H)-yl. octahydro-6H-pyrrolo[3,4-b]pyridin-6-yl, and 1,4-diazepan-1-yl, Heterocyclic groups also include substituted and unsubstituted azabicyclo and oxaazabicyclo groups, for example, 2,5-diazabicyclo[2.2.1]hept-2-yl, methyl-2,5-diazabicyclo[2.2.1]hept-2-yl, trifluoroethyl-2,5-diazabicyclo[2.2.1]hept-2-yl, 2-oxa-5-azabicyclo[2.2.1]hept-5yl, 5-methyl-2,5-diazabicyclo[2.2.1]hept-2-yl, 1,4-diazabicyclo[3.2.2]non-4-yl, 5-methyl-2,5-diazabicyclo[2.2.2]oct-2-yl, 8-methyl-3,8-diazabicyclo[3.2.1]oct-3-yl, 5-cyclopropyl-2,5-diazabicyclo[2.2.1]hept-2-yl, and 5-(cyclopropylcarbonyl)-2,5-diazabicyclo[2.2.1]hept-2-yl.

Substituted heterocyclic groups refer to the heterocyclic groups described above, which are substituted in one or more places by, for example, halogen, aryl, alkyl, alkoxy, cyano, trifluoromethyl, nitro, oxo, amino, alkylamino, and/or dialkylamino. Suitable substituted heterocyclic groups include 2-methylpiperazin-1-y, 3-methylpiperazin-1-yl, 4-methylpiperazin-1-yl, 3,4-dimethylpiperazin-1-yl, 4-methyl-1,4-diazepan-1-yl, 3-methoxypyrrolidin-1-yl, 1-methylpyrrolidin-3-yl, 1-methyl-4,5-dihydro-1H-imidazol-2-yl, 3-(cyclopropylmethoxy)pyrrolidin-1-yl, 6-chloroisothiazolo[5,4-b]pyridinyl, 4-(cyclopropylcarbonyl)piperazin-1-yl, and 1-(cyclopropylcarbonyl)octahydro-6H-pyrrolo[3,4-b]pyridin-6-yl.

Substituted radicals are, in each case, substituted one or more times, and preferably have 1 to 3 substituents, especially 1 or 2 substituents of the exemplified substituents. These substituents are in each case independently selected. Thus, the substituents can be the same or different. Halogenated radicals such as halogenated alkyls are preferably fluorinated and include but are not limited to perhalo radicals such as trifluoromethyl.

According to another compound and/or method aspect of the invention, R is not $NH_2$ or $NHCH_3$. According to a further aspect of the invention, R is not $NH_2$, $NHCH_3$, or $N(CH_3)_2$.

According to a further aspect of the invention, R is not $NH_2$, monoalkylamino, or dialkylamino.

According to a compound and/or method aspect of the invention, $R^2$ is Het-NH—CO—. According to another compound and/or method aspect of the invention, when $R^2$ is Het-NH—CO—, the Het group is preferably an azabicyclo group, for example, 1-azabicyclo[2.2.2]oct-3-yl.

According to a compound and/or method aspect of the invention, Het is substituted by cycloalkylalkyl having 4 to 7 carbon atoms (e.g., cyclopropylmethyl). According to another compound and/or method aspect of the invention, when Het is substituted by cycloalkylalkyl, the cycloalkyl portion preferably has 3 to 5 carbon atoms (e.g., cyclopropyl), and the alkyl portion preferably has 1 to 2 carbon atoms. Additionally, the Het group is preferably an azabicyclo group, for example, 2,5-diazabicyclo[2.2.1]hept-2-yl.

According to a further compound and/or method aspect of the invention, Het is a heterocyclic group, which is fully saturated, partially saturated or fully unsaturated, having 5 to 10 ring atoms in which at least 1 ring atom is a N, O or S atom, and which is substituted, wherein at least one of the substituents is halogenated alkoxy having 1 to 8 carbon atoms (e.g., $OCHF_2$), cycloalkoxy having 3 to 7 carbon atoms, cycloalkylalkoxy having 4 to 7 carbon atoms (e.g., cyclopropylmethyloxy), cycloalkylalkyl having 4 to 7 carbon atoms (e.g., cyclopropylmethyl), halogenated alkyl other than trifluoromethyl (e.g., halogenated alkyl having 2 to 8 or 3 to 8 carbon atoms such as trifluoroethyl and trifluoropropyl), alkoxyalkyl having 2 to 8 carbon atoms (e.g., $CH_3OCH_2$), alkyl(halogenated alkyl)amino wherein each alkyl group has 1 to 8 carbon atoms, di(halogenated alkyl)amino wherein each alkyl group has 1 to 8 carbon atoms, or (halogenated alkyl)amino having 1 to 8 carbon atoms.

According to a further compound and/or method aspect of the invention, the compound is selected from Formula I-IV wherein at least one R, $R^1$, $R^3$, $R^4$, and $R^5$ group is Het or OHet in which the Het group is selected from, in each case substituted or unsubstituted, azabicyclooctyl (e.g., 1-azabicyclo[2.2.2]oct-3-yl), oxa-azabicycloheptyl (e.g., 2-oxa-5-azabicyclo[2.2.1]heptyl), diazabicycloheptyl (e.g., 2,5-diazabicyclo[2.2.1]hept-2-yl, 5-methyl-2,5-diazabicyclo[2.2.1]hept-2-yl, trifluoroethyl-2,5-diazabicyclo[2.2.1]hept-2-yl, and 5-(cyclopropylcarbonyl)-2,5-diazabicyclo[2.2.1]hept-2-yl), diazabicyclononyl (e.g., 1,4-diazabicyclo[3.2.2]non-4-yl), diazabicyclooctyl (e.g., 5-methyl-2,5-diazabicyclo[2.2.2]oct-2-yl and 8-methyl-3,8-diazabicyclo[3.2.1]oct-3-yl), pyrazolyl, dihydroimidazolyl, 1,4-diazepanyl (e.g., 1,4-diazepan-1-yl and 4-methyl-1,4-diazepan-1-yl), hexahydropyrrolopyrazinyl (e.g., hexahydropyrrolo[1,2-a]pyrazin-2(1H)-yl), and octahydropyrrolopyridinyl (e.g., 1-(cyclopropylcarbonyl)-octahydro-6H-pyrrolo[3,4-b]pyridin-6-yl).

According to a further compound and/or method aspect of the invention, at least one of $X^1$, $X^2$, $X^3$, and $X^4$ is N; least one of $X^5$, $X^6$, $X^7$, and $X^8$ is N; at least one of $X^9$, $X^{10}$, $X^{11}$, and $X^{12}$ is N; and/or at least one of $X^{13}$, $X^{14}$, $X^{15}$, and $X^{16}$ is N. According to a further embodiment of this aspect of the invention, at least one of $X^1$, $X^2$, $X^3$, and $X^4$ is N, and 1 or 2 of the remaining $X^1$—$X^4$ are $CR^1$. According to a further embodiment of this aspect of the invention, at least one of $X^5$, $X^6$, $X^7$, and $X^8$ is N, and 1 or 2 of the remaining $X^5$—$X^8$ are $CR^3$. According to a further embodiment of this aspect of the invention, at least one of $X^9$, $X^{10}$, $X^{11}$, and $X^{12}$ is N, and 1 or 2 of the remaining $X^9$—$X^{12}$ are $CR^4$. According to a further embodiment of this aspect of the invention, at least one of $X^{13}$, $X^{14}$, $X^{15}$ and X16 is N, and 1 or 2 of the remaining $X^{13}$—$X^{16}$ are CR.

According to a further compound and/or method aspect of the invention, $X^4$ is N and $X^1$, $X^2$, and $X^3$ are each CH or $CR^1$. According to a further compound and/or method aspect of the invention, $X^3$ is N and $X^1$, $X^2$, and $X^4$ are each CH or $CR^1$.

According to a further compound and/or method aspect of the invention, $X^{12}$ is N and $X^9$, $X^{10}$, and $X^{11}$ are each CH or $CR^4$.

According to a further compound and/or method aspect of the invention, Het is a heterocyclic group, which is fully saturated, partially saturated or fully unsaturated, having 5 to 10 ring atoms in which at least 1 ring atom is a N, O or S atom, and which is substituted, wherein at least one of the substituents is halogenated alkoxy having 1 to 8 carbon atoms (e.g., $OCHF_2$), cycloalkoxy having 3 to 7 carbon atoms, cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl and trifluoropropyl), alkoxyalkyl having 2 to 8 carbon atoms (e.g., $CH_3OCH_2$), alkyl(halogenated alkyl)amino wherein each alkyl group has 1 to 8 carbon atoms, di(halogenated alkyl)amino wherein each alkyl group has 1 to 8 C atoms, or (halogenated alkyl)amino having 1 to 8 carbon atoms.

According to a further compound and/or method aspect of the invention, Het is a heterocyclic group, which is fully saturated and which is substituted, wherein at least one of the substituents is halogenated alkoxy having 1 to 8 C atoms (e.g., $OCHF_2$), cycloalkoxy having 3 to 7 carbon atoms, cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl and trifluoropropyl), alkoxyalkyl having 2 to 8 carbon atoms (e.g., $CH_3OCH_2$), alkyl(halogenated alkyl)amino wherein each alkyl group has 1 to 8 C atoms, di(halogenated alkyl)amino wherein each alkyl group has 1 to 8 C atoms, or (halogenated alkyl)amino having 1 to 8 carbon atoms.

According to a further compound and/or method aspect of the invention, Het is a heterocyclic group, which is fully saturated, partially saturated or fully unsaturated, having 5 to 10 ring atoms in which at least 1 ring atom is a N, O or S atom, and which is substituted wherein at least one of the substituents is halogenated alkoxy having 1 to 8 carbon atoms (e.g., $OCHF_2$), cycloalkylalkoxy having 4 to 7 carbon atoms (e.g., cyclopropylmethyloxy) halogenated alkyl other than trifluoromethyl (e.g., halogenated alkyl having 2 to 8 or 3 to 8 carbon atoms such as trifluoroethyl and trifluoropropyl), alkoxyalkyl having 2 to 8 carbon atoms (e.g., $CH_3OCH_2$), or alkyl(halogenated alkyl)amino wherein each alkyl group has 1 to 8 carbon atoms.

According to a further compound and/or method aspect of the invention, Het is a fully saturated heterocyclic group, which is substituted, wherein at least one of the substituents is halogenated alkoxy having 1 to 8 carbon atoms (e.g., $OCHF_2$), cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl and trifluoropropyl), alkoxyalkyl having 2 to 8 carbon atoms (e.g., $CH_3OCH_2$), or alkyl(halogenated alkyl)amino wherein each alkyl group has 1 to 8 carbon atoms.

According to a further compound and/or method aspect of the invention, A is of formula (a) having at least one $R^1$ substituent that is a heterocyclic group, which is fully saturated, partially saturated or fully unsaturated, having 5 to 10 ring atoms in which at least 1 ring atom is a N, O or S atom, and which is substituted, wherein at least one of the substituents is halogenated alkoxy having 1 to 8 carbon atoms (e.g., $OCHF_2$), cycloalkoxy having 3 to 7 carbon atoms, cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl and trifluoropropyl), alkoxyalkyl having 2 to 8 carbon atoms (e.g., $CH_3OCH_2$), alkyl(halogenated alkyl)amino wherein each alkyl group has 1 to 8 carbon atoms, di(halogenated alkyl)amino wherein each alkyl group has 1 to 8 carbon atoms, or (halogenated alkyl)amino having 1 to 8 C atoms.

According to a further compound and/or method aspect of the invention, A is of formula (a) having at least one $R^1$ substituent that is a fully saturated heterocyclic group which is substituted, wherein at least one of the substituents is halogenated alkoxy having 1 to 8 C atoms (e.g., $OCHF_2$), cycloalkoxy having 3 to 7 carbon atoms, cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl and trifluoropropyl), alkoxyalkyl having 2 to 8 carbon atoms (e.g., $CH_3OCH_2$), or alkyl(halogenated alkyl)amino wherein each alkyl group has 1 to 8 carbon atoms.

According to a further compound and/or method aspect of the invention, A is of formula (c) having at least one $R^4$ substituent that is a heterocyclic group, which is fully saturated, partially saturated or fully unsaturated, having 5 to 10 ring atoms in which at least 1 ring atom is a N, O or S atom, and which is substituted, wherein at least one of the substituents is halogenated alkoxy having 1 to 8 carbon atoms (e.g., $OCHF_2$), cycloalkoxy having 3 to 7 carbon atoms, cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl and trifluoropropyl), alkoxyalkyl having 2 to 8 carbon atoms (e.g., $CH_3OCH_2$), alkyl(halogenated alkyl)amino, wherein each alkyl group has 1 to 8 carbon atoms, di(halogenated alkyl)amino wherein each alkyl group has 1 to 8 carbon atoms, or (halogenated alkyl)amino having 1 to 8 carbon atoms.

According to a further compound and/or method aspect of the invention, A is of formula (c) having at least one $R^4$ substituent that is a fully saturated heterocyclic group which is substituted, wherein at least one of the substituents is halogenated alkoxy having 1 to 8 carbon atoms (e.g., $OCHF_2$), cycloalkoxy having 3 to 7 carbon atoms, cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl and trifluoropropyl), alkoxyalkyl having 2 to 8 carbon atoms (e.g., $CH_3OCH_2$), or alkyl(halogenated alkyl)amino wherein each alkyl group has 1 to 8 carbon atoms.

According to a further compound and/or method aspect of the invention, A is of formula (d) having at least one R substituent that is OH, O—($C_{1-6}$-alkyl-O)$_{1-2}$—$C_{1-6}$-alkyl, —O—$C_{1-6}$-alkyl-NR$^6$R$^7$, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, OAr, OHet, Carbo-O, Ar—$C_{1-6}$-alkyl-O—, Het-$C_{1-6}$-alkyl-O—, or Ar—$C_{1-6}$-alkyl-Het-O—.

According to a further compound and/or method aspect of the invention, A is of formula (d) having at least one R substituent that is OH, O—($C_{1-6}$-alkyl-O)$_{1-2}$—$C_{1-6}$-alkyl, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), fluorinated alkoxy having 1 to 4 carbon atoms (e.g., $OCF_3$, $OCHF_2$), hydroxyalkoxy having 2 to 4 carbon atoms, or fluorinated hydroxyalkoxy.

According to a further compound and/or method aspect of the invention, A is of formula (d) having at least one R substituent that is OH, alkoxy having 1 to 4 carbon atoms (e.g., $OCH_3$), fluorinated alkoxy having 1 to 4 carbon atoms (e.g., $OCF_3$, $OCHF_2$), hydroxyalkoxy having 2 to 4 carbon atoms, or fluorinated hydroxyalkoxy.

According to a further compound and/or method aspect of the invention, A is of formula (a) having at least one $R^1$ substituent that is dihydroimidazolyl.

According to a further compound and/or method aspect of the invention, A is of formula (a) having at least one $R^1$ substituent that is Het other than thiazolyl, and wherein $R^2$ is alkyl having 2 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-SO$_2$—, $C_{1-4}$-alkyl-O—$C_{1-4}$-alkyl- (e.g., $CH_2CH_2$—O—$CH_3$), or Ar—$C_{1-4}$-alkyl-NH—CO—.

According to a further compound and/or method aspect of the invention, A is of formula (c) having at least one $R^4$ substituent that is imidazolyl (e.g., imidazol-1-yl), pyrrolyl, pyrazolyl, $C_{1-8}$alkyl-pyrazolyl (e.g., 3-methyl-1H-pyrazol-1-yl, 5-methyl-1H-pyrazol-1-yl), oxa-azabicycloheptyl (e.g., 2-oxa-5-azabicyclo[2.2.1]heptyl), diazabicycloheptyl (e.g., 2,5-diazabicyclo[2.2.1]hept-2-yl), $C_{1-8}$alkyl-diazabicycloheptyl (e.g., 5-methyl-2,5-diazabicyclo[2.2.1]hept-2-yl), halogenated $C_{1-8}$alkyl-diazabicycloheptyl (e.g. trifluoroethyl-2,5-diazabicyclo[2.2.1]hept-2-yl, piperidinyl substituted by amino, monoalkylamino ($C_{1-8}$alkyl-NH—), or dialkylamino (($C_{1-8}$alkyl)$_2$N—) (e.g., (4-dimethylamino)piperidin-1-yl), or pyrrolidinyl substituted by hydroxy, halogenated alkoxy, cycloalkylalkoxy, amino, monoalkylamino ($C_{1-8}$alkyl-NH—), dialkylamino (($C_{1-8}$alkyl)$_2$N—), alkoxyalkyl, or alkyl (fluorinated alkyl)amino (e.g., 3-(cyclopropylmethoxy)pyrrolidin-1-yl, 3-(hydroxy)pyrrolidin-1-yl (such as 3-(3R)-hydroxypyrrolidin-1-yl, 3-(3S)-hydroxypyrrolidin-1-yl), 3-(difluoromethoxy)pyrrolidin-1-yl), 3-(dimethylamino)pyrrolidin-1-yl (such as 3-(3S)-(dimethylamino)pyrrolidin-1-yl, 3-(3R)-(dimethylamino)pyrrolidin-1-yl), 3-methylaminopyrrolidin-1yl, 3-(methoxymethyl)pyrrolidin-1-yl, 3-[methyl(2,2,2-trifluoroethyl)amino]pyrrolidin-1-yl).

According to a further aspect of the invention, the compound is of formulas I to IV, but the 1-azabicyclo group is in the form of a quaternary ammonium salt of the subformula:

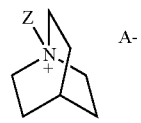

wherein Z is alkyl having 1 to 4 carbon atoms (e.g., methyl, ethyl, propyl), halogenated alkyl having 1 to 4 carbon atoms (e.g., chloromethyl, chloroethyl), cycloalkylalkyl having 4 to 7 carbon atoms (e.g., cyclopropylmethyl), or arylalkyl having 7 to 16 carbon atoms (e.g., benzyl), and anion A is, for example, iodide, bromide, chloride, triflate, tosylate, or mesylate. In this embodiment, group A is preferably of formula (a) or (c). Also, $X^1$ to $X^4$ are each, preferably, CH or $CR^1$, and $X^9$ to $X^{12}$ are each, preferably, CH or $CR^4$.

According to a further aspect of the invention, the compound is selected from formula Ip according to the following subgenera:
- (i) $X^{13}$-$X^{16}$ are independently CH or CR wherein at least one of $X^{13}$-$X^{16}$ is other than CH;
  X is O;
  R is H, alkyl (e.g., $CH_3$ or $C_2H_5$, particularly $CH_3$) or cycloalkylalkyl (e.g., cyclopropylmethyl, cyclobutylmethyl, cyclopentylmethyl or cyclopropylethyl, particularly cyclopropylmethyl); and
  at least one R is alkoxy (e.g., $OCH_3$) or Het (e.g., 3-methoxy-pyrrolidin-1-yl [such as (3R)-3-methoxy-pyrrolidin-1-yl. (3S)-3-methoxypyrrolidin-1-yl, According to a further aspect of the invention, the compound is selected from formula Ia or Ij according to the following subgenera:
- (i) X is O;
  one of $X^1$-$X^4$ is N or one of $X^9$-$X^{12}$ is N and the others of $X^1$-$X^4$ or of $X^9$-$X^{12}$ are CH, $CR^1$ or $CR^4$;
  R' is H, alkyl (e.g., $CH_3$ or $C_2H_5$, particularly $CH_3$) or cycloalkylalkyl (e.g., cyclopropylmethyl, cyclobutylmethyl, cyclopentylmethyl or cyclopropylethyl, particularly cyclopropylmethyl);
  $R^2$ is H; and
  $R^1$ and $R^4$ are independently selected from H, halogen (e.g., Cl or F), Ar (e.g., phenyl) or Het (e.g., 3-dimethylaminopyrrolidin-1-yl.

According to a further compound and/or method aspect of the invention, the compound is selected from the following subgenera:
- (a) a compound according to formula I wherein at least one of $X^1$, $X^2$, $X^3$, and $X^4$ is N;
- (b) a compound according to formula Ia wherein at least one of $X^1$, $X^2$, $X^3$, and $X^4$ is N;
- (c) a compound according to formula Ij wherein at least one of $X^1$, $X^2$, $X^3$, and $X^4$ is N;
- (d) a compound according to formula I wherein at least one of $X^5$, $X^6$, $X^7$, and $X^8$ is N;
- (e) a compound according to formula I wherein at least one of $X^9$, $X^{10}$, $X^{11}$, and $X^{12}$ is N;
- (f) a compound according to formula I wherein at least one of $X^{13}$, $X^{14}$, $X^{15}$, and $X^{16}$ is N;
- (g) a compound according to formula I wherein at least one of $X^1$, $X^2$, $X^3$, and $X^4$ is N, and 1 or 2 of the remaining $X^1$-$X^4$ are $CR^1$;
- (h) a compound according to formula Ia wherein at least one of $X^1$, $X^2$, $X^3$, and $X^4$ is N, and 1 or 2 of the remaining $X^1$-$X^4$ are $CR^1$;
- (i) a compound according to formula Ij wherein at least one of $X^1$, $X^2$, $X^3$, and $X^4$ is N, and 1 or 2 of the remaining $X^1$-$X^4$ are $CR^1$;
- (j) a compound according to formula I wherein at least one of $X^5$, $X^6$, $X^7$, and $X^8$ is N, and 1 or 2 of the remaining $X^5$-$X^8$ are $CR^3$;
- (k) a compound according to formula I wherein at least one of $X^9$, $X^{10}$, $X^{11}$, and $X^{12}$ is N, and 1 or 2 of the remaining $X^9$-$X^{12}$ are $CR^4$;
- (l) a compound according to formula I wherein at least one of $X^{13}$, $X^{14}$, $X^{15}$, and $X^{16}$ is N, and 1 or 2 of the remaining $X^{13}$-$X^{16}$ are CR;
- (m) a compound according to formula I wherein $X^4$ is N and $X^1$, $X^2$, and $X^3$ are each CH or $CR^1$;
- (n) a compound according to formula Ia wherein $X^4$ is N and $X^1$, $X^2$, and $X^3$ are each CH or $CR^1$;
- (o) a compound according to formula Ij wherein $X^{12}$ is N and $X^9$, $X^{10}$, and $X^{11}$ are each CH or $CR^4$;
- (p) a compound according to formula Ia wherein $X^3$ is N and $X^1$, $X^2$, and $X^4$ are each CH or $CR^1$;
- (q) a compound according to formula Ia or Ij having at least one $R^1$ or $R^4$ which is substituted Het and at least one of the Het substituents is halogenated alkoxy having 1 to 8 carbon atoms (e.g., $OCHF_2$), cycloalkoxy having 3 to 7 carbon atoms, cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl), alkoxyalkyl having 2 to 8 carbon atoms (e.g., $CH_2OCH_3$). alkyl(halogenated alkyl)amino, wherein each alkyl group has 1 to 8 carbon atoms di(halogenated alkyl)amino wherein each alkyl group has 1 to 8 carbon atoms, or (halogenated alkyl)amino having 1 to 8 C atoms;
- (r) a compound according to formula Ia or Ij having at least one $R^1$ or $R^4$ which is substituted Het and at least one of the Het substituents is halogenated alkoxy having 1 to 8 carbon atoms (e.g., $OCHF_2$), cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl), alkoxyalkyl having 2 to 8 carbon atoms (e.g., $CH_2OCH_3$), or alkyl(halogenated alkyl)amino, wherein each alkyl group has 1 to 8 carbon atoms;
- (s) a compound according to formula Ia or Ij having at least one $R^1$ or $R^4$ which is a substituted fully saturated Het group (e.g., pyrrolidinyl or piperidinyl) and at least one of the Het substituents is halogenated alkoxy having 1 to 8 carbon atoms (e.g., $OCHF_2$), cycloalkoxy having 3 to 7 carbon atoms, cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl), alkoxyalkyl having 2 to 8 carbon atoms (e.g., $CH_2OCH_3$), alkyl(halogenated alkyl)amino, wherein each alkyl group has 1 to 8 carbon atoms, di(halogenated alkyl)amino wherein each alkyl group has 1 to 8 carbon atoms, or (halogenated alkyl)amino having 1 to 8 carbon atoms;
- (t) a compound according to formula Ia or Ij having at least one $R^1$ or $R^4$ which is substituted fully saturated Het group (e.g., pyrrolidinyl) and at least one of the Het substituents is halogenated alkoxy having 1 to 8 carbon atoms (e.g., $OCHF_2$), cycloalkylalkoxy having 4 to 7 carbon atoms (e.g., cyclopropylmethyloxy), halogenated alkyl other than trifluoromethyl (e.g., halogenated alkyl having 2 to 8 or 3 to 8 carbon atoms such as trifluoroethyl), alkoxyalkyl having 2 to 8 carbon atoms (e.g., $CH_2OCH_3$), or alkyl(halogenated alkyl)amino, wherein each alkyl group has 1 to 8 carbon atoms;
- (u) a compound according to formula Ip having at least one R substituent that is OH, O—$(C_{1-6}$-alkyl-O$)_{1-2}$—$C_{1-6}$-alkyl, —O—$C_{1-6}$-alkyl-$NR^6R^7$, alkoxy having 1 to 4 carbon atoms (e.g., $OCH_3$), cycloalkoxy having 3 to 7 carbon atoms, cycloalkylalkoxy having 4 to 7 carbon atoms (e.g., cyclopropylmethoxy), fluorinated alkoxy having 1 to 4 carbon atoms (e.g., $OCF_3$, $OCHF_2$), hydroxyalkyl having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, OAr, OHet, Carbo-O, Ar—C$_{1-6}$-alkyl-O—, Het-C$_{1-6}$-alkyl-O—, or Ar—C$_{1-6}$-alkyl-Het-O—;

(v) a compound according to formula Ip having at least one R substituent that is OH, O—(C$_{1-6}$-alkyl-O)$_{1-2}$—C$_{1-6}$-alkyl, alkoxy having 1 to 4 carbon atoms (e.g., OCH$_3$), cycloalkoxy having 3 to 7 carbon atoms, cycloalkylalkoxy having 4 to 7 carbon atoms (e.g., cyclopropylmethoxy), fluorinated alkoxy having 1 to 4 carbon atoms (e.g., OCF$_3$, OCHF$_2$), hydroxyalkoxy having 2 to 4 carbon atoms, or fluorinated hydroxyalkoxy;

(w) a compound according to formula Ip having at least one R substituent that is OH, alkoxy having 1 to 4 carbon atoms (e.g., OCH$_3$), fluorinated alkoxy having 1 to 4 carbon atoms (e.g., OCF$_3$, OCHF$_2$), hydroxyalkoxy having 2 to 4 carbon atoms, or fluorinated hydroxyalkoxy;

(x) a compound according to formula Ia having at least one R substituent that is dihydroimidazolyl;

(y) a compound according to formula Ia having at least one R$^1$ substituent that is Het other than thiazolyl, and wherein R$^2$ is alkyl having 2 to 4 carbon atoms, fluorinated alkyl having 1 to 4 carbon atoms, cycloalkyl having 3 to 7 carbon atoms, cycloalkylalkyl having 4 to 7 carbon atoms, fluorinated C$_{1-4}$-alkyl-CO—, C$_{3-7}$-cycloalkyl-CO—, C$_{1-4}$-alkyl-NH—CO—, C$_{3-7}$-cycloalkyl-NH—CO—, Het, Ar—C$_{1-4}$-alkyl-, Ar—C$_{1-4}$-alkyl-CO—, Ar—C$_{1-4}$-alkyl-SO$_2$—, C$_{1-4}$-alkyl-O—C$_{1-4}$-alkyl- (e.g., CH$_2$CH$_2$—O—CH$_3$), or Ar—C$_{14}$-alkyl-NH—CO—;

(z) a compound according to formula Ij having at least one R$^4$ substituent that is imidazolyl (e.g., imidazol-1-yl), pyrrolyl, pyrazolyl, C$_{1-8}$alkyl-pyrazolyl (e.g., 3-methyl-1H-pyrazol-1-yl, 5-methyl-1H-pyrazol-1-yl), oxoazabicycloheptyl (e.g., 2-oxo-5-azabicyclo[2.2.1]heptyl), 2,5-diazabicyclo[2.2.1]hept-2-yl, C$_{1-8}$alkyl-diazabicycloheptyl (e.g., 5-methyl-2,5-diazabicyclo[2.2.1]hept-2-yl), halogenated C$_{1-8}$alkyl-diazabicycloheptyl (e.g. trifluoroethyl-2,5-diazabicyclo[2.2.1]hept-2-yl), piperidinyl substituted by amino, monoalkylamino (C$_{1-8}$alkyl-NH—), or dialkylamino ((C$_{1-8}$alkyl)$_2$N—) (e.g., (4-dimethylamino)piperidin-1-yl), or pyrrolidinyl substituted by hydroxy, halogenated alkoxy, cycloalkylalkoxy, amino, monoalkylamino(C$_{1-8}$alkyl-NH—), dialkylamino ((C$_{1-8}$alkyl)$_2$N—), alkoxyalkyl, or alkyl (fluorinated alkyl)amino (e.g., 3-(cyclopropylmethoxy)pyrrolidin-1-yl, 3-(hydroxy)pyrrolidin-1-yl (such as 3-(3R)-hydroxypyrrolidin-1-yl, 3-(3S)-hydroxypyrrolidin-1-yl), 3-(difluoromethoxy)pyrrolidin-1-yl), 3-(dimethylamino)pyrrolidin-1-yl, (such as 3-(3S)-(dimethylamino)pyrrolidin-1-yl, 3-(3R)-(dimethylamino)pyrrolidin-1-yl), 3-methylaminopyrrolidin-1yl, 3-(methoxymethyl)pyrrolidin-1-yl, 3-[methyl(2,2,2-trifluoroethyl)amino]pyrrolidin-1-yl)

(aa) a subgenus according to any of subgenus (a)-(z) above wherein X is O; and (ab) a subgenus according to any of subgenus (a)-(aa) above wherein R' is H or alkyl, especially H.

According to a compound and/or method aspect of the invention, the compound of formulas I-IV is selected from:

1) (3S)-3-({[6-(Cyclopropylmethoxy)-1,2-benzisothiazol-3-yl]carbonyl}amino)-1-(cyclopropylmethyl)-1-azoniabicyclo[2.2.2]octane bromide or formate, 2) N-[(3S)-1-Azabicyclo[2.2.2]oct-3-yl]-6-(3-methoxypyrrolidin-1-yl)-1,2-benzisothiazole-3-carboxamide, 3) N-[(3S)-1-Azabicyclo[2.2.2]oct-3-yl]-5,6-dimethoxy-1H-indazole-3-carboxamide hydroformate, 4) N-[(3S)-1-Azabicyclo[2.2.2]oct-3-yl]-1-propyl-6-(1,3-thiazol-2-yl)-1H-indazole-3-carboxamide, 5) N-[(3S)-1-Azabicyclo[2.2.2]oct-3-yl]-1-isopropyl-6-(1,3-thiazol-2-yl)-1H-indazole-3-carboxamide, 6) N-[(3S)-1-Azabicyclo[2.2.2]oct-3-yl]-6-(tetrahydrofuran-3-yloxy)-1H-indazole-3-carboxamide hydroformate, 7) N-[(3S)-1-Azabicyclo[2.2.2]oct-3-yl]-6-(tetrahydro-2H-pyran-4-yloxy)-1H-indazole-3-carboxamide hydroformate, 8) N-[(3S)-1-Azabicyclo[2.2.2]oct-3-yl]-6-[(1-methylpyrrolidin-3-yl)oxy]-1H-indazole-3-carboxamide hydroformate, 9) N-[(3S)-1-Azabicyclo[2.2.2]oct-3-yl]-4-hydroxy-1H-indazole-3-carboxamide hydroformate, 10) N-[(3S)-1-Azabicyclo[2.2.2]oct-3-yl]-5-bromo-4-hydroxy-1H-indazole-3-carboxamide hydroformate, 11) N-[(3S)-1-Azabicyclo[2.2.2]oct-3-yl]-5,7-dibromo-4-hydroxy-1H-indazole-3-carboxamide hydroformate, 12) N-[(3S)-1-Azabicyclo[2.2.2]oct-3-yl]-5-hydroxy-1,2-benzisothiazole-3-carboxamide hydroformate, 13) (3S)-3-{[(5-Hydroxy-1,2-benzisothiazol-3-yl)carbonyl]amino}-1-methyl-1-azoniabicyclo[2.2.2]octane iodide or formate, 14) N-[(3S)-1-Azabicyclo[2.2.2]oct-3-yl]-6-(3-furylmethoxy)-1,2-benzisothiazole-3-carboxamide hydroformate, 15) N-[(3S)-1-Azabicyclo[2.2.2]oct-3-yl]-1-ethyl-6-(2-oxopyrrolidin-1-yl)-1H-indazole-3-carboxamide hydroformate, 16) N-[(3S)-1-Azabicyclo[2.2.2]oct-3-yl]-7-hydroxy-1H-indazole-3-carboxamide hydroformate, 17) N-[(3R)-1-Azabicyclo[2.2.2]oct-3-yl]-6-methoxy-N-methyl-1H-indazole-3-carboxamide hydroformate, 18) N-[(3S)-1-Azabicyclo[2.2.2]oct-3-yl]-1-methyl-6-{[(propylamino)carbonyl]amino}-1H-indazole-3-carboxamide hydroformate, 19) N-[(3S)-1-Azabicyclo[2.2.2]oct-3-yl]-1-ethyl-6-methoxy-1H-indazole-3-carboxamide, 20) N-[(3R)-1-Azabicyclo[2.2.2]oct-3-yl]-1-ethyl-6-methoxy-1H-indazole-3-carboxamide, 21) N-[(3S)-1-Azabicyclo[2.2.2]oct-3-yl]-1-(difluoromethyl)-6-methoxy-1H-indazole-3-carboxamide, 22) N-[(3S)-1-Azabicyclo[2.2.2]oct-3-yl]-1-(difluoromethyl)-6-(1,3-thiazol-2-yl)-1H-indazole-3-carboxamide, 23) N-[(3S)-1-Azabicyclo[2.2.2]oct-3-yl]-6-[(cyclopropylcarbonyl)amino]-1-methyl-1H-indazole-3-carboxamide hydroformate, 24) N-[(3S)-1-Azabicyclo[2.2.2]oct-3-yl]-6-[(cyclopropylcarbonyl)amino]-1-(difluoromethyl)-1H-indazole-3-carboxamide hydroformate, 25) N-[(3S)-1-Azabicyclo[2.2.2]oct-3-yl]-1-(difluoromethyl)-6-{[(propylamino)carbonyl]amino}-1H-indazole-3-carboxamide hydroformate, 26) N-[(3S)-1-Azabicyclo[2.2.2]oct-3-yl]-1-cyclopropyl-6-(1,3-thiazol-2-yl)-1H-indazole-3-carboxamide, 27) N-[(3S)-1-Azabicyclo[2.2.2]oct-3-yl]-6-(1,3-thiazol-2-yl)-1-(3-thienyl)-1H-indazole-3-carboxamide, 28) N-[(3S)-1-Azabicyclo[2.2.2]oct-3-yl]-N-methyl-6-(1,3-oxazol-2-yl)-1H-indazole-3-carboxamide, 29) N-[(3S)-1-Azabicyclo[2.2.2]oct-3-yl]-N-methyl-6-(1,3-thiazol-2-yl)-1H-indazole-3-carboxamide, 30) N-[(3S)-1-Azabicyclo[2.2.2]oct-3-yl]-1-ethyl-6-(1,3-oxazol-2-yl)-1H-indazole-3-carboxamide, 31) N-[(3S)-1-Azabicyclo[2.2.2]oct-3-yl]-1-(cyclopropylmethyl)-6-(1,3-oxazol-2-yl)-1H-indazole-3-carboxamide, 32) N-[(3S)-1-Azabicyclo[2.2.2]oct-3-yl]-6-(1,3-oxazol-2-yl)-1-propyl-1H-indazole-3-carboxamide, 33) N-[(3S)-1-Azabicyclo[2.2.2]oct-3-yl]-1-ethyl-N-methyl-6-(1,3-oxazol-2-yl)-1H-indazole-3-carboxamide,
34) N-[(3S)-1-Azabicyclo[2.2.2]oct-3-yl]-N-methyl-6-(tetrahydro-2H-pyran-4-yl)-1H-indazole-3-carboxamide,
35) N-[(3S)-1-Azabicyclo[2.2.2]oct-3-yl]-N-methyl-5-(tetrahydro-2H-pyran-4-yl)-1H-indazole-3-carboxamide,
36) N-[(3S)-1-Azabicyclo[2.2.2]oct-3-yl]-5-(difluoromethoxy)-N-methyl-1H-indazole-3-carboxamide,
37) N-[(3S)-1-Azabicyclo[2.2.2]oct-3-yl]-6-(difluoromethoxy)-N-methyl-1H-indazole-3-carboxamide,
38) N-[(3S)-1-Azabicyclo[2.2.2]oct-3-yl]-1-cyclopropyl-6-[(cyclopropylcarbonyl) amino]-1H-indazole-3-carboxamide,
39) N-[(3S)-1-Azabicyclo[2.2.2]oct-3-yl]-1-cyclopropyl-6-{[(propylamino)carbonyl]amino}-1H-indazole-3-carboxamide,
40) N-[(3S)-1-Azabicyclo[2.2.2]oct-3-yl]-5-methoxy-N-methyl-1H-indazole-3-carboxamide,
41) N-[(3S)-1-Azabicyclo[2.2.2]oct-3-yl]-6-[(4S)-4-hydroxy-2-oxopyrrolidin-1-yl]-1H-indazole-3-carboxamide hydroformate,
42) N-[(3R)-1-Azabicyclo[2.2.2]oct-3-yl]-5-methoxy-N-methyl-1H-indazole-3-carboxamide hydroformate,
43) N-[(3R)-1-Azabicyclo[2.2.2]oct-3-yl]-5-(difluoromethoxy)-N-methyl-1H-indazole-3-carboxamide hydroformate,
44) N-[(3R)-1-Azabicyclo[2.2.2]oct-3-yl]-6-(difluoromethoxy)-N-methyl-1H-indazole-3-carboxamide hydroformate,
45) N-[(3R)-1-Azabicyclo[2.2.2]oct-3-yl]-N-methyl-6-(tetrahydro-2H-pyran-4-yl)-1H-indazole-3-carboxamide hydroformate,
46) N-[(3R)-1-Azabicyclo[2.2.2]oct-3-yl]-N-methyl-5-(tetrahydro-2H-pyran-4-yl)-1H-indazole-3-carboxamide hydroformate,
47) N-[(3R)-1-Azabicyclo[2.2.2]oct-3-yl]-N-methyl-6-(1,3-thiazol-2-yl)-1H-indazole-3-carboxamide hydroformate,
48) N-[(3R)-1-Azabicyclo[2.2.2]oct-3-yl]-6-methoxy-N-methyl-1,2-benzisothiazole-3-carboxamide hydroformate,
49) N-[(3S)-1-Azabicyclo[2.2.2]oct-3-yl]-6-(3-methoxypyrrolidin-1-yl)-1,2-benzisothiazole-3-carboxamide hydrochloride,
50) N-[(3S)-1-Azabicyclo[2.2.2]oct-3-yl]-6-hydroxy-1,2-benzisothiazole-3-carboxamide,
51) N-[(3R)-1-Azabicyclo[2.2.2]oct-3-yl]-6-methoxy-1,2-benzisothiazole-3-carboxamide hydrochloride,
52) N-[(3S)-1-Azabicyclo[2.2.2]oct-3-yl]-6-methoxy-1,2-benzisothiazole-3-carboxamide hydrochloride,
53) N-[(3S)-1-Azabicyclo[2.2.2]oct-3-yl]-7-methoxy-1,2-benzisothiazole-3-carboxamide hydrochloride,
54) N-[(3S)-1-Azabicyclo[2.2.2]oct-3-yl]-6-(2-oxo-3-propylimidazolidin-1-yl)-1,2-benzisothiazole-3-carboxamide hydrochloride,
55) N-[(3S)-1-Oxido-1-azabicyclo[2.2.2]oct-3-yl]-5-(trifluoromethoxy)-1H-indazole-3-carboxamide, and
56) 6-Methoxy-N-[(3S)-1-oxido-1-azabicyclo[2.2.2]oct-3-yl]-1,2-benzisothiazole-3-carboxamide,
wherein salts listed above can also be in free base form or in the form of another pharmaceutically acceptable salt, and free base forms listed above can also be in the form of a pharmaceutically acceptable salt,
wherein a compound listed above (in either a free base form or in the form of a pharmaceutically acceptable salt) can also be in the form of a solvate (such as a hydrate),
wherein a compound listed above (in either a free base form or in the form of a pharmaceutically acceptable salt) can also be in the form of an N-oxide,
wherein a compound listed above (in a free base form or solvate or N-oxide thereof, or in the form of a pharmaceutically acceptable salt or solvate thereof) can also be in the form of a polymorph, and
wherein if the compound exhibits chirality it can be in the form of a mixture of enantiomers such as a racemate or a mixture of diastereomers, or can be in the form of a single enantiomer or a single diastereomer.

According to a further compound and/or method aspect of the invention, the compound of formulas I-IV is selected from:
1) (3S)-3-({[6-(Cyclopropylmethoxy)-1,2-benzisothiazol-3-yl]carbonyl}amino)-1-(cyclopropylmethyl)-1-azoniabicyclo[2.2.2]octane bromide or formate,
2) N-[(3S)-1-Azabicyclo[2.2.2]oct-3-yl]-6-(3-methoxypyrrolidin-1-yl)-1,2-benzisothiazole-3-carboxamide,
3) N-[(3S)-1-Azabicyclo[2.2.2]oct-3-yl]-5,6-dimethoxy-1H-indazole-3-carboxamide hydroformate,
4) N-[(3S)-1-Azabicyclo[2.2.2]oct-3-yl]-1-propyl-6-(1,3-thiazol-2-yl)-1H-indazole-3-carboxamide,
5) N-[(3S)-1-Azabicyclo[2.2.2]oct-3-yl]-1-isopropyl-6-(1,3-thiazol-2-yl)-1H-indazole-3-carboxamide,
6) N-[(3S)-1-Azabicyclo[2.2.2]oct-3-yl]-6-(tetrahydrofuran-3-yloxy)-1H-indazole-3-carboxamide hydroformate,
7) N-[(3S)-1-Azabicyclo[2.2.2]oct-3-yl]-6-(tetrahydro-2H-pyran-4-yloxy)-1H-indazole-3-carboxamide hydroformate,
8) N-[(3S)-1-Azabicyclo[2.2.2]oct-3-yl]-6-[(1-methylpyrrolidin-3-yl)oxy]-1H-indazole-3-carboxamide hydroformate,
9) N-[(3S)-1-Azabicyclo[2.2.2]oct-3-yl]-4-hydroxy-1H-indazole-3-carboxamide hydroformate,
10) N-[(3S)-1-Azabicyclo[2.2.2]oct-3-yl]-5-bromo-4-hydroxy-1H-indazole-3-carboxamide hydroformate,
11) N-[(3S)-1-Azabicyclo[2.2.2]oct-3-yl]-5,7-dibromo-4-hydroxy-1H-indazole-3-carboxamide hydroformate,
12) N-[(3S)-1-Azabicyclo[2.2.2]oct-3-yl]-5-hydroxy-1,2-benzisothiazole-3-carboxamide hydroformate,
13) (3S)-3-{[(5-Hydroxy-1,2-benzisothiazol-3-yl)carbonyl]amino}-1-methyl-1-azoniabicyclo[2.2.2]octane iodide or formate,
14) N-[(3S)-1-Azabicyclo[2.2.2]oct-3-yl]-6-(3-furylmethoxy)-1,2-benzisothiazole-3-carboxamide hydroformate,
15) N-[(3S)-1-Azabicyclo[2.2.2]oct-3-yl]-1-ethyl-6-(2-oxopyrrolidin-1-yl)-1H-indazole-3-carboxamide hydroformate,
16) N-[(3S)-1-Azabicyclo[2.2.2]oct-3-yl]-7-hydroxy-1H-indazole-3-carboxamide hydroformate,
17) N-[(3R)-1-Azabicyclo[2.2.2]oct-3-yl]-6-methoxy-N-methyl-1H-indazole-3-carboxamide hydroformate,
18) N-[(3S)-1-Azabicyclo[2.2.2]oct-3-yl]-1-methyl-6-{[(propylamino)carbonyl]amino}-1H-indazole-3-carboxamide hydroformate,
19) N-[(3S)-1-Azabicyclo[2.2.2]oct-3-yl]-1-ethyl-6-methoxy-1H-indazole-3-carboxamide,
20) N-[(3R)-1-Azabicyclo[2.2.2]oct-3-yl]-1-ethyl-6-methoxy-1H-indazole-3-carboxamide,
21) N-[(3S)-1-Azabicyclo[2.2.2]oct-3-yl]-1-(difluoromethyl)-6-methoxy-1H-indazole-3-carboxamide,
22) N-[(3S)-1-Azabicyclo[2.2.2]oct-3-yl]-1-(difluoromethyl)-6-(1,3-thiazol-2-yl)-1H-indazole-3-carboxamide, 23) N-[(3S)-1-Azabicyclo[2.2.2]oct-3-yl]-6-[(cyclopropylcarbonyl)amino]-1-methyl-1H-indazole-3-carboxamide hydroformate,
24) N-[(3S)-1-Azabicyclo[2.2.2]oct-3-yl]-6-[(cyclopropylcarbonyl)amino]-1-(difluoromethyl)-1H-indazole-3-carboxamide hydroformate,
25) N-[(3S)-1-Azabicyclo[2.2.2]oct-3-yl]-1-(difluoromethyl)-6-{[(propylamino)carbonyl]amino}-1H-indazole-3-carboxamide hydroformate,
26) N-[(3S)-1-Azabicyclo[2.2.2]oct-3-yl]-1-cyclopropyl-6-(1,3-thiazol-2-yl)-1H-indazole-3-carboxamide,
27) N-[(3S)-1-Azabicyclo[2.2.2]oct-3-yl]-6-(1,3-thiazol-2-yl)-1-(3-thienyl)-1H-indazole-3-carboxamide,
28) N-[(3S)-1-Azabicyclo[2.2.2]oct-3-yl]-N-methyl-6-(1,3-oxazol-2-yl)-1H-indazole-3-carboxamide,
29) N-[(3S)-1-Azabicyclo[2.2.2]oct-3-yl]-N-methyl-6-(1,3-thiazol-2-yl)-1H-indazole-3-carboxamide,
30) N-[(3S)-1-Azabicyclo[2.2.2]oct-3-yl]-1-ethyl-6-(1,3-oxazol-2-yl)-1H-indazole-3-carboxamide,
31) N-[(3S)-1-Azabicyclo[2.2.2]oct-3-yl]-1-(cyclopropylmethyl)-6-(1,3-oxazol-2-yl)-1H-indazole-3-carboxamide,
32) N-[(3S)-1-Azabicyclo[2.2.2]oct-3-yl]-6-(1,3-oxazol-2-yl)-1-propyl-1H-indazole-3-carboxamide,
33) N-[(3S)-1-Azabicyclo[2.2.2]oct-3-yl]-1-ethyl-N-methyl-6-(1,3-oxazol-2-yl)-1H-indazole-3-carboxamide,
34) N-[(3S)-1-Azabicyclo[2.2.2]oct-3-yl]-N-methyl-6-(tetrahydro-2H-pyran-4-yl)-1H-indazole-3-carboxamide,
35) N-[(3S)-1-Azabicyclo[2.2.2]oct-3-yl]-N-methyl-5-(tetrahydro-2H-pyran-4-yl)-1H-indazole-3-carboxamide,
36) N-[(3S)-1-Azabicyclo[2.2.2]oct-3-yl]-5-(difluoromethoxy)-N-methyl-1H-indazole-3-carboxamide,
37) N-[(3S)-1-Azabicyclo[2.2.2]oct-3-yl]-6-(difluoromethoxy)-N-methyl-1H-indazole-3-carboxamide,
38) N-[(3S)-1-Azabicyclo[2.2.2]oct-3-yl]-1-cyclopropyl-6-[(cyclopropylcarbonyl)amino]-1H-indazole-3-carboxamide,
39) N-[(3S)-1-Azabicyclo[2.2.2]oct-3-yl]-1-cyclopropyl-6-{[(propylamino)carbonyl]amino}-1H-indazole-3-carboxamide,
40) N-[(3S)-1-Azabicyclo[2.2.2]oct-3-yl]-5-methoxy-N-methyl-1H-indazole-3-carboxamide,
41) N-[(3S)-1-Azabicyclo[2.2.2]oct-3-yl]-6-[(4S)-4-hydroxy-2-oxopyrrolidin-1-yl]-1H-indazole-3-carboxamide hydroformate,
42) N-[(3R)-1-Azabicyclo[2.2.2]oct-3-yl]-5-methoxy-N-methyl-1H-indazole-3-carboxamide hydroformate,
43) N-[(3R)-1-Azabicyclo[2.2.2]oct-3-yl]-5-(difluoromethoxy)-N-methyl-1H-indazole-3-carboxamide hydroformate,
44) N-[(3R)-1-Azabicyclo[2.2.2]oct-3-yl]-6-(difluoromethoxy)-N-methyl-1H-indazole-3-carboxamide hydroformate,
45) N-[(3R)-1-Azabicyclo[2.2.2]oct-3-yl]-N-methyl-6-(tetrahydro-2H-pyran-4-yl)-1H-indazole-3-carboxamide hydroformate,
46) N-[(3R)-1-Azabicyclo[2.2.2]oct-3-yl]-N-methyl-5-(tetrahydro-2H-pyran-4-yl)-1H-indazole-3-carboxamide hydroformate,
47) N-[(3R)-1-Azabicyclo[2.2.2]oct-3-yl]-N-methyl-6-(1,3-thiazol-2-yl)-1H-indazole-3-carboxamide hydroformate,
48) N-[(3R)-1-Azabicyclo[2.2.2]oct-3-yl]-6-methoxy-N-methyl-1,2-benzisothiazole-3-carboxamide hydroformate,
49) N-[(3S)-1-Azabicyclo[2.2.2]oct-3-yl]-6-(3-methoxypyrrolidin-1-yl)-1,2-benzisothiazole-3-carboxamide hydrochloride, and
50) N-[(3S)-1-Azabicyclo[2.2.2]oct-3-yl]-6-hydroxy-1,2-benzisothiazole-3-carboxamide, wherein salts listed above can also be in free base form or in the form of another pharmaceutically acceptable salt, and free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

According to a further compound and/or method aspect of the invention, the compound of formulas I-IV is selected from:

57) N-[(3S)-1-Azabicyclo[2.2.2]oct-3-yl]-6-fluoro-1H-pyrazolo[3,4-b]pyridine-3-carboxamide hydroformate,
58) N-[(3S)-1-Azabicyclo[2.2.2]oct-3-yl]-6-[3-(cyclopropylmethoxy)pyrrolidin-1-yl]-1H-indazole-3-carboxamide hydroformate,
59) N-[(3S)-1-Azabicyclo[2.2.2]oct-3-yl]-1H-pyrazolo[4,3-c]pyridine-3-carboxamide,
60) N-[(3S)-1-Azabicyclo[2.2.2]oct-3-yl]-1H-pyrazolo[3,4-c]pyridine-3-carboxamide hydroformate,
61) N-[(3R)-1-Azabicyclo[2.2.2]oct-3-yl]-6-[3-(cyclopropylmethoxy)pyrrolidin-1-yl]-1H-indazole-3-carboxamide hydroformate,
62) N-[(3R)-1-Azabicyclo[2.2.2]oct-3-yl]-6-(3-methoxypyrrolidin-1-yl)-1H-indazole-3-carboxamide hydroformate,
63) N-[(3R)-1-Azabicyclo[2.2.2]oct-3-yl]-6-(2-oxo-3-propylimidazolidin-1-yl)-1H-indazole-3-carboxamide hydroformate,
64) N-[(3S)-1-Azabicyclo[2.2.2]oct-3-yl]-6-pyrrolidin-1-yl-1,2-benzisothiazole-3-carboxamide,
65) N-[(3S)-1-Azabicyclo[2.2.2]oct-3-yl]-6-(3-methyl-2-oxopyrrolidin-1-yl)-1,2-benzisothiazole-3-carboxamide,
66) N-[(3S)-1-Azabicyclo[2.2.2]oct-3-yl]-6-(1H-pyrrol-1-yl)-1,2-benzisothiazole-3-carboxamide,
67) N-[(3S)-1-Azabicyclo[2.2.2]oct-3-yl]-6-(3-ethyl-2-oxoimidazolidin-1-yl)-1,2-benzisothiazole-3-carboxamide,
68) N-[(3S)-1-Azabicyclo[2.2.2]oct-3-yl]-6-[3-(cyclopropylmethoxy)pyrrolidin-1-yl]-1,2-benzisothiazole-3-carboxamide,
69) N-[(3S)-1-Azabicyclo[2.2.2]oct-3-yl]-6-(3-methoxypyrrolidin-1-yl)-1,2-benzisoxazole-3-carboxamide,
70) N-[(3S)-1-Azabicyclo[2.2.2]oct-3-yl]-7-(3-methoxypyrrolidin-1-yl)-1,2-benzisothiazole-3-carboxamide,
71) N-[(3S)-1-Azabicyclo[2.2.2]oct-3-yl]-6-methoxy-1,2-benzisoxazole-3-carboxamide hydrochloride
72) N-[(3R)-1-Azabicyclo[2.2.2]oct-3-yl]-6-(3-methoxypyrrolidin-1-yl)-1,2-benzisothiazole-3-carboxamide,
73) N-[(3R)-1-Azabicyclo[2.2.2]oct-3-yl]-1-ethyl-6-(1,3-oxazol-2-yl)-1H-indazole-3-carboxamide hydroformate,
74) N-[(3S)-1-Azabicyclo[2.2.2]oct-3-yl]-1-ethyl-6-(1,3-oxazol-2-yl)-1H-indazole-3-carboxamide hydrochloride,
75) N-[(3S)-1-Azabicyclo[2.2.2]oct-3-yl]-6-[(3R)-3-methoxypyrrolidin-1-yl]-1,2-benzisothiazole-3-carboxamide,
76) N-[(3S)-1-Azabicyclo[2.2.2]oct-3-yl]-6-[(3S)-3-methoxypyrrolidin-1-yl]-1,2-benzisothiazole-3-carboxamide,
77) N-[(3S)-1-Azabicyclo[2.2.2]oct-3-yl]-6-(2-oxo-3-propylimidazolidin-1-yl)-1H-indazole-3-carboxamide, 78) N-[(3S)-1-Azabicyclo[2.2.2]oct-3-yl]-6-(3-hydroxypyrrolidin-1-yl)-1,2-benzisothiazole-3-carboxamide,
79) N-[(3S)-1-Azabicyclo[2.2.2]oct-3-yl]-6-[-3-(difluoromethoxy)pyrrolidin-1-yl]-1,2-benzisothiazole-3-carboxamide,
80) N-[(3S)-1-Azabicyclo[2.2.2]oct-3-yl]-6-(1H-imidazol-1-yl)-1,2-benzisothiazole-3-carboxamide,
81) N-[(3S)-1-Azabicyclo[2.2.2]oct-3-yl]-6-(1H-pyrazol-1-yl)-1,2-benzisothiazole-3-carboxamide,
82) N-[(3S)-1-Azabicyclo[2.2.2]oct-3-yl]-6-(3-methyl-1H-pyrazol-1-yl)-1,2-benzisothiazole-3-carboxamide,
83) N-[(3S)-1-Azabicyclo[2.2.2]oct-3-yl]-6-(5-methyl-1H-pyrazol-1-yl)-1,2-benzisothiazole-3-carboxamide,
84) N-[(3R)-1-Azabicyclo[2.2.2]oct-3-yl]-6-[(3R)-3-methoxypyrrolidin-1-yl]-1,2-benzisothiazole-3-carboxamide,
85) N-[(3R)-1-Azabicyclo[2.2.2]oct-3-yl]-6-[(3S)-3-methoxypyrrolidin-1-yl]-1,2-benzisothiazole-3-carboxamide,
86) N-[(3R)-1-Azabicyclo[2.2.2]oct-3-yl]-6-methoxy-1,2-benzisoxazole-3-carboxamide,
87) N-[(3S)-1-Azabicyclo[2.2.2]oct-3-yl]-6-(3-ethoxypyrrolidin-1-yl)-7-fluoro-1,2-benzisothiazole-3-carboxamide,
88) N-[(3S)-1-Azabicyclo[2.2.2]oct-3-yl]-6-phenyl-1H-pyrazolo[3,4-b]pyridine-3-carboxamide,
89) N-[(3R)-1-Azabicyclo[2.2.2]oct-3-yl]-6-(4,5-dihydro-1H-imidazol-2-yl)-1H-indazole-3-carboxamide,
90) N-[(3S)-1-Azabicyclo[2.2.2]oct-3-yl]-6-[3-(dimethylamino)pyrrolidin-1-yl]-1H-pyrazolo[3,4-b]pyridine-3-carboxamide,
91) N-[(3R)-1-Azabicyclo[2.2.2]oct-3-yl]-6-[3-(dimethylamino)pyrrolidin-1-yl]-1H-pyrazolo[3,4-b]pyridine-3-carboxamide,
92) N-[(3R)-1-Azabicyclo[2.2.2]oct-3-yl]-7-fluoro-6-(3-methoxypyrrolidin-1-yl)-1,2-benzisothiazole-3-carboxamide,
93) N-[(3S)-1-Azabicyclo[2.2.2]oct-3-yl]-7-fluoro-6-(3-methoxypyrrolidin-1-yl)-1,2-benzisothiazole-3-carboxamide,
94) N-[(3S)-1-Azabicyclo[2.2.2]oct-3-yl]-6-[(3R)-3-hydroxypyrrolidin-1-yl]-1,2-benzisothiazole-3-carboxamide,
95) N-[(3S)-1-Azabicyclo[2.2.2]oct-3-yl]-6-[(3S)-3-hydroxypyrrolidin-1-yl]-1,2-benzisothiazole-3-carboxamide,
96) N-[(3S)-1-Azabicyclo[2.2.2]oct-3-yl]-6-[(3S)-3-(dimethylamino)pyrrolidin-1-yl]-1,2-benzisothiazole-3-carboxamide,
97) N-[(3S)-1-Azabicyclo[2.2.2]oct-3-yl]-6-[(1S,4S)-2-oxa-5-azabicyclo[2.2.1]hept-5-yl]-1,2-benzisothiazole-3-carboxamide,
98) N-[(3R)-1-Azabicyclo[2.2.2]oct-3-yl]-6-[(3R)-3-hydroxypyrrolidin-1-yl]-1,2-benzisothiazole-3-carboxamide,
99) N-[(3R)-1-Azabicyclo[2.2.2]oct-3-yl]-6-[(3S)-3-hydroxypyrrolidin-1-yl]-1,2-benzisothiazole-3-carboxamide,
100) N-[(3R)-1-Azabicyclo[2.2.2]oct-3-yl]-6-[(3S)-3-(dimethylamino)pyrrolidin-1-yl]-1,2-benzisothiazole-3-carboxamide,
101) N-[(3S)-1-Azabicyclo[2.2.2]oct-3-yl]-7-[(3R)-3-hydroxypyrrolidin-1-yl]-1,2-benzisothiazole-3-carboxamide,
102) N-[(3S)-1-Azabicyclo[2.2.2]oct-3-yl]-7-[(3S)-3-hydroxypyrrolidin-1-yl]-1,2-benzisothiazole-3-carboxamide,
103) N-[(3S)-1-Azabicyclo[2.2.2]oct-3-yl]-7-[(3S)-3-(dimethylamino)pyrrolidin-1-yl]-1,2-benzisothiazole-3-carboxamide,
104) N-[(3S)-1-Azabicyclo[2.2.2]oct-3-yl]-7-[(1S,4S)-2-oxa-5-azabicyclo[2.2.1]hept-5-yl]-1,2-benzisothiazole-3-carboxamide,
105) N-[(3R)-1-Azabicyclo[2.2.2]oct-3-yl]-7-[(3S)-3-(dimethylamino)pyrrolidin-1-yl]-1,2-benzisothiazole-3-carboxamide,
106) N-[(3R)-1-Azabicyclo[2.2.2]oct-3-yl]isothiazolo[5,4-b]pyridine-3-carboxamide hydroformate,
107) N-[(3R)-1-Azabicyclo[2.2.2]oct-3-yl]isothiazolo[5,4-b]pyridine-3-carboxamide hydroformate,
108) N-[(3S)-1-Azabicyclo[2.2.2]oct-3-yl]-6-[(3R)-3-methoxypyrrolidin-1-yl]-1,2-benzisoxazole-3-carboxamide,
109) N-[(3S)-1-Azabicyclo[2.2.2]oct-3-yl]-6-[(3S)-3-methoxypyrrolidin-1-yl]-1,2-benzisoxazole-3-carboxamide,
110) N-[(3R)-1-Azabicyclo[2.2.2]oct-3-yl]-7-[(3R)-3-methoxypyrrolidin-1-yl]-1,2-benzisothiazole-3-carboxamide hydroformate,
111) N-[(3R)-1-Azabicyclo[2.2.2]oct-3-yl]-7-[(3S)-3-methoxypyrrolidin-1-yl]-1,2-benzisothiazole-3-carboxamide,
112) N-[(3S)-1-Azabicyclo[2.2.2]oct-3-yl]-7-[(3R)-3-methoxypyrrolidin-1-yl]-1,2-benzisothiazole-3-carboxamide hydroformate,
113) N-[(3S)-1-Azabicyclo[2.2.2]oct-3-yl]-7-[(3S)-3-methoxypyrrolidin-1-yl]-1,2-benzisothiazole-3-carboxamide hydroformate,
114) N-[(3S)-1-Azabicyclo[2.2.2]oct-3-yl]-7-fluoro-6-methoxy-1,2-benzisothiazole-3-carboxamide,
115) N-[(3R)-1-Azabicyclo[2.2.2]oct-3-yl]-7-fluoro-6-methoxy-1,2-benzisothiazole-3-carboxamide,
116) N-[(3R)-1-Azabicyclo[2.2.2]oct-3-yl]-6-[(1S,4S)-5-methyl-2,5-diazabicyclo[2.2.1]hept-2-yl]-1,2-benzisothiazole-3-carboxamide,
117) N-[(3S)-1-Azabicyclo[2.2.2]oct-3-yl]-6-[(1S,4S)-5-methyl-2,5-diazabicyclo[2.2.1]hept-2-yl]-1,2-benzisothiazole-3-carboxamide,
118) N-[(3R)-1-Azabicyclo[2.2.2]oct-3-yl]-6-[(1S,4S)-2,5-diazabicyclo[2.2.1]hept-2-yl]-1,2-benzisothiazole-3-carboxamide,
119) N-[(3S)-1-Azabicyclo[2.2.2]oct-3-yl]-6-[(1S,4S)-2,5-diazabicyclo[2.2.1]hept-2-yl]-1,2-benzisothiazole-3-carboxamide,
120) N-[(3S)-1-Azabicyclo[2.2.2]oct-3-yl]-6-[3-(methylamino)pyrrolidin-1-yl]-1,2-benzisothiazole-3-carboxamide,
121) N-[(3R)-1-Azabicyclo[2.2.2]oct-3-yl]-6-[3-(methylamino)pyrrolidin-1-yl]-1,2-benzisothiazole-3-carboxamide,
122) N-[(3R)-1-Azabicyclo[2.2.2]oct-3-yl]-6-[(1S,4S)-5-(2,2,2-trifluoroethyl)-2,5-diazabicyclo[2.2.1]hept-2-yl]-1,2-benzisothiazole-3-carboxamide,
123) N-[(3R)-1-Azabicyclo[2.2.2]oct-3-yl]-6-{3-[methyl(2,2,2-trifluoroethyl)amino]pyrrolidin-1-yl}-1,2-benzisothiazole-3-carboxamide,
124) N-[(3S)-1-Azabicyclo[2.2.2]oct-3-yl]-6-{3-[methyl(2,2,2-trifluoroethyl)amino]pyrrolidin-1-yl}-1,2-benzisothiazole-3-carboxamide,
125) N-[(3S)-1-Azabicyclo[2.2.2]oct-3-yl]-6-[3-(methoxymethyl)pyrrolidin-1-yl]-1,2-benzisothiazole-3-carboxamide,
126) N-[(3R)-1-Azabicyclo[2.2.2]oct-3-yl]-6-[3-(methoxymethyl)pyrrolidin-1-yl]-1,2-benzisothiazole-3-carboxamide,
127) N-[(3R)-1-Azabicyclo[2.2.2]oct-3-yl]-6-[(3R)-3-(dimethylamino)pyrrolidin-1-yl]-1,2-benzisothiazole-3-carboxamide, 128) N-[(3S)-1-Azabicyclo[2.2.2]oct-3-yl]-6-[(3R)-3-(dimethylamino)pyrrolidin-1-yl]-1,2-benzisothiazole-3-carboxamide,
129) N-[(3S)-1-Azabicyclo[2.2.2]oct-3-yl]-6-[4-(dimethylamino)piperidin-1-yl]-1,2-benzisothiazole-3-carboxamide, and
130) N-[(3R)-1-Azabicyclo[2.2.2]oct-3-yl]-6-[4-(dimethylamino)piperidin-1-yl]-1,2-benzisothiazole-3-carboxamide, wherein salts listed above can also be in free base form or in the form of another pharmaceutically acceptable salt, and free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

According to a further compound and/or method aspect of the invention, the compound of formulas I-IV is:
131) N-[(3R)-1-Azabicyclo[2.2.2]oct-3-yl]-6-(2-oxo-3-propylimidazolidin-1-yl)-1,2-benzisothiazole-3-carboxamide or pharmaceutically acceptable salt thereof, wherein the compound listed above (in either a free base form or in the form of a pharmaceutically acceptable salt) can also be in the form of a solvate (such as a hydrate), wherein the compound listed above (in either a free base form or in the form of a pharmaceutically acceptable salt) can also be in the form of an N-oxide, wherein the compound listed above (in a free base form or solvate or N-oxide thereof, or in the form of a pharmaceutically acceptable salt or solvate thereof) can also be in the form of a polymorph.

According to a further compound and/or method aspect of the invention, the compound of formulas I-IV is selected from:
132) N-[(3S)-1-Azabicyclo[2.2.2]oct-3-yl]-N-methyl-6-[(1S,4S)-5-methyl-2,5-diazabicyclo[2.2.1]hept-2-yl]-1,2-benzisothiazole-3-carboxamide dihydroformate
133) N-[(3R)-1-Azabicyclo[2.2.2]oct-3-yl]-N-methyl-6-[(1S,4S)-5-methyl-2,5-diazabicyclo[2.2.1]hept-2-yl]-1,2-benzisothiazole-3-carboxamide dihydroformate
134) N-[(3R)-1-Azabicyclo[2.2.2]oct-3-yl]-6-[(1R,4R)-5-methyl-2,5-diazabicyclo[2.2.1]hept-2-yl]-1,2-benzisothiazole-3-carboxamide
135) N-[(3S)-1-Azabicyclo[2.2.2]oct-3-yl]-6-[(1R,4R)-5-methyl-2,5-diazabicyclo[2.2.1]hept-2-yl]-1,2-benzisothiazole-3-carboxamide
136) N-[(3R)-1-Azabicyclo[2.2.2]oct-3-yl]-6-(1,4-diazabicyclo[3.2.2]non-4-yl)-1,2-benzisothiazole-3-carboxamide dihydroformate
137) N-[(3S)-1-Azabicyclo[2.2.2]oct-3-yl]-6-(1,4-diazabicyclo[3.2.2]non-4-yl)-1,2-benzisothiazole-3-carboxamide dihydroformate
138) N-[(3R)-1-Azabicyclo[2.2.2]oct-3-yl]-6-pyrrolidin-1-yl-1,2-benzisothiazole-3-carboxamide
139) N-[(3R)-1-Azabicyclo[2.2.2]oct-3-yl]-6-(4-methylpiperazin-1-yl)-1,2-benzisothiazole-3-carboxamide
140) N-[(3S)-1-Azabicyclo[2.2.2]oct-3-yl]-6-(4-methylpiperazin-1-yl)-1,2-benzisothiazole-3-carboxamide
141) N-[(3R)-1-Azabicyclo[2.2.2]oct-3-yl]-6-(4-methyl-1,4-diazepan-1-yl)-1,2-benzisothiazole-3-carboxamide
142) N-[(3S)-1-Azabicyclo[2.2.2]oct-3-yl]-6-(4-methyl-1,4-diazepan-1-yl)-1,2-benzisothiazole-3-carboxamide
143) N-[(3R)-1-Azabicyclo[2.2.2]oct-3-yl]-6-(hexahydropyrrolo[1,2-a]pyrazin-2(1H)-yl)-1,2-benzisothiazole-3-carboxamide
144) N-[(3S)-1-Azabicyclo[2.2.2]oct-3-yl]-6-(hexahydropyrrolo[1,2-a]pyrazin-2(1H)-yl)-1,2-benzisothiazole-3-carboxamide
145) N-[(3R)-1-Azabicyclo[2.2.2]oct-3-yl]-6-(5-methyl-2,5-diazabicyclo[2.2.2]oct-2-yl)-1,2-benzisothiazole-3-carboxamide
146) N-[(3S)-1-Azabicyclo[2.2.2]oct-3-yl]-6-(5-methyl-2,5-diazabicyclo[2.2.2]oct-2-yl)-1,2-benzisothiazole-3-carboxamide
147) N-[(3R)-1-Azabicyclo[2.2.2]oct-3-yl]-6-(8-methyl-3,8-diazabicyclo[3.2.1]oct-3-yl)-1,2-benzisothiazole-3-carboxamide
148) N-[(3S)-1-Azabicyclo[2.2.2]oct-3-yl]-6-(8-methyl-3,8-diazabicyclo[3.2.1]oct-3-yl)-1,2-benzisothiazole-3-carboxamide
149) N-[(3R)-1-Azabicyclo[2.2.2]oct-3-yl]-6-[(1S,4S)-5-cyclopropyl-2,5-diazabicyclo[2.2.1]hept-2-yl]-1,2-benzisothiazole-3-carboxamide
150) N-[(3S)-1-Azabicyclo[2.2.2]oct-3-yl]-6-[(1S,4S)-5-cyclopropyl-2,5-diazabicyclo[2.2.1]hept-2-yl]-1,2-benzisothiazole-3-carboxamide
151) N-[(3R)-1-Azabicyclo[2.2.2]oct-3-yl]-6-[(1S,4S)-5-(cyclopropylmethyl)-2,5-diazabicyclo[2.2.1]hept-2-yl]-1,2-benzisothiazole-3-carboxamide
152) N-[(3S)-1-Azabicyclo[2.2.2]oct-3-yl]-6-[(1S,4S)-5-(cyclopropylmethyl)-2,5-diazabicyclo[2.2.1]hept-2-yl]-1,2-benzisothiazole-3-carboxamide
153) N-[(3S)-1-Azabicyclo[2.2.2]oct-3-yl]-5-(4-methyl-1,4-diazepan-1-yl)-1,2-benzisothiazole-3-carboxamide
154) N-[(3R)-1-Azabicyclo[2.2.2]oct-3-yl]-5-[(3R)-3-methoxypyrrolidin-1-yl]-1,2-benzisothiazole-3-carboxamide
155) N-[(3S)-1-Azabicyclo[2.2.2]oct-3-yl]-5-[(3R)-3-methoxypyrrolidin-1-yl]-1,2-benzisothiazole-3-carboxamide
156) N-[(3R)-1-Azabicyclo[2.2.2]oct-3-yl]-5-[(3S)-3-methoxypyrrolidin-1-yl]-1,2-benzisothiazole-3-carboxamide
157) N-[(3R)-1-Azabicyclo[2.2.2]oct-3-yl]-6-[(1-methylpyrrolidin-3-yl)oxy]-1,2-benzisothiazole-3-carboxamide
158) N-[(3S)-1-Azabicyclo[2.2.2]oct-3-yl]-6-[(1-methylpyrrolidin-3-yl)oxy]-1,2-benzisothiazole-3-carboxamide
159) N-[(3R)-1-Azabicyclo[2.2.2]oct-3-yl]-6-(1-azabicyclo[2.2.2]oct-3-yloxy)-1,2-benzisothiazole-3-carboxamide
160) N-[(3S)-1-Azabicyclo[2.2.2]oct-3-yl]-6-(1-azabicyclo[2.2.2]oct-3-yloxy)-1,2-benzisothiazole-3-carboxamide
161) N,N'-di-(3S)-1-Azabicyclo[2.2.2]oct-3-yl-1H-indazole-1,3-dicarboxamide
162) N-[(3R)-1-Azabicyclo[2.2.2]oct-3-yl]-6-(1-methyl-4,5-dihydro-1H-imidazol-2-yl)-1H-indazole-3-carboxamide
163) N-[(3S)-1-Azabicyclo[2.2.2]oct-3-yl]-6-(1-methyl-4,5-dihydro-1H-imidazol-2-yl)-1H-indazole-3-carboxamide
164) N-[(3S)-1-Azabicyclo[2.2.2]oct-3-yl]-5-[(3S)-3-(cyclopropylmethoxy)pyrrolidin-1-yl]-1H-indazole-3-carboxamide 165) (3S)-1-(Chloromethyl)-3-[(1H-indazol-3-ylcarbonyl)amino]-1-azoniabicyclo[2.2.2]octane chloride
166) N-[(3S)-1-Azabicyclo[2.2.2]oct-3-yl]-5-[(3S)-3-methoxypyrrolidin-1-yl]-1H-indazole-3-carboxamide dihydroformate
167) N-[(3S)-1-Azabicyclo[2.2.2]oct-3-yl]-6-chloroisothiazolo[5,4-b]pyridine-3-carboxamide
168) N-[(3R)-1-Azabicyclo[2.2.2]oct-3-yl]-6-(3-methylpiperazin-1-yl)-1,2-benzisothiazole-3-carboxamide
169) N-[(3R)-1-Azabicyclo[2.2.2]oct-3-yl]-6-(octahydro-6H-pyrrolo[3,4-b]pyridin-6-yl)-1,2-benzisothiazole-3-carboxamide
170) N-[(3S)-1-Azabicyclo[2.2.2]oct-3-yl]-6-(octahydro-6H-pyrrolo[3,4-b]pyridin-6-yl)-1,2-benzisothiazole-3-carboxamide
171) N-[(3S)-1-Azabicyclo[2.2.2]oct-3-yl]-6-piperazin-1-yl-1,2-benzisothiazole-3-carboxamide
172) N-[(3R)-1-Azabicyclo[2.2.2]oct-3-yl]-6-piperazin-1-yl-1,2-benzisothiazole-3-carboxamide
173) N-[(3R)-1-Azabicyclo[2.2.2]oct-3-yl]-6-(1,4-diazepan-1-yl)-1,2-benzisothiazole-3-carboxamide
174) N-[(3S)-1-Azabicyclo[2.2.2]oct-3-yl]-6-(1,4-diazepan-1-yl)-1,2-benzisothiazole-3-carboxamide
175) N-[(3R)-1-Azabicyclo[2.2.2]oct-3-yl]-6-(2-methylpiperazin-1-yl)-1,2-benziosthiazole-3-carboxamide
176) N-[(3S)-1-Azabicyclo[2.2.2]oct-3-yl]-6-(2-methylpiperazin-1-yl)-1,2-benzisothiazole-3-carboxamide
177) N-[(3R)-1-Azabicyclo[2.2.2]oct-3-yl]-6-[4-(cyclopropylcarbonyl)piperazin-1-yl]-1,2-benzisothiazole-3-carboxamide
178) N-[(3S)-1-Azabicyclo[2.2.2]oct-3-yl]-6-[4-(cyclopropylcarbonyl)piperazin-1-yl]-1,2-benzisothiazole-3-carboxamide
179) N-[(3R)-1-Azabicyclo[2.2.2]oct-3-yl]-6-[1-(cyclopropylcarbonyl)octahydro-6H-pyrrolo[3,4-b]pyridin-6-yl]-1,2-benzisothiazole-3-carboxamide
180) N-[(3S)-1-Azabicyclo[2.2.2]oct-3-yl]-6-[1-(cyclopropylcarbonyl)octahydro-6H-pyrrolo[3,4-b]pyridin-6-yl]-1,2-benzisothiazole-3-carboxamide
181) N-[(3R)-1-Azabicyclo[2.2.2]oct-3-yl]-6-[(1S,4S)-5-(cyclopropylcarbonyl)-2,5-diazabicyclo[2.2.1]hept-2-yl]-1,2-benzisothiazole-3-carboxamide
182) N-[(3S)-1-Azabicyclo[2.2.2]oct-3-yl]-6-[(1S,4S)-5-(cyclopropylcarbonyl)-2,5-diazabicyclo[2.2.1]hept-2-yl]-1,2-benzisothiazole-3-carboxamide
183) N-[(3R)-1-Azabicyclo[2.2.2]oct-3-yl]-6-(3,4-dimethylpiperazin-1-yl)-1,2-benzisothiazole-3-carboxamide
184) N-[(3S)-1-Azabicyclo[2.2.2]oct-3-yl]-6-cyano-1H-indazole-3-carboxamide,
185) 3-[(3S)-1-Azabicyclo[2.2.2]oct-3-ylamino]carbonyl-1H-indazole-6-carboxylic acid hydrochloride,
186) N(3)-[(3S)-1-Azabicyclo[2.2.2]oct-3-yl]-N(6),N(6)-dimethyl-1H-indazole-3,6-dicarboxamide,
187) N-[(3S)-1-Azabicyclo[2.2.2]oct-3-yl]-6-[(4-methylpiperazin-1-yl)carbonyl]-1H-indazole-3-carboxamide,
188) N-[(3S)-1-Azabicyclo[2.2.2]oct-3-yl]-6-[(3R)-3-methoxypyrrolidin-1-yl]carbonyl-1H-indazole-3-carboxamide,
189) N-[(3S)-1-Azabicyclo[2.2.2]oct-3-yl]-6-methoxyisothiazolo[5,4-b]pyridine-3-carboxamide,
190) N-[(3R)-1-Azabicyclo[2.2.2]oct-3-yl]-5-(tetrahydro-2H-pyran-4-yloxy)-1H-indazole-3-carboxamide, wherein salts listed above can also be in free base form or in the form of another pharmaceutically acceptable salt, and free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in either a free base form or in the form of a pharmaceutically acceptable salt) can also be in the form of an N-oxide, wherein a compound listed above (in a free base form or solvate or N-oxide thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

The following table presents the structures for selected compounds of Formulas I-IV in accordance with the present invention:

| Compound | Structure |
|---|---|
| 1) | 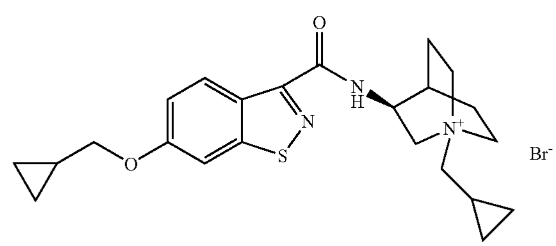 |
| 2) | 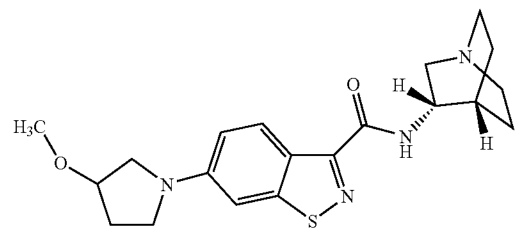 |

-continued
| Compound | Structure |
|---|---|
| 3) | 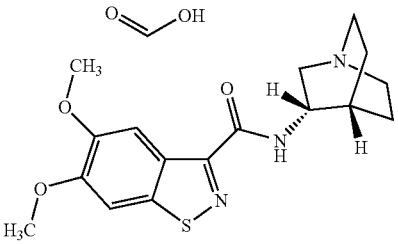 |
| 4) | 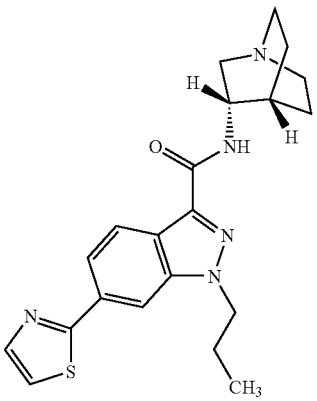 |
| 5) | 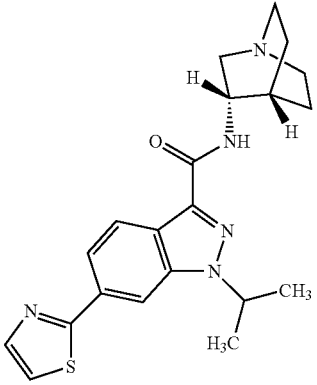 |
| 6) | 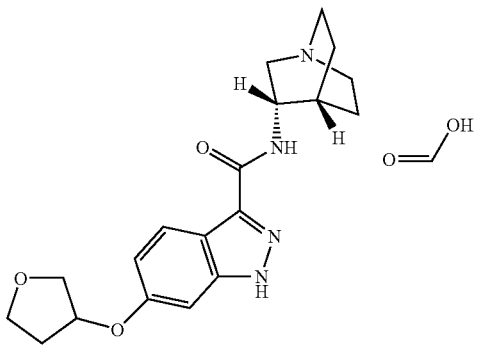 |

| Compound | Structure |
|---|---|
| 7) | 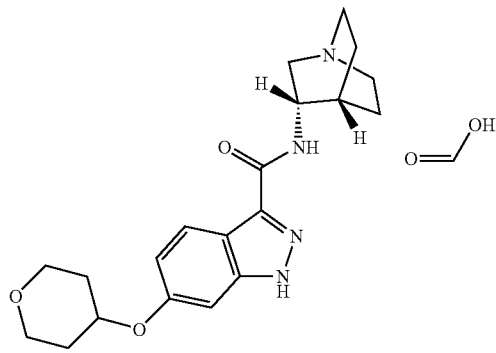 |
| 8) | 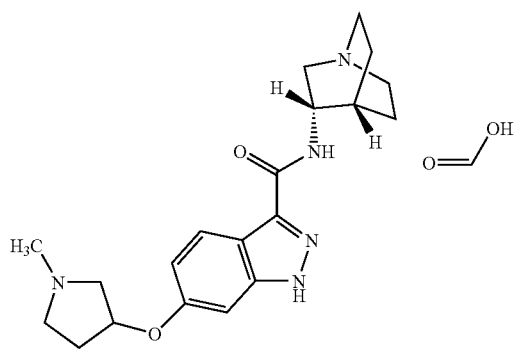 |
| 9) | 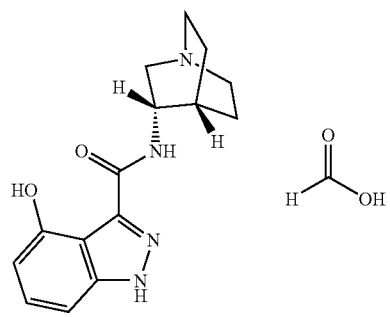 |
| 10) | 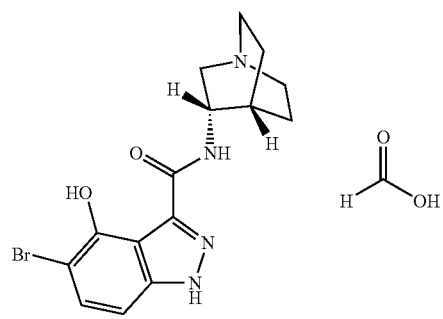 |

-continued

| Compound | Structure |
|---|---|
| 11) | (chemical structure: N-(quinuclidin-3-yl)-5,7-dibromo-4-hydroxy-1H-indazole-3-carboxamide with formic acid) |
| 12) | (chemical structure: N-(quinuclidin-3-yl)-5-hydroxybenzo[d]isoxazole-3-carboxamide with formic acid) |
| 13) | (chemical structure: N-(1-methylquinuclidin-1-ium-3-yl)-5-hydroxybenzo[d]isothiazole-3-carboxamide iodide) |
| 14) | (chemical structure: N-(quinuclidin-3-yl)-6-(furan-3-ylmethoxy)benzo[d]isothiazole-3-carboxamide with formic acid) |
| 15) | (chemical structure: N-(quinuclidin-3-yl)-1-ethyl-6-(2-oxopyrrolidin-1-yl)-1H-indazole-3-carboxamide with formic acid) |

-continued
| Compound | Structure |
| --- | --- |
| 16) | 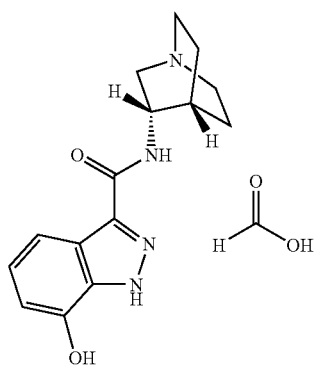 |
| 17) | 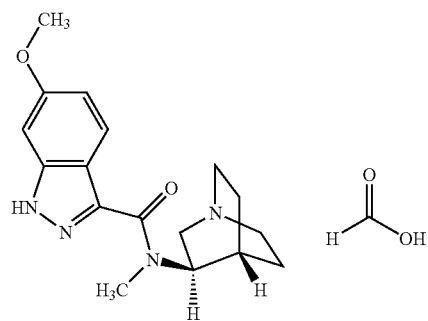 |
| 18) | 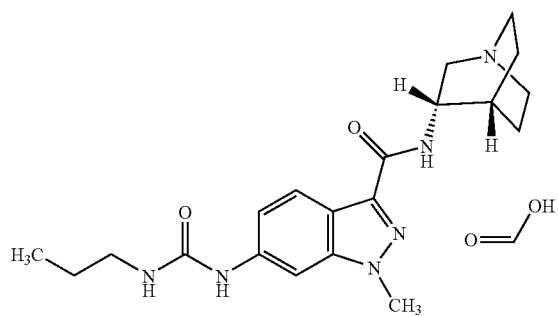 |
| 19) | 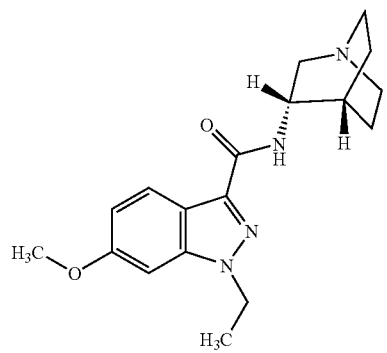 |

-continued
| Compound | Structure |
|---|---|
| 20) | 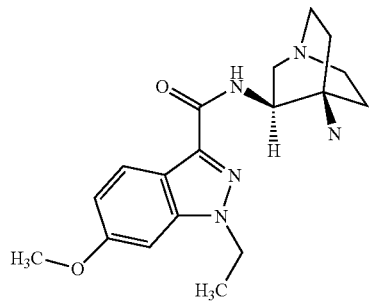 |
| 21) | 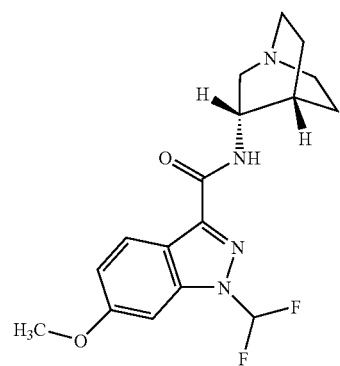 |
| 22) | 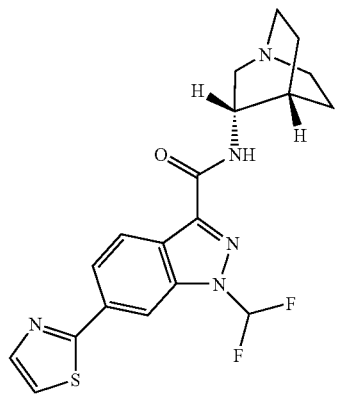 |
| 23) | 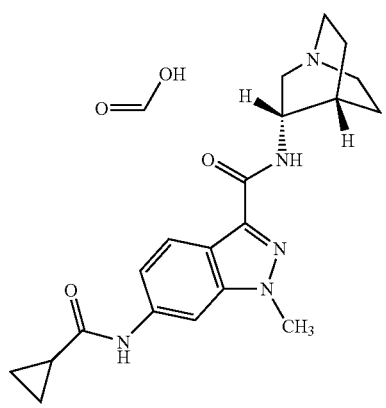 |

| Compound | Structure |
|---|---|
| 24) | 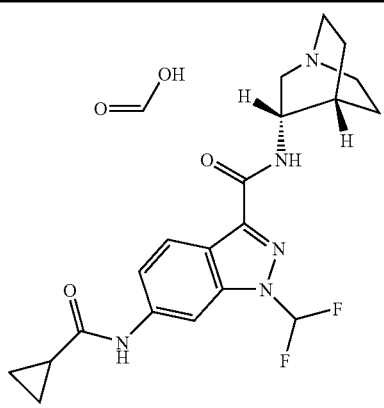 |
| 25) | 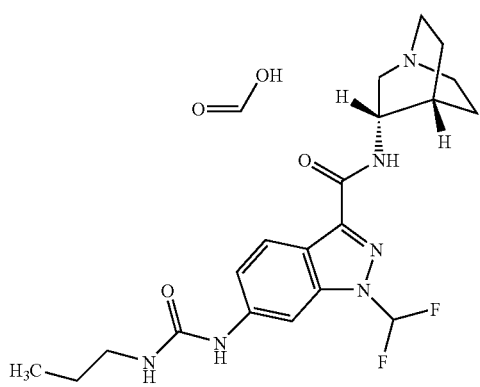 |
| 26) | 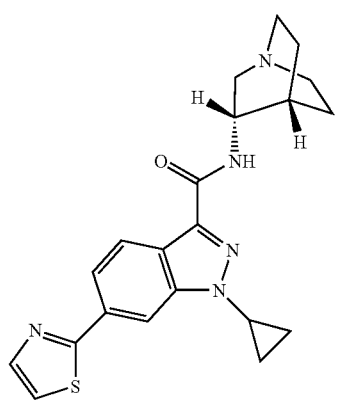 |
| 27) | 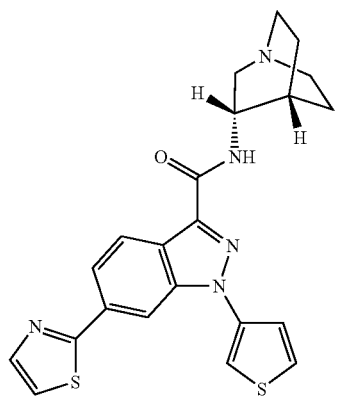 |

| Compound | Structure |
|---|---|
| 28) | 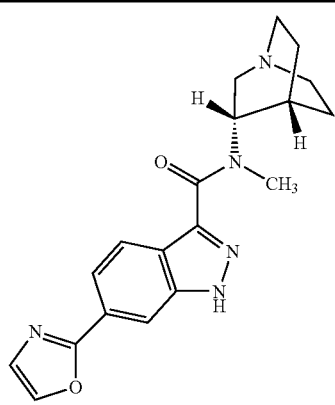 |
| 29) | 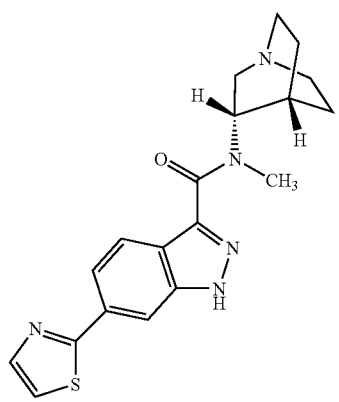 |
| 30) | 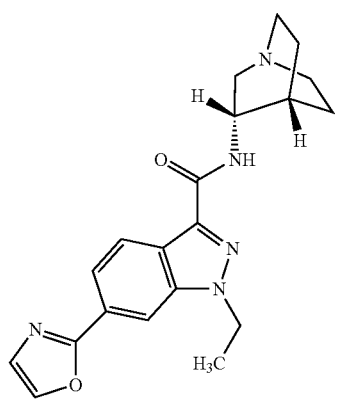 |
| 31) | 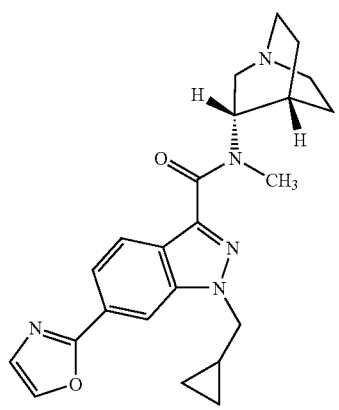 |

-continued
| Compound | Structure |
|---|---|
| 32) | 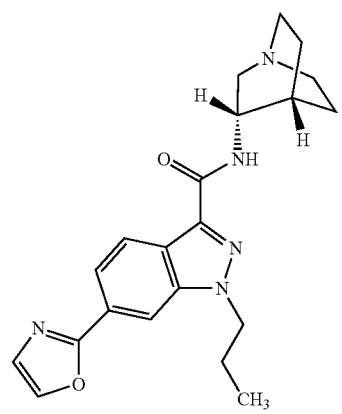 |
| 33) | 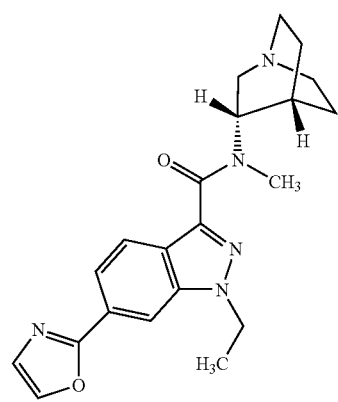 |
| 34) | 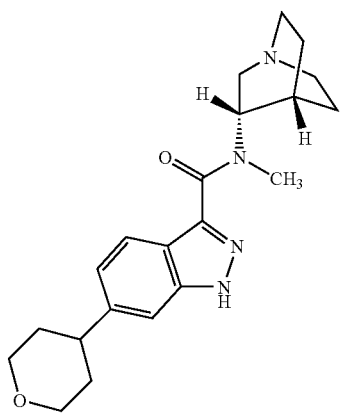 |
| 35) | 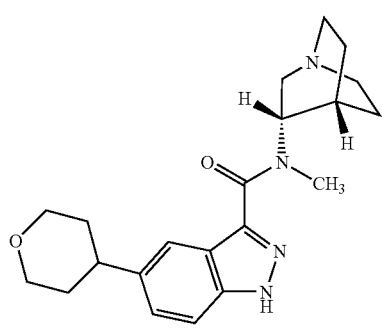 |

-continued
| Compound | Structure |
|---|---|
| 36) | 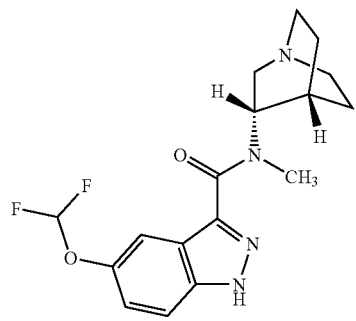 |
| 37) | 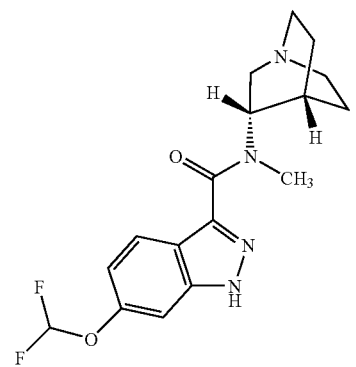 |
| 38) | 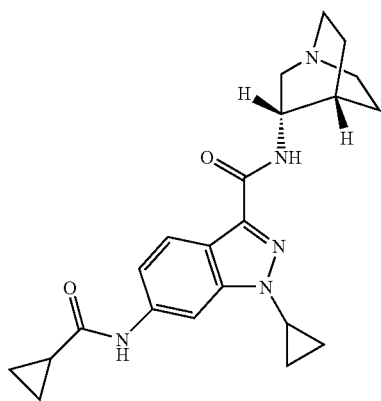 |
| 39) | 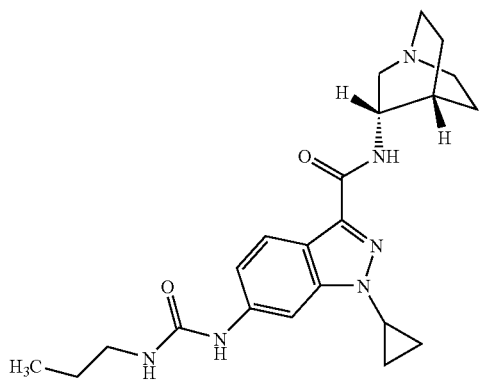 |

| Compound | Structure |
|---|---|
| 40) | 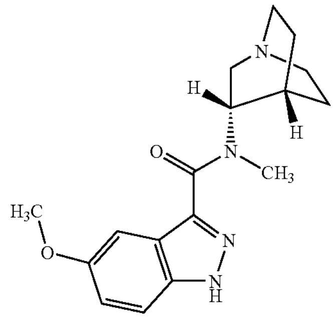 |
| 41) | 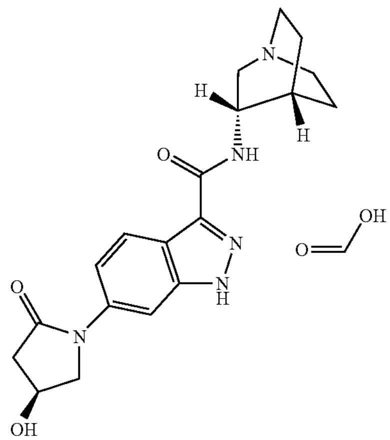 |
| 42) | 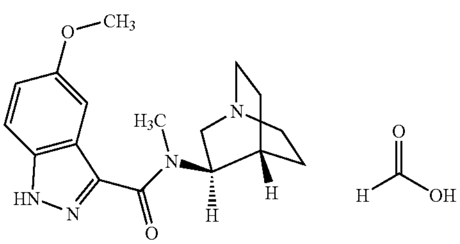 |
| 43) | 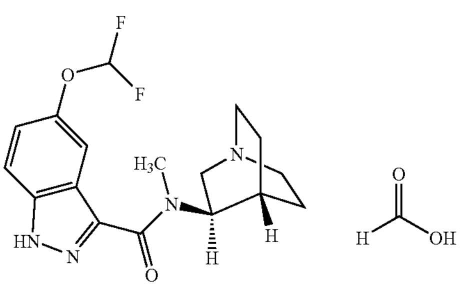 |
| 44) | 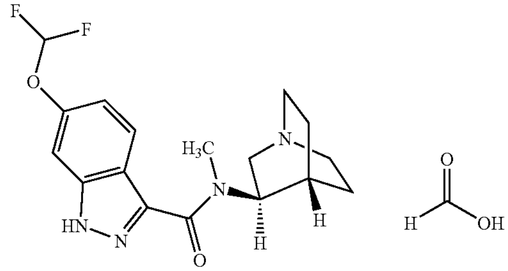 |

-continued

| Compound | Structure |
|---|---|
| 45) | [structure: 6-(tetrahydropyran-4-yl)-1H-indazole-3-carboxylic acid N-methyl-N-quinuclidin-3-yl amide · formic acid] |
| 46) | [structure: 5-(tetrahydropyran-4-yl)-1H-indazole-3-carboxylic acid N-methyl-N-quinuclidin-3-yl amide · formic acid] |
| 47) | [structure: 6-(thiazol-2-yl)-1H-indazole-3-carboxylic acid N-methyl-N-quinuclidin-3-yl amide · formic acid] |
| 48) | [structure: 6-methoxy-1H-indazole-3-carboxylic acid N-methyl-N-quinuclidin-3-yl amide · formic acid] |
| 49) | [structure: 6-(3-methoxypyrrolidin-1-yl)benzo[d]isothiazole-3-carboxylic acid N-quinuclidin-3-yl amide · HCl] |
| 50) | [structure: 6-hydroxybenzo[d]isothiazole-3-carboxylic acid N-quinuclidin-3-yl amide] |

-continued
| Compound | Structure |
|---|---|
| 51) | 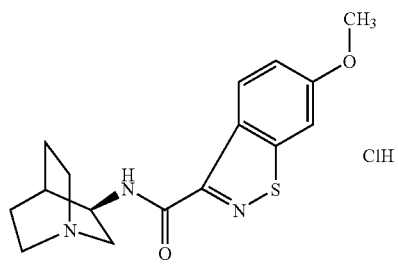 ClH |
| 52) | 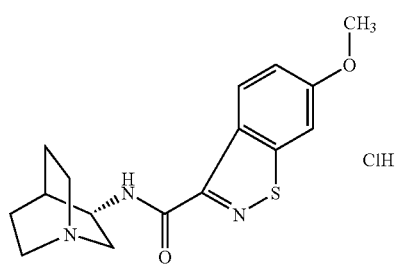 ClH |
| 53) | 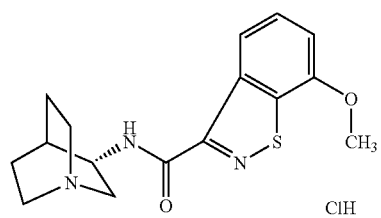 ClH |
| 54) | 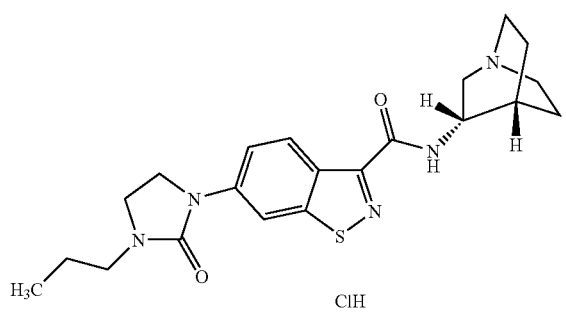 ClH |
| 55) | 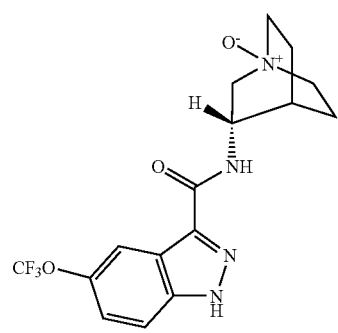 |

-continued
| Compound | Structure |
|---|---|
| 56) | 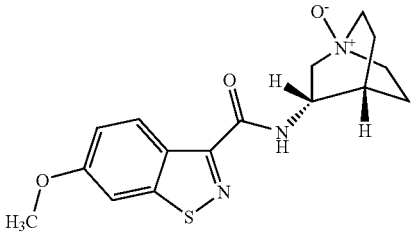 |
| 57) | 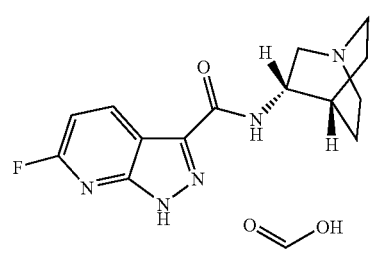 |
| 58) | 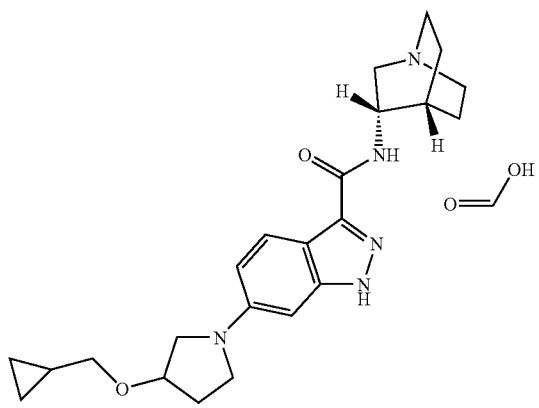 |
| 59) | 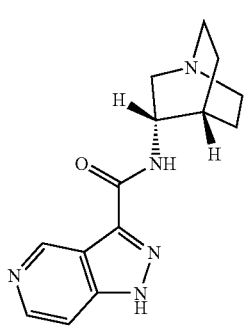 |
| 60) | 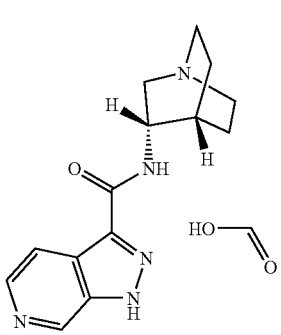 |

-continued
| Compound | Structure |
|---|---|
| 61) | 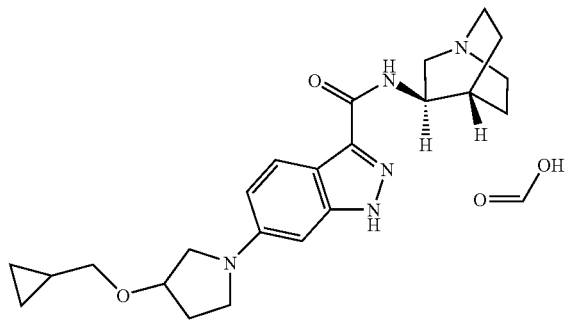 |
| 62) | 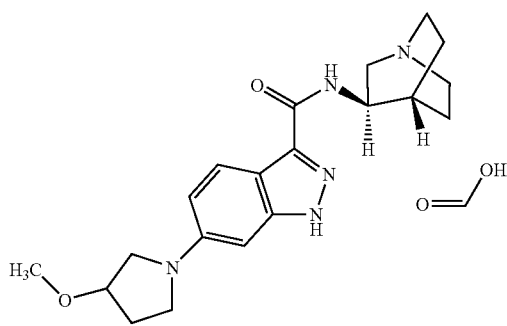 |
| 63) | 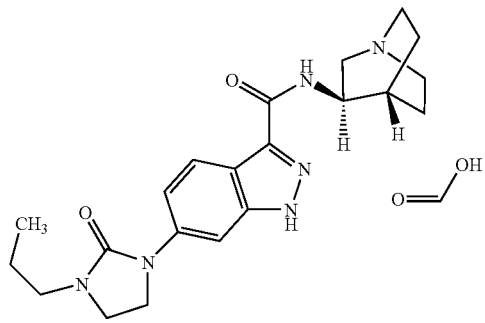 |
| 64) | 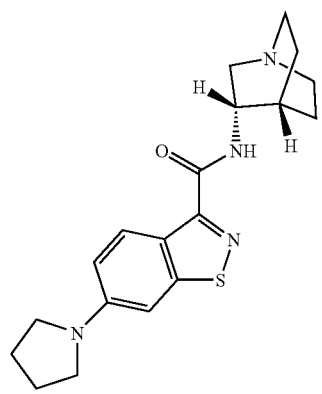 |

| Compound | Structure |
|---|---|
| 65) | 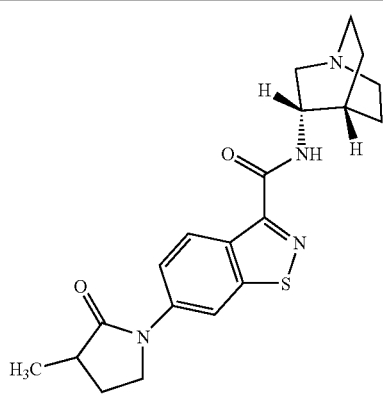 |
| 66) | 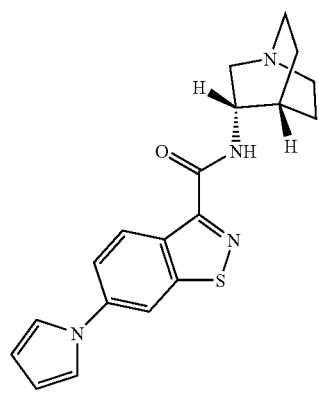 |
| 67) | 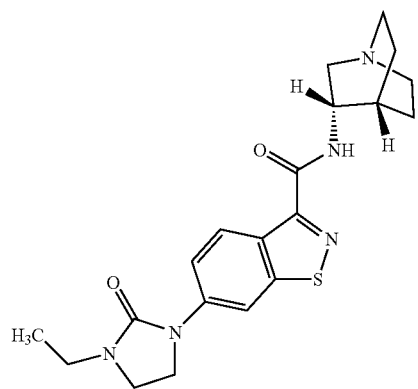 |
| 68) | 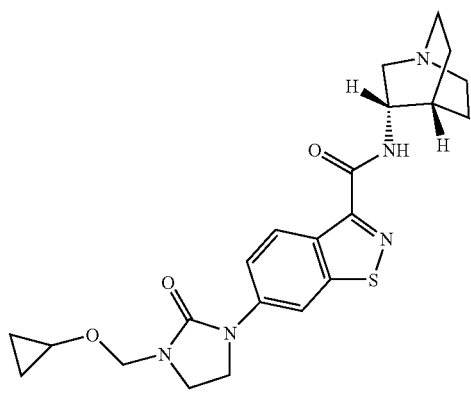 |

-continued
| Compound | Structure |
|---|---|
| 69) | 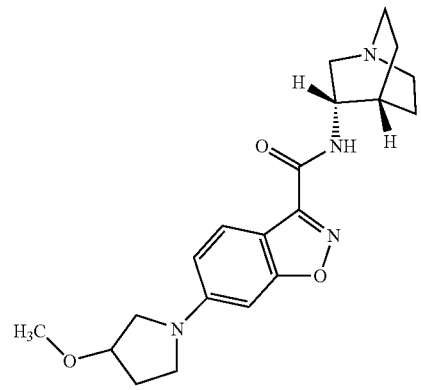 |
| 70) | 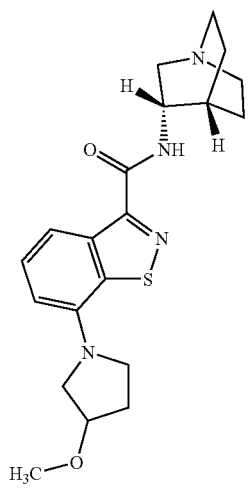 |
| 71) | 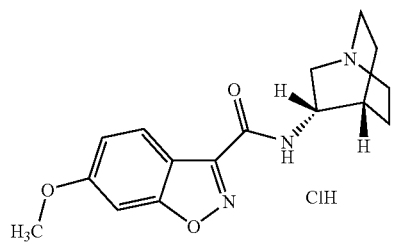 |
| 72) | 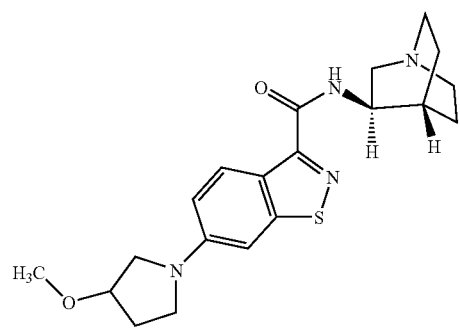 |

-continued
| Compound | Structure |
|---|---|
| 73) | 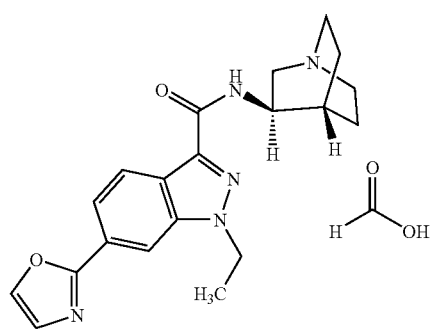 |
| 74) | 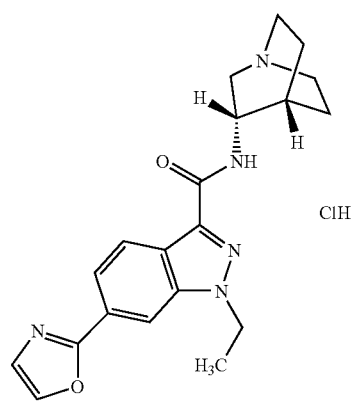 |
| 75) | 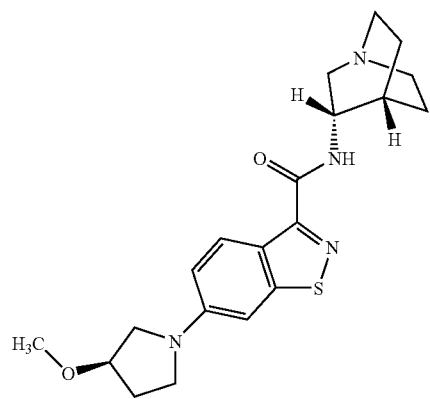 |
| 76) | 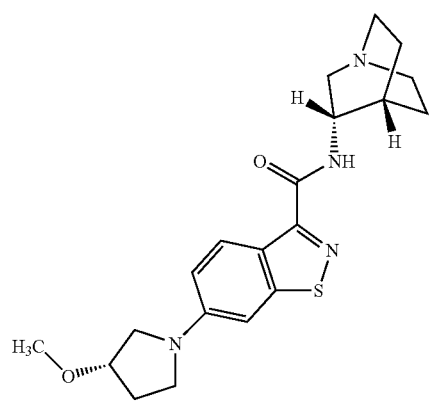 |

-continued
| Compound | Structure |
|---|---|
| 77) | 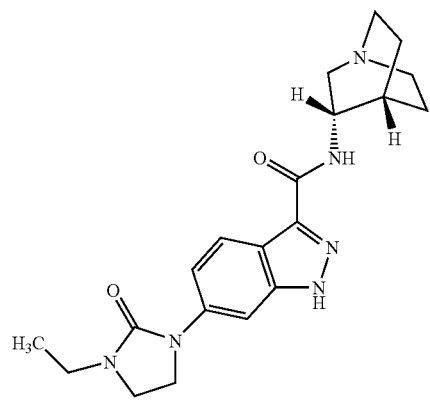 |
| 78) | 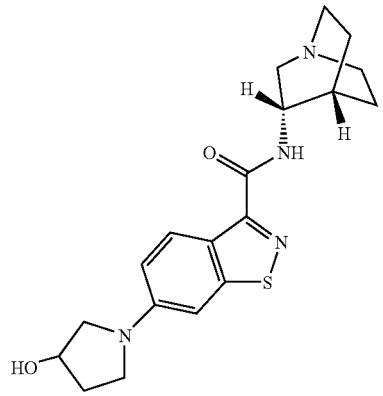 |
| 79) | 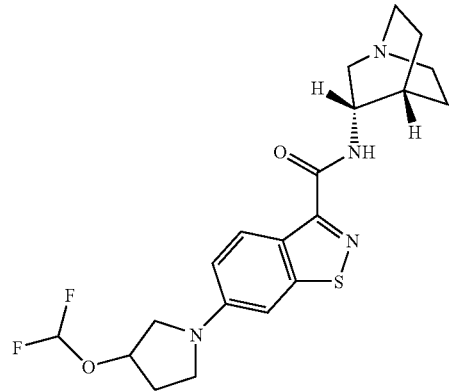 |
| 80) | 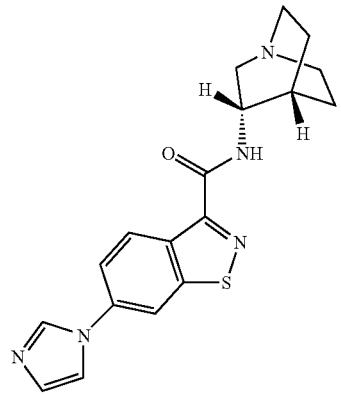 |

| Compound | Structure |
|---|---|
| 81) | 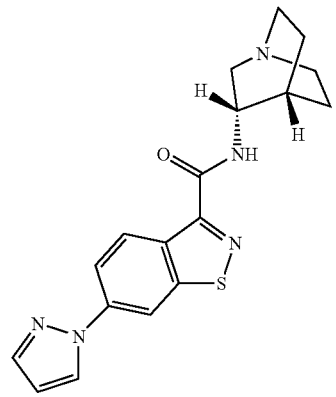 |
| 82) | 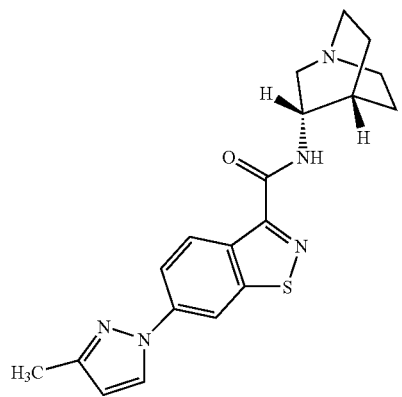 |
| 83) | 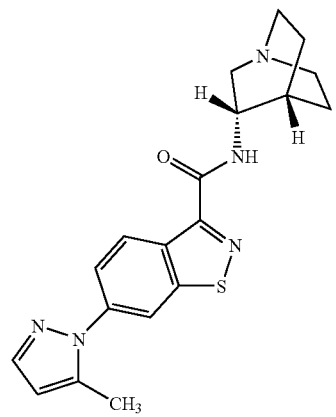 |
| 84) | 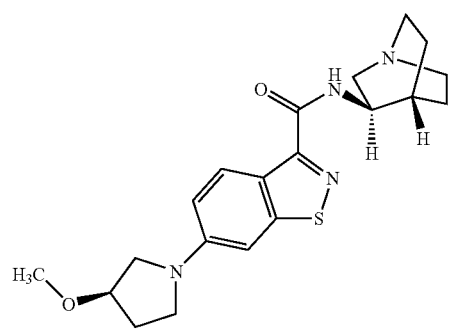 |

| Compound | Structure |
|---|---|
| 85) | 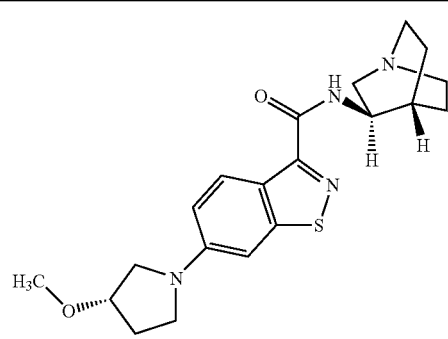 |
| 86) | 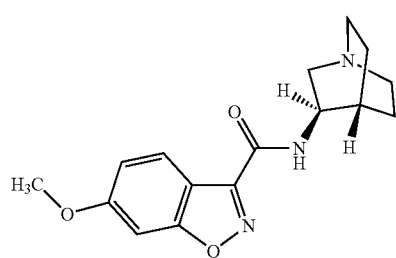 |
| 87) | 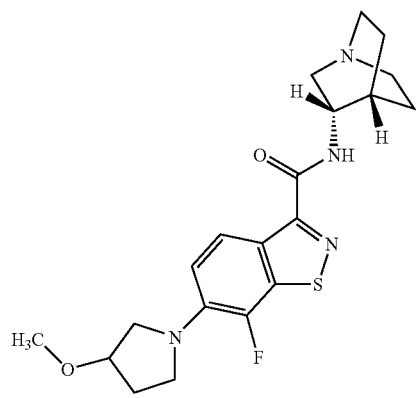 |
| 88) | 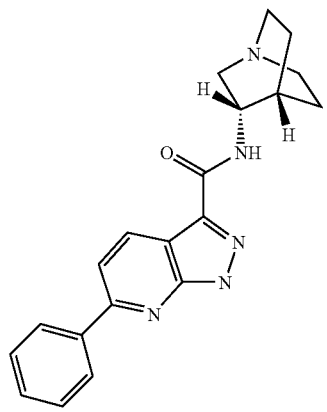 |

-continued
| Compound | Structure |
|---|---|
| 89) | 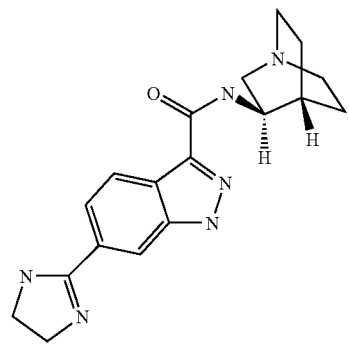 |
| 90) | 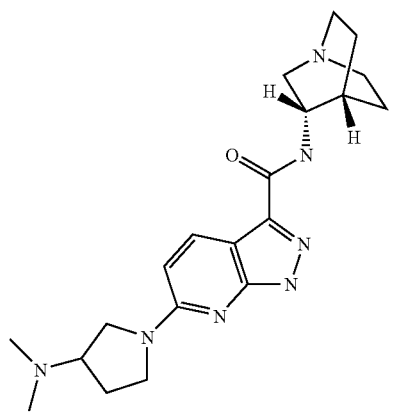 |
| 91) | 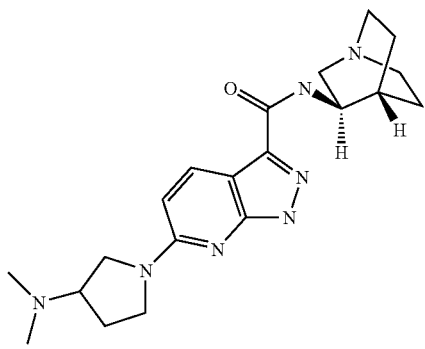 |
| 92) | 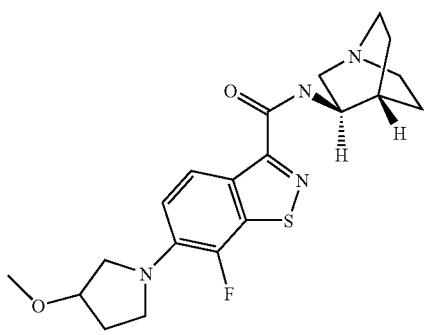 |

| Compound | Structure |
|---|---|
| 93) | 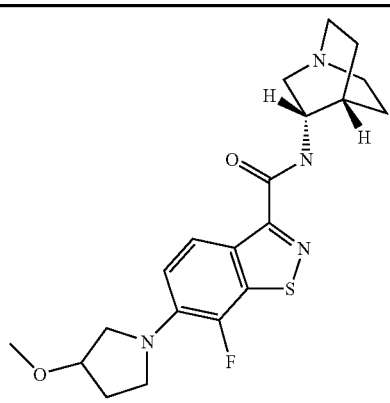 |
| 94) | 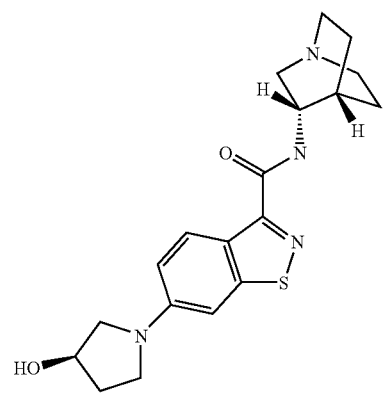 |
| 95) | 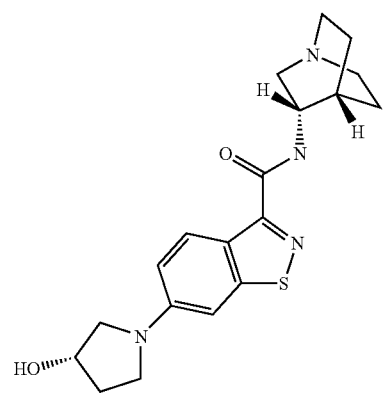 |
| 96) | 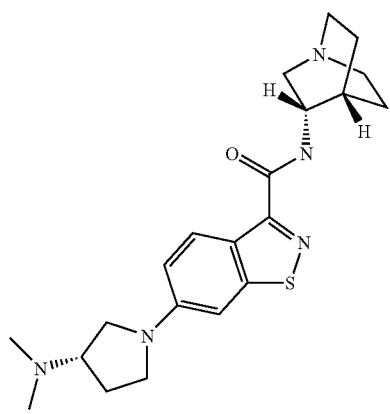 |

| Compound | Structure |
|---|---|
| 97) | 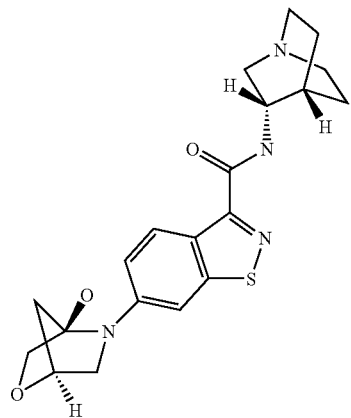 |
| 98) | 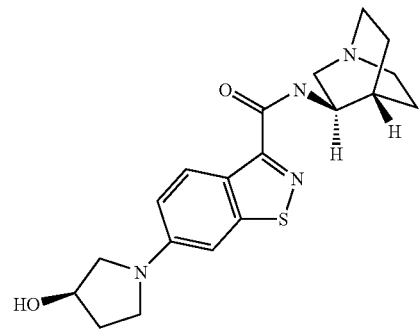 |
| 99) | 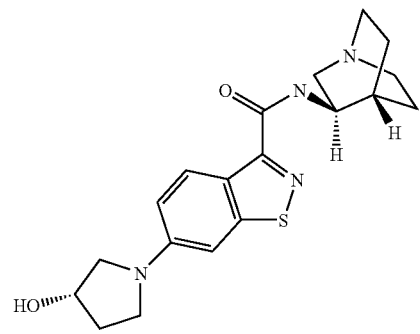 |
| 100) | 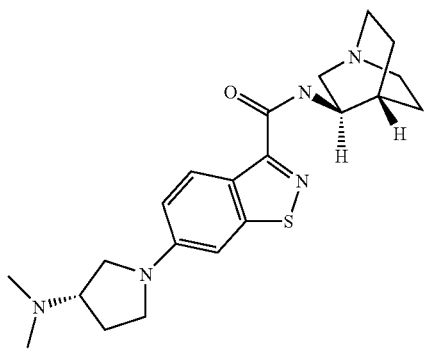 |

| Compound | Structure |
|---|---|
| 101) | 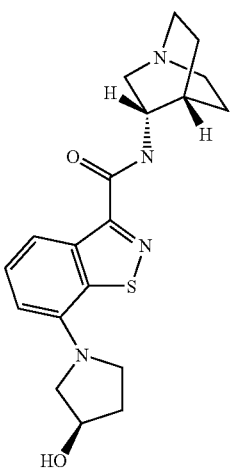 |
| 102) | 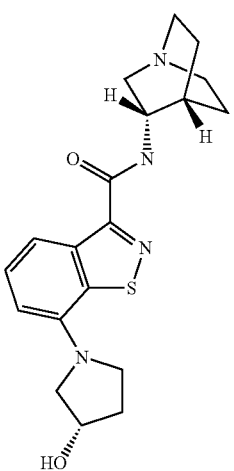 |
| 103) | 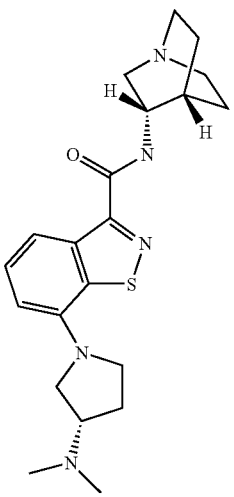 |

-continued
| Compound | Structure |
|---|---|
| 104) | 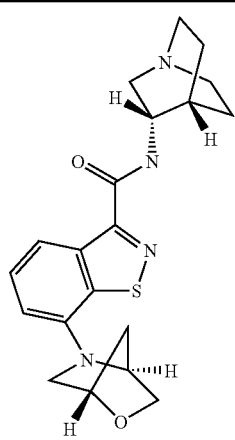 |
| 105) | 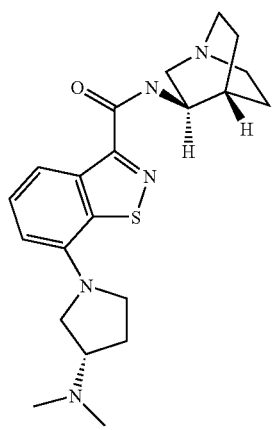 |
| 106) | 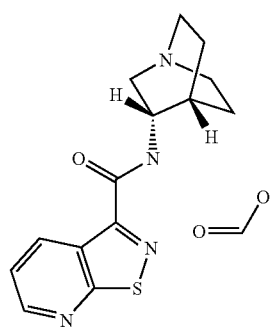 |
| 107) | 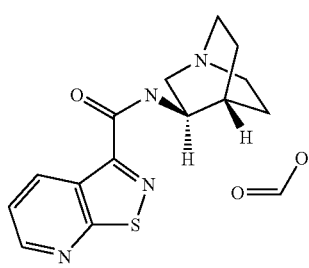 |

-continued
| Compound | Structure |
|---|---|
| 108) | 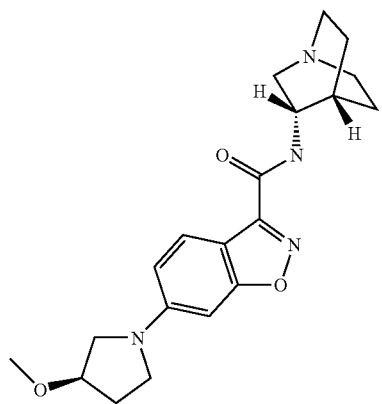 |
| 109) | 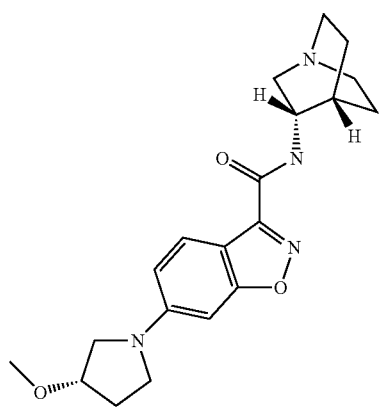 |
| 110) | 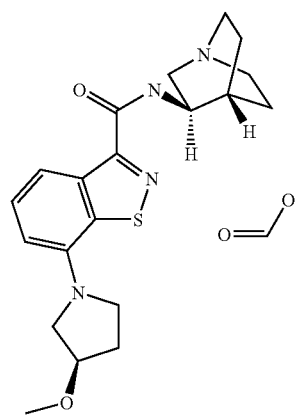 |

| Compound | Structure |
|---|---|
| 111) | 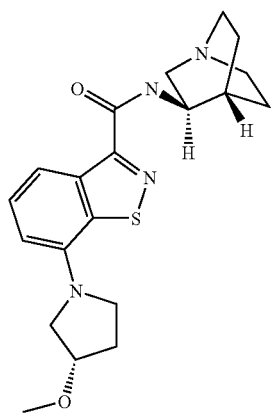 |
| 112) | 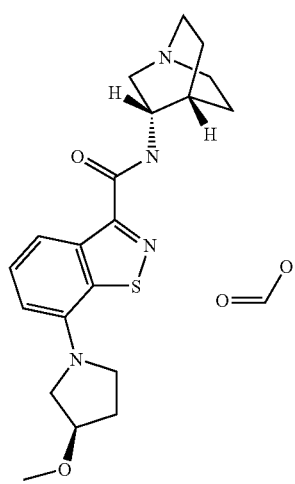 |
| 113) | 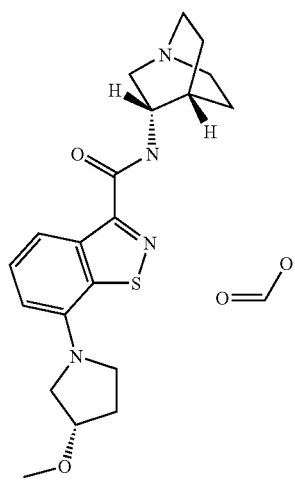 |

-continued
| Compound | Structure |
|---|---|
| 114) | 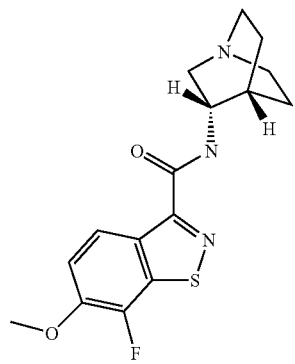 |
| 115) | 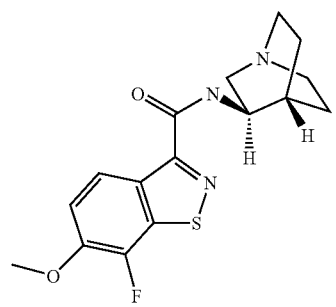 |
| 116) | 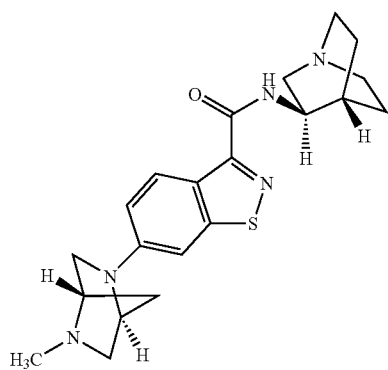 |
| 117) | 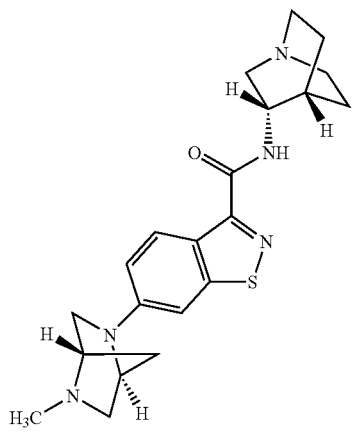 |

-continued
| Compound | Structure |
|---|---|
| 118) | 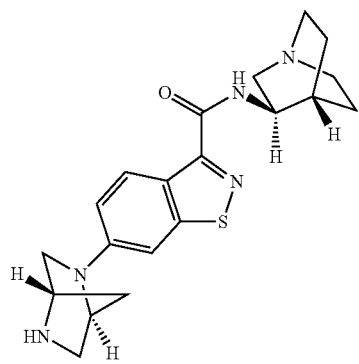 |
| 119) | 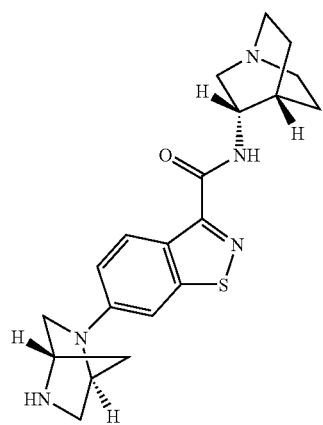 |
| 120) | 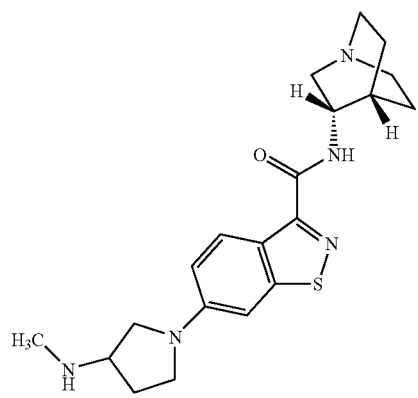 |
| 121) | 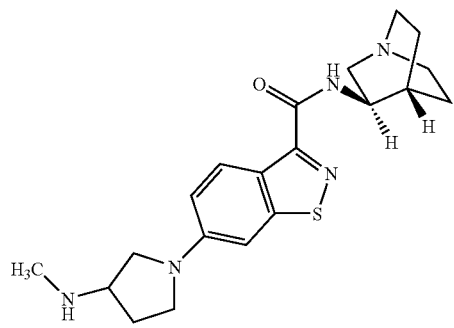 |

-continued
| Compound | Structure |
|---|---|
| 122) | 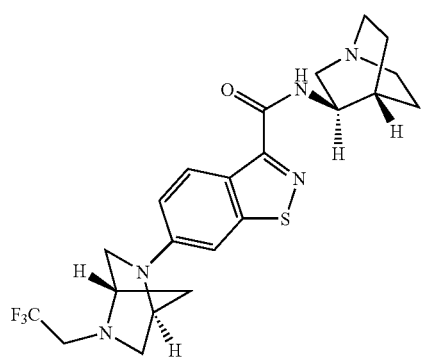 |
| 123) | 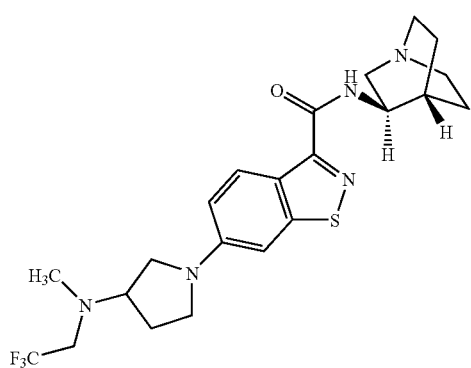 |
| 124) | 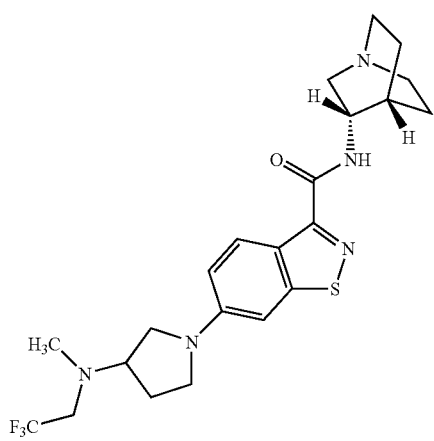 |
| 125) | 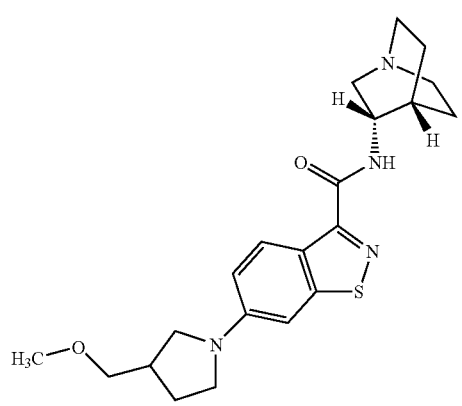 |

-continued
| Compound | Structure |
|---|---|
| 126) | 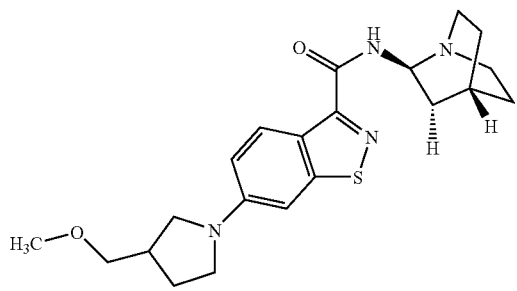 |
| 127) | 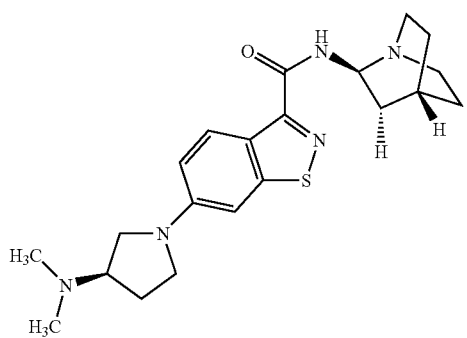 |
| 128) | 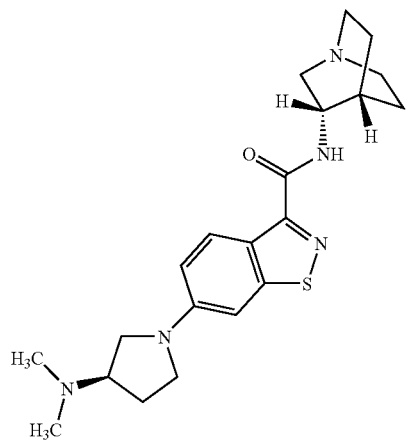 |
| 129) | 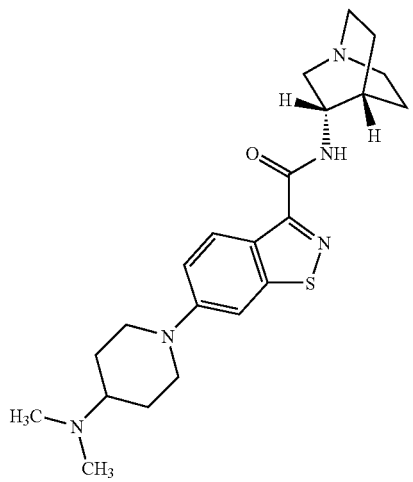 |

-continued
| Compound | Structure |
|---|---|
| 130) | 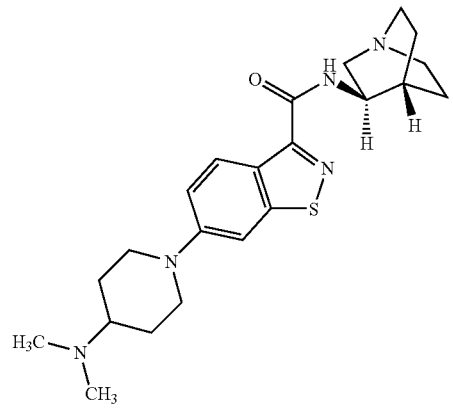 |
| 131) | 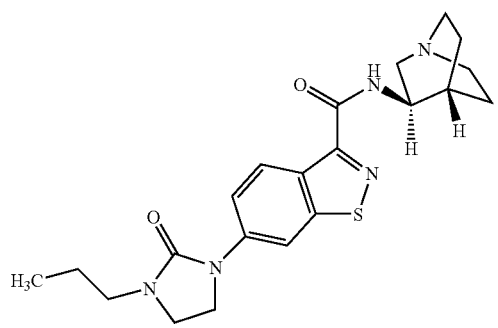 |
| 132) | 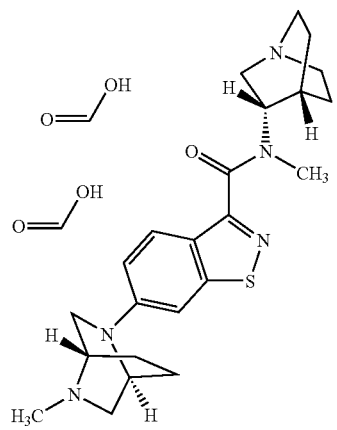 |
| 133) | 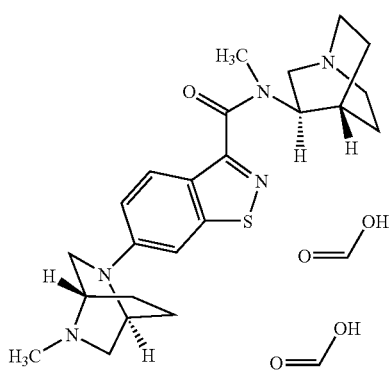 |

-continued
| Compound | Structure |
|---|---|
| 134) | 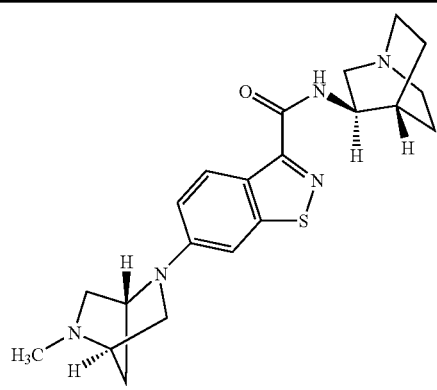 |
| 135) | 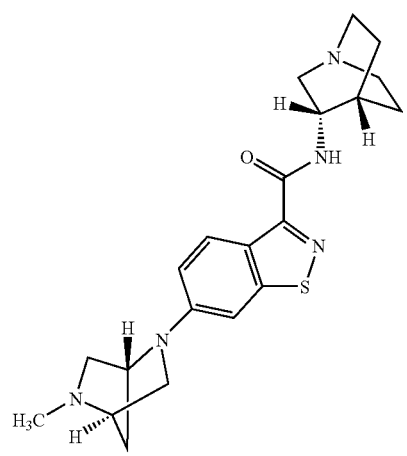 |
| 136) | 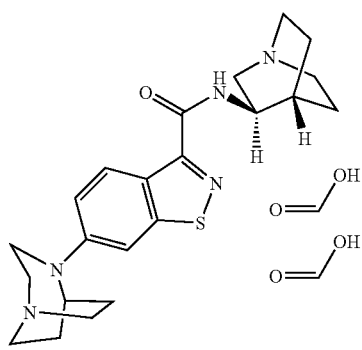 |
| 137) | 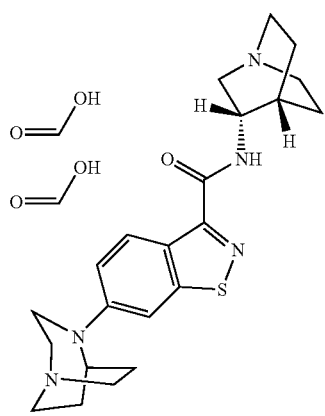 |

| Compound | Structure |
|---|---|
| 138) | 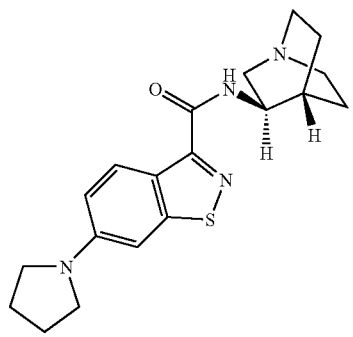 |
| 139) | 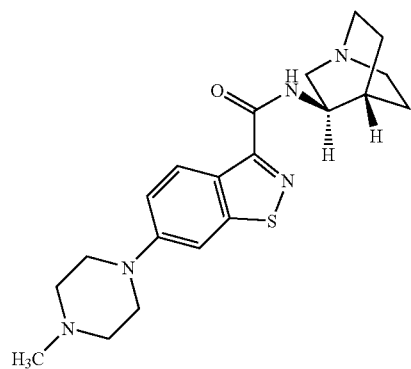 |
| 140) | 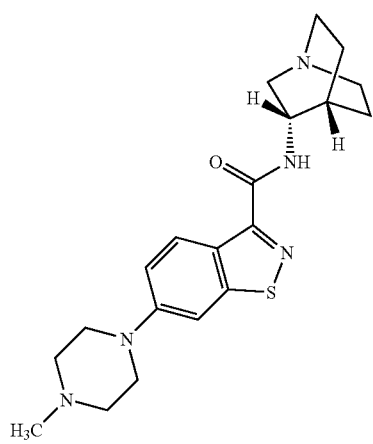 |
| 141) | 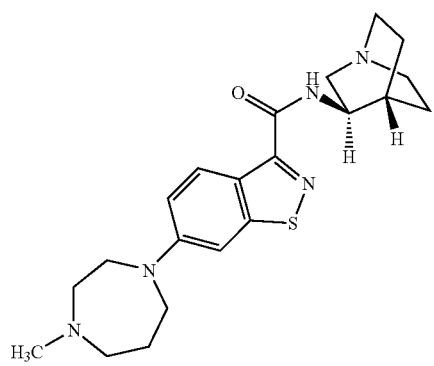 |

-continued
| Compound | Structure |
|---|---|
| 142) | 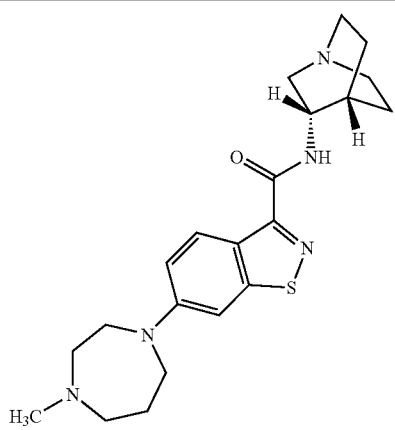 |
| 143) | 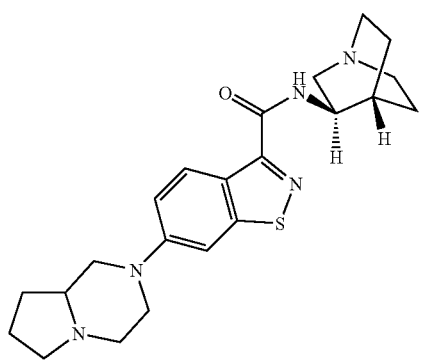 |
| 144) | 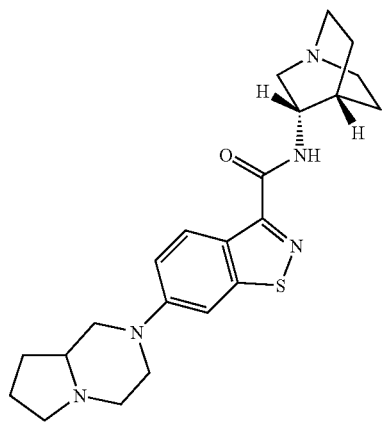 |
| 145) | 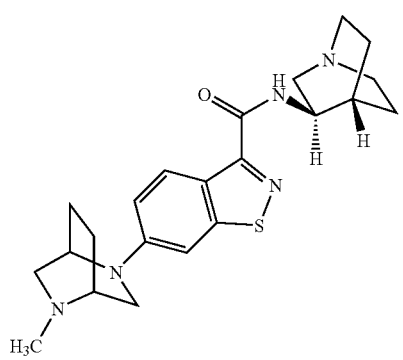 |

-continued
| Compound | Structure |
|---|---|
| 146) | 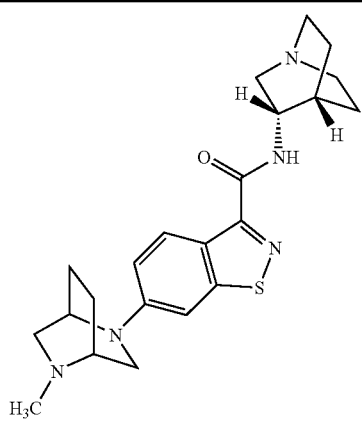 |
| 147) | 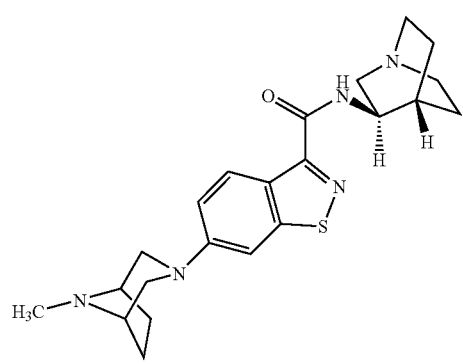 |
| 148) | 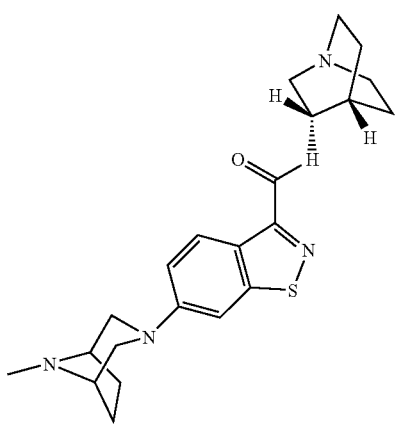 |
| 149) | 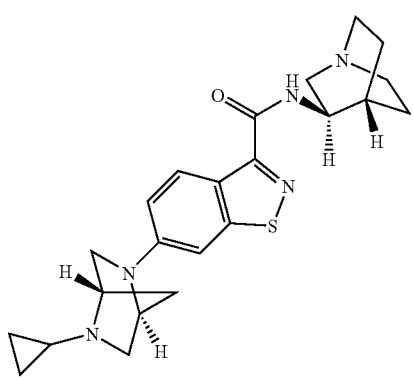 |

-continued
| Compound | Structure |
|---|---|
| 150) | 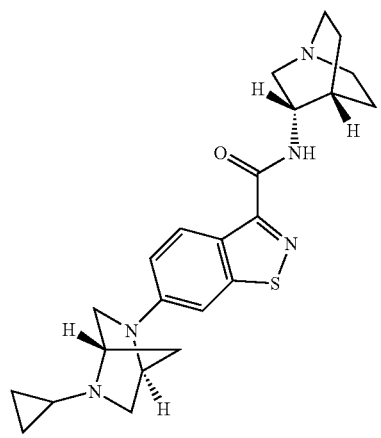 |
| 151) | 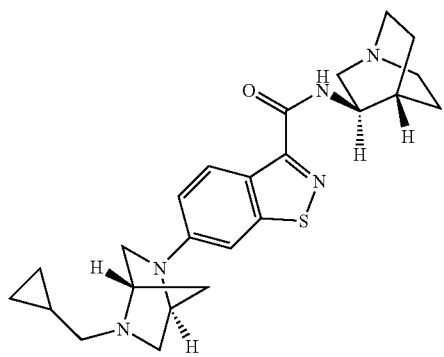 |
| 152) | 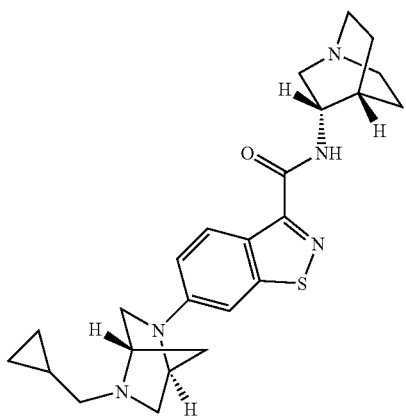 |
| 153) | 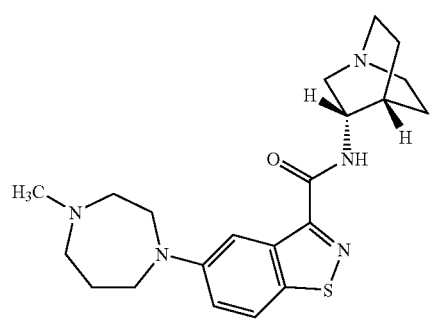 |

| Compound | Structure |
|---|---|
| 154) | 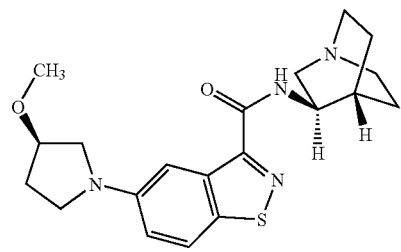 |
| 155) | 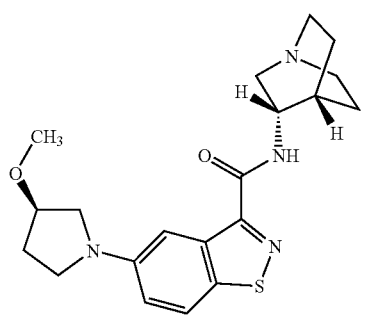 |
| 156) | 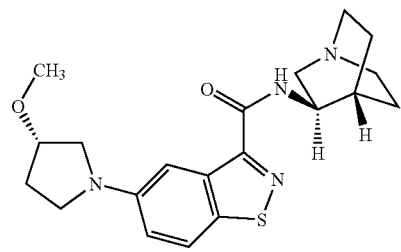 |
| 157) | 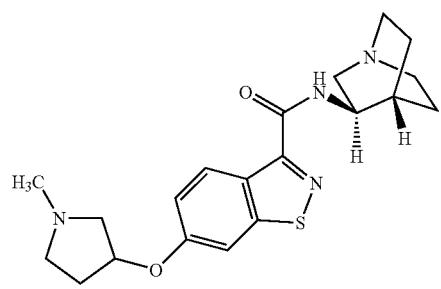 |
| 158) | 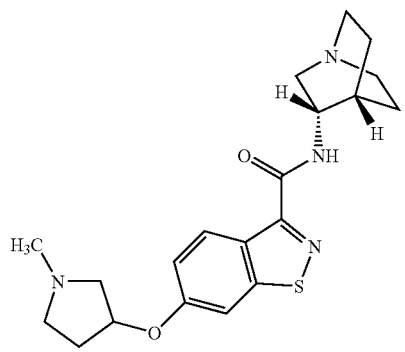 |

-continued
| Compound | Structure |
|---|---|
| 159) | 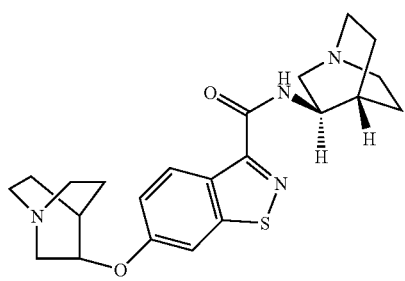 |
| 160) | 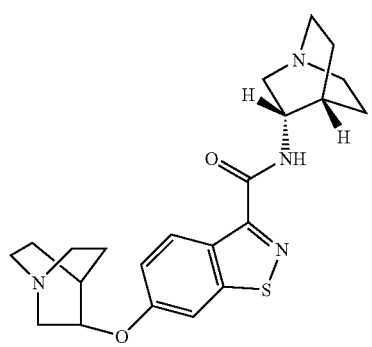 |
| 161) | 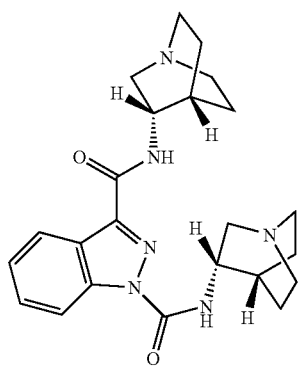 |
| 162) | 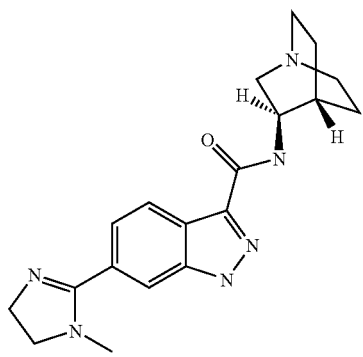 |

| Compound | Structure |
|---|---|
| 163) | 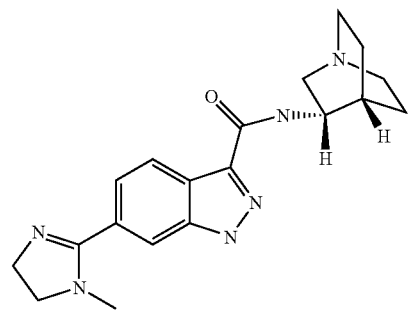 |
| 164) | 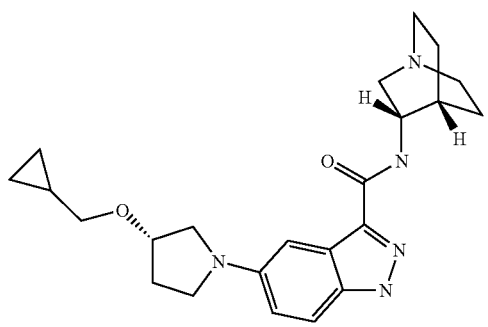 |
| 165) | 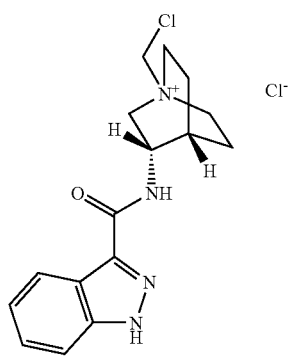 |
| 166) | 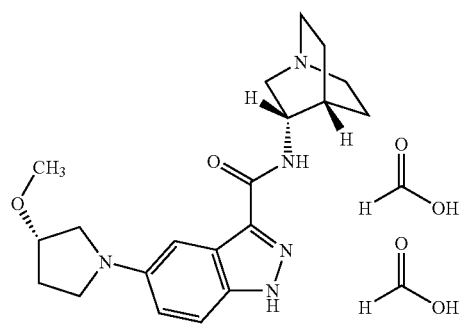 |

-continued
| Compound | Structure |
|---|---|
| 167) | 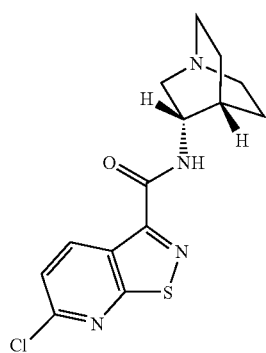 |
| 168) | 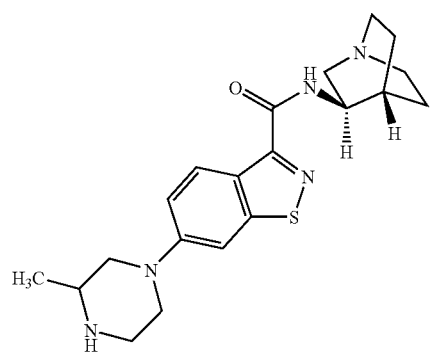 |
| 169) | 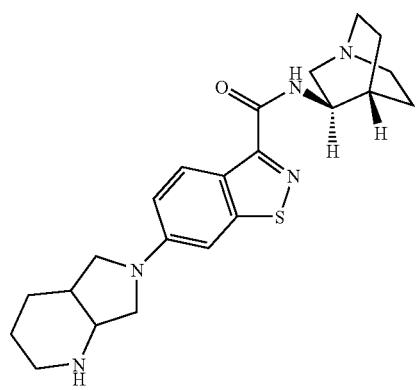 |
| 170) | 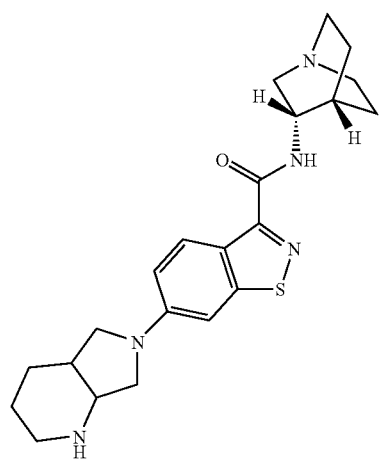 |

| Compound | Structure |
|---|---|
| 171) | 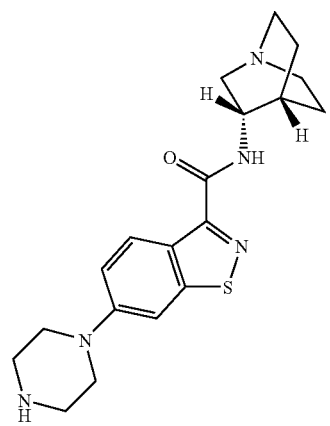 |
| 172) | 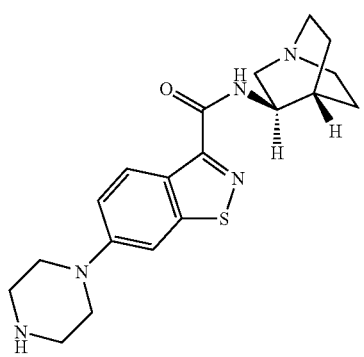 |
| 173) | 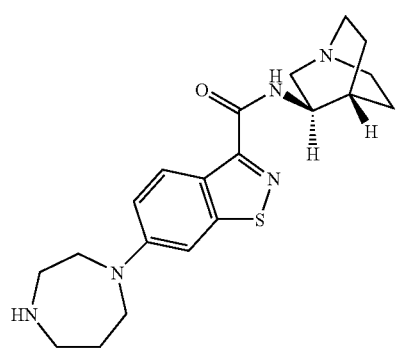 |
| 174) | 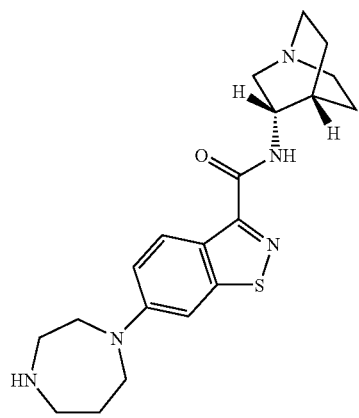 |

-continued
| Compound | Structure |
|---|---|
| 175) | 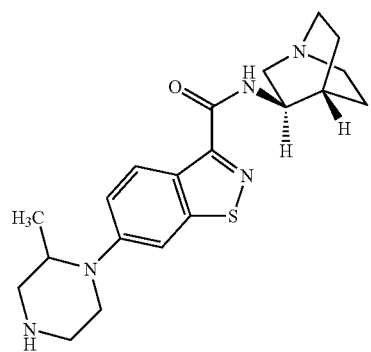 |
| 176) | 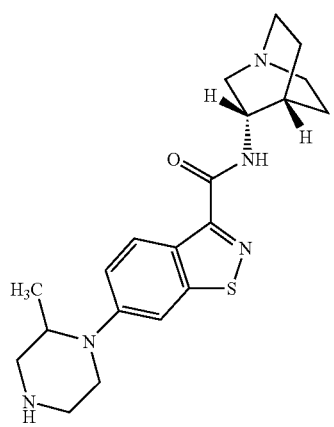 |
| 177) | 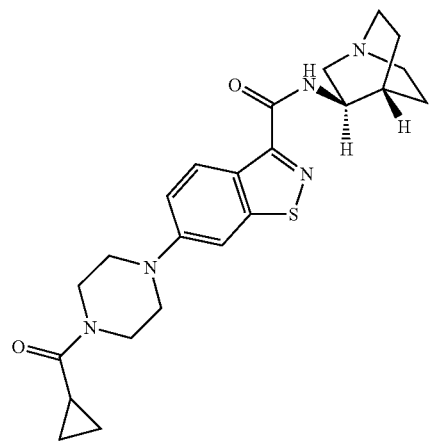 |

| Compound | Structure |
|---|---|
| 178) | 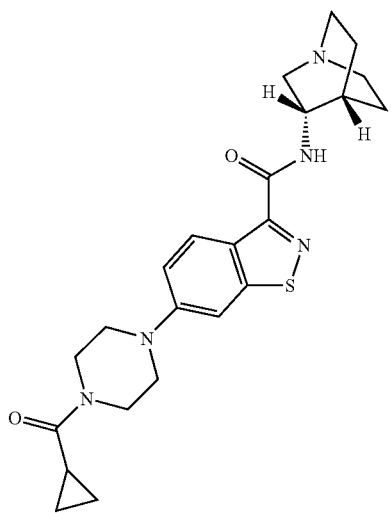 |
| 179) | 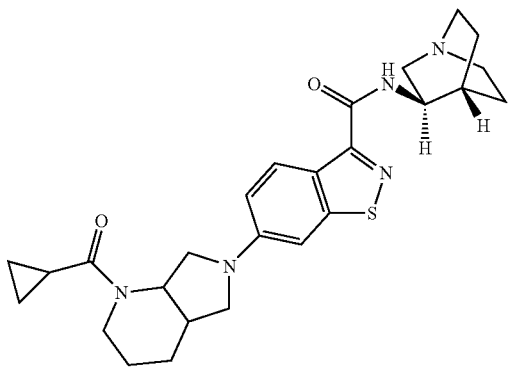 |
| 180) | 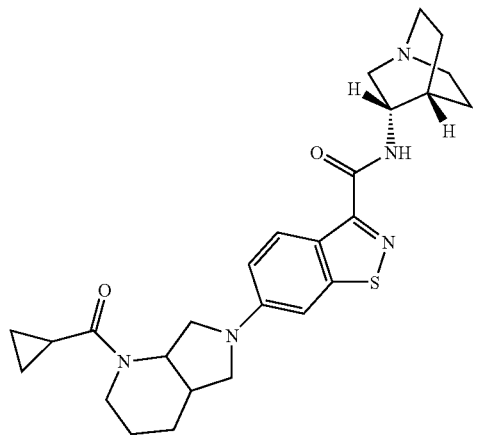 |

| Compound | Structure |
|---|---|
| 181) | 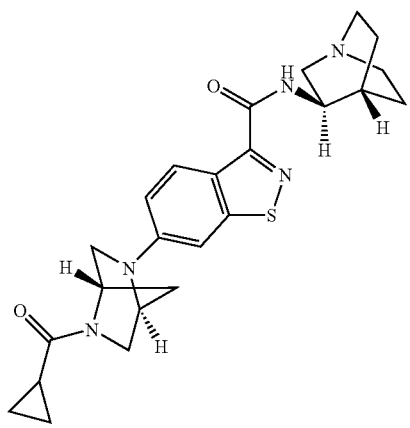 |
| 182) | 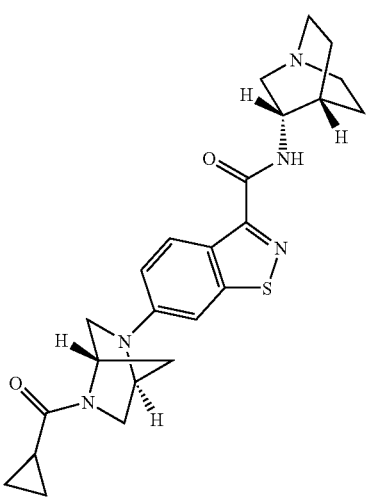 |
| 183) | 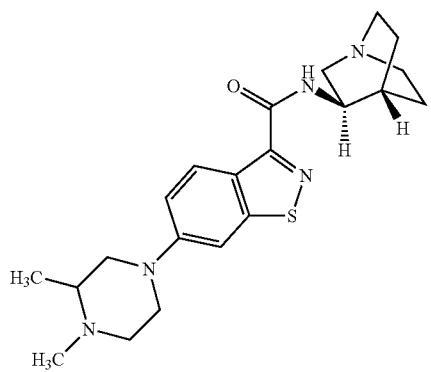 |

-continued
| Compound | Structure |
|---|---|
| 184) | 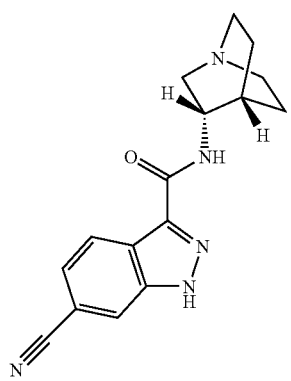 |
| 185) | 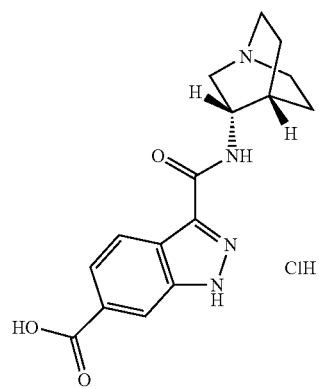 |
| 186) | 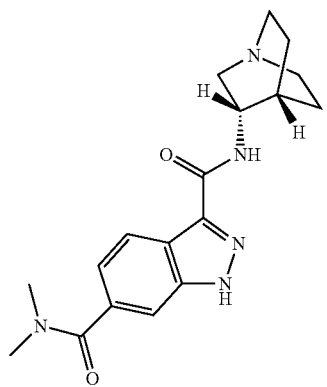 |
| 187) | 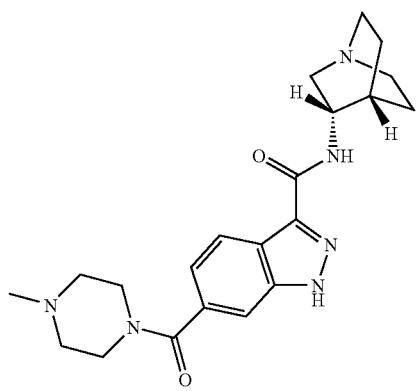 |

-continued

| Compound | Structure |
|---|---|
| 188) | 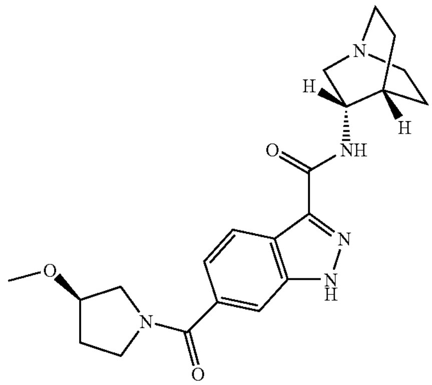 |
| 189) | 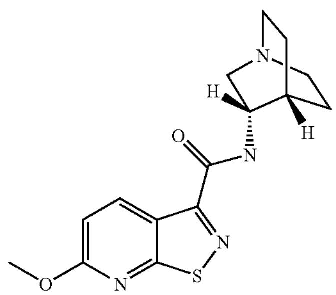 |
| 190) | 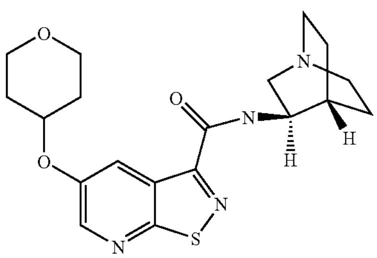 |

Additional aspects include pharmaceutical compositions comprising a compound of this invention and a pharmaceutically acceptable carrier and, optionally, another active agent as discussed below; a method of stimulating or activating inhibiting alpha-7 nicotinic receptors, e.g., as determined by a conventional assay or one described herein, either in vitro or in vivo (in an animal, e.g., in an animal model, or in a mammal or in a human); a method of treating a neurological syndrome, e.g., loss of memory, especially long-term memory, cognitive impairment or decline, memory impairment, etc. method of treating a disease state modulated by nicotinic alpha-7 activity, in a mammal, e.g., a human, e.g., those mentioned herein.

The compounds of the present invention may be prepared conventionally. Some of the known processes that can be used are described below. All starting materials are known or can be conventionally prepared from known starting materials by one of ordinary skill Acids that were used in the preparation of the bicyclobase amides were commercially available or were prepared by known procedures described in the literature or as described below. For example, indazole-3-carboxylic acid was commercially available. A variety of the simple substituted indazole-3-acids, such as the bromoindazole acids, were prepared from the corresponding isatins by basic hydrolysis, diazotization, and reduction (Snyder, H. R. et al., *J. Am. Chem. Soc.* 1952, 74, 2009).

Several substituted indazole-3-acids were prepared by modifying existing indazole acids or esters. For example, N(1)- and N(2)-protected indazole acids were prepared from the ester through reaction with methoxyethoxymethyl chloride (MEM-Cl) or trimethylsilylethoxymethyl chloride (SEM-Cl) and either sodium hydride or di-isopropylethylamine. N(1)-Alkylated indazole-3-carboxylic acids were prepared from the corresponding indazole esters by standard alkylation or Mitsunobu procedures. N(1)-Arylated indazole-3-carboxylic acids were prepared from the corresponding indazole esters by copper mediated cross couplings with boronic acids. Non-aromatic heterocyclic derivatives were prepared from the corresponding bromides by metal-halogen exchange, trapping of indazole aryllithiums with ketones, followed by reduction or acid mediated elimination. Aromatic substituted indazole-3-acids were prepared from the corresponding bromides via palladium mediated cross-coupling with boronic acids or aryl zinc reagents (Reeder, M. R.; et. al. *Org. Proc. Res. Devel.* 2003, 7, 696). Amino indazole acids were prepared using a palladium mediated cross-coupling reaction with secondary amines. Phenol derivatives were prepared from the corresponding methoxy acids using boron tribromide. 6-Amino- and 6-phenyl-7-azaindazole-3-carboxylic acids were prepared from the commercially available 6-fluoro material by reaction with a secondary amine or by nickel mediated cross-coupling with aryl Grignard reagents.

Several substituted indazole-3-acids were prepared from benzene derivatives. For example, 5-difluoromethoxyindazole-3-acid was prepared from 3-bromo-4-nitrophenol by reaction with ethyl difluoroacetate, reaction with diethyl malonate, decarboxylative saponification, esterification, reduction of the nitro group, and diazotization. 6-Difluoromethoxyindazole-3-acid was prepared in a similar manner from 2-bromo-5-difluoromethoxynitrobenzene. The 2-bromo-5-difluoromethoxynitrobenzene was prepared from 4-nitrophenol by ether formation, nitro reduction with concomitant protection as the amide, nitration, amide hydrolysis, and a Sandmeyer reaction with copper (I) bromide. 6-Benzyloxyindazole-3-carboxylic acid and ester were prepared from 4-methoxynitrobenzene by nitro reduction with concomitant protection as the amide, nitration, amide hydrolysis, Sandmeyer reaction with copper (I) bromide, and demethylation. The phenol was alkylated with benzyl bromide and the arylbromide was subjected to reaction with diethyl malonate, decarboxylative saponification, esterification, reduction of the nitro group, and diazotization. The 5-benzyloxy analog was prepared in a similar manner from 4-benzyloxy-2-bromonitrobenzene (Parker, K. A.; Mindt, T. L. *Org. Lett.* 2002, 4, 4265. ) The benzyl group was removed by hydrogenolysis and the resulting phenol was transformed to ether derivatives via either alkylation or Mitsunobu reaction conditions. 4-Methoxyindazole acid was prepared from 4-methoxyaniline by amide formation, nitration, amide hydrolysis, Sandmeyer reaction with copper (I) bromide, nitro reduction, isatin formation and rearrangement to the indazole, followed by hydrogenolytic removal of the bromine. 5-Azaindazole-3-acid was prepared from 4-chloropyridine by metallation and trapping with diethyloxalate, cyclization with hydrazine, and saponification. 6-Azaindazole-3-acid was prepared from 4-chloro-3-nitropyridine by reaction with a malonate anion, decarboxylation, nitro reduction, diazotization, and saponification.

The benziosoxazole esters were prepared from simple benzene derivatives using similar techniques. For example, ethyl 6-bromobenzisoxazole-3-carboxylate was prepared from 2-nitro-1,4-dibromobenzene by reaction with dimethylmalonate, a saponification/decarboxylation sequence, esterification, and reaction with isoamyl nitrite under basic conditions. The 6-methoxybenzisoxazole ester compound was prepared, analogously, from 2,4-dinitrochlorobenzene. Reduction of the resultant 6-nitro group followed by diazotization and oxidation provided the 6-hydroxy compound. The ether was obtained by simple alkylation.

The benzisothiazole carboxylic acids were also prepared using similar strategies outlined for the indazole acids. For example, 6-methoxybenzisothiazole-3-carboxylic acid was prepared from 3-methoxythiophenol by reaction with oxalyl chloride and aluminum chloride followed by treatment with hydroxylamine, hydrogen peroxide, and sodium hydroxide. Amino substituted benzisothiazole acids were prepared from the requisite bromide by a palladium mediated cross-coupling reaction with secondary amines or benzophenone imine. The primary and secondary amines generated this way serve as intermediates for other ligands. For example, the amines were transformed into tertiary amines and amides using standard reductive amination and acylation reactions practiced by those of ordinary skill in the art. 7-Azabenzisothiazole-3-carboxylic acid was prepared from 2-chloronicotinoyl chloride by reaction with the diethylmalonate anion and decarboxylation followed by reaction of the ketone with sulfer, ammonium hydroxide, and ammonia to generate the 7-aza-3-methylbenzisothiazole core. The acid was installed using a benzylic oxidation with N-bromosuccinamide and hydrolysis, followed by basic permanganate oxidation of the alcohol. 7-Aza-6-chlorobenzisothiazole-3-acid was synthesized from the 7-aza-3-methylbenzisothiazole core by oxidation of the pyridine ring nitrogen followed by a rearrangement reaction mediated by triphosgene to install a chlorine atom at the 6-position. The synthesis was completed by a benzylic oxidation in a similar manner to the unsubstituted azabenzisothiazole acid.

The bicycloamines, 3-aminoquinuclidine and the R- and S-enantiomers thereof, used in the preparation of the bicyclobase amides were commercially available. The N-alkylated quinuclidines were prepared by acylation of 3-aminoquinuclidine followed by reduction of the amide.

The bicyclobase amides were prepared from the acids and the bicycloamines using standard peptide coupling agents, such as O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), O-(benzotriazol-1-yl)-N,N,N',N'-tetramethyluronium tetrafluoroborate (TBTU), hydroxybenztriazole (HOBt) and N-(3-dimethylaminopropyl)-N'-ethylcarbodiimide (EDCI), carbonyl diimidazole (CDI), and 2-chloro-1,3,-dimethylimidazolinium hexafluorophosphate (CIP), or by converting the acids to the corresponding acid chloride followed by reaction with the bicycloamine (Macor, J. E.; Gurley, D.; Lanthorn, T.; Loch, J.; Mack, R. A.; Mullen, G.; Tran, O.; Wright, N.; and J. E. Macor et al., "The 5-HT3-Antagonist Tropisetron (ICS 205-930) was a Potent and Selective α-7 Nicotinic Receptor Partial Agonist," *Bioorg. Med. Chem. Lett.* 2001, 9, 319-321). The couplings were generally performed at room temperature for 18-24 hours. The resultant adducts were isolated and purified by standard techniques practiced by those of ordinary skill in the art, such as chromatography or recrystallization.

The nicotinic ligands can, alternatively, be prepared by modification of other nicotinic ligands. For example, the cyclic urea ligand was prepared from the corresponding bromide ligand by a palladium-catalyzed cross-coupling reaction. Amino-substituted ligands were prepared by similar palladium mediated coupling reactions with secondary amines or benzophenone imine. The primary and secondary amines generated this way serve as intermediates for other ligands, as understood by those of ordinary skill in the art. 5-Alkoxybenzisothiazole ligands were prepared by palladium mediated cross coupling with pinacolborane dimer followed by oxidation and alkylation. In some cases, the indazole quinuclidine carboxamides were derivatized at the indazole nitrogen under Mitsunobu conditions or through the copper mediated coupling with boronic acids. Quaternary quinuclidine salts were prepared by the reaction of the final product with alkylating agents. N-Oxides were prepared by the reaction of the final product with oxidants.

One of ordinary skill in the art will recognize that compounds of Formulas I-IV can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulas I-IV can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made by the procedures described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, including free base forms and pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, or a maleate.

The salts of the present invention also include quaternary ammonium salts obtained by reacting the main compound, functioning as a nucleophile, with agents bearing nucleofugal groups. Examples of those agents include, but are not limited to, methyl iodide, methyl bromide, methyl chloride, methyl triflate, methyl tosylate, methyl mesylate, ethyl iodide, ethyl bromide, ethyl chloride, ethyl triflate, ethyl tosylate, ethyl mesylate, propyl iodide, propyl bromide, propyl chloride, cyclopropylmethyl bromide, benzyl bromide, methylene chloride, and dichloroethane. One skilled in the art will recognize that the list of example agents presented is non-exhaustive and can be expanded within reason.

For example, the quaternary ammonium salt can be formed at the N atom of the azabicyclo structute as shown in the following formula:

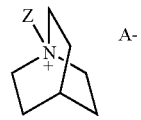

wherein Z is, for example, methyl, chloromethyl, ethyl, chloroethyl, propyl, cyclopropylmethyl, or benzyl, and the corresponding anion A is, for example, iodide, bromide, chloride, triflate, tosylate, or mesylate. See, for example, compounds 1, 13, and 165.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. For example, alkyl halide addition salts (e.g., salts formed by reaction with methyl iodide) may be envisaged. The free base can then, if desired, be converted to a pharmaceutically acceptable acid addition salt.

One of ordinary skill in the art will also recognize that some of the compounds of Formulas I, II, III, and IV can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of Formulas I, II, III, and IV can exist in different solvate forms. Solvates of the compounds of the invention may also form when solvent molecules are incorporated into the crystalline lattice structure of the compound molecule during the crystallization process.

The compounds of the invention can be administered alone or as an active ingredient of a formulation. Thus, the present invention also includes pharmaceutical compositions of compounds of Formulas I-IV, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their alpha-7 stimulating activity and, preferably their high degree of selectivity, the compounds of the present invention can be administered to anyone needing stimulation of alpha-7 receptors. Administration may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or memory loss, e.g., other α-7 agonists, PDE4 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and glanthanamine). In such combinations, each active ingredient can be administered either in accordance with their usual dosage range or a dose below their usual dosage range.

The compounds of the invention can be used in conjunction with "positive modulators" which enhance the efficacy of nicotinic receptor agonists. See, e.g., the positive modulators disclosed in WO 99/56745, WO 01/32619, and WO 01/32622. Such combinational therapy can be used in treating conditions/diseases associated with reduced nicotinic transmission.

Further the compounds may be used in conjunction with compounds that bind to Aβ peptides and thereby inhibit the binding of the peptides to α7nACh receptor subtypes. See, e.g., WO 99/62505.

The present invention further includes methods of treatment that involve activation of α-7 nicotinic receptors. Thus, the present invention includes methods of selectively activating/stimulating α-7 nicotinic receptors in a patient (e.g., a mammal such as a human) wherein such activation/stimulation has a therapeutic effect, such as where such activation may relieve conditions involving neurological syndromes, such as the loss of memory, especially long-term memory. Such methods comprise administering to a patient (e.g., a mammal such as a human), an effective amount of a compound of Formulas I-IV, alone or as part of a formulation, as disclosed herein.

In accordance with a method aspect of the invention, there is provided a method of treating a patient (e.g., a mammal such as a human) suffering from a disease state (e.g., memory impairment) comprising administering to the patient a compound according to Formulas I-IV. Preferably, the disease state involves decreased nicotinic acetylcholine receptor activity.

In accordance with a method aspect of the invention there is provided a method for the treatment or prophylaxis of a disease or condition resulting from dysfunction of nicotinic acetylcholine receptor transmission in a patient (e.g., a mammal such as a human) comprising administering an effective amount of a compound according to Formulas I-IV.

In accordance with a method aspect of the invention there is provided a method for the treatment or prophylaxis of a disease or condition resulting from defective or malfunctioning nicotinic acetylcholine receptors, particularly α7nACh receptors, in a patient (e.g., a mammal such as a human) comprising administering an effective amount of a compound according to Formulas I-IV.

In accordance with a method aspect of the invention there is provided a method for the treatment or prophylaxis of a disease or condition resulting from suppressed nicotinic acetylcholine receptor transmission in a patient (e.g., a mammal such as a human) comprising administering an amount of a compound according to Formulas I-IV effective to activate α7nACh receptors.

In accordance with another method aspect of the invention there is provided a method for the treatment or prophylaxis of a psychotic disorder, a cognition impairment (e.g., memory impairment), or neurodegenerative disease in a patient (e.g., a mammal such as a human) comprising administering an effective amount of a compound according to Formulas I-IV.

In accordance with another method aspect of the invention there is provided a method for the treatment or prophylaxis of a disease or condition resulting from loss of cholinergic synapses in a patient (e.g., a mammal such as a human) comprising administering an effective amount of a compound according to Formulas I-IV.

In accordance with another method aspect of the invention there is provided a method for the treatment or prophylaxis of a neurodegenerative disorder by activation of α7nACh receptors in a patient (e.g., a mammal such as a human) comprising administering an effective amount of a compound according to Formulas I-IV.

In accordance with another method aspect of the invention there is provided a method for protecting neurons in a patient (e.g., a mammal such as a human) from neurotoxicity induced by activation of α7nACh receptors comprising administering an effective amount of a compound according to Formulas I-IV.

In accordance with another method aspect of the invention there is provided a method for the treatment or prophylaxis of a neurodegenerative disorder by inhibiting the binding of Aβ peptides to α7nACh receptors in a patient (e.g., a mammal such as a human) comprising administering an effective amount of a compound according to Formulas I-IV.

In accordance with another method aspect of the invention there is provided a method for protecting neurons in a patient (e.g., a mammal such as a human) from neurotoxicity induced by Aβ peptides comprising administering an effective amount of a compound according to Formulas I-IV.

In accordance with another method aspect of the invention there is provided a method for alleviating inhibition of cholinergic function induced by Aβ peptides in a patient (e.g., a mammal such as a human) comprising administering an effective amount of a compound according to Formulas I-IV.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the present invention are nicotinic alpha-7 ligands, preferably agonists, especially partial agonists, for the alpha-7 nicotinic acetylcholine receptor. Assays for determining nicotinic acetylcholine activity are known within the art. See, e.g., Davies, A. R., et al., *Characterisation of the binding of [3H]methyllycaconitine: a new radioligand for labelling alpha 7-type neuronal nicotinic acetylcholine receptors*. Neuropharmacology, 1999. 38(5): p. 679-90. As agonists for α7nACh receptors, the compounds are useful in the prophylaxis and treatment of a variety of diseases and conditions associated with the central nervous system. Nicotinic acetylcholine receptors are ligand-gastrol ion-channel receptors that are composed of five subunit proteins which form a central ion-conducting pore. Presently, there are eleven known neuronal nAch receptor subunits (α2-α9 and β2-β4). There are also five further subunits expressed in the peripheral nervous system (α1, β1, γ, δ, ε).

The nACh receptor subtypes can be homopentameric or heteropentameric. The subtype which has received considerable attention is the homopentameric α7 receptor subtype formed from five α7 subunits. The α7nACh receptors exhibit a high affinity for nicotine (agonist) and for α-bungarotoxin (antagonist). Studies have shown the α7nACh receptor agonists can be useful in the treatment of psychotic diseases, neurodegenerative diseases, and cognitive impairments, among other things. While nicotine is a known agonist, there is a need for the development of other α7nACh receptor agonists, especially selective agonists, which are less toxic or exhibit fewer side effects than nicotine.

The compound anabaseine, i.e., 2-(3-pyridyl)-3,4,5,6-tetrahydropyridine is a naturally occurring toxin in certain marine worms (nemertine worms) and ants. See, e.g., Kem et al., Toxicon, 9:23, 1971. Anabaseine is a potent activator of mammalian nicotinic receptors. See, e.g., Kem, Amer. Zoologist, 25, 99, 1985. Certain anabaseine analogs such as anabasine and DMAB (3-[4-(dimethylamino)benzylidene]-3,4,5,6-tetrahydro-2',3'-bipyridine) are also known nicotinic receptor agonists. See, e.g., U.S. Pat. No. 5,602,257 and WO 92/15306. One particular anabaseine analog, (E-3-[2,4-dimethoxy-benzylidene]-anabaseine, also known as GTS-21 and DMXB (see, e.g., U.S. Pat. No. 5,741,802), is a selective partial α7nACh receptor agonist that has been studied extensively. For example, abnormal sensory inhibition is a sensory processing deficit in schizophrenics and GTS-21 has been found to increase sensory inhibition through interaction with α7nACh receptors. See, e.g., Stevens et al., Psychopharmacology, 136: 320-27 (1998).

Another compound which is known to be a selective α7nACh receptor agonist is Tropisetron, i.e., 1αH, 5αH-tropan-3α-yl indole-3-carboxylate. See J. E. Macor et al., *The 5-HT3-Antagonist Tropisetron (ICS 205-930) is a Potent and Selective A7 Nicotinic Receptor Partial Agonist*. Bioorg. Med. Chem. Lett. 2001, 319-321).

Agents that bind to nicotinic acetylcholine receptors have been indicated as useful in the treatment and/or prophylaxis of various diseases and conditions, particularly psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, and treating jetlag. See, e.g., WO 97/30998; WO 99/03850; WO 00/42044; WO 01/36417; Holladay et al., J. Med. Chem., 40:26, 4169-94 (1997); Schmitt et al., Annual Reports Med. Chem., Chapter 5, 41-51 (2000); Stevens et al., Psychopharmatology, (1998) 136: 320-27; and Shytle et al., Molecular Psychiatry, (2002), 7, pp. 525-535.

Thus, in accordance with the invention, there is provided a method of treating a patient, especially a human, suffering from psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound according to Formulas I-IV.

Neurodegenerative disorders included within the methods of the present invention include, but are not limited to, treatment and/or prophylaxis of Alzheimer's diseases, Pick's disease, diffuse Lewy Body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Sträussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, α7nACh receptor agonists, such as the compounds of the present invention can be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia. See, e.g., WO 99/62505. Thus, in accordance with the invention, there is provided a method of treating a patient, especially a human, suffering from age-related dementia and other dementias and conditions with memory loss comprising administering to the patient an effective amount of a compound according to Formulas I-IV.

Thus, in accordance with a further embodiment, the present invention includes methods of treating patients suffering from memory impairment due to, for example, Alzheimer's disease, mild cognitive impairment due to aging, schizophrenia, Parkinson's disease, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formulas I-IV.

Amyloid precursor protein (APP) and Aβ peptides derived therefrom, e.g., $A\beta_{1-40}$, $A\beta_{1-42}$, and other fragments, are known to be involved in the pathology of Alzheimer's disease. The $A\beta_{1-42}$ peptides are not only implicated in neurotoxicity but also are known to inhibit cholinergic transmitter function. Further, it has been determined that Aβ peptides bind to α7nACh receptors. Thus, agents which block the binding of the Aβ peptides to α-7 nAChRs are useful for treating neurodegenerative diseases. See, e.g., WO 99/62505. In addition, stimulation α7nACh receptors can protect neurons against cytotoxicity associated with Aβ peptides. See, e.g., Kihara, T. et al., Ann. Neurol., 1997, 42, 159.

Thus, in accordance with an embodiment of the invention there is provided a method of treating and/or preventing dementia in an Alzheimer's patient which comprises administering to the subject a therapeutically effective amount of a compound according to Formulas I-IV to inhibit the binding of an amyloid beta peptide (preferably, $A\beta_{1-42}$) with nACh receptors, preferable α7nACh receptors, most preferably, human α7nACh receptors (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The present invention also provides methods for treating other amyloidosis diseases, for example, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, and Finnish and Iowa amyloidosis.

In addition, nicotinic receptors have been implicated as playing a role in the body's response to alcohol ingestion. Thus, agonists for α7nACh receptors can be used in the treatment of alcohol withdrawal and in anti-intoxication therapy. Thus, in accordance with an embodiment of the invention there is provided a method of treating a patient for alcohol withdrawal or treating a patient with anti-intoxication therapy comprising administering to the patient an effective amount of a compound according to Formulas I-IV.

Agonists for the α7nACh receptor subtypes can also be used for neuroprotection against damage associated with strokes and ischemia and glutamate-induced excitotoxicity. Thus, in accordance with an embodiment of the invention there is provided a method of treating a patient to provide for neuroprotection against damage associated with strokes and ischemia and glutamate-induced excitotoxicity comprising administering to the patient an effective amount of a compound according to Formulas I-IV.

As noted above, agonists for the α7nACh receptor subtypes can also be used in the treatment of nicotine addiction, inducing smoking cessation, treating pain, and treating jetlag, obesity, diabetes, and inflammation. Thus, in accordance with an embodiment of the invention there is provided a method of treating a patient suffering from nicotine addiction, pain, jetlag, obesity, diabetes, and/or inflammation, or a method of inducing smoking cessation in a patient comprising administering to the patient an effective amount of a compound according to Formulas I-IV.

The inflammatory reflex is an autonomic nervous system response to an inflammatory signal. Upon sensing an inflammatory stimulus, the autonomic nervous system responds through the vagus nerve by releasing acetylcholine and activating nicotinic α7 receptors on macrophages. These macrophages in turn release cytokines. Dysfunctions in this pathway have been linked to human inflammatory diseases including rheumatoid arthritis, diabetes and sepsis. Macrophages express the nicotinic α7 receptor and it is likely this receptor that mediates the cholinergic anti-inflammatory response. Therefore, compounds with affinity for the α7nACh receptor on macrophages may be useful for human inflammatory diseases including rheumatoid arthritis, diabetes and sepsis. See, e.g., Czura, C J et al., J. Intern. Med., 2005, 257(2), 156-66.

Thus, in accordance with an embodiment of the invention there is provided a method of treating a patient (e.g., a mammal, such as a human) suffering from an inflammatory disease or disorder, such as, but not limited to, rheumatoid arthritis, diabetes or sepsis, comprising administering to the patient an effective amount of a compound according to Formulas I-IV.

In addition, due to their affinity to α7nACh receptors, labeled derivatives of the compounds of Formulas I-IV (e.g., $C^{11}$ or $F^{18}$ labeled derivatives), can be used in neuroimaging of the receptors within, e.g., the brain. Thus, using such labeled agents in vivo imaging of the receptors can be performed using, e.g., PET imaging.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeldt-Jakob disease, HIV, cardiovascular disease, and head trauma as well as age-related cognitive decline.

Thus, in accordance with an embodiment of the invention there is provided a method of treating a patient suffering from, for example, mild cognitive impairment (MCI), vascular dementia (VaD), age-associated cognitive decline (AACD), amnesia associated w/open-heart-surgery, cardiac arrest, and/or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia, drug/substance induced memory impairments, Dementia Puglistica (Boxer Syndrome), and animal dementia (e.g., dogs, cats, horses, etc.) comprising administering to the patient an effective amount of a compound according to Formulas I-IV.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention can be administered to patients, e.g., mammals, particularly humans, at typical dosage levels customary for α-7 nicotinic receptor agonists such as the known α-7 nicotinic receptor agonist compounds mentioned above. For example, the compounds can be administered, in single or multiple doses, by oral administration at a dosage level of, for example, 0.0001-10 mg/kg/day, e.g., 0.01-10 mg/kg/day. Unit dosage forms can contain, for example, 1-200 mg of active compound. For intravenous administration, the compounds can be administered in single or multiple dosages.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

Using the following procedures and further procedures described below, the following compounds were prepared. The syntheses of related compounds are also described in U.S. patent application Ser. Nos. 11/089,533 and 10/669,645, which are hereby incorporated by reference in their entireties.

EXAMPLES

All spectra were recorded at 300 MHz on a Bruker Instruments NMR unless otherwise stated. Coupling constants (J) are in Hertz (Hz) and peaks are listed relative to TMS (δ 0.00 ppm). Microwave reactions were performed using a Personal Chemistry Optimizer™ microwave reactor in 2.5 mL or 5 mL Personal Chemistry microwave reactor vials. All reactions were performed at 200° C. for 600 s with the fixed hold time ON unless otherwise stated. Sulfonic acid ion exchange resins (SCX) were purchased from Varian Technologies. Analytical HPLC was performed on 4.6 mm×100 mm Xterra $RP_{18}$ 3.5μ columns using a gradient of 20/80 to 80/20 acetonitrile (0.1% formic acid)/water (0.1% formic acid) over 6 min. For compound 57, a gradient of 5/95 to 60/40 acetonitrile (0.1% formic acid)/water (0.1% formic acid) was used. For compounds 116-130, a gradient of 10/90 to 80/20 acetonitrile (0.1% formic acid)/water (0.1% formic acid) over 8 min was used.

Preparative HPLC was performed on 30 mm×100 mm Xterra Prep $RP_{18}$ 5μ columns using (i) an 8 min gradient of 20/80 to 80/20 acetonitrile (0.1% formic acid)/water (0.1% formic acid) (compounds 1-50, 54-57, 59, 60, 63-77, 79-131, and 149-185), (ii) a 30 min gradient of 5/95 to 95/5 acetonitrile (0.05% trifluoroacetic acid)/water (0.05% trifluoroacetic acid) (compounds 51-53), (iii) an 8 min gradient of 10/90 to 60/40 acetonitrile (0.1% formic acid)/water (0.1% formic acid) (compounds 58, 61, 62, 78, and 132-137), (iv) an 8 min gradient of 5/95 to 60/40 acetonitrile (0.1% formic acid)/water (0.1% formic acid) (compounds 186-190), or (v) an 8 min gradient of 10/90 to 80/20 acetonitrile (0.1% formic acid)/water (0.1% formic acid) (compounds 138-148).

Acid Preparations.

The following procedures (1-29) detail the preparation of the indazole, benzisoxazole, and benzisothiazole acids and esters that were not commercially available.

Procedure 1

Procedure 1 provides a preparation of substituted benzisothiazole-3-carboxylic acids from the corresponding thiophenols.

To a solution of 3-methoxythiophenol (26.7 mmol) in ether (20 mL) was added oxalyl chloride (43 mmol) dropwise. The mixture was heated at reflux for 1.5 h, cooled to rt (room temperature), and concentrated in vacuo. The resulting yellow oil was dissolved in dichloromethane (50 mL), cooled to 0° C., and was treated with aluminum chloride (32.0 mmol) in portions. The mixture was heated at reflux for 30 min, cooled to rt, and poured onto ice water with stifling. The organic layer was separated and successively washed with saturated, aqueous sodium bicarbonate, water, and brine. The organic layer was dried over magnesium sulfate, filtered and concentrated in vacuo. The residue was purified by chromatography (4/1 ethyl acetate/hexane), thus providing 6-methoxy-1-benzothiophene-2,3-dione in 47% yield as an orange solid.

To a mixture of the dione (0.44 mmol) in 30% aqueous solution of ammonium hydroxide (2.0 mL) was added 35% aqueous solution hydrogen peroxide (0.2 mL) and the reaction mixture was maintained for 12 h. The precipitated pink solids were isolated by filtration, washed with water, and dried under high vacuum, thus providing the amide in 42% yield.

To a solution of the amide (5.46 mmol) in methanol (100 mL) was added 10 N sodium hydroxide (12 mL). The mixture was heated at reflux for 12 h, cooled to rt, and was acidified to pH<2 by the slow addition of conc. hydrochloric acid. The organic layer was extracted with dichloromethane (2×) and was dried over sodium sulfate. The crude product was purified by chromatography (300/50/1 dichloromethane/methanol/formic acid), thus providing the acid in 89% as a pink solid.

The following acids were prepared using this method:
6-Bromobenzisothiazole-3-carboxylic acid.
5-Bromobenzisothiazole-3-carboxylic acid.
6-Methoxybenzisothiazole-3-carboxylic acid.
7-Bromobenzisothiazole-3-carboxylic acid.

The following esters were prepared from the acid using ethanol and sulfuric acid:
Ethyl 6-bromobenzisothiazole-3-carboxylate.
Ethyl 6-methoxybenzisothiazole-3-carboxylate.
tert-Butyl 5-bromo-1,2-benzisothiazole-3-carboxylate.

The following procedure was used to prepare benzisothiazole tert-butyl esters:

Di-tert-butyldicarbonate (128 mmol) was added to a suspension of 6-bromo-1,2-benzisothiazole-3-carboxylic acid (46.5 mmol) and 4-dimethylaminopyridine (4.26 mmol) in tert-butyl alcohol (40.0 mL) and tetrahydrofuran (40.0 mL) and the reaction mixture was heated at 65° C. for 16 hours. There was vigorous carbon dioxide evolution which gradually subsided as the mixture become homogeneous. The reaction mixture was concentrated and the residue was dissolved in dichloromethane. The dichloromethane solution was filtered through silica gel (ca. 50 g) and the eluent was concentrated to provide the ester product in 99% yield.

The following ester was prepared using this method:
tert-Butyl 6-bromo-1,2-benzisothiazole-3-carboxylate.

Procedure 2

Procedure 2 provides a method for the preparation of isatins from anilines and the conversion of the isatins to the corresponding indazole-3-carboxylic acids.

A solution of the substituted aniline (565 mL) in 6N hydrochloric acid (106 mL) was added to a suspension of 2,2,2-trichloro-1-ethoxyethanol (678 mL) and sodium sulfate (3.15 mol) in water (1.4 L) and the reaction mixture was stirred vigorously for 1 h. A solution of hydroxylamine hydrochloride (2.08 mol) in water (650 mL) was added in one portion and the reaction mixture was heated at 80° C. for 1.5 h. The reaction mixture was cooled to 10° C. and the precipitated solids were collected by filtration, washed with water, and dried to provide the amide in 91% yield.

The amide was added to sulfuric acid (1.9L) and the reaction mixture was heated at 60° C. for 6h. The reaction mixture was allowed to cool to room temperature and was cautiously poured onto ice (7 kg). The precipitated solids were collected by filtration, washed with water, and dried to provide the isatin in 61% yield.

The conversion of the substituted isatins to the corresponding indazole-3-carboxylic acids is essentially the same method as described for indazole-3-carboxylic acid: Snyder, H. R., et. al. *J. Am. Chem. Soc.* 1952, 74, 2009. The substituted isatin (22.1 mmol) was diluted with 1 N sodium hydroxide (24 mL) and was heated at 50° C. for 30 min. The burgundy solution was allowed to cool to rt and was maintained for 1 h. The reaction mixture was cooled to 0° C. and was treated with a 0° C. solution of sodium nitrite (22.0 mmol) in water (5.5 mL). This solution was added through a pipet submerged below the surface of a vigorously stirred solution of sulfuric acid (2.3 mL) in water (45 mL) at 0° C. The addition took 15 min and the reaction was maintained for an additional 30 min. A cold (0° C.) solution of tin (II) chloride dihydrate (52.7 mmol) in concentrated hydrochloric acid (20 mL) was added to the reaction mixture over 10 min and the reaction mixture was maintained for 60 min. The precipitated solids were isolated by filtration, washed with water, and dried to give a quantitative mass balance. This material was of sufficient purity ($^1$H NMR and LC/MS) to use in the next step without further purification. Alternatively, the acid was recrystallized from acetic acid to provide pure material.

The following acids were prepared using this method:
6-Bromo-1H-indazole-3-acid.
5-Methoxy-1H-indazole-3-acid.
6-Methoxy-1H-indazole-3-acid.

Procedure 3

Procedure 3 provides a method for the trapping of indazole aryllithiums with ketones and the coupling with 3-aminoquinuclidine to form heterocyclic derivatives.

tert-Butyl 6-bromoindazole-3-carboxylate was prepared from the acid by reaction with a 2-fold excess of di-tert-butyldicarbonate followed by treatment with sodium hydroxide. To a suspension of sodium hydride (60% mineral oil dispersion) (4.8 mmol) in tetrahydrofuran (40 mL) at 0° C. was slowly added a solution of tert-butyl 6-bromoindazole-3-carboxylate (4.0 mmol) in tetrahydrofuran (4 mL). After stifling for 0.5 h at 0° C., the mixture was cooled to −78° C. and a 1.7 M solution of tert-butyllithium in pentane (5.1 mmol) was added. After 0.5 h at −78° C., a solution of tetrahydropyran-4-one (5 mmol) in tetrahydrofuran (1 mL) was added dropwise. The mixture was stirred at −78° C. for 1 h and warmed to 0° C. The reaction mixture was quenched with saturated aqueous ammonium chloride and the mixture was partitioned between ethyl acetate (100 mL) and water (100 mL). The organic layer was separated, washed with brine (50 mL), dried (magnesium sulfate), and concentrated. The residue was purified by chromatography (70/30 ethyl acetate/hexanes) to yield 6-(4-hydroxytetrahydropyran-4-yl)-1H-indazole-3-carboxylic acid tert-butyl ester (68%) as a colorless solid.

6-(4-Hydroxytetrahydropyran-4-yl)-1H-indazole-3-carboxylic acid tert-butyl ester (0.86 mmol) was dissolved in trifluoroacetic acid (3 mL) and the mixture was maintained at room temperature for 16 h. The solvent was removed in vacuo and the residue was triturated with ethyl acetate to provide 6-(3,6-dihydro-2H-pyran-4-yl)-1H-indazole-3-carboxylic acid (76%). The acids were coupled with quinuclidine amine according to procedure A.

6-(4-Hydroxytetrahydropyran-4-yl)-1H-indazole-3-carboxylic acid tert-butyl ester (1.0 mmol) was taken up in trifluoroacetic acid (5 mL), triethylsilane (2 mL), and dichloromethane (3 mL) and the mixture was refluxed for 16 h. The solvent was removed in vacuo and the residue was triturated with ethyl acetate to provide 6-(tetrahydropyran-4-yl)-1H-indazole-3-carboxylic acid (60%) as a tan solid.

The following acids and esters were prepared using this method:
5-(Tetrahydro-2H-pyran-4-yl)-1H-indazole-3-carboxylic acid.
6-(Tetrahydro-2H-pyran-4-yl)-1H-indazole-3-carboxylic acid.
tert-Butyl 6-formal-1H-indazole-3-carboxylic acid.
tert-Butyl 6-formal-1H-indazole-3-carboxylate.
Procedure 4

Procedure 4 provides a method for the preparation of N-1-alkylated indazole-3-carboxylic acids from the corresponding indazole ester.

To a solution of ethyl 5-methoxyindazole-3-carboxylate (1.50 mmol) in acetonitrile (15 mL) was added potassium carbonate (5.99 mmol) and methyl iodide (3.00 mol). The reaction was heated at 60° C. for 4 hours, allowed to cool to ambient temperature, and was partitioned between water (50 mL) and ethyl acetate (50 mL). The layers were separated and the organic later was washed with brine (25 mL), dried (magnesium sulfate), and concentrated. The residue was purified by chromatography using a gradient of 95/5 to 80/20 hexanes/ethyl acetate to provide the 2-substituted indazole (17%) and the 1-substituted indazole (44%). The 1-substituted indazole (61 mg, 0.26 mmol) was suspended in ethanol (5.0 mL) and was warmed to facilitate dissolution. An aliquot of a 5.0 M solution of sodium hydroxide in water (2.00 mL) was added and the reaction mixture was maintained at ambient temperature for 16 h. The reaction mixture was diluted with water (50 mL) and was acidified with 6.0 N hydrochloric acid. The aqueous layer was extracted with ethyl acetate (3×50 mL) and the combined organic layers were washed with brine (25 mL), dried (magnesium sulfate), and concentrated, thus providing the acid in 95% yield.

The following acids were prepared using this method:
6-Bromo-1-methyl-1H-indazole-3-carboxylic acid.
6-Bromo-1-ethyl-1H-indazole-3-carboxylic acid.
1-Ethyl-6-methoxy-1H-indazole-3-carboxylic acid.
Procedure 5

Procedure 5 provides a method for the preparation of 5-difluoromethoxyindazole-3-acid from 3-bromo-4-nitrophenol.

3-Bromo-4-nitrophenol (10.0 mmol) was added to a suspension of sodium hydroxide (29.0 mmol) in N,N-dimethylformamide (15 mL) and the suspension was maintained for 15 min at rt. The reaction mixture was cooled to 0° C. and was treated with ethyl chlorodifluoroacetate (20.0 mmol). The reaction mixture was heated at 70° C. for 16 h and was concentrated. The residue was diluted with ice water (200 mL) and was extracted with ethyl acetate (3×100 mL). The combined organic layers were dried (magnesium sulfate) and concentrated to provide the difluoromethyl ether in 75% yield as a yellow oil.

Diethyl malonate (328 mmol) was added dropwise to a suspension of sodium hydride (328 mmol) in dimethylsulfoxide (40 mL) at 0° C. The reaction mixture was warmed to 60° C. and maintained for 0.5 h. A solution of the difluoromethyl ether (149 mmol) in dimethylsulfoxide (80 mL) was added dropwise and the reaction mixture was heated at 100° C. for 5 h. The cooled solution was poured onto ice water, and the aqueous layer was extracted with dichloromethane (3×100 mL). The combined organic layers were dried (magnesium sulfate) and concentrated to give the crude diester in 112% yield as an oil. The diester (167 mmol), sodium hydroxide (500 mmol), and water (335 mL) were combined and heated at 60° C. for 1 h. The reaction mixture was allowed to cool to rt and the aqueous layer was washed with dichloromethane (3×100 mL). The pH of the aqueous layer was cautiously adjusted to 1 with concentrated hydrochloric acid and the reaction mixture was heated at 60° C. for 1 h. The suspension was cooled to 5° C. and the solids were collected by filtration and dried to provide the acid in 61% yield.

Acetyl chloride (203 mmol) was added dropwise to ethanol (300 mL) at 0° C. After 0.5 h, the acid (101 mmol) was added and the reaction mixture was heated at reflux for 15 h. The reaction mixture was concentrated and the residue was partitioned between dichloromethane (200 mL) and saturated sodium bicarbonate (100 mL). The aqueous layer was further extracted with dichloromethane (2×200 mL) and the combined organic layers were dried (magnesium sulfate) and concentrated to provide the ester in 60% yield as a brown oil.

The ester (60.4 mmol) was dissolved in ethanol (103 mL), diluted with water (71 mL), and was treated with ammonium chloride (243 mmol) and iron powder (301 mmol). The reaction mixture was heated at reflux for 10 minutes and the suspension was filtrated through Celite and the filter cake was washed with ethanol three times. The filtrate was concentrated, the residue was suspended in 2 N hydrochloric acid and was stirred vigorously for 0.5 h. The aqueous layer was washed with ethyl acetate (3×50mL) and the pH adjusted to 9-10 with 5 M sodium hydroxide. The aqueous layer was extracted with chloroform (3×100mL) and the combined organic layers were dried (magnesium sulfate). Acetic anhydride (392 mmol), isoamyl nitrite (291 mmol), and potassium acetate (51.0 mmol) were added to the organic layer and the suspension was heated at reflux for 16 h. The solution was evaporated and the residue was partitioned between saturated sodium bicarbonate (50 mL) and dichloromethane (100 mL). The aqueous layer was further extracted with dichloromethane (2×100 mL) and the combined organic layers were dried (magnesium sulfate) and concentrated to provide the N-acetylindazole ester in 79% yield as a brown oil.

The ester (63.8 mmol), sodium hydroxide (193 mmol), and water (65 mL) were combined and the reaction was maintained for 24 h at 60° C. After cooling to rt, the aqueous layer was washed with dichloromethane (3×50mL). The aqueous layer was adjusted to pH 1 with concentrated hydrochloric acid. The precipitated solids were collected by filtration, washed with water and dichloromethane, and dried to provide the acid in 27% yield.

The following acid was prepared according to this method:
5-(Difluoromethoxy)-1H-indazole-3-carboxylic acid.
Procedure 6

Procedure 6 provides a method for the preparation of 6-difluoromethoxyindazole-3-acid from 4-nitrophenol.

4-Nitrophenol (162 mmol) was added to a suspension of sodium hydroxide (485 mmol) in N,N-dimethylformamide (150 mL) and the suspension was maintained for 15 min at rt. The reaction mixture was cooled to 0° C. and was treated with ethyl chlorodifluoroacetate (329 mmol). The reaction mixture was heated at 70° C. for 16 h and was concentrated. The residue was diluted with ice water (200 mL) and was extracted with ethyl acetate (3×100 mL). The combined organic layers were dried (magnesium sulfate) and concentrated to provide the difluoromethyl ether in 59% yield as a yellow oil.

The nitro ether (149 mmol) was dissolved in ethanol (37.5 mL), diluted with water (25 mL), and was treated with ammonium chloride (84.7 mmol) and iron powder (105 mmol). The reaction mixture was heated at reflux for 30 minutes and the suspension was filtered through Celite. The filter cake was washed with ethanol three times and the combined filtrates were concentrated. The residue was dissolved in water and the pH adjusted to 9-10 with 5 M sodium hydroxide. The aqueous layer was extracted with ethyl acetate (3×100mL) and the combined organic layers were dried (magnesium sulfate) and concentrated to a yellow oil. The oil was dissolved in acetic anhydride (23.5 mmol) and the reaction mixture was maintained at rt for 16 h. The reaction mixture was diluted with water (50 mL) and was neutralized with solid sodium bicarbonate. The precipitated solids were isolated by filtration, washed with water, and dried to provide the acetamide in 62% yield as a light yellow solid.

Acetic anhydride (19.6 mmol) was added to a solution of the acetamide (13.2 mmol) in chloroform (20 mL) and the reaction mixture was warmed to reflux. Fuming nitric acid (16.0 mmol) was added dropwise and the reaction mixture was maintained at reflux for 30 min. The cooled solution was diluted with water (20 mL) and the aqueous layer was extracted with dichloromethane (3×10 mL). The combined organic layers were dried (magnesium sulfate) and concentrated to provide the nitro-amide in 83% yield.

The amide (11.0 mmol), sodium hydroxide (43.8 mmol), and water (10 mL) were combined and the reaction mixture was maintained for 1.5 hour at 60° C. the reaction was allowed to cool to rt and the precipitated solids were isolated by filtration, and washed with water, and dried to provide the aniline in 98% yield as a light yellow solid.

The aniline (15.7 mmol) was mixed with 40% hydrobromic acid (14.3 g) and water (10 mL) and the reaction mixture was warmed to 80-90° C. in order to completely dissolve the aniline. The reaction mixture was cooled to 0° C. and a solution of sodium nitrite (23.2 mmol) in water (5.3 mL) was added during a 15 min period. The solution was maintained for 40 minutes at 0-5° C. and filtered. Copper (I) bromide (18.8 mmol) was dissolved in 40% hydrobromic acid (21 mL) and was cooled to 0° C. The solution of the diazo salt was added slowly to the copper solution and the mixture was maintained for 30 min at 0-10° C. The reaction mixture was heated at 60° C. for 30 min and then at 100° C. for 10 min to ensure completion. The reaction mixture was allowed to cool to rt and was extracted with dichloromethane (3×40 mL). The combined organic layers were washed with 1 M sodium hydroxide, water, 1 N hydrochloric acid, and water. The organic layer was dried (magnesium sulfate) and concentrated to provide the nitro bromide in 76% yield as a light yellow solid.

Diethyl malonate (25.7 mmol) was added dropwise to a suspension of sodium hydride (25.8 mmol) in dimethylsulfoxide (5 mL) at 0° C. The reaction mixture was warmed to 60° C. and maintained for 30 min. A solution of the nitro bromide (11.7 mmol) in dimethylsulfoxide (7 mL) was added dropwise and the reaction mixture was heated at 100° C. for 5 h. The cooled solution was poured onto ice water and the aqueous layer was extracted with dichloromethane (3×100 mL). The combined organic layers were dried (magnesium sulfate) and concentrated to give the crude diester as an oil. The diester (11.7 mmol), sodium hydroxide (35 mmol), and water (20 mL) were combined and heated at 60° C. for 1 h. The reaction mixture was allowed to cool to rt and the aqueous layer was washed with dichloromethane (3×100 mL). The pH of the aqueous layer was cautiously adjusted to 1 with concentrated hydrochloric acid and the reaction mixture was heated at 60° C. for 1 h. The suspension was cooled to 0° C. and the solids were collected by filtration and dried to provide the acid in 64% yield.

Acetyl chloride (15.3 mmol) was added dropwise to ethanol (50 mL) at 0° C. After 30 min, the acid (7.69 mmol) was added and the reaction mixture was heated at reflux for 15 h. The reaction mixture was concentrated and the residue was partitioned between dichloromethane (20 mL) and saturated sodium bicarbonate (10 mL). The aqueous layer was further extracted with dichloromethane (2×20 mL) and the combined organic layers were dried (magnesium sulfate) and concentrated to provide the ester in 94% yield as a brown oil.

Acetic anhydride (6.0 mL) was added to a suspension of the ester (3.64 mmol), and acetic acid (7.0 mL) at 0° C. Zinc dust (14.6 mmol) was added in portions over 15 min and the reaction mixture was maintained for 30 min at 0° C. and then for 1.5 h at rt. Additional zinc powder (6.15 mmol) was added and the reaction maintained for 3 h. The suspension was filtered through Celite and the filtrate was concentrated. The residue was partitioned between saturated sodium bicarbonate (10 mL) and ethyl acetate (20 mL). The aqueous layer was further extracted with ethyl acetate (3×20 mL) and the combined organic layers were dried (magnesium sulfate) and concentrated to provide the acetamide in 92% yield as a brown oil.

Acetic anhydride (13.7 mmol), isoamyl nitrite (13.7 mmol), and potassium acetate (2.04 mmol) were added to a solution of the acetamide (3.92 mmol) in chloroform (20 mL) and the suspension was heated at reflux for 16 h. The solution was evaporated and the residue was partitioned between saturated sodium bicarbonate (10 mL) and dichloromethane (20 mL). The aqueous layer was further extracted with dichloromethane (2×20 mL) and the combined organic layers were dried (magnesium sulfate) and concentrated to provide the crude N-acetylindazole ester as a brown oil.

The ester (3.36 mmol), sodium hydroxide (10 mmol) and water (5 mL) were combined and the reaction was maintained for 24 h at 60° C. After cooling to rt, the aqueous layer was washed with dichloromethane (3×30 mL). The aqueous layer was adjusted to pH 1 with concentrated hydrochloric acid and the precipitated solids were collected by filtration, washed with water and dichloromethane, and dried to provide the acid in 26% yield.

The following acid was prepared according to this method: 6-(Difluoromethoxy)-1H-indazole-3-carboxylic acid.

Procedure 7

Procedure 7 provides a method for the coupling between brominated benzisothiazole-3-carboxylic esters and brominated indazole-3-carboxylic esters and Grignard reagents to form heteroaromatic-substituted acids.

A 0.5 M solution of Grignard reagent (75.0 mmol) in tetrahydrofuran was diluted with tetrahydrofuran (150 mL), cooled to 5° C., and treated with solid zinc chloride (165 mmol). The reaction mixture was allowed to warm to rt and the brominated ester (28.2 mmol) and tetrakis(triphenylphosphine)palladium (0) (1.64 mmol) were added. The suspension was heated at 65° C. for 16 h and was concentrated. The reaction was partitioned between ethyl acetate (250 mL) and 7 M ammonium chloride (500 mL). The aqueous layer was extracted with ethyl acetate (3×250 mL) and the combined extracts were dried over sodium sulfate and concentrated to dryness. The residue was purified by chromatography using a gradient of 100/0 to 97/3 chloroform/methanol to provide the ester in 80% yield. The ester was suspended in methanol (100 mL) and was treated with 8 M sodium hydroxide (30 mL). The mixture was heated at 60° C. for 3 h, cooled to rt, filtered, and was acidified to pH<2 by the slow addition of conc. hydrochloric acid. The aqueous layer was concentrated and the residue was triturated with water. The resultant solid was recrystallized from water to give the acid in 81% yield.

The Grignard reagent of thiazole is commercially available. Alternatively, the aryllithium and the corresponding arylzinc reagent can be generated according to the procedure outlined by Reeder, M. R.; et. al., *Org. Proc. Res. Devel.* 2003, 7, 696. The zinc reagent of oxazole was prepared according to this procedure.

The following acids were prepared using this method:
6-(1,3-Thiazol-2-yl)-1H-indazole-3-carboxylic acid.
6-(1,3-Oxazol-2-yl)-1H-indazole-3-carboxylic acid.
1-Ethyl-6-(1,3-oxazol-2-yl)-1H-indazole-3-carboxylic acid.

Procedure 8

Procedure 8 provides a method for the preparation of N-methoxyethoxymethyl and N-trimethylsilylethoxymethyl protected indazole acids and esters from the corresponding indazole esters using alkylation conditions.

Representative Procedure for N(1)-alkylation: A solution of ethyl 5-(benzyloxy)-1H-indazole-3-carboxylate (2.70 mmol) in tetrahydrofuran (10 mL) was added dropwise to a 0° C. suspension of sodium hydride (60% mineral oil dispersion, 8.1 mmol) in tetrahydrofuran (54.0 mL). The reaction was maintained at 0° C. for 1 h. [β-(Trimethylsilyl)ethoxy]methyl chloride (3.2 mmol) was added and the reaction mixture was maintained for 1 h. The reaction was partitioned between water (50 mL) and ethyl acetate (50 mL) and the organic layer was washed with brine (25 mL), dried (magnesium sulfate), and concentrated. The residue was purified by chromatography (95/5 to 85/15 hexanes/ethyl acetate to provide the protected indazole in 89% yield.

Representative Procedure for N(2)-alkylation: 2-Methoxyethoxy methyl chloride (48.0 mmol) was added slowly to a suspension of ethyl 6-bromo-1H-indazole-3-carboxylate (40.0 mmol) and N,N-diisopropylethylamine (80.0 mmol) in methylene chloride (80.0 mL). The reaction became homogeneous and was maintained for 4 h at rt. The reaction mixture was concentrated and the residue was partitioned between water (50 mL) and ethyl acetate (100 mL). The layers were separated and the organic layer was washed with brine (25 mL), dried (magnesium sulfate), and concentrated to give sufficiently pure product (89%) as a 2/1 mixture of N(2)- and N(1)-regioisomers as a yellow oil.

5.0 M of Sodium hydroxide (52 mL) was added to a solution of ethyl 6-bromo-1-[(2-methoxyethoxy)methyl]-1H-indazole-3-carboxylate (18.2 mmol) and the reaction mixture were maintained for 16 h. The solution was diluted with 50 mL water (50 mL) and acidified with 6.0 N hydrochloric acid. The slurry was extracted with ethyl acetate (50 mL) and the organic layer was washed with brine (25 mL), dried (magnesium sulfate), and concentrated. The residue was recrystallized from toluene to give a colorless solid (82%) as a mixture of regioisomers.

The following esters and acids were prepared using this method:
6-Bromo-1-[(2-methoxyethoxy)methyl]-1H-indazole-3-carboxylic acid.
Ethyl 6-bromo-1-[(2-methoxyethoxy)methyl]-1H-indazole-3-carboxylate.
Ethyl 6-benzyloxy-1-[(2-methoxyethoxy)methyl]-1H-indazole-3-carboxylate.
6-Bromo-1-{[2-(trimethylsilyl)ethoxy]methyl}-1H-indazole-3-carboxylic acid.
Ethyl 6-bromo-1-{[2-(trimethylsilyl)ethoxy]methyl}-1H-indazole-3-carboxylic acid.
5-Bromo-1-{[2-(trimethylsilyl)ethoxy]methyl}-1H-indazole-3-carboxylic acid.
6-Bromo-2-{[2-(trimethylsilyl)ethoxy]methyl}-1H-indazole-3-carboxylic acid.
5-Bromo-2-{[2-(trimethylsilyl)ethoxy]methyl}-1H-indazole-3-carboxylic acid.
Ethyl 6-bromo-2-{[2-(trimethylsilyl)ethoxy]methyl}-1H-indazole-3-carboxylic acid.
Ethyl 5-bromo-2-{[2-(trimethylsilyl)ethoxy]methyl}-1H-indazole-3-carboxylic acid.
Ethyl 5-bromo-1-{[2-(trimethylsilyl)ethoxy]methyl}-1H-indazole-3-carboxylic acid Procedure 9

Procedure 9 provides a method for the preparation of alkoxy indazole acids from the corresponding benzyloxy indazole esters using Mitsunobu conditions.

Ethyl 6-benzyloxy-1-[(2-methoxyethoxy)methyl]-1H-indazole-3-carboxylate (9.38 mmol) was added to a suspension of 10% palladium on carbon (249 mg) in ethanol (66.7 mL). The reaction was shaken under an atmosphere of hydrogen (50 psi) for 4.0 h. The reaction was filtered through Celite and concentrated to give the phenol in 87% yield as a white solid.

Diisopropyl azodicarboxylate (0.841 mmol) was added dropwise to a solution of ethyl 6-hydroxy-1-[(2-methoxyethoxy)methyl]-1H-indazole-3-carboxylate (0.765 mmol), 1-methyl-3-pyrrolidinol (0.917 mmol), and triphenylphosphine (1.15 mmol) in tetrahydrofuran (4.6 mL). The reaction was maintained for 16 h and was concentrated. The residue was purified by chromatography (100/0 to 90/10 ethyl acetate/[70/30/2 ethyl acetate/methanol/dimethylethylamine] to provide the ether product in 28% yield. The ester was saponified to provide the acid which was coupled to the bicyclobase using Procedure C.

The following acids were prepared using this method:
Ethyl 6-hydroxy-1-[(2-methoxyethoxy)methyl]-1H-indazole-3-carboxylate.
1-[(2-Methoxyethoxy)methyl]-6-[(1-methylpyrrolidin-3-yl)oxy]-1H-indazole-3-carboxylic acid.
1-[(2-Methoxyethoxy)methyl]-6-(tetrahydrofuran-3-yloxy)-1H-indazole-3-carboxylic acid.
1-[(2-Methoxyethoxy)methyl]-6-(tetrahydro-2H-pyran-4-yloxy)-1H-indazole-3-carboxylic acid.
6-[(1-Methylpyrrolidin-3-yl)oxy]-1,2-benzisothiazole-3-carboxylic acid.
6-(1-Azabicyclo[2.2.2]oct-3-yloxy)-1,2-benzisothiazole-3-carboxylic acid Procedure 10

Procedure 10 provides a method for the preparation of 4-methoxyindazole acid from 4-methoxyaniline.

A solution of 4-methoxyaniline (1.63 mol) in acetic acid (244 mL) was treated with acetic anhydride (244 mL) and zinc powder (30.8 mmol) and the reaction mixture was heated at reflux for 30 min. The suspension was allowed to cool to rt and was filtered and concentrated. The residue was diluted with water (200 mL) and the pH of the solution was adjusted to 8 with 10% sodium hydroxide. The precipitated solids were collected by filtration, washed with water (1 L), and dried to give the acetamide in 94% yield as a purple solid.

Concentrated nitric acid (210 mL) was added dropwise to a solution of the acetamide (1.52 mol) in dichloromethane (1.5 L) at rt. The reaction mixture was heated at reflux for 1 h and was allowed to cool to rt. The reaction mixture was washed with water (1.0 L), saturated sodium carbonate (1.0 L), and water (1.0 L). The organic layer was dried over anhydrous sodium sulfate and concentrated to provide the nitroacetamide in 83% yield as an orange solid.

A solution of the nitroacetamide (1.27 mol) in water (1.27 L) was treated with sodium hydroxide (5.07 mol) and the reaction mixture was heated at 60° C. for 2 h. The precipitated solids were collected by filtration, washed with water, and dried to provide the nitroaniline in 85% yield as an orange solid.

A solution of sodium nitrite (1.48 mol) in water (250 mL) was added to a cold (0-5° C.) solution of the nitroaniline (1.08 mol) in hydrobromic acid (4.87 mol) (prepared by heating the reaction mixture at 90° C. for 2 h). The reaction mixture was maintained for 40 min and was filtered. The filtrate was added dropwise to a cold (0-5° C.) solution of copper (I) bromide (1.81 mol) in hydrobromic acid (640 mL) and the reaction mixture was maintained for 30 min. The reaction mixture was warmed to 60° C. and was maintained for 30 min. The reaction mixture was warmed to reflux and was maintained for 1 h. The reaction mixture was diluted with water (2 L) and was extracted with dichloromethane (3×1 L). The combined organic layers were washed with 10% sodium hydroxide (1.0 L), water (2.0 L), 10% hydrochloric acid (1.6 L) and water (2.0 L), dried (magnesium sulfate) and concentrated. The residue was recrystallized from ethanol to provide the bromide in 50% yield as a yellow solid.

Iron powder (1.08 mol) and ammonium chloride (862 mmol) were added to a solution of the bromide (216 mmol) in ethanol (200 mL) and water (140 mL) and the reaction mixture was heated at reflux for 1 h. The suspension was filtered and concentrated and the residue was extracted with ethyl acetate (3×200 mL). The combined organic layers were dried (sodium sulfate) and concentrated to give the bromoaniline in 96% yield as a yellow liquid.

A solution of the bromoaniline (208 mmol) in 50% hydrochloric acid (40 mL) was added to a solution of trichloroacetaldehyde hydrate (312 mmol) and sodium sulfate (967 mmol) in water (450 mL) and the reaction mixture was maintained for 1 h. A solution of hydroxylamine hydrochloride (793 mmol) in water (240 mL) was added and the reaction mixture was heated at 60° C. for 2 h. The aqueous layer was decanted and the residual red oil, which solidifies upon standing, was purified by chromatography (6/6/1 petroleum ether/dichloromethane/ethyl acetate) to provide the cc-oxime amide in 29% yield as a light yellow solid.

The α-oxime amide (58.6 mmol) was added in one portion to warm (40° C.) 90% sulfuric acid (16 mL) and the reaction mixture was heated at 60° C. for 30 min. The reaction mixture was allowed to cool to rt and was poured into ice water. The precipitated orange solids were collected by filtration and dried. The crude product was purified by chromatography (15/1 petroleum ether/ethyl acetate) to provide the isatin in 57% yield as a yellow solid.

The isatin (20.7 mmol) was mixed with 1 M sodium hydroxide (23 mL) and the reaction mixture was heated to 30-40° C. for 30 min. The reaction mixture was cooled to 0° C. and treated with a solution of sodium nitrite (20.7 mmol) in water (5.1 mL) and was maintained for 20 min. That solution was added dropwise to a cold (0-5° C.) solution of concentrated sulfuric acid (2.24 mL) in water (43.3 mL) and the reaction mixture was maintained for 0.5 h. A solution of tin (II) chloride (50.5 mmol) in concentrated hydrochloric acid (19.6 mL) was added dropwise and the reaction mixture was maintained at 0-5° C. for 1 h. The precipitated solids were isolated by filtration and dried to provide the indazole acid as a yellow solid (100% by mass).

Acetylchloride (18 mL) was added to methanol (180 mL) at 0° C. and the reaction mixture maintained for 1 h. The indazole acid (21.8 mmol) was added and the reaction mixture was heated at reflux for 3 h. The solution was concentrated to dryness and the residue was suspended in water and the pH adjusted to 7 with saturated sodium hydrogen carbonate. The mixture was extracted with ethyl acetate (3×100 mL), and the combined organic layers were dried (magnesium sulfate) and concentrated. The crude product was purified by chromatography (2/1 petroleum ether/ethyl acetate) to provide the indazole ester in 5% yield (two steps) as a yellow solid.

The indazole ester (1.02 mmol) was combined with 10% palladium on carbon (30mg) and methanol (20 mL) under an atmosphere of hydrogen gas for 30 min at rt. The catalyst was removed by filtration and the eluent was concentrated to afford the de-brominated indazole ester in 24%yield as an orange solid.

1 M Sodium hydroxide (1.5 mL) was added to a solution of the de-brominated indazole ester (0.243 mmol) in methanol (3.0 mL) and the reaction mixture was heated at 60° C. for 3 h. The solution was concentrated, the pH adjusted to 1-2, and the solids collected by filtration to provide the indazole acid in 100% yield as a yellow solid.

The following acid was prepared using this procedure:
4-Methoxy-1H-indazole-3-carboxylic acid.

Procedure 11

Procedure 11 provides a method for the preparation of benzyloxy-substituted indazole-3-carboxylic acids and esters from the corresponding bromo nitrobenzenes.

Acetic anhydride (34 mL) and zinc dust (4.59 mmol) were added to a solution of 4-methoxynitrobenzene (230 mmol) in glacial acetic acid (34 mL) and the reaction mixture was heated at reflux for 0.5 h. The reaction mixture was poured into water (340 mL) and the pH of the solution was adjusted to 8 with 10% sodium hydroxide. The precipitated solids were isolated by filtration, washed with water (100 mL), and dried to provide the acetamide in 88% yield.

65% Nitric acid (22 mL) was added dropwise over 0.5 h to a solution of the acetamide (200 mmol) in dichloromethane (200 mL). The reaction mixture was maintained for 1 h at rt and was heated at reflux for 1 h. The reaction mixture was washed with water (200 mL), saturated sodium carbonate solution (100 mL), and water (200 mL). The combined organic layers were dried (magnesium sulfate) and concentrated to provide the nitro acetamide in 90% as a yellow solid.

The nitroacetamide (180 mmol) was added to 4 M sodium hydroxide (180 mL) and the reaction mixture was maintained for 2 h at 60° C. The precipitated solids were isolated by filtration, washed with water, and dried to provide the nitroaniline in 70% yield as a red solid.

A solution of sodium nitrite (11.8 g) in water (28 mL) was added dropwise over 0.5 h to a solution of the nitroaniline (125 mmol) in 40%. hydrobromic acid (110g) at 10° C. The reaction mixture was maintained for 40 min at 0-10° C. and was filtered. The filtrate was added dropwise over 1 h to a 0° C., purple solution of copper (I) bromide (209 mmol) in hydrobromic acid (74 mL). The reaction mixture was allowed to warm to and maintained at rt for 30 min, was maintained at 60° C. for 0.5 h, and was heated at reflux for 1 h. The reaction mixture was partitioned between water (2.0 L) and dichloromethane (600 mL) and the aqueous layer was further extracted with dichloromethane (300 mL). The combined organic layers were washed with 10% sodium hydroxide (200 mL), water (600 mL), 10% hydrochloric acid (300 mL), and water (600 mL), dried (magnesium sulfate) and concentrated to provide the nitrobromide in 83% yield as a yellow oil.

A solution of boron tribromide (250 mmol) in dichloromethane (200 mL) was added drop wise over 1 h to a solution of the nitrobromide (100 mmol) in dichloromethane (250 mL) at −78° C. The reaction mixture was allowed to warm to rt and was maintained for 30 h. The reaction mixture was cooled to 0° C., quenched with water (300 mL) and the aqueous layer was extracted with ethyl acetate (2×300 mL).

The combined organic layers were washed with saturated sodium bicarbonate (2×300 mL), dried (magnesium sulfate), and concentrated to provide the nitrophenol in 87% yield as a brown crystalline solid.

Benzyl bromide (131 mmol) and potassium carbonate (130 mmol) were added to a solution of the nitrophenol (87.0 mmol) in 2/1 acetonitrile/acetone (840 mL). The reaction mixture was heated at reflux for 17 h and was concentrated to dryness. The residue was suspended in ethyl acetate (756 mL), filtered, and the organic layer was washed with water (567 mL), 1 M hydrochloric acid (2×567 mL), and brine (567 mL). The organic layer was dried (magnesium sulfate) and concentrated to the benzyl ether in 78% yield.

Diethyl malonate (890 mmol) was added drop wise over 1 h to a suspension of sodium hydride (520 mmol) in dimethylsulfoxide (100 mL) at 0° C. The benzyl ether (44.0 mmol) was added and the reaction mixture was heated at 100° C. for 5 h. The reaction mixture was poured into ice water and was extracted with ethyl acetate (3×70 mL). The combined organic layers were dried (magnesium sulfate) and concentrated to provide the diethylmalonate addition product. The diethylmalonate addition product was diluted with a 4 M solution of sodium hydroxide (100 mL) and the reaction mixture was heated at 60° C. for 6 h. The solution was extracted with dichloromethane (3×50 mL) and the aqueous layer was adjusted to pH 1 with concentrated hydrochloric acid. The reaction mixture was heated at 60° C. for 1 h, allowed to cool to rt, and was extracted with ethyl acetate (3×50 mL). The combined organic layers were dried (magnesium sulfate) and concentrated to provide the phenylacetic acid in 78% yield as a solid.

The phenylacetic acid (350 mmol) was added to a freshly prepared solution of ethanolic hydrochloric acid [acetyl chloride (5 mL) was added to ethanol (100 mL)]and the reaction mixture was heated at reflux for 20 h. The reaction mixture was concentrated to dryness and the residue was partitioned between saturated sodium bicarbonate (200 mL) and ethyl acetate (150 mL). The aqueous layer was extracted with ethyl acetate (2×50 mL) and the combined organic layers were dried (magnesium sulfate), filtered and concentrated to provide the ester in 77% yield.

The nitro ester (27.0 mmol) was dissolved in acetic acid (60 mL) and acetic anhydride (44 mL) and was cooled to 0° C. Zinc dust (153 mmol) was added and the reaction mixture was allowed to warm to rt and was maintained for 2 h. Additional quantities of zinc dust (2×45.9 mmol) were added during a 3 h course of time. After 1 h, the reaction mixture was filtered and the filter cake was washed with ethanol (100 mL). The combined filtrates were concentrated and the residue was partitioned between saturated sodium bicarbonate and ethyl acetate (50 mL). The solution was extracted with ethyl acetate (2×50 mL) and the combined organic layers were dried (magnesium sulfate), filtered and concentrated to provide the acetamide in 82% yield.

Isoamyl nitrite (47.2g) was added dropwise over 30 min to a solution of the acetamide (21.0 mmol) in chloroform (80 mL) and acetic anhydride (45 mL). Solid potassium acetate (7.13 mmol) was added in several portions and the reaction mixture was heated at reflux for 1.5 h. The reaction mixture was washed with water (2×80 mL) and brine (80 mL), dried (magnesium sulfate), and concentrated to provide the acetylated indazole ester in 68% yield.

The acetylated indazole ester (15.0 mmol) was suspended in 2 M sodium hydroxide (35 mL) and the reaction mixture was heated at 60° C. for 24 h. The pH of the solution was adjusted to 1-2 with concentrated hydrochloric acid and the solids were collected by filtration and dried to provide 6-benzyloxy-1H-indazole-3-carboxylic acid in 28% yield as a yellow solid.

6-Benzyloxy-1H-indazole-3-carboxylic acid (1.85 mmol) was added to a freshly prepared solution of ethanolic hydrochloric acid [prepared from ethanol (20 mL) and acetyl chloride (5 mL)]and the reaction mixture was heated at reflux for 25 h and was concentrated. The residue was partitioned between saturated sodium bicarbonate (20 mL) and ethyl acetate (20 mL) and the layers were separated. The aqueous layer was extracted with ethyl acetate (2×20 mL) and the combined organic layers were dried (magnesium sulfate) and concentrated. The residue was purified by chromatography (300/1 dichloromethane/methanol) to provide the product in 36.4% yield. Alternatively, the ester can be obtained from the acetylated indazole ester by maintaining the acetylated material in 2 M ammonia in methanol for 30 min.

The following acids were prepared using this method:
6-Benzyloxy-1H-indazole-3-carboxylic acid.
5-Benzyloxy-1H-indazole-3-carboxylic acid (from 4-benzyloxy-2-bromonitrobenzene:
see Parker, K. A.; Mindt, T. L. *Org. Lett.*, 2002, 4, 4265).
Ethyl 6-benzyloxy-1H-indazole-3-carboxylate.
Ethyl 5-benzyloxy-1H-indazole-3-carboxylate.
Procedure 12

Procedure 12 provides a method for the preparation of N(1)-difluoromethylindazole acids from the corresponding indazole-3-carboxylic acids.

Acetyl chloride (141 mmol) was added dropwise to a solution of 6-methoxy-3-indazole-carboxylic acid (26.0 mmol) in ethanol (200 mL) and the reaction mixture was heated at reflux for 16 h. The reaction mixture was allowed to cool to rt and was concentrated. The residue was dissolved in ethyl acetate (300 mL) and was washed with aqueous sodium bicarbonate (2×50 mL). The combined aqueous layers were back-extracted with ethyl acetate (2×200 mL). The combined organic layers were washed with brine (50 mL), dried (sodium sulfate), concentrated, and dried under vacuum to afford 4.91 g (86%) of the ester as a solid.

A solution of ethyl 6-methoxy-1H-indazole-3-carboxylate (4.54 mmol) in N,N-dimethylformamide (6.11 mL) was added dropwise to a suspension of sodium hydride (5.45 mmol) and N,N-dimethylformamide (12.2 mL) and the reaction mixture was maintained at room temperature for 30 min. Chlorodifluoromethane (17.0 mol) was bubbled into the reaction and the mixture was warmed to 80° C. and maintained for 2 h. The mixture was diluted with water (200 mL) and the precipitates were collected to give a white solid. The solid was dissolved in ethanol (20.0 mL) and a 5.0 M solution of sodium hydroxide (3.6 mL) was added. The reaction mixture was maintained at rt for 2 h, diluted with water (50 mL) and acidified with 6.0 N hydrochloric acid. The precipitate was collected and dried to provide the acid in 65% yield.

The following acids were prepared using this method:
1-(Difluoromethyl)-6-methoxy-1H-indazole-3-carboxylic acid.
6-Bromo-1-(difluoromethyl)-1H-indazole-3-carboxylic acid.
Procedure 13

Procedure 13 provides a preparation of 5-azaindazole-3-carboxlic acid from 4-chloropyridine.

A saturated aqueous sodium bicarbonate solution was carefully added to a solution of 4-chloropyridine hydrochloride (56.7 mmol) in water (20 mL) until the solution was basic. The mixture was extracted with hexanes (3×25 mL).

The combined organic layers were dried over magnesium sulfate and concentrated to a volume of ca. 25 mL to give a solution of the free base.

n-Butyllithium (2.0 M in Pentane, 68 mmol) was added dropwise to a solution of N,N-diisopropylamine (62.3 mmol) in tetrahydrofuran (61.6 mmol) at 0° C. and the reaction mixture was maintained for 30 min. The reaction mixture was cooled to −78° C. and the hexanes solution of 4-chloropyridine was added dropwise and the mixture was maintained for 1 h. Diethyl oxalate (56.7 mmol) was added to the orange homogeneous solution and the mixture was allowed to warm to rt. Analysis by LC/MS revealed that the main product was not the ethyl oxalate, but the N,N-diisopropylamide. The reaction was partitioned between water (50 mL) and ethyl acetate (50 mL). The layers were separated and the organic washed with brine (25 mL), dried (magnesium sulfate), and concentrated. The residue was dissolved in ethanol (50.0 mL), treated with hydrazine (160 mmol) and the mixture was heated at reflux for 1 h. The reaction mixture was concentrated and the residue was titrated with dichloromethane to give 1.20 g (8.6%) of hydrazone product.

A mixture of N,N-diisopropyl-1H-pyrazolo[4,3-c]pyridine-3-carboxamide (0.800 g, 0.00325 mol) and aqueous hydrogen chloride (10 M, 3.00 mL) in a microwave reaction vessel was heated at 120° C. for 10 min. The mixture had to be heated on the high absorbance setting to avoid pressure build-up. The reaction was diluted with water and neutralized with 3 N sodium hydroxide. The resultant white precipitate was collected and found to be a mixture of the acid (47%) and the mono-isopropyl amide (25%). The mixture was used without further purification.

The following acid was prepared using this method:
1H-Pyrazolo[4,3-c]pyridine-3-carboxylic acid.
Procedure 14

Procedure 14 provides a preparation of 6-azaindazole-3-carboxlic acid from 4-chloro-3-nitropyridine.

tert-Butyl ethyl propane-1,3-dioate (26.6 mmol) was added to a suspension of sodium hydride (1.11 g) in tetrahydrofuran (50.0 mL) at 0° C. The reaction mixture was allowed to warm to rt and was maintained for 30 min. The reaction mixture was then cooled to 0° C. and a solution of 4-chloro-3-nitropyridine (12.6 mmol) in tetrahydrofuran/N,N-dimethylformamide (9/1, 10 mL) was added dropwise. The mixture was allowed to warm to rt and was maintained for 1 h. The reaction was quenched with water (50 mL) and was neutralized with acetic acid to a pH of 5 (the color went from dark brown to yellow on neutralization). The mixture was extracted with ethyl acetate (50 mL) and the combined organic layers were washed with brine (25 mL), dried (magnesium sulfate), and concentrated to provide the product in 94% yield.

The crude tert-butyl ethyl (3-nitropyridin-4-yl)malonate (12.6 mmol) was dissolved in 4/1 dichloromethane/trifluoroacetic acid (25.0 mL) and the mixture was heated at reflux for 2 h. The reaction mixture was concentrated and the residue was partitioned between saturated aqueous sodium bicarbonate (50 mL) and ethyl acetate (50 mL). The layers were separated and the ethyl acetate layer was washed with brine (25 mL), dried (magnesium sulfate), and concentrated. The residue was purified by chromatography (95/5 dichloromethane/ethyl acetate) to provide the product in 77% yield.

Ethyl (3-nitropyridin-4-yl)acetate (9.66 mmol) and 10% palladium on carbon (2.10 g) were diluted with ethanol (25.0 mL) in a Parr pressure reactor. The reaction mixture was shaken under an atmosphere of hydrogen (30 psi) for 3 h. The reaction mixture was filtered (Celite) and concentrated to provide the product in 97% yield.

Amyl Nitrite (18.9 mmol) was added to a solution of ethyl (3-aminopyridin-4-yl)acetate (9.43 mmol), potassium acetate (11.3 mmol), and acetic anhydride (28.3 mmol) in chloroform (10.0 mL) and the reaction was heated at 60° C. for 16 h. The cooled reaction mixture was carefully diluted with aqueous sodium bicarbonate and was extracted with dichloromethane (2×50 mL). The combined organic layers were washed with brine (25 mL), dried (magnesium sulfate), and concentrated. The residue was pre-purified by chromatography (50/50 to 0/100 hexanes/ethyl acetate) to yield a complex mixture of products. The mixture was dissolved in ethanol (10.0 mL), diluted with 5.0 M sodium hydroxide (5.00 mL), and the reaction mixture was maintained for 16 h. The reaction mixture was concentrated to ~5 mL, diluted with water (20 mL), and was neutralized with acetic acid. The yellow solid was collected by filtration to provide the desired product in 18% yield.

The following acid was prepared using this method:
1H-pyrazolo[3,4-c]pyridine-3-carboxylic acid.
Procedure 15

Procedure 15 provides a preparation of aminobenzisothiazole-3-carboxlic acids from the ester.

Cesium carbonate (3.18 mmol), palladium(II) acetate (0.24 mmol), and 2-dicyclohexylphosphino-2',4',6'-tri-i-propyl-1,1'-biphenyl (0.24 mmol) were combined in a microwave vessel and the vessel was flushed with nitrogen. A solution of (R)-(+)-3-pyrrolidinol (3.18 mol) and tert-butyl 6-bromo-1,2-benzisothiazole-3-carboxylate (1.59 mol) in tetrahydrofuran (20.0 mL) was added. The vessel was sealed and was heated at 135° C. for 30 minutes. The reaction mixture was filtered through Celite (ethyl acetate) and the filtrate was concentrated. The residue was purified by chromatography (70/30 to 50/50 hexanes/ethyl acetate) to provide the purified ester. The ester was dissolved in dichloromethane/trifluoroacetic acid (4:1, 2.00 mL) and was maintained for 16 h. The reaction mixture was concentrated to provide the product in 23% yield. The product was used without further purification.

Alternatively, when ethyl 6-bromo-1,2-benzisothiazole-3-carboxylate was used, a solution of the ester in ethanol was saponified using 5N sodium hydroxide. The acid was collected by filtration after diluting with water and neutralizing with acetic acid.

The following acids and esters were prepared using this method:
6-[(3R)-3-Hydroxypyrrolidin-1-yl]-1,2-benzisothiazole-3-carboxylic acid.
6-[(3S)-3-Hydroxypyrrolidin-1-yl]-1,2-benzisothiazole-3-carboxylic acid.
6-[(3R)-3-Methoxypyrrolidin-1-yl]-1,2-benzisothiazole-3-carboxylic acid.
6-[(3S)-3-Methoxypyrrolidin-1-yl]-1,2-benzisothiazole-3-carboxylic acid.
6-(3-Methoxypyrrolidin-1-yl)-1,2-benzisothiazole-3-carboxylic acid.
6-[(3S)-3-Dimethylaminopyrrolidin-1-yl]-1,2-benzisothiazole-3-carboxylic acid.
6-[(3R)-3-Dimethylaminopyrrolidin-1-yl]-1,2-benzisothiazole-3-carboxylic acid.
6-(3-Ethoxypyrrolidin-1-yl)-1,2-benzisothiazole-3-carboxylic acid.
6-[(1S,4S)-2-Oxa-5-azabicyclo[2.2.1]hept-5-yl]-1,2-benzisothiazole-3-carboxylic acid.
tert-Butyl 7-bromo-1,2-benzisothiazole-3-carboxylate.
7-[(3R)-3-Hydroxypyrrolidin-1-yl]-1,2-benzisothiazole-3-carboxylic acid.

7-[(3S)-3-Hydroxypyrrolidin-1-yl]-1,2-benzisothiazole-3-carboxylic acid.
6-[(1S,4S)-5-(tert-Butoxycarbonyl)-2,5-diazabicyclo [2.2.1]hept-2-yl]-1,2-benzisothiazole-3-carboxylic acid
6-[(1S,4S)-5-Methyl-2,5-diazabicyclo[2.2.1]hept-2-yl]-1,2-benzisothiazole-3-carboxylic acid
6-[3-[tert-Butoxycarbonyl)(methyl)amino]pyrrolidin-1-yl]-1,2-benzisothiazole-3-carboxylic acid
6-[3-(Methoxymethyl)pyrrolidin-1-yl]-1,2-benzisothiazole-3-carboxylicacid
6-[4-(Dimethylamino)piperidine-1-yl]-1,2-benzisothiazole-3-carboxylicacid
6-(1,4-Diazabicyclo[3.2.2]non-4-yl)-1,2-benzisothiazole-3-carboxylic acid.
6-[(1S,4S)-5-Methyl-2,5-diazabicyclo[2.2.1]hept-2-yl]-1,2-benzisothiazole-3carboxylic acid.
6-[(1R,4R)-5-Methyl-2,5-diazabicyclo[2.2.1]hept-2-yl]-1,2-benzisothiazole-3-carboxylic acid.
6-(Pyrrolidin-1-yl)-1,2-benzisothiazole-3-carboxylic acid.
6-(4-Methylpiperazin-1-yl)-1,2-benzisothiazole-3-carboxylic acid.
6-(4-Methyl-1,4-diazepan-1-yl)-1,2-benzisothiazole-3-carboxylic acid.
6-(Hexahydropyrrolo[1,2-a]pyrazin-2(1H)-yl)-1,2-benzisothiazole-3-carboxylic acid.
6-(5-Methyl-2,5-diazabicyclo[2.2.2]oct-2-yl)-1,2-benzisothiazole-3-carboxylic acid.
6-(8-Methyl-3,8-diazabicyclo[3.2.1]oct-3-yl)-1,2-benzisothiazole-3-carboxylic
5-(4-Methyl-1,4-diazepan-1-yl)-1,2-benzisothiazole-3-carboxylic acid.
5-[(3R)-3-Methoxypyrrolidin-1-yl]-1,2-benzisothiazole-3-carboxylic acid.
5-[(3S)-3-Methoxypyrrolidin-1-yl]-1,2-benzisothiazole-3-carboxylic acid.
5-[(3S)-3-(Cyclopropylmethoxy)pyrrolidin-1-yl]-2-{[2-(trimethylsilyl)ethoxy]methyl}-1H-indazole-3-carboxylic acid.
5-[(3S)-3-(Methoxy)pyrrolidin-1-yl]-2-{[2-(trimethylsilyl)ethoxy]methyl}-1H-indazole-3-carboxylic acid.
5-((3R)-3-{[2-(Trimethylsilyl)ethoxy]methoxy}pyrrolidin-1-yl)-1,2-benzisothiazole-3-carboxylic acid.
5-((3S)-3-{[2-(Trimethylsilyl)ethoxy]methoxy}pyrrolidin-1-yl)-1,2-benzisothiazole-3-carboxylic acid.
6-[4-(tert-Butoxycarbonyl)-3-methylpiperazin-1-yl]-1,2-benzisothiazole-3-carboxylic acid.
6-[1-(tert-Butoxycarbonyl)octahydro-6H-pyrrolo[3,4-b]pyridin-6-yl]-1,2-benzisothiazole-3-carboxylic acid.
5-[(3S)-3-methoxypyrrolidin-1-yl]-1-{[2-(trimethylsilyl)ethoxy]methyl}-1H-indazole-3-carboxylic acid.
6-[4-(tert-Butoxycarbonyl)-3-methylpiperazin-1-yl]-1,2-benzisothiazole-3-carboxylic acid.
6-[1-(tert-Butoxycarbonyl)octahydro-6H-pyrrolo[3,4-b]pyridin-6-yl]-1,2-benzisothiazole-3-carboxylic acid.
6-[4-(tent-Butoxycarbonyl)piperazin-1-yl]-1,2-benzisothiazole-3-carboxylic acid.
Ethyl 6-[4-(tert-butoxycarbonyl)-1,4-diazepan-1-yl]-1,2-benzisothiazole-3-carboxylate.
6-[4-(tert-Butoxycarbonyl)-2-methylpiperazin-1-yl]-1,2-benzisothiazole-3-carboxylic acid.
6-(3,4-Dimethylpiperazin-1-yl)-1,2-benzisothiazole-3-carboxylic acid.
Ethyl 6-[3-[tert-butoxycarbonyl)(methyl)amino]pyrrolidin-1-yl]-1,2-benzisothiazole-3-carboxylate
The following esters were prepared from the N-Boc intermediates using trifluoroacetic acid:

Ethyl 6-[(1S,4S)-2,5-diazabicyclo[2.2.1]hept-2-yl]-1,2-benzisothiazole-3-carboxylate
Ethyl 6-(octahydro-6H-pyrrolo[3,4-b]pyridin-6-yl)-1,2-benzisothiazole-3-carboxylate.
Ethyl 6-piperazin-1-yl-1,2-benzisothiazole-3-carboxylate.

Procedure 16

Procedure 16 provides a preparation of 6-amino-7-azaindazole-3-carboxlic acids from tert-butyl 6-fluoro-1H-pyrazolo [3,4-b]pyridine-3-carboxylate.

3-Pyrrolidinol (24.7 mmol) was added to a solution of tert-butyl 6-fluoro-1H-pyrazolo[3,4-b]pyridine-3-carboxylate (4.22 mmol) in toluene (4.00 mL) in a microwave reaction vessel. The reaction mixture was subjected to microwave irradiation at 120° C. for 300 s. The reaction mixture was partitioned between water (100 mL) and ethyl acetate (200 mL) and the layers were separated. The organic layer was washed with water (2×50 mL) and brine (25 mL) and was filtered through silica gel (50 g). The silica was washed with 100 mL EtOAc and the combined EtOAc solutions were concentrated to provide the product in 63% yield.

Methanesulfonyl chloride (5.52 mmol) was added dropwise to a cold (0° C.) solution of tert-butyl 6-(3-hydroxypyrrolidin-1-yl)-1H-pyrazolo [3,4-b]pyridine-3-carboxylate (2.63 mmol) and triethylamine (6.57 mmol) in dichloromethane (2.7 mL). The reaction mixture was maintained at rt for 16 h and was diluted with water (25 mL). The dichloromethane layer was separated and was transferred to a silica gel column. The column was eluted using a gradient of 90/10 to 0/100 hexanes/ethyl acetate to provide the bis-mesylate in 60% yield and the monomesylate in 28% yield.

tert-Butyl 1-(methylsulfonyl)-6-3-[(methylsulfonyl)oxy]pyrrolidin-1-yl-1H-pyrazolo[3,4-b]pyridine-3-carboxylate (0.380 mmol) was diluted with a 2.0 M solution of dimethylamine in tetrahydrofuran (5.0 mL) in a microwave vessel. The reaction mixture was subjected to microwave irradiation at 135° C. for 80 min. The reaction mixture was concentrated and the residue was purified by chromatography {100/0 to 90/10 ethyl acetate/[(50/50/2) ethyl acetate/methanol/dimethylethylamine]} to provide the purified ester. The ester was dissolved in 4/1 dichloromethane/trifluoroacetic acid (5.00 mL) and the mixture was maintained at rt for 16 h. The volatiles were removed and the residue was dissolved in water. The mixture was neutralized with half saturated sodium bicarbonate and the solid precipitate was collected by filtration to provide the product in 79% yield.

The following acid was prepared using this method:
6-[3-(Dimethylamino)pyrrolidin-1-yl]-1H-pyrazolo[3,4-b]pyridine-3-carboxylic acid.

Procedure 17

Procedure 17 provides a preparation of fluorinated benzisothiazole-3-carboxlic acids from the ester of the corresponding benzisothiazole-3-carboxlic acid.

1-Fluoro-2,6-dichloropyridinium triflate (2.25 mmol) was added to a solution of ethyl 6-(3-methoxypyrrolidin-1-yl)-1,2-benzisothiazole-3-carboxylate (1.87 mmol) in dichloromethane (20.0 mL) and the reaction mixture was maintained at rt for 6 h. The reaction mixture was filtered through silica gel (10 g, dichloromethane wash) and the eluent was concentrated. The residue was purified by chromatography 90/10 to 70/30 hexanes/ethyl acetate to provide the product in 22% yield.

A solution of ethyl 7-fluoro-6-(3-methoxypyrrolidin-1-yl)-1,2-benzisothiazole-3-carboxylate (0.177 mmol) in ethanol (1.5 mL) was treated with a 5.0 M solution of sodium hydroxide (3.0 mmol). Within minutes, a gelatinous solid precipitated. The reaction mixture was diluted with water (50 mL) and was acidified with 6.0 N hydrochloric acid. The precipitate was collected by filtration to provide the product in 80% yield. The acid was used without further purification.

The following acid was prepared using this method:
7-Fluoro-6-(3-methoxypyrrolidin-1-yl)-1,2-benzisothiazole-3-carboxylic acid.
7-Fluoro-6-(3-ethoxypyrrolidin-1-yl)-1,2-benzisothiazole-3-carboxylic acid.
7-Fluoro-6-methoxy-1,2-benzisothiazole-3-carboxylic acid.
Procedure 18

Procedure 18 provides a preparation of 6-phenyl-1H-pyrazolo[3,4-b]pyridine-3-carboxylic acid from tert-butyl 6-phenyl-1H-pyrazolo[3,4-b]pyridine-3-carboxylate.

[1,3-Bis(diphenylphosphino)propane]nickel(II) chloride (0.0999 mmol) and tert-butyl 6-fluoro-1H-pyrazolo[3,4-b]pyridine-3-carboxylate (0.999 mmol) were dissolved in tetrahydrofuran (20.0 mL) and the reaction mixture was cooled to 0° C. A 1.00 M solution of phenylmagnesium bromide in tetrahydrofuran (2.40 mL) was added and the reaction mixture was allowed to warm to rt and was maintained for 4 h. The reaction was partitioned between water (50 mL) and ethyl acetate (50 mL). The layers were separated and the organic washed with brine (25 mL), dried (magnesium sulfate), and concentrated. The residue was purified by chromatography (95/5 to 85/15 hexanes/ethyl acetate) to provide the product in 56% yield.

tert-Butyl 6-phenyl-1H-pyrazolo[3,4-b]pyridine-3-carboxylate (0.555 mmol) was dissolved in a 4/1 dichloromethane/trifluoroacetic acid solution (2.00 mL) and the reaction was maintained for 16 h at rt. The reaction mixture was concentrated and the residue was diluted with water (5 mL). The reaction mixture was neutralized to pH 5-7, stirred vigorously for 1 h, and the precipitated solids were collected by filtration to provide the acid in 92% yield.

The following acid was prepared using this method:
6-Phenyl-1H-pyrazolo[3,4-b]pyridine-3-carboxylic acid.
Procedure 19

Procedure 19 details the preparation of ethyl 6-bromobenzisoxazole-3-carboxylate from 2,5-dibromonitrobenzene.

Diethyl malonate (12.6 g, 79 mmol) was added to a suspension of sodium hydride (3.16 g, 132 mmol) in dimethylsulfoxide (60 ml) over 30 min. The temperature of the reaction rose to 60° C. and the mixture clarified. 1,4-Dibromo-2-nitrobenzene (10 g, 36.0 mmol) was added and the solution was maintained for 2 h at 100° C. The reaction mixture was allowed to cool to rt and was poured into ice (300 g-400 g). The precipitated solids were isolated by filtration and dried to provide 11.0 g of the product (89%).

The ester (11.0 g, 32.0 mmol) was diluted with a 2 N solution of sodium hydroxide (32 mL, 63 mmol) and the reaction mixture was maintained at room temperature for 16 h. The aqueous layer was extracted with dichloromethane (20 mL) and was acidified. The precipitated solids were isolated by filtration and dried to provide 7.00 g of the acid (89%).

Sulfuric acid (1 mL) was added to a solution of the acid (7.00 g, 27.0 mmol) in ethanol (60 ml). The reaction mixture was warmed to reflux, maintained for 2 h, and was concentrated under reduce pressure. The residue was partitioned between ethyl acetate (250 mL) and saturated sodium carbonate (50 mL) and the organic layer was washed with saturated sodium carbonate (50 mL) and brine (50 mL). The organic layer was dried (sodium sulfate) and concentrated to provide 8.00 g (98%) of the ester as a liquid.

Isoamylnitrite (225 mL) was added to a solution of the ester (420 g, 1.46 mol) in ethanol (3 L) in a 10 L three-necked round bottom flask and the mixture was warmed to 60° C. A solution of sodium ethoxide, prepared from sodium metal (33.5 g, 1.46 mmol) in ethanol (1 L) was added dropwise and the reaction mixture was maintained for 2 h. The reaction mixture was allowed to cool to rt and was neutralized with 2 N hydrochloric acid. The reaction mixture was extracted with ethyl acetate (4×2L) and the combined organic layers were washed with water (2×1 L) and brine (2×1 L) and dried (sodium sulfate). The residue was purified by chromatography (1/1 to 0/1 hexane/ethyl acetate) to provide 110 g of the product (28%).

See, for example, International Publication Number WO 2004/010995.

The following ester was prepared using this method:
Ethyl 6-bromo-1,2-benzisoxazole-3-carboxylate.
Procedure 20

Procedure 20 details the preparation of ethyl 6-methoxybenzisoxazole-3-carboxylate from 1-chloro-2,4-dinitrobenzene.

Sodium hydride (417 mmol) was added to a solution of ethyl 3-oxobutanoate (129 mmol) in tetrahydrofuran (350 mL). 1-Chloro-2,4-dinitrobenzene (123 mmol) was added and the resulting suspension was maintained for 24 h at rt. The pH was adjusted to 5 by the addition of 3 M hydrochloric acid and the resulting solution was extracted with diethyl ether (300 mL). The organic layer was washed with water (3×300 mL), dried (magnesium sulfate), and concentrated to provide ethyl 2-(2,4-dinitrophenyl)-3-oxobutanoate in 98% yield as a brown solid.

Propan-1-amine (136 mmol) was added to a solution of ethyl 2-(2,4-dinitrophenyl)-3-oxobutanoate (135 mmol) in chloroform (500 mL). The reaction mixture was maintained for 12 h at rt and was concentrated. The residue was purified by chromatography 20/1 hexane/ethyl acetate to provide ethyl 2-(2,4-dinitrophenyl)acetate in 99% yield as a brown oil.

A solution of ethyl 2-(2,4-dinitrophenyl)acetate (18.1 mmol) and 3-methylbutanyl nitrite (73.5 mmol) in ethanol (70 mL) was warmed to 60° C. A solution of sodium ethoxide, prepared from sodium (21.7 mmol) and ethanol (70 mL), was added and the reaction mixture was maintained for 1 h. The reaction mixture was cooled to 0° C. and the pH adjusted to 7 by the addition of 5% hydrochloric acid. The resulting solution was diluted with water (500 mL) and was extracted with ethyl acetate (200 mL). The organic layer was washed with brine (4×200 mL), dried (magnesium sulfate), and concentrated. The residue was purified by chromatography (30/1 petroleum ether/ethyl acetate) to provide 6-nitrobenzo[d]isoxazole-3-carboxylate in 70% yield as a orange solid.

Ethyl 6-nitrobenzo[d]isoxazole-3-carboxylate (12.7 mmol), iron (53.6 mmol), and ammonium chloride (56.1 mmol) were combined and diluted with ethanol (150 mL) and water (20 mL). The resulting suspension was heated at reflux, with vigorous stirring, for 2 h. The reaction mixture was filtered through Celite, diluted with brine (200 mL), and the resulting solution was extracted with ethyl acetate (200 mL). The organic layer was washed with of brine (3×200 mL), dried (magnesium sulfate), and concentrated. The residue was purified by chromatography (20/1 petroleum ether/ethyl acetate) to provide ethyl 6-aminobenzo[d]isoxazole-3-carboxylate 49.6% yield as a orange solid Ethyl 6-aminobenzo[d]isoxazole-3-carboxylate (2.43 mmol) was diluted with a solution of sulfuric acid (2.5 mL) in water (2.5 mL) and the resulting mixture was maintained at rt for 30 min. A solution of sodium nitrite (2.67 mmol) in water (2.5 ml) was added dropwise at 0° C. and the resulting mixture was maintained for 30 min at 0° C. This aqueous solution was added to a cold (0° C.) solution of copper (II) nitrate (149 mmol) in water (80 mL) and the reaction mixture was allowed to warm to rt. After 5 min., copper (I) oxide (2.78 mmol) was added to the mixture and the reaction mixture was maintained for 1 h at rt. The reaction mixture was extracted with ethyl acetate (3×100 mL) and the combined organic layers were dried (magnesium sulfate) and concentrated to provide crude ethyl 6-hydroxybenzo[d]isoxazole-3-carboxylate in 99% yield as a brown oil.

Potassium carbonate (9.42 mmol) and iodomethane (8.45 mmol) were added to a solution of crude ethyl 6-hydroxybenzo[d]isoxazole-3-carboxylate (2.42 mmol) in N,N-dimethylformamide (30 mL) and the reaction mixture was maintained for 48 h at rt in the dark. The reaction mixture was diluted with water (100 mL) and was extracted with ethyl acetate (2×100 mL). The combined organic layers were washed with brine (3×100 mL), dried (magnesium sulfate), and concentrated. The residue was purified by chromatography (30/1 petroleum ether/ethyl acetate) to provide ethyl 6-methoxybenzo[d]isoxazole-3-carboxylate in 19% yield as a yellow solid.

The following ester was prepared using this method:
Ethyl 6-methoxybenzo[d]isoxazole-3-carboxylate.
Procedure 21

Procedure 21 provides a preparation of 7-azabenzisothiazole-3-carboxlic acid from 2-chloronicotinic acid.

2-Chloronicotinic acid (317 mmol) was diluted with oxalyl chloride (130 mL) and the resulting solution was heated at reflux for 18 h. The volatiles were removed by evaporation to provide 2-chloronicotinoyl chloride in 98% yield as a white solid.

Magnesium chloride (221 mmol) and triethylamine (752 mmol) were added to a solution of diethyl malonate (375 mmol) in toluene (250 ml) and the reaction mixture was maintained for 1 h at 25° C. A solution of 2-chloronicotinoyl chloride (313 mmol) in toluene (80 mL) was added dropwise over the course of 2 h. The reaction mixture was maintained at rt for 3.5 h and was quenched with cold (0° C.) water (500 mL). The resulting solution was extracted with ethyl acetate (500 mL) and the organic layers combined. The organic layer was washed with brine (3×300 mL), dried (sodium sulfate), and was concentrated to provide diethyl 2-(2-chloronicotinoyl)malonate in 85% yield as a brown oil.

A solution of diethyl 2-(2-chloronicotinoyl)malonate (267 mmol) in dimethylsulfoxide (100 ml) was added dropwise over 1.5 h to a 130° C. solution of water (10 mL) in dimethylsulfoxide (260 mL). The reaction mixture was maintained at 130° C. for an additional 2 h and was allowed to cool to rt. The reaction mixture was diluted with cold (0° C.) water (500 mL) and was extracted with ethyl acetate (3×200 mL). The combined organic layers were washed with brine (5×200 mL), dried (sodium sulfate), and concentrated. The residue was purified by chromatography (10/1 petroleum ether/ethyl acetate) to provide 1-(2-chloropyridin-3-yl)ethanone 52% yield as yellow oil.

A solution of 1-(2-chloropyridin-3-yl)ethanone (129 mmol) in ammonium hydroxide (130 mL) and ethanol (500 mL) was added to a 1 L high pressure steel vessel under an atmosphere of ammonia. Sulfur (129 mmol) was added to the reaction mixture, the vessel was sealed, and the reaction mixture was heated at 130° C. for 16 h. The reaction mixture was filtered through Celite and the eluent was extracted with ethyl acetate (300 mL). The organic layer was washed with brine (100 mL), dried (sodium sulfate) and concentrated. The residue was purified by chromatography (20/1 petroleum ether/ethyl acetate) to provide 3-methylisothiazolo[5,4-b]pyridine in 22% yield as a white solid.

N-Bromosuccinamide (10.7 mmol) was added to a solution of 3-methylisothiazolo[5,4-b]pyridine (10.0 mmol) in carbontetrachloride (20 mL). Benzoyl peroxide (0.82 mmol) was added and the reaction mixture was heated at reflux for 48 h. The reaction mixture was filtered through Celite (ethyl acetate) and the eluent was concentrated to provide crude 3-(bromomethyl)isothiazolo[5,4-b]pyridine as a yellow solid.

A solution of the crude 3-(bromomethyl)isothiazolo[5,4-b]pyridine (3.49 mmol) in dimethylsulfoxide (20 mL) was treated with water (4 mL) and the reaction mixture was heated at 80° C. for 1.5 h. The reaction mixture was diluted with water (100 mL), filtered through Celite, and was extracted with ethyl acetate (3×30 mL). The combined organic layers were washed with water, dried (magnesium sulfate), and concentrated to provide isothiazolo[5,4-b]pyridin-3-ylmethanol in 31% yield as yellow oil.

Potassium permanganate (2.25 mmol) and potassium hydroxide (1.79 mmol) were added to a solution of isothiazolo[5,4-b]pyridin-3-ylmethanol (1.08 mmol) in water (4 mL) and the resulting solution was allowed to react for 3 h at rt. The reaction mixture was filtered through Celite and was extracted with ethyl acetate (3×10 mL). The pH of the combined aqueous layers was adjusted to 2 by the addition of 0.6 M hydrochloric acid. The slurry was stirred for 5 min and the solids were collected by filtration to provide isothiazolo[5,4-b]pyridine-3-carboxylic acid in 42% yield as a light yellow solid.

The following acid was prepared using this method:
Isothiazolo[5,4-b]pyridine-3-carboxylic acid.
Procedure 22

The following procedure provides a method for the preparation of 2,2,2-trifluoroethyl substituted acids.

A mixture of ethyl 6-[(1S,4S)-5-(tert-butoxycarbonyl)-2,5-diazabicyclo[2.2.1]hept-2-yl]-1,2-benzisothiazole-3-carboxylate (1.16 mmol) in 4/1 methylene chloride/trifluoroacetic acid (10.00 mL) was maintained at room temperature for 16 h. The reaction mixture was concentrated and the residue was loaded onto a SCX column (10 g) and flushed with 5 volumes of methanol. The partially purified product was then eluted using 2.0 M ammonia in methanol to provide the amine in 68% yield.

2,2,2-Trifluoroethylmethanesulfonate (0.330 mmol) was added to a solution of ethyl 6-[(1S,4S)-2,5-diazabicyclo[2.2.1]hept-2-yl]-1,2-benzisothiazole-3-carboxyl (0.165 mmol) in N,N-diisopropylethylamine (0.20 mL) and acetonitrile (15 mL) and the resulting mixture was maintained for 16 h at room temperature. The reaction mixture was concentrated and the residue was purified by chromatography (90/10 to 70/30 hexanes/ethyl acetate) to yield the purified ester. The ester was dissolved in ethanol (5.0 mL) and an aqueous solution of sodium hydroxide (5.0 M, 2.0 mL) was added. The reaction was maintained at room temperature for 4 h, then diluted with water (50 mL) and neutralized with acetic acid. The precipitate was collected by filtration to provide 6-[(1S,4S)-5-(2,2,2-trifluoroethyl)-2,5-diazabicyclo[2.2.1]hept-2-yl]-1,2-benzisothiazole-3-carboxylic acid in 29% yield.

The following acid was prepared using a similar procedure:
6-{3-[Methyl(2,2,2-trifluoroethyl)amino]pyrrolidin-1-yl}-1,2-benzisothiazole-3-carboxylic acid
Procedure 23

Procedure 23 provides a preparation of amidine substituted indazole-3-carboxylic acids from the corresponding aldehydes.

N-Methyl-1,2-ethanediamine (4.7 mmol) was added to a solution of tert-butyl 6-formal-1-1H-indazole-3-carboxylate (4.2 mmol) in tert-butanol (40 mL) and the reaction mixture was maintained for 30 min. Potassium carbonate (10 mmol) and iodine (5.3 mmol) were added and the slurry was heated at 70° C. for 3 h. The reaction mixture was allowed to cool to rt and was quenched with aqueous sodium thiosulfate (40 mL). The aqueous layer was extracted with 9/1 dichloromethane/methanol and the combined organic layers were dried (magnesium sulfate) and concentrated. The residue was purified by chromatography [100/0 to 60/40 dichloromethane/(8/1/1 dichloromethane/methanol/7 M ammonia in methanol) to provide the amidine in 51% yield.

tert-Butyl 6-(1-methyl-4,5-dihydro-1H-imidazol-2-yl)-1H-indazole-3-carboxylate (2.2 mmol) was diluted with trifluoroacetic acid (3.7 mL) and the reaction mixture was maintained for 16 h at rt. The precipitated product was isolated by filtration to provide the acid in 93% yield.

The following acid was prepared using this method:
6-(1-Methyl-4,5-dihydro-1H-imidazol-2-yl)-1H-indazole-3-carboxylic acid.

Procedure 24

Procedure 24 provides a preparation of N-alkyl aminobenzisothiazole-3-carboxylic acids from the corresponding aminobenzisothiazole-3-carboxylic esters.

Sodium cyanoborohydride (8.57 mmol) was added to a solution of ethyl 6-[(1S,4S)-2,5-diazabicyclo[2.2.1]hept-2-yl]-1,2-benzisothiazole-3-carboxylate (0.260 g, 0.857 mmol) and 1-ethoxy-1-(trimethylsilyloxy)cyclopropane (8.57 mmol) in ethanol (11.2 mL) and the reaction mixture was heated at 60° C. for 6 h. The reaction mixture was diluted with water (50 mL) and was extracted with ethyl acetate (2 ×50 mL). The combined organic layers were washed with brine (25 mL), dried (magnesium sulfate), and were concentrated. The residue was purified by chromatography (ethyl acetate) to yield the ester. A 5.0 M solution of sodium hydroxide in water (4.00 mL) was added to a solution of the ester in ethanol (10.0 mL) and the reaction mixture was maintained for 16 h. The reaction was neutralized with acetic acid and was loaded onto a SCX column. The column was flushed with water (200 mL) and methanol (100 mL) and the product was eluted with 2.0 M ammonia in methanol (60 mL) to provide the acid in 56% yield. The acid was used without further purification.

The following acid was prepared using this method:
6-[(1S,4S)-5-Cyclopropyl-2,5-diazabicyclo[2.2.1]hept-2-yl]-1,2-benzisothiazole-3-carboxylic acid.

Procedure 25

Procedure 25 provides a preparation of N-alkyl aminobenzisothiazole-3-carboxylic acids from the corresponding aminobenzisothiazole-3-carboxylic esters.

Cyclopropylmethyl bromide (1.71 mmol) was added to a suspension of ethyl 6-[(1S,4S)-2,5-diazabicyclo[2.2.1]hept-2-yl]-1,2-benzisothiazole-3-carboxylate (0.857 mmol) and sodium bicarbonate (3.43 mmol) in acetonitrile (10.0 mL) and the reaction mixture was heated at 60° C. for 6 h. The acetonitrile was decanted from the solids and the solids were washed with acetonitrile (2×5 mL). The acetonitrile solution was transferred to a silica gel column and the mixture was purified by chromatography {9/1 to 7/3 ethyl acetate/[(50/50/2) ethyl acetate/methanol/dimethylethylamine]} to yield the purified ester. A 5.0 M solution of sodium hydroxide in water (2.00 mL) was added to a solution of the ester in ethanol (5.0 mL) and the reaction mixture was maintained for 16 h. The reaction was neutralized with acetic acid and the reaction mixture was transferred to a SCX column (10 g). The column was flushed with water (200 mL) and methanol (100 mL) and the product was eluted with 2.0 M ammonia in methanol to provide the product in 50% yield. The acid was used without further purification.

The following acid was prepared using this method:
6-[(1S,4S)-5-(Cyclopropylmethyl)-2,5-diazabicyclo[2.2.1]hept-2-yl]-1,2-benzisothiazole-3-carboxylic acid.

Procedure 26

Procedure 26 provides a preparation of 6-hydroxybenzisothiazole-3-carboxylic acid and the ester from the corresponding anisole.

A 1.0 M solution of boron tribromide in methylene chloride (20.00 mL) was added dropwise to a 0° C. solution of ethyl 6-methoxy-1,2-benzisothiazole-3-carboxylate (12.6 mmol) in methylene chloride (30.0 mL). The reaction mixture was allowed to warm to rt and was maintained for 16 h. The reaction mixture was poured into 100 mL of ice cold 2 N sodium hydroxide and the mixture was stirred vigorously for 20 min. The precipitated solids were removed by filtration and the eluent was washed with ethyl acetate (2×50 mL). The aqueous layer was neutralized with 6 N hydrochloric acid and the precipitated tan solid was collected by filtration to give a mixture of the methoxy (~48% yield) and hydroxy acids (~37% yield).

Thionyl chloride (27.0 mmol) was added dropwise to a round bottom flask containing ethanol (50.0 mL) at 0° C. The reaction mixture was allowed to warm to rt and the mixture of hydroxy and methoxy acids was added after 30 min. The reaction mixture was heated at 95° C. for 4 h and was concentrated to ca. 25 mL. The reaction mixture was partitioned between ethyl acetate (100 mL) and saturated aqueous sodium bicarbonate (100 mL) and the organic layer was washed with brine and concentrated. The residue was purified by chromatography using a gradient of 80/20 to 60/40 hexanes/ethyl acetate to provide the product in 82% yield.

The following acids and esters were prepared using this method:
6-Hydroxy-1,2-benzisothiazole-3-carboxylic acid.
6-Methoxybenzo[d]isothiazole-3-carboxylic acid.
Ethyl 6-hydroxy-1,2-benzisothiazole-3-carboxylate.

Procedure 27

Procedure 27 provides a preparation of 7-aza-6-chlorobenzisothiazole-3-carboxylic acid from 2-chloronicotinoyl chloride.

Magnesium metal (1.25 mol) was diluted with ethanol (250 mL) and carbon tetrachloride (5 mL) and the suspension was heated at 70-80° C. for 1 h. A solution of diethylmalonate (1.21 mol) in toluene (200 mL) was added dropwise and the reaction mixture was maintained for 2 h. The reaction mixture was cooled to 0° C. and a solution of 2-chloronicotinoyl chloride (313 mmol) in toluene (200 mL) was added dropwise, while maintaining the temperature between 0 and 5° C. The resulting solution was allowed to warm to rt and was maintained for 2 h. The reaction mixture was diluted with 50 mL of water and the precipitated solids were collected by filtration to provide 104 g of crude diethyl 2-(2-chloronicotinoyl) malonate as a pink solid.

Water (1.3 mL) was added to a solution of diethyl 2-(2-chloronicotinoyl)malonate (31.7 mmol) in dimethylsulfoxide (50 mL). The pH of the reaction mixture was added adjusted to 5-6 by the addition of hydrochloric acid and the reaction mixture was heated at 130° C. for 2 h. The reaction mixture was then quenched with ice water (300 mL) and the aqueous layer was extracted with ethyl acetate (3×50 mL). The combined organic layers were washed with brine, dried (sodium sulfate), and concentrated. The residue was purified by chromatography (1/20 ethyl acetate/petroleum ether to provide 1-(2-chloropyridin-3-yl)ethanone in 56% yield as light yellow oil.

Ammonium hydroxide (368 mL) was added to a mixture of sulfur (386 mmol) and 1-(2-chloropyridin-3-yl)ethanone (350 mmol) and the slurry was diluted with methanol (960 mL). Ammonia gas was bubbled through the reaction mixture for 10 min and the reaction mixture was heated at 110° C. for 24 h. The reaction mixture was concentrated to dryness and the residue was extracted with water (3×500 mL). The aqueous layer was extracted with ethyl acetate (5×500 mL) and the combined organic layers were dried (magnesium sulfate) and concentrated. The residue was purified by chromatography (1/25 ethyl acetate/petroleum ether to provide 3-methylisothiazolo[5,4-b]pyridine in 67% yield as a light yellow solid.

A solution of m-chloroperbenzoic acid (160 mmol) in acetic acid (200 mL) was added dropwise to a solution of 3-methylisothiazolo[5,4-b]pyridine (107 mmol) in dichloromethane (200 mL). The reaction mixture was maintained for 6 h at 25° C. The reaction mixture was diluted with water (100 mL), the pH was adjusted to 8 with 10% sodium hydroxide, and the layers were separated. The aqueous layer was extracted with ethyl acetate (10×100 mL) and the combined organic layers were dried (magnesium sulfate) and concentrated to provide 3-methylisothiazolo[5,4-b]pyridine-N-oxide in 62% yield as a yellow solid.

A solution of triphosgene (190 mmol) in dichloromethane (200 mL) was added dropwise over 20 min to a solution of 3-methylisothiazolo [5,4-b]pyridine-N-oxide (47.4 mmol) in dichloromethane (150 mL) at −20° C. A solution of diisopropylamine (190 mmol) in dichloromethane (200 mL) was added dropwise over 1 h. The reaction mixture was allowed to warm to rt and was maintained for 16 h. The reaction mixture was quenched with water (40 mL) of water and the pH was adjusted to 7 by the addition of 10% sodium hydroxide. The organic layer was washed with water (100 mL). The combined aqueous layers were extracted with dichloromethane (10×100 mL) and the combined organic layers were dried (magnesium sulfate) and concentrated. The residue was purified by chromatography (1/80 ethyl acetate/petroleum ether) to provide 6-chloro-3-methylisothiazolo[5,4-b]pyridine in 46% yield as a colorless solid.

AIBN (1.35 mmol) was added to a solution of 6-chloro-3-methylisothiazolo[5,4-b]pyridine (13.5 mmol) and N-bromosuccinamide (27.1 mmol) in carbon tetrachloride (25 mL). The reaction mixture was heated at 80° C. for 6 h, allowed to cool to rt, and the precipitated solids were removed by filtration. The filtrate was concentrated to provide crude 3-(bromomethyl)-6-chloroisothiazolo[5,4-b]pyridine as yellow oil.

Water (8 mL) was added to a solution of 3-(bromomethyl)-6-chloroisothiazolo[5,4-b]pyridine (19.0 mmol) in dimethylsulfoxide (40 mL) and the reaction mixture was heated at 80° C. for 1.5 h. The reaction mixture was then quenched with water (50 mL) and the resulting solution was extracted with ethyl acetate (3×40 mL). The combined organic layers were dried (magnesium sulfate) and concentrated to provide the crude (6-chloroisothiazolo[5,4-b]pyridin-3-yl) methanol as a yellow solid.

Potassium permanganate (1.69 mmol) was added in several batches a solution of (6-chlorobenzo[d]isothiazol-3-yl) methanol (2.50 mmol) in water (3 mL). Potassium carbonate (2.90 mmol) was added and the reaction mixture was maintained for 30 min at 25° C. The insoluble materials were removed by filtration and the aqueous layer was extracted with ethyl acetate (3×10 mL). The pH of the aqueous layer was adjusted to 3-4 by the addition of 1 N hydrochloric acid and the reaction mixture was maintained for 10 min. The solids were collected by filtration to provide 6-chlorobenzo [d]isothiazole-3-carboxylic acid in 15% yield as a white solid.

The following acid was made using this method:
6-Chloroisothiazolo[5,4-b]pyridine-3-carboxylic acid.
Procedure 28

Procedure 28 provides a preparation of N-acylated aminobenzisothiazole-3-carboxylic acids from the corresponding aminobenzisothiazole-3-carboxylic esters.

Cyclopropanecarbonyl chloride (0.37 mmol) and N,N-diisopropylethylamine (0.49 mmol) were added to a solution of ethyl 6-piperazin-1-yl-1,2-benzisothiazole-3-carboxylate (0.12 mmol) in methylene chloride (3.0 mL) and the reaction mixture was maintained for 1 h at rt. The reaction mixture was quenched with methanol (10 mL) and the mixture was maintained for an additional 30 min. The reaction mixture was poured onto a 5 g SCX column and the product was eluted with methanol (20 mL). A 5.0 M solution of sodium hydroxide in water (1.2 mL) was added to the methanol solution and the mixture was maintained for 2 h. The reaction mixture was diluted with water (50 mL) and neutralized with a 6N solution of hydrochloric acid (1.5 mL). The pH was further adjusted to between 5 and 7 with acetic acid. The precipitated solids were collected by filtration to provide the acid in 88% yield.

The following acids were prepared using this method:
6-[4-(Cyclopropylcarbonyl)piperazin-1-yl]-1,2-benzisothiazole-3-carboxylic acid.
6-[1-(Cyclopropylcarbonyl)octahydro-6H-pyrrolo [3,4-b] pyridin-6-yl]-1,2-benzisothiazole-3-carboxylic acid.
6-[(1S,4S)-5-(Cyclopropylcarbonyl)-2,5-diazabicyclo [2.2.1]hept-2-yl]-1,2-benzisothiazole-3-carboxylic acid.
Procedure 29

Procedure 29 provides a preparation of nitrile substituted indazole-3-carboxylic acids from the corresponding bromoindazole-3-carboxylic esters.

Zinc Cyanide (1.00 mmol) was added to a solution of ethyl 6-bromo-1H-indazole-3-carboxylate (0.502 mmol) and tetrakis(triphenylphosphine)palladium(0) (0.0502 mmol) in N,N-dimethylformamide (5.00 mL) and the reaction mixture was heated at 100° C. for 16 h. The reaction mixture was diluted with ethyl acetate and water and the layers were separated. The aqueous layer was extracted with ethyl acetate (2×) and the combined organic layers were washed with brine and dried (sodium sulfate). The residue was purified by chromatography 70/30 to 50/50 hexane/ethyl acetate to provide the nitrile in 65% yield. The ester was hydrolyzed with sodium hydroxide in ethanol to provide the acid.

The following acid and ester were prepared using this procedure:
Ethyl 6-cyano-1H-indazole-3-carboxylate.
6-Cyano-1H-indazole-3-carboxylic acid.
Base Preparations.

The following procedures (30-35) detail the preparation of the bicyclobases and amines that were not commercially available.
Procedure 30

Procedure 30 provides a method for the preparation of N-alkylated 3-aminoquinuclidines from 3-aminoquinuclidine.

Acetyl chloride (12 mmol) was added dropwise to a solution of (R)-3-aminoquinuclidine (10 mmol) and N,N-diisopropylethylamine (30 mmol) in dichloromethane (100 mL). The resulting solution was maintained at rt for 4 h and was evaporated to dryness. The crude amide was dissolved in tetrahydrofuran (150 mL) and was treated with lithium aluminum hydride (66 mmol) in small portions. The reaction mixture was quenched with sodium sulfate decahydrate and the resulting slurry was diluted with tetrahydrofuran and filtered through Celite. The filtrate was concentrated and the residue was then diluted with freshly prepared methanolic hydrogen chloride (generated by the dropwise addition of 3 mL of acetyl chloride into 30 mL of methanol) and maintained at rt for 15 min. The residue obtained by the removal of the volatiles was recrystallized (2-propanol/methanol) to provide the secondary amine in 41% yield as a colorless solid.

The following bases were prepared using this method:
(3R)-N-(Methyl)quinuclidin-3-amine dihydrochloride.
(3S)-N-(Methyl)quinuclidin-3-amine dihydrochloride.
Procedure 31

Procedure 31 provides a method for the preparation of cyclic ureas from diamines.

Carbonic acid, dimethyl ester (10.0 mmol) was added dropwise to a mixture of N-propyl-1,2-ethanediamine(10.0 mmol) and cesium carbonate (2.00 mmol) and the reaction mixture was heated at 70° C. for 1 h. The reaction mixture was concentrated and the residue was heated at 130° C. for 3 h. The reaction mixture was concentrated and the residue was purified by chromatography [(50/50 to 0/100)hexane/ethyl acetate] to provide the product (60%) as an oil.

The following cyclic urea was prepared using this method:
1-Propylimidazolidin-2-one.
1-Ethylimidazolidin-2-one.
Procedure 32

Procedure 32 provides a method for the preparation of 3-alkoxypyrrolidines from N-Boc-3-hydroxypyrrolidine.

1-Boc-3-hydroxypyrrolidine (16.1 mmol) was added in portions to a suspension of sodium hydride (22.0 mmol) in tetrahydrofuran (40 mL) at 0° C. The reaction mixture was diluted with tetrahydrofuran (60 mL) and allowed to warm to rt. Methyl iodide (21.0 mmol) was added to the cloudy suspension after 1 h and the reaction mixture was maintained at rt for 6 h. The reaction mixture was concentrated and redissolved in ethyl acetate (100 mL). The extract was washed with saturated ammonium chloride (20 mL), water (20 mL), and brine (20 mL) and was dried (sodium sulfate). The residue was purified by chromatography (1/4 ethyl acetate/hexane) to give the ether. The N-Boc product was dissolved in tetrahydrofuran (30 mL) and 6 N hydrochloric acid (20 mL) was added. The resultant mixture was stirred for 1 h and was concentrated to give an oil. Toluene (10 mL) and ethanol (10 mL) were added and the mixture was concentrated to give 1.79 g of brownish, very hygroscopic solid. The solid was suspended in ethyl acetate and stirred vigorously for 12 h. The solids were quickly collected by filtration and dried under high vacuum to give the product (81%) as a colorless solid.

An alternative procedure used for the removal of the N-Boc groups entails exposure to trifluoroacetic acid for 4 h. followed by concentration of the reaction mixture. This procedure may be useful for the production of the amine as a free base.

The following amine was prepared using this procedure:
3-Methoxypyrrolidine hydrochloride.

The free base was obtained by neutralization of the salt residue with saturated sodium carbonate (5 mL), extraction with 9/1 dichloromethane/methanol (3×20 mL), drying (potassium carbonate), and concentration, followed by capturing the amine on a SCX column and eluting with 2M ammonia in methanol:
3-Methoxypyrrolidine.
3-Ethoxypyrrolidine.
(3R)-3-Methoxypyrrolidine.
(3S)-3-Methoxypyrrolidine.
3-(Methoxymethyl)pyrrolidine
Procedure 33

Procedure 33 provides a preparation of SEM protected hydroxypyrrolidines from hydroxypyrrolidine.

A solution of 1-Boc-3-hydroxy-pyrrolidine (26.7 mmol) in tetrahydrofuran (20 mL) was added slowly to a suspension of sodium hydride (30.8 mmol) in tetrahydrofuran (78 mL) and the reaction mixture was maintained for 30 min. A solution of [β-(trimethylsilyl)ethoxy]methyl chloride (30.7 mmol) in tetrahydrofuran (4.4 mL) was added and the reaction mixture was maintained for 18 h. The reaction was partitioned between water (50 mL) and ethyl acetate (50 mL) and the layers were separated. The organic layer was washed with brine (25 mL), dried (magnesium sulfate), and concentrated. The residue was purified by chromatography 95/5 to 80/20 hexanes/ethyl acetate to provide the Boc-protected product. The residue was heated neat at 350° C. for 3 h. The resulting brown oil was purified by chromatography [100/0 to 80/20 ethyl acetate/(50/50/2 ethyl acetate/methanol/dimethylethylamine)] to give a brown oil after concentration. The oil was dissolved in ethanol and the solution was treated with activated carbon, filtered, and concentrated to provide the product in 52% yield.

The following amine was prepared using this method:
3-{[2-(Trimethylsilyl)ethoxy]methoxy}pyrrolidine.
Procedure 34

Procedure 34 provides a preparation of 3-trifluoromethoxypyrrolidine from hydroxypyrrolidine.

A solution of 1-Boc-3-hydroxypyrrolidine (26.7 mmol) in tetrahydrofuran (20 mL) was added slowly to a suspension of sodium hydride (30.8 mmol) in tetrahydrofuran (78 mL) at 0° C. Chlorodifluoromethane (30.7 mmol) was added to the reaction and the reaction mixture was allowed to warm to rt where it was maintained for 18 h. The reaction was partitioned between water (50 mL) and ethyl acetate (50 mL) and the layers were separated. The organic layer was washed with brine (25 mL), dried (magnesium sulfate), and concentrated. The residue was purified by chromatography 95/5 to 80/20 hexanes/ethyl acetate to provide the Boc-protected product. The purified product (ca. 2 g) was dissolved in a 4/1 mixture of dichloromethane/trifluoroacetic acid (20.0 mL) and was maintained for 4 h. The solvent was removed and the residue was purified by chromatography [100/0 to 90/10 ethyl acetate/(50/50/2 ethyl acetate/methanol/dimethylethylamine)]. The product was unexpectedly volatile and much of it was lost on concentration. The final yield for the product was 2%.

The following amine was prepared using this method:
3-(Difluoromethoxy)pyrrolidine.
Procedure 35

Procedure 35 provides a preparation of 3-cyclopropylmethoxypyrrolidine from hydroxypyrrolidine.

A solution of 3-hydroxy-pyrrolidine-hydrochloride (162 mmol) in tetrahydrofuran (100 mL) was treated with potassium carbonate (210 mmol) and a solution of benzyl chloroformate (210 mmol) in tetrahydrofuran (50 mL). The resulting solution was maintained for 16 h at rt. The reaction mixture was concentrated and the residue was dissolved in ethyl acetate (200 mL). The solution was washed with brine (3×100 mL), dried (magnesium sulfate), and concentrated to provide the protected amine in 90% yield as a yellow liquid.

Sodium hydride (280 mmol) was added in portions to a cold (0° C.) solution of benzyl 3-hydroxypyrrolidine-1-carboxylate (76.9 mmol) in N,N-dimethylformamide (100 mL). The mixture was maintained for 60 min and was then treated with a solution of (bromomethyl)cyclopropane (231 mmol) in N,N-dimethylformamide (100 mL) and potassium iodide (0.66 mmol). The reaction mixture was allowed to warm to rt where it was maintained for 30 min. The reaction mixture was subjected to microwave irradiation for 2 h at 90° C. The reaction mixture was concentrated and the residue was diluted with ethyl acetate (200 mL) and water (200 mL) and the layers were separated. The aqueous layer was extracted with ethyl acetate (3×200 mL) and the combined organic layers were washed with brine (2×200 mL) and dried (magnesium sulfate). The residue was purified by chromatography (20/1 petroleum ether/ethyl acetate) to provide the product in 81% yield.

A suspension of benzyl 3-(cyclopropylmethoxy)pyrrolidine-1-carboxylate (17.4 mmol) and 10% palladium on carbon (600 mg) in ethyl acetate (20 mL) and methanol (20 mL) was placed under an atmosphere of hydrogen gas. The reaction mixture was maintained for 16 h and was filtered through Celite. The filtrate was concentrated to provide the product in 86% yield as a yellow liquid.

The following amine was prepared using this method:
3-(Cyclopropylmethoxy)pyrrolidine.
Representative Procedures.

The following procedures (A-AA) detail the preparation of the bicyclobase analogs.

Procedure A

Procedure A provides a method for the coupling between 3-aminoquinuclidine and benzisoxazole carboxylic esters to form carboxamide derivatives.

The suspension of (S)-3-aminoquinuclidine hydrochloride (3.50 mmol) in ethanol (5 mL) was treated with N,N-diisopropylethylamine (4.00 mmol). Ethyl 6-bromo-1,2-benzisoxazole-3-carboxylate (1.86 mmol) was added and the suspension was heated at 85° C. for 3 d. The reaction mixture was allowed to cool to rt, was diluted with dichloromethane (30 mL), and was washed with 10 mL of saturated sodium bicarbonate. The aqueous layer was back-extracted with dichloromethane (30 mL) and the combined organic layers were washed with brine and dried (sodium sulfate). The organic layer was loaded on a 10 g SCX column. The column was washed with methanol (50 mL), 2 M ammonia in methanol (60 mL) and the ammonia wash was concentrated. The residue was purified by chromatography [40/60 to 0/100 ethyl acetate/(70/30/1 ethyl acetate/methanol/ammonium hydroxide)] to provide the product in 63% yield as a colorless oil.

The following compound was prepared using this method:
86) N-[(3R)-1-Azabicyclo[2.2.2]oct-3-yl]-6-methoxy-1,2-benzisoxazole-3-carboxamide, $^1$H NMR (CD$_3$OD) δ 7.94 (d, 1H, J=8.8), 7.24 (d, 1H, J=2), 7.06 (dd, 1H, J=2.1, 8.7), 4.51 (m, 1H), 3.91 (s, 1H), 3.84 (m, 1H), 3.38 (m, 1H), 2.38 (m, 1H), 2.22 (m, 1H), 2.09 (m, 2H), 1.94 (m, 1H); LC/MS (EI) $t_R$ 3.37, m/z 302.1 (M$^+$+1):
N-[(3S)-1-Azabicyclo[2.2.2]oct-3-yl]-6-bromo-1,2-benzisoxazole-3-carboxamide.

Procedure B

Procedure B provides a method for the coupling between 3-aminoquinuclidine and benzisothiazole carboxylic acids to form carboxamide derivatives.

To a solution of the benzisothiazole-3-carboxylic acid (0.30 mmol) in a 5/1 mixture of tetrahydrofuran/N,N-dimethylformamide (12 mL) was added diisopropylethylamine (1.1 mmol) and (R)-3-aminoquinuclidine dihydrochloride (0.6 mmol). The mixture was cooled to 0° C., and HATU (0.3 mmol) was added in one portion. The reaction mixture was allowed to warm to rt and was maintained for 16 h. The mixture was partitioned between saturated aqueous potassium carbonate solution and a 95/5 mixture of dichloromethane/methanol. The aqueous layer was extracted with 95/5 dichloromethane/methanol (2X), and the combined organic layers were washed with brine and dried over sodium sulfate. Alternatively, the reaction mixture was loaded on a 10 g SCX column and the column was washed with methanol (50 mL), 2 M ammonia in methanol (60 mL) and the ammonia wash was concentrated. The crude product was purified by chromatography 100/0 to 30/70 ethyl acetate/[(50/50/2)ethyl acetate/methanol/dimethylethylamine] or by preparative HPLC, thus providing the amide in 75% yield as a colorless solid.

The following compounds were prepared using this method:

84) N-[(3R)-1-Azabicyclo[2.2.2]oct-3-yl]-6-[(3R)-3-methoxypyrrolidin-1-yl]-1,2-benzisothiazole-3-carboxamide, $^1$H NMR (CD$_3$OD) δ 8.47 (d, J=9.1, 1H); 6.98 (d, J=1.9, 1H); 6.88 (dd, J=2.0/9.2, 1H); 4.30 (m, 1H); 4.16 (m, 1H); 3.60-3.35 (m, 5H); 3.38 (s, 3H); 3.3-2.95 (m, 5H); 2.30-2.00 (m, 4H); 1.92 (m, 2H); 1.61 (m, 1H); LC/MS (EI) $t_R$ 3.84, m/z 387.2 (M$^+$+1):

85) N-[(3R)-1-Azabicyclo[2.2.2]oct-3-yl]-6-[(3S)-3-methoxypyrrolidin-1-yl]-1,2-benzisothiazole-3-carboxamide, LC/MS (EI) $t_R$ 3.91, m/z 387.2 (M$^+$+1);

87) N-[(3S)-1-Azabicyclo[2.2.2]oct-3-yl]-6-(3-ethoxypyrrolidin-1-yl)-7-fluoro-1,2-benzisothiazole-3-carboxamide, LC/MS (EI) $t_R$ 4.82, m/z 419.1 (M$^+$+1);

92) N-[(3R)-1-Azabicyclo[2.2.2]oct-3-yl]-7-fluoro-6-(3-methoxypyrrolidin-1-yl)-1,2-benzisothiazole-3-carboxamide, LC/MS (EI) $t_R$ 5.11, m/z 405.2 (M$^+$+1);

93) N-[(3S)-1-Azabicyclo[2.2.2]oct-3-yl]-7-fluoro-6-(3-methoxypyrrolidin-1-yl)-1,2-benzisothiazole-3-carboxamide, LC/MS (EI) $t_R$ 5.08, m/z 405.2 (M$^+$+1);

94) N-[(3S)-1-Azabicyclo[2.2.2]oct-3-yl]-6-[(3R)-3-hydroxypyrrolidin-1-yl]-1,2-benzisothiazole-3-carboxamide, LC/MS (EI) $t_R$ 4.25, m/z 373.1 (M$^+$+1);

95) N-[(3S)-1-Azabicyclo[2.2.2]oct-3-yl]-6-[(3S)-3-hydroxypyrrolidin-1-yl]-1,2-benzisothiazole-3-carboxamide, LC/MS (EI) $t_R$ 4.23, m/z 373.1 (M$^+$+1);

96) N-[(3S)-1-Azabicyclo[2.2.2]oct-3-yl]-6-[(3S)-3-(dimethylamino)pyrrolidin-1-yl]-1,2-benzisothiazole-3-carboxamide, LC/MS (EI) $t_R$ 1.92, m/z 400.2 (M$^+$+1);

97) N-[(3S)-1-Azabicyclo[2.2.2]oct-3-yl]-6-[(1S,4S)-2-oxa-5-azabicyclo[2.2.1]hept-5-yl]-1,2-benzisothiazole-3-carboxamide, LC/MS (EI) $t_R$ 4.26, m/z 385.1 (M$^+$+1);

98) N-[(3R)-1-Azabicyclo[2.2.2]oct-3-yl]-6-[(3R)-3-hydroxypyrrolidin-1-yl]-1,2-benzisothiazole-3-carboxamide, LC/MS (EI) $t_R$ 4.27, m/z 373.1 (M$^+$+1);

99) N-[(3R)-1-Azabicyclo[2.2.2]oct-3-yl]-6-[(3S)-3-hydroxypyrrolidin-1-yl]-1,2-benzisothiazole-3-carboxamide, LC/MS (EI) $t_R$ 4.23, m/z 373.1 (M$^+$+1);

100) N-[(3R)-1-Azabicyclo[2.2.2]oct-3-yl]-6-[(3S)-3-(dimethylamino)pyrrolidin-1-yl]-1,2-benzisothiazole-3-carboxamide, LC/MS (EI) $t_R$ 1.89, m/z 400.2 (M$^+$+1);

101) N-[(3S)-1-Azabicyclo[2.2.2]oct-3-yl]-7-[(3R)-3-hydroxypyrrolidin-1-yl]-1,2-benzisothiazole-3-carboxamide, LC/MS (EI) $t_R$ 4.27, m/z 373.1 (M$^+$+1);

102) N-[(3S)-1-Azabicyclo[2.2.2]oct-3-yl]-7-[(3S)-3-hydroxypyrrolidin-1-yl]-1,2-benzisothiazole-3-carboxamide, LC/MS (EI) $t_R$ 4.26, m/z 373.1 (M$^+$+1);

103) N-[(3S)-1-Azabicyclo[2.2.2]oct-3-yl]-7-[(3S)-3-(dimethylamino)pyrrolidin-1-yl]-1,2-benzisothiazole-3-carboxamide, LC/MS (EI) $t_R$ 1.92, m/z 400.2 (M$^+$+1);

104) N-[(3S)-1-Azabicyclo[2.2.2]oct-3-yl]-7-[(1S,4S)-2-oxa-5-azabicyclo[2.2.1]hept-5-yl]-1,2-benzisothiazole-3-carboxamide, LC/MS (EI) $t_R$ 4.36, m/z 385.1 (M$^+$+1);

105) N-[(3R)-1-Azabicyclo[2.2.2]oct-3-yl]-7-[(3S)-3-(dimethylamino)pyrrolidin-1-yl]-1,2-benzisothiazole-3-carboxamide, LC/MS (EI) $t_R$ 1.81, m/z 400.2 (M$^+$+1);

106) N-[(3S)-1-Azabicyclo[2.2.2]oct-3-yl]isothiazolo[5,4-b]pyridine-3-carboxamide hydroformate, LC/MS (EI) $t_R$ 2.71, m/z 289.1 (M$^+$+1);

107) N-[(3R)-1-Azabicyclo[2.2.2]oct-3-yl]isothiazolo[5,4-b]pyridine-3-carboxamide hydroformate, LC/MS (EI) $t_R$ 2.48, m/z x289.1 (M$^+$+1);

114) N-[(3S)-1-Azabicyclo[2.2.2]oct-3-yl]-7-fluoro-6-methoxy-1,2-benzisothiazole-3-carboxamide, LC/MS (EI) $t_R$ 3.8, m/z 336.1 (M$^+$+1);

115) N-[(3R)-1-Azabicyclo[2.2.2]oct-3-yl]-7-fluoro-6-methoxy-1,2-benzisothiazole-3-carboxamide, LC/MS (EI) $t_R$ 3.81, m/z 336.1 (M$^+$+1);.

116) N-[(3R)-1-Azabicyclo[2.2.2]oct-3-yl]-6-[(1S,4S)-5-methyl-2,5-diazabicyclo[2.2.1]hept-2-yl]-1,2-benzisothiazole-3-carboxamide, LC/MS (EI) $t_R$ 1.84, m/z 398.2 (M$^+$+1);

117) N-[(3S)-1-Azabicyclo[2.2.2]oct-3-yl]-6-[(1S,4S)-5-methyl-2,5-diazabicyclo[2.2.1]hept-2-yl]-1,2-benzisothiazole-3-carboxamide, LC/MS (EI) $t_R$ 1.87, m/z 398.2 (M$^+$+1);

122) N-[(3R)-1-Azabicyclo[2.2.2]oct-3-yl]-6-[(1S,4S)-5-(2,2,2-trifluoroethyl)-2,5-diazabicyclo[2.2.1]hept-2-yl]-1,2-benzisothiazole-3-carboxamide, LC/MS (EI) $t_R$ 4.69, m/z 466.1 (M$^+$+1);

123) N-[(3R)-1-Azabicyclo[2.2.2]oct-3-yl]-6-{3-[methyl(2,2,2-trifluoroethyl)amino]pyrrolidin-1-yl}-1,2-benzisothiazole-3-carboxamide, LC/MS (EI) $t_R$ 4.77, m/z 468.1 (M$^+$+1);

124) N-[(3S)-1-Azabicyclo[2.2.2]oct-3-yl]-6-{3-[methyl(2,2,2-trifluoroethyl)amino]pyrrolidin-1-yl}-1,2-benzisothiazole-3-carboxamide, LC/MS (EI) $t_R$ 4.75, m/z 468.1 (M$^+$+1);

125) N-[(3S)-1-Azabicyclo[2.2.2]oct-3-yl]-6-[3-(methoxymethyl)pyrrolidin-1-yl]-1,2-benzisothiazole-3-carboxamide, LC/MS (EI) $t_R$ 4.98, m/z 401.1 (M$^+$+1);

126) N-[(3R)-1-Azabicyclo[2.2.2]oct-3-yl]-6-[3-(methoxymethyl)pyrrolidin-1-yl]-1,2-benzisothiazole-3-carboxamide, LC/MS (EI) $t_R$ 4.94, m/z 401.1 (M$^+$+1);

127) N-[(3R)-1-Azabicyclo[2.2.2]oct-3-yl]-6-[(3R)-3-(dimethylamino)pyrrolidin-1-yl]-1,2-benzisothiazole-3-carboxamide, LC/MS (EI) $t_R$ 1.55, m/z 400.2 (M$^+$+1);

128) N-[(3S)-1-Azabicyclo[2.2.2]oct-3-yl]-6-[(3R)-3-(dimethylamino)pyrrolidin-1-yl]-1,2-benzisothiazole-3-carboxamide, LC/MS (EI) $t_R$ 1.55, m/z 400.1 (M$^+$+1);

129) N-[(3S)-1-Azabicyclo[2.2.2]oct-3-yl]-6-[4-(dimethylamino)piperidin-1-yl]-1,2-benzisothiazole-3-carboxamide LC/MS (EI) $t_R$ 1.59, m/z 414.1 (M$^+$+1).;

130) N-[(3R)-1-Azabicyclo[2.2.2]oct-3-yl]-6-[4-(dimethylamino)piperidin-1-yl]-1,2-benzisothiazole-3-carboxamide, LC/MS (EI) $t_R$ 1.61, m/z 414.2 (M$^+$+1);

177) N-[(3R)-1-Azabicyclo[2.2.2]oct-3-yl]-6-[4-(cyclopropylcarbonyl)piperazin-1-yl]-1,2-benzisothiazole-3-carboxamide, LC/MS (EI) $t_R$ 3.30, m/z 440 (M$^+$+1);

178) N-[(3S)-1-Azabicyclo[2.2.2]oct-3-yl]-6-[4-(cyclopropylcarbonyl)piperazin-1-yl]-1,2-benzisothiazole-3-carboxamide, LC/MS (EI) $t_R$ 3.30, m/z 440 (M$^+$+1);

179) N-[(3R)-1-Azabicyclo[2.2.2]oct-3-yl]-6-[1-(cyclopropylcarbonyl)octahydro-6H-pyrrolo[3,4-b]pyridin-6-yl]-1,2-benzisothiazole-3-carboxamide, LC/MS (EI) $t_R$ 3.81, m/z 480 (M$^+$+1);

180) N-[(3S)-1-Azabicyclo[2.2.2]oct-3-yl]-6-[1-(cyclopropylcarbonyl)octahydro-6H-pyrrolo[3,4-b]pyridin-6-yl]-1,2-benzisothiazole-3-carboxamide, LC/MS (EI) $t_R$ 3.85, m/z 480 (M$^+$+1);

181) N-[(3R)-1-Azabicyclo[2.2.2]oct-3-yl]-6-[(1S,4S)-5-(cyclopropylcarbonyl)-2,5-diazabicyclo[2.2.1]hept-2-yl]-1,2-benzisothiazole-3-carboxamide, LC/MS (EI) $t_R$ 3.97, m/z 452 (M$^+$+1);

182) N-[(3S)-1-Azabicyclo[2.2.2]oct-3-yl]-6-[(1S,4S)-5-(cyclopropylcarbonyl)-2,5-diazabicyclo[2.2.1]hept-2-yl]-1,2-benzisothiazole-3-carboxamide, LC/MS (EI) $t_R$ 3.04, m/z 452 (M$^+$+1);

183) N-[(3R)-1-Azabicyclo[2.2.2]oct-3-yl]-6-(3,4-dimethylpiperazin-1-yl)-1,2-benzisothiazole-3-carboxamide, LC/MS (EI) $t_R$ 1.30, m/z 400 (M$^+$+1);

132) N-[(3S)-1-Azabicyclo[2.2.2]oct-3-yl]-N-methyl-6-[(1S,4S)-5-methyl-2,5-diazabicyclo[2.2.1]hept-2-yl]-1,2-benzisothiazole-3-carboxamide dihydroformate, LC/MS (EI) $t_R$ 3.27, m/z 412.2 (M$^+$+1);

133) N-[(3R)-1-Azabicyclo[2.2.2]oct-3-yl]-N-methyl-6-[(1S,4S)-5-methyl-2,5-diazabicyclo[2.2.1]hept-2-yl]-1,2-benzisothiazole-3-carboxamide dihydroformate, LC/MS (EI) $t_R$ 3.19, m/z 412.2 (M$^+$+1);

134) N-[(3R)-1-Azabicyclo[2.2.2]oct-3-yl]-6-[(1R,4R)-5-methyl-2,5-diazabicyclo[2.2.1]hept-2-yl]-1,2-benzisothiazole-3-carboxamide, LC/MS (EI) $t_R$ 3.26, m/z 398.2 (M$^+$+1);

135) N-[(3S)-1-Azabicyclo[2.2.2]oct-3-yl]-6-[(1R,4R)-5-methyl-2,5-diazabicyclo[2.2.1]hept-2-yl]-1,2-benzisothiazole-3-carboxamide, LC/MS (EI) $t_R$ 3.2, m/z 398.2 (M$^+$+1);

136) N-[(3R)-1-Azabicyclo[2.2.2]oct-3-yl]-6-(1,4-diazabicyclo[3.2.2]non-4-yl)-1,2-benzisothiazole-3-carboxamide dihydroformate, LC/MS (EI) $t_R$ 1.61, m/z 412.2 (M$^+$+1);

137) N-[(3S)-1-Azabicyclo[2.2.2]oct-3-yl]-6-(1,4-diazabicyclo[3.2.2]non-4-yl)-1,2-benzisothiazole-3-carboxamide dihydroformate, LC/MS (EI) $t_R$ 3.51, m/z 412.1 (M$^+$+1);

138) N-[(3R)-1-Azabicyclo[2.2.2]oct-3-yl]-6-pyrrolidin-1-yl-1,2-benzisothiazole-3-carboxamide, LC/MS (EI) $t_R$ 4.66, m/z 357.2 (M$^+$+1);

139) N-[(3R)-1-Azabicyclo[2.2.2]oct-3-yl]-6-(4-methylpiperazin-1-yl)-1,2-benzisothiazole-3-carboxamide, LC/MS (EI) $t_R$ 1.67, m/z 386.2 (M$^+$+1);

140) N-[(3S)-1-Azabicyclo[2.2.2]oct-3-yl]-6-(4-methylpiperazin-1-yl)-1,2-benzisothiazole-3-carboxamide, LC/MS (EI) $t_R$ 1.63, m/z 386.2 (M$^+$+1);

141) N-[(3R)-1-Azabicyclo[2.2.2]oct-3-yl]-6-(4-methyl-1,4-diazepan-1-yl)-1,2-benzisothiazole-3-carboxamide, LC/MS (EI) $t_R$ 1.8, m/z 400.2(M$^+$+1);

142) N-[(3S)-1-Azabicyclo[2.2.2]oct-3-yl]-6-(4-methyl-1,4-diazepan-1-yl)-1,2-benzisothiazole-3-carboxamide, LC/MS (EI) $t_R$ 1.84, m/z 400.2 (M$^+$+1);

143) N-[(3R)-1-Azabicyclo[2.2.2]oct-3-yl]-6-(hexahydropyrrolo[1,2-a]pyrazin-2(1H)-yl)-1,2-benzisothiazole-3-carboxamide, LC/MS (EI) $t_R$ 1.79, m/z 412.1 (M$^+$+1);

144) N-[(3S)-1-Azabicyclo[2.2.2]oct-3-yl]-6-(hexahydropyrrolo[1,2-a]pyrazin-2(1H)-yl)-1,2-benzisothiazole-3-carboxamide, LC/MS (EI) $t_R$ 1.81, m/z 412.2 (M$^+$+1);

145) N-[(3R)-1-Azabicyclo[2.2.2]oct-3-yl]-6-(5-methyl-2,5-diazabicyclo[2.2.2]oct-2-yl)-1,2-benzisothiazole-3-carboxamide, LC/MS (EI) $t_R$ 1.88, m/z 412.2 (M$^+$+1);

146) N-[(3S)-1-Azabicyclo[2.2.2]oct-3-yl]-6-(5-methyl-2,5-diazabicyclo[2.2.2]oct-2-yl)-1,2-benzisothiazole-3-carboxamide, LC/MS (EI) $t_R$ 1.88, m/z 412.2 (M$^+$+1);

147) N-[(3R)-1-Azabicyclo[2.2.2]oct-3-yl]-6-(8-methyl-3,8-diazabicyclo[3.2.1]oct-3-yl)-1,2-benzisothiazole-3-carboxamide, LC/MS (EI) $t_R$ 1.95, m/z 412.2 (M$^+$+1);

148) N-[(3S)-1-Azabicyclo[2.2.2]oct-3-yl]-6-(8-methyl-3,8-diazabicyclo[3.2.1]oct-3-yl)-1,2-benzisothiazole-3-carboxamide, LC/MS (EI) $t_R$ 1.93, m/z 412.2 (M$^+$+1);

149) N-[(3R)-1-Azabicyclo[2.2.2]oct-3-yl]-6-[(1S,4S)-5-cyclopropyl-2,5-diazabicyclo[2.2.1]hept-2-yl]-1,2-benzisothiazole-3-carboxamide, LC/MS (EI) $t_R$ 3.08, m/z 424.1 (M$^+$+1);

150) N-[(3S)-1-Azabicyclo[2.2.2]oct-3-yl]-6-[(1S,4S)-5-cyclopropyl-2,5-diazabicyclo[2.2.1]hept-2-yl]-1,2-benzisothiazole-3-carboxamide, LC/MS (EI) $t_R$ 3.24, m/z 424.1 (M$^+$+1);

151) N-[(3R)-1-Azabicyclo[2.2.2]oct-3-yl]-6-[(1S,4S)-5-(cyclopropylmethyl)-2,5-diazabicyclo[2.2.1]hept-2-yl]-1,2-benzisothiazole-3-carboxamide, LC/MS (EI) $t_R$ 1.31, m/z 438.2 (M$^+$+1);

152) N-[(3S)-1-Azabicyclo[2.2.2]oct-3-yl]-6-[(1S,4S)-5-(cyclopropylmethyl)-2,5-diazabicyclo[2.2.1]hept-2-yl]-1,2-benzisothiazole-3-carboxamide, LC/MS (EI) $t_R$ 1.31, m/z 438.2 (M$^+$+1);

153) N-[(3S)-1-Azabicyclo[2.2.2]oct-3-yl]-5-(4-methyl-1,4-diazepan-1-yl)-1,2-benzisothiazole-3-carboxamide, LC/MS (EI) $t_R$ 2.14, m/z 400.2 (M$^+$+1);

154) N-[(3R)-1-Azabicyclo[2.2.2]oct-3-yl]-5-[(3R)-3-methoxypyrrolidin-1-yl]-1,2-benzisothiazole-3-carboxamide, LC/MS (EI) $t_R$ 3.57, m/z 387.2 (M$^+$+1);

155) N-[(3S)-1-Azabicyclo[2.2.2]oct-3-yl]-5-[(3R)-3-methoxypyrrolidin-1-yl]-1,2-benzisothiazole-3-carboxamide, LC/MS (EI) $t_R$ 3.57, m/z 387.2 (M$^+$+1);

156) N-[(3R)-1-Azabicyclo[2.2.2]oct-3-yl]-5-[(3S)-3-methoxypyrrolidin-1-yl]-1,2-benzisothiazole-3-carboxamide, LC/MS (EI) $t_R$ 3.56, m/z 387.2 (M$^+$+1);

157) N-[(3R)-1-Azabicyclo[2.2.2]oct-3-yl]-6-[(1-methylpyrrolidin-3-yl)oxy]-1,2-benzisothiazole-3-carboxamide, LC/MS (EI) $t_R$ 1.25, m/z 387.2 (M$^+$+1);

158) N-[(3S)-1-Azabicyclo[2.2.2]oct-3-yl]-6-[(1-methylpyrrolidin-3-yl)oxy]-1,2-benzisothiazole-3-carboxamide, LC/MS (EI) $t_R$ 1.25, m/z 387.2 (M$^+$+1);

159) N-[(3R)-1-Azabicyclo[2.2.2]oct-3-yl]-6-(1-azabicyclo[2.2.2]oct-3-yloxy)-1,2-benzisothiazole-3-carboxamide, LC/MS (EI) $t_R$ 1.33, m/z 413.2 (M$^+$+1);

160) N-[(3S)-1-Azabicyclo[2.2.2]oct-3-yl]-6-(1-azabicyclo[2.2.2]oct-3-yloxy)-1,2-benzisothiazole-3-carboxamide, LC/MS (EI) $t_R$ 1.32, m/z 413.2 (M$^+$+1);

N-[(3S)-1-Azabicyclo[2.2.2]oct-3-yl]-5-(bromo)-1,2-benzisothiazole-3-carboxamide;

N-[(3S)-1-Azabicyclo[2.2.2]oct-3-yl]-6-(bromo)-1,2-benzisothiazole-3-carboxamide;

N-[(3R)-1-Azabicyclo[2.2.2]oct-3-yl]-6-(bromo)-1,2-benzisothiazole-3-carboxamide;

N-[(3S)-1-Azabicyclo[2.2.2]oct-3-yl]-6-(methoxy)-1,2-benzisothiazole-3-carboxamide.

The following compounds were prepared using this procedure, followed by treatment with trifluoroacetic acid, isolation by ion exchange, and purification by chromatography or preparative HPLC as described above:

118) N-[(3R)-1-Azabicyclo[2.2.2]oct-3-yl]-6-[(1S,4S)-2,5-diazabicyclo[2.2.1]hept-2-yl]-1,2-benzisothiazole-3-carboxamide, LC/MS (EI) $t_R$ 1.87, m/z 384.1 (M$^+$+1);

119) N-[(3S)-1-Azabicyclo[2.2.2]oct-3-yl]-6-[(1S,4S)-2,5-diazabicyclo[2.2.1]hept-2-yl]-1,2-benzisothiazole-3-carboxamide, LC/MS (EI) $t_R$ 1.87, m/z 384.1 (M$^+$+1);

120) N-[(3S)-1-Azabicyclo[2.2.2]oct-3-yl]-6-[3-(methylamino)pyrrolidin-1-yl]-1,2-benzisothiazole-3-carboxamide, LC/MS (EI) $t_R$ 1.96, m/z 386.1 (M$^+$+1);

121) N-[(3R)-1-Azabicyclo[2.2.2]oct-3-yl]-6-[3-(methylamino)pyrrolidin-1-yl]-1,2-benzisothiazole-3-carboxamide, LC/MS (EI) $t_R$ 1.94, m/z 386.2 (M$^+$+1);

168) N-[(3R)-1-Azabicyclo[2.2.2]oct-3-yl]-6-(3-methylpiperazin-1-yl)-1,2-benzisothiazole-3-carboxamide, LC/MS (EI) $t_R$ 1.28, m/z 386.2 (M$^+$+1);

169) N-[(3R)-1-Azabicyclo[2.2.2]oct-3-yl]-6-(octahydro-6H-pyrrolo[3,4-b]pyridin-6-yl)-1,2-benzisothiazole-3-carboxamide, LC/MS (EI) $t_R$ 1.33, m/z 412.2 (M$^+$+1);

170) N-[(3S)-1-Azabicyclo[2.2.2]oct-3-yl]-6-(octahydro-6H-pyrrolo [3,4-b]pyridin-6-yl)-1,2-benzisothiazole-3-carboxamide, LC/MS (EI) $t_R$ 1.35, m/z 412.2 (M$^+$+1);

171) N-[(3S)-1-Azabicyclo[2.2.2]oct-3-yl]-6-piperazin-1-yl-1,2-benzisothiazole-3-carboxamide, LC/MS (EI) $t_R$ 1.29, m/z 372 (M$^+$+1);

172) N-[(3R)-1-Azabicyclo[2.2.2]oct-3-yl]-6-piperazin-1-yl-1,2-benzisothiazole-3-carboxamide, LC/MS (EI) $t_R$ 1.47, m/z 372 (M$^+$+1);

173) N-[(3R)-1-Azabicyclo[2.2.2]oct-3-yl]-6-(1,4-diazepan-1-yl)-1,2-benzisothiazole-3-carboxamide, LC/MS (EI) $t_R$ 1.74, m/z 386 (M$^+$+1);

174) N-[(3S)-1-Azabicyclo[2.2.2]oct-3-yl]-6-(1,4-diazepan-1-yl)-1,2-benzisothiazole-3-carboxamide, LC/MS (EI) $t_R$ 1.70, m/z 386 (M$^+$+1);

175) N-[(3R)-1-Azabicyclo[2.2.2]oct-3-yl]-6-(2-methylpiperazin-1-yl)-1,2-benzisothiazole-3-carboxamide, LC/MS (EI) $t_R$ 1.57, m/z 386 (M$^+$+1);

176) N-[(3S)-1-Azabicyclo[2.2.2]oct-3-yl]-6-(2-methylpiperazin-1-yl)-1,2-benzisothiazole-3-carboxamide, LC/MS (EI) $t_R$ 1.55, m/z 386 (M$^+$+1).

Procedure C

Procedure C provides a method for the coupling between 3-aminoquinuclidine and carboxylic acids to form carboxamide derivatives.

To a solution of the carboxylic acid (16.1 mmol) in N,N-dimethylformamide (65 mL) was added HBTU (16.1 mmol), catalytic amount of dimethylaminopyridine, N,N-diisopropylethylamine (96.6 mmol) and 4 Å activated molecular sieves (2.6 g). The reaction mixture was maintained at room temperature for 2 h under nitrogen and then 3-aminoquinuclidine dihydrochloride (16.1 mmol) was added. After 18 h, the solvent was removed under reduced pressure. The oily residue was partitioned between saturated, aqueous sodium bicarbonate (25 mL) and dichloromethane (100 mL). The aqueous layer was further extracted with 9/1 dichloromethane/methanol (5×100 mL) and the combined organic layers were concentrated. The residue was purified by chromatography [90/10/1 dichloromethane/methanol/ammonium hydroxide or 1/1 to 0/1 ethyl acetate/(70/30/1 ethyl acetate/methanol/ammonium hydroxide)]or by preparative HPLC, thus providing the product in 30%-70% yield.

The following compounds were prepared using this method:

42) N-[(3R)-1-Azabicyclo[2.2.2]oct-3-yl]-5-methoxy-N-methyl-1H-indazole-3-carboxamide hydroformate. $^1$H NMR (CD$_3$OD) δ 8.42 (br s, 1H), 7.49 (d, J=9.1, 1H), 7.38 (d, J=2.1, 1H), 7.09 (dd, J=9.1, 2.4, 1H), 4.89 (m, 1H), 3.85 (s, 3H), 3.83 (m, 2H), 3.60-3.46 (m, 1H), 3.38-3.30 (m, 2H), 2.57 (m, 2H), 2.36-2.30 (m, 1H), 2.10-1.97 (m, 3H); LC/MS (EI) $t_R$ 2.56, m/z 315 (M$^+$+1);

43) N-[(3R)-1-Azabicyclo[2.2.2]oct-3-yl]-5-(difluoromethoxy)-N-methyl-1H-indazole-3-carboxamide hydroformate. LC/MS (EI) $t_R$ 2.82, m/z 351 (M$^+$+1);

44) N-[(3R)-1-Azabicyclo[2.2.2]oct-3-yl]-6-(difluoromethoxy)-N-methyl-1H-indazole-3-carboxamide hydroformate. LC/MS (EI) $t_R$ 2.9, m/z 351 (M$^+$+1);

45) N-[(3R)-1-Azabicyclo[2.2.2]oct-3-yl]-N-methyl-6-(tetrahydro-2H-pyran-4-yl)-1H-indazole-3-carboxamide hydroformate. LC/MS (EI) $t_R$ 2.55, m/z 369 (M$^+$+1);

46) N-[(3R)-1-Azabicyclo[2.2.2]oct-3-yl]-N-methyl-5-(tetrahydro-2H-pyran-4-yl)-1H-indazole-3-carboxamide hydroformate. LC/MS (EI) $t_R$ 2.89, m/z 369 (M$^+$+1);

47) N-[(3R)-1-Azabicyclo[2.2.2]oct-3-yl]-N-methyl-6-(1,3-thiazol-2-yl)-1H-indazole-3-carboxamide hydroformate. LC/MS (EI) $t_R$ 3.33, m/z 368 (M$^+$+1);

48) N-[(3R)-1-Azabicyclo[2.2.2]oct-3-yl]-6-methoxy-N-methyl-1,2-benzisothiazole-3-carboxamide hydroformate. LC/MS (EI) $t_R$ 3.21, m/z 348 (M$^+$+1);

N-[(3S)-1-Azabicyclo[2.2.2]oct-3-yl]-7-methoxy-1H-indazole-3-carboxamide.

Procedure D

Procedure D provides a method for the coupling between 3-aminoquinuclidine and carboxylic acids to form carboxamide derivatives.

To a solution of the carboxylic acid (4.77 mmol) in N,N-dimethylformamide (14 mL) was added N,N-diisopropylethylamine (19 mmol) and 3-aminoquinuclidine dihydrochloride (4.29 mmol). The reaction mixture was maintained at room temperature for 30 min under nitrogen and then HATU (4.76 mol) was added. After 18 h, the reaction mixture was filtered through Celite (methanol rinse) and was divided equally amongst 3 SCX columns. The columns were washed with methanol (100 mL each) and the basic components were eluted with 2 M ammonia in methanol (100 mL each) and concentrated. The residue was purified by chromatography [1/1 to 0/1 ethyl acetate/(70/30/1 ethyl acetate/methanol/ammonium hydroxide)]or by preparative HPLC, thus providing the product in 15%-50% yield.

The following compounds were prepared using this method:

3) N-[(3S)-1-Azabicyclo[2.2.2]oct-3-yl]-5,6-dimethoxy-1H-indazole-3-carboxamide hydroformate. $^1$H NMR (CD$_3$OD) δ 8.33 (bs, 2H), 7.55 (s, 1H), 7.05 (s, 1H), 4.52 (m, 1H), 3.87 (s, 3H), 3.86 (s, 3H), 3.79 (m, 1H), 3.37 (m, 6H), 2.38 (m, 4H), 2.11 (m, 5H); LC/MS (EI) $t_R$ 2.48, m/z 331 (M$^+$+1);

17) N-[(3R)-1-Azabicyclo[2.2.2]oct-3-yl]-6-methoxy-N-methyl-1H-indazole-3-carboxamide hydroformate. LC/MS (EI) $t_R$ 2.53, m/z 315 (M$^+$+1);

19) N-[(3S)-1-Azabicyclo[2.2.2]oct-3-yl]-1-ethyl-6-methoxy-1H-indazole-3-carboxamide. LC/MS (EI) $t_R$ 3.55, m/z 329 (M$^+$+1);

20) N-[(3R)-1-Azabicyclo[2.2.2]oct-3-yl]-1-ethyl-6-methoxy-1H-indazole-3-carboxamide. LC/MS (EI) $t_R$ 3.54, m/z 329 (M$^+$+1);

21) N-[(3S)-1-Azabicyclo[2.2.2]oct-3-yl]-1-(difluoromethyl)-6-methoxy-1H-indazole-3-carboxamide. LC/MS (EI) $t_R$ 3.75, m/z 351 (M$^+$+1);

28) N-[(3S)-1-Azabicyclo[2.2.2]oct-3-yl]-N-methyl-6-(1,3-oxazol-2-yl)-1H-indazole-3-carboxamide. LC/MS (EI) $t_R$ 3.09, m/z 352 (M$^+$+1);

29) N-[(3S)-1-Azabicyclo[2.2.2]oct-3-yl]-N-methyl-6-(1,3-thiazol-2-yl)-1H-indazole-3-carboxamide. LC/MS (EI) $t_R$ 3.33, m/z 368 (M$^+$+1);

34) N-[(3S)-1-Azabicyclo[2.2.2]oct-3-yl]-N-methyl-6-(tetrahydro-2H-pyran-4-yl)-1H-indazole-3-carboxamide. LC/MS (EI) $t_R$ 2.52, m/z 369 (M$^+$+1);

35) N-[(3S)-1-Azabicyclo[2.2.2]oct-3-yl]-N-methyl-5-(tetrahydro-2H-pyran-4-yl)-1H-indazole-3-carboxamide. LC/MS (EI) $t_R$ 2.85, m/z 369 (M$^+$+1);

36) N-[(3S)-1-Azabicyclo[2.2.2]oct-3-yl]-5-(difluoromethoxy)-N-methyl-1H-indazole-3-carboxamide. LC/MS (EI) $t_R$ 3.4, m/z 351 (M$^+$+1);

37) N-[(3S)-1-Azabicyclo[2.2.2]oct-3-yl]-6-(difluoromethoxy)-N-methyl-1H-indazole-3-carboxamide. LC/MS (EI) $t_R$ 3.48, m/z 351 (M$^+$+1);

40) N-[(3S)-1-Azabicyclo[2.2.2]oct-3-yl]-5-methoxy-N-methyl-1H-indazole-3-carboxamide. LC/MS (EI) $t_R$ 2.51, m/z 315 (M$^+$+1);

57) N-[(3S)-1-Azabicyclo[2.2.2]oct-3-yl]-6-fluoro-1H-pyrazolo[3,4-b]pyridine-3-carboxamide hydroformate, LC/MS (EI) $t_R$ 2.47, m/z 290 (M$^+$+1);

59) N-[(3S)-1-Azabicyclo[2.2.2]oct-3-yl]-1H-pyrazolo[4,3-c]pyridine-3-carboxamide, LC/MS (EI) $t_R$ 1.29, m/z 272.2 (M$^+$+1);

60) N-[(3S)-1-Azabicyclo[2.2.2]oct-3-yl]-1H-pyrazolo[3,4-c]pyridine-3-carboxamide hydroformate, LC/MS (EI) $t_R$ 1.59, m/z 272.2 (M$^+$+1);

73) N-[(3R)-1-Azabicyclo[2.2.2]oct-3-yl]-1-ethyl-6-(1,3-oxazol-2-yl)-1H-indazole-3-carboxamide hydroformate, LC/MS (EI) $t_R$ 3.13, m/z 366 (M$^+$+1);

88) N-[(3S)-1-Azabicyclo[2.2.2]oct-3-yl]-6-phenyl-1H-pyrazolo[3,4-b]pyridine-3-carboxamide, LC/MS (EI) $t_R$ 4.18, m/z 348.1 (M$^+$+1);

90) N-[(3S)-1-Azabicyclo[2.2.2]oct-3-yl]-6-[3-(dimethylamino)pyrrolidin-1-yl]-1H-pyrazolo[3,4-b]pyridine-3-carboxamide, LC/MS (EI) $t_R$ 2.64, m/z 384.2 (M$^+$+1);

91) N-[(3R)-1-Azabicyclo[2.2.2]oct-3-yl]-6-[3-(dimethylamino)pyrrolidin-1-yl]-1H-pyrazolo[3,4-b]pyridine-3-carboxamide, LC/MS (EI) $t_R$ 2.62, m/z 384.2 (M$^+$+1);

N-[(3S)-1-Azabicyclo[2.2.2]oct-3-yl]-6-(bromo)-1H-indazole-3-carboxamide;

N-[(3S)-1-Azabicyclo[2.2.2]oct-3-yl]-4-methoxy-1H-indazole-3-carboxamide.

N-[(3S)-1-Azabicyclo[2.2.2]oct-3-yl]-6-bromo-1-ethyl-1H-indazole-3-carboxamide;

N-[(3S)-1-Azabicyclo[2.2.2]oct-3-yl]-6-bromo-1-methyl-1H-indazole-3-carboxamide;

N-[(3S)-1-Azabicyclo[2.2.2]oct-3-yl]-6-bromo-1-difluoromethyl-1H-indazole-3-carboxamide;

N-[(3S)-1-Azabicyclo[2.2.2]oct-3-yl]-6-(1,3-thiazol-2-yl)-1H-indazole-3-carboxamide;

N-[(3S)-1-Azabicyclo[2.2.2]oct-3-yl]-6-(1,3-oxazol-2-yl)-1H-indazole-3-carboxamide;

N-[(3S)-1-Azabicyclo[2.2.2]oct-3-yl]-6-bromo-1-[(2-methoxyethoxy)methyl]-1H-indazole-3-carboxamide;

N-[(3S)-1-Azabicyclo[2.2.2]oct-3-yl]-6-bromo-1-{[2-(trimethylsilyl)ethoxy]methyl}-1H-indazole-3-carboxamide;

N-[(3R)-1-Azabicyclo[2.2.2]oct-3-yl]-6-bromo-1-{[2-(trimethylsilyl)ethoxy]methyl}-1H-indazole-3-carboxamide;

N-[(3S)-1-Azabicyclo[2.2.2]oct-3-yl]-6-bromo-2-{[2-(trimethylsilyl)ethoxy]methyl}-1H-indazole-3-carboxamide;

N-[(3R)-1-Azabicyclo[2.2.2]oct-3-yl]-6-bromo-2-{[2-(trimethylsilyl)ethoxy]methyl}-1H-indazole-3-carboxamide.

The following compounds were prepared using this procedure, followed by removal of the protecting group using 6 N hydrochloric acid, isolation by ion exchange, and purification by preparative HPLC:

6) N-[(3S)-1-Azabicyclo[2.2.2]oct-3-yl]-6-(tetrahydrofuran-3-yloxy)-1H-indazole-3-carboxamide hydroformate. LC/MS (EI) $t_R$ 2.68, m/z 357 (M$^+$+1);

7) N-[(3S)-1-Azabicyclo[2.2.2]oct-3-yl]-6-(tetrahydro-2H-pyran-4-yloxy)-1H-indazole-3-carboxamide hydroformate. LC/MS (EI) $t_R$ 2.73, m/z 371 (M$^+$+1);

8) N-[(3S)-1-Azabicyclo[2.2.2]oct-3-yl]-6-[(1-methylpyrrolidin-3-yl)oxy]-1H-indazole-3-carboxamide hydroformate. LC/MS (EI) $t_R$ 1.4, m/z 370 (M$^+$+1).

The following compound was prepared using this procedure, followed by treatment with tetrabutylammonium fluoride:

164) N-[(3S)-1-Azabicyclo[2.2.2]oct-3-yl]-5-[(3S)-3-(cyclopropylmethoxy)pyrrolin-1-yl]-1H-indazole-3-carboxamide, LC/MS (EI) $t_R$ 3.67, m/z 410 (M$^+$+1);

166) N-[(3S)-1-Azabicyclo[2.2.2]oct-3-yl]-5-[(3S)-3-methoxypyrrolidin-1-yl]-1H-indazole-3-carboxamide dihydroformate, LC/MS (EI) $t_R$ 2.44, m/z 369 ($M^+$+1).

Procedure E

Procedure E provides a method for the coupling between 3-aminoquinuclidine and carboxylic acids, amines, and indazoles to form amide and urea derivatives.

A mixture of 6-(1-methyl-4,5-dihydro-1H-imidazol-2-yl)-1H-indazole-3-carboxylic acid (0.500 mmol), TBTU (0.624 mmol), and (3R)-quinuclidin-3-amine dihydrochloride (0.706 mmol) was diluted with N,N-dimethylformamide (4 mL) and N,N-diisopropylethylamine (2.34 mmol) was added. The reaction mixture was maintained for 16 h at rt. The reaction mixture was loaded onto a SCX column (10 g) and was washed with methanol (100 mL). The partially purified product was then eluted using 2.0M ammonia in methanol (60 mL). The solvent was removed and the residue was purified by preparative HPLC, thus providing the product in 20% yield.

The following compounds were prepared using this method:

162) N-[(3R)-1-Azabicyclo[2.2.2]oct-3-yl]-6-(1-methyl-4,5-dihydro-1H-imidazol-2-yl)-1H-indazole-3-carboxamide, $^1$H NMR (CD$_3$OD) δ 8.53 (s, 2H), 8,46 (d, J=8.5, 1H, rotamer), 8.40 (d, J=8.4, 1H, rotamer), 8.06 (s, 1H, rotamer), 7.90 (s, 1H, rotamer), 7.50 (d, J=8.3, 1H, rotamer), 7.35 (d, J=8.4, 1H, rotamer), 4.91 (s, 1H), 4.20 (m, 3H), 4.03 (m, 3H), 3.82 (m, 1H), 3.33 (m, 6H), 3.19 (s, 3H), 2.39 (m, 1H), 2.38 (m, 1H), 2.11 (m, 2H), 1.22 (m, 1H); LC/MS (EI) $t_R$ 1.43, m/z 352 ($M^+$+1);

163) N-[(3S)-1-Azabicyclo[2.2.2]oct-3-yl]-6-(1-methyl-4,5-dihydro-1H-imidazol-2-yl)-1H-indazole-3-carboxamide, LC/MS (EI) $t_R$ 1.26, m/z 352 ($M^+$+1);

167) N-[(3S)-1-Azabicyclo[2.2.2]oct-3-yl]-6-chloroisothiazolo[5,4-b]pyridine-3-carboxamide, LC/MS (EI) $t_R$ 2.46, m/z 322 ($M^+$+1);

184) N-[(3S)-1-Azabicyclo[2.2.2]oct-3-yl]-6-cyano-1H-indazole-3-carboxamide, LC/MS (EI) $t_R$ 2.50, m/z 2.96 ($M^+$+1).

Procedure F

Procedure F provides a method for the coupling between 3-aminoquinuclidine and carboxylic acids, amines, and indazoles to form amide and urea derivatives.

N,N-Carbonyldiimidazole (0.62 mmol) was added to a solution of (S) 3-aminoquinuclidine hydrochloride (0.500 mmol) in N,N-dimethylformamide (3.0 mL). N,N-Diisopropylethylamine (1.48 mmol) was added dropwise and the reaction mixture was maintained for 2 h at rt. N-[(3S)-1-Azabicyclo[2.2.2]oct-3-yl]-1H-indazole-3-carboxamide (0.370 mmol) was added and the reaction mixture was maintained for 16 h. The reaction mixture was transferred to a SCX column (10 g) and the column was flushed with 5 volumes of methanol. The partially purified product was then eluted using 5% dimethylethylamine in methanol. The residue was purified by chromatography using 50/50 to 30/70 ethyl acetate/[(50/50/2) ethyl acetate/methanol/dimethylethylamine]to provide the urea in 61% yield.

The following compound was prepared using this method:

161) N,N'-di-(3S)-1-Azabicyclo[2.2.2]oct-3-yl-1H-indazole-1,3-dicarboxamide, $^1$H NMR (CD$_3$OD) δ 8.34 (d, J=8.5, 1H); 8.27 (d, J=8.2, 1H); 7.57 (t, J=7.3, 1H); 7.40 (t, J=7.3,1H); 4.21 (m,1H); 4.11 (m, 1H); 3.39 (m, 2H); 3.1-2.7 (m, 10H); 2.12 (m, 2H); 1.97 (m, 2H); 1.81 (m, 4H); 1.59 (m,2H); LC/MS (EI) $t_R$ 1.38, m/z 423.2 ($M^+$+1);

N-[(3S)-1-Azabicyclo[2.2.2]oct-3-yl]-6-(bromo)-1,2-benzisothiazole-3-carboxamide.

N-[(3R)-1-Azabicyclo[2.2.2]oct-3-yl]-5-(tetrahydro-2H-pyran-4-yloxy)-1-[2-(trimethylsilyl)ethoxy]methyl-1H-indazole-3-carboxamide The following compound was prepared using this procedure, followed by treatment with tetrabutylammonium fluoride:

190) N-[(3R)-1-Azabicyclo[2.2.2]oct-3-yl]-5-(tetrahydro-2H-pyran-4-yloxy)-1H-indazole-3-carboxamide,); LC/MS (EI) $t_R$ 4.46, m/z 370.4 ($M^+$+1);

Procedure G

Procedure G provides a method for the coupling between 3-aminoquinuclidine and carboxylic acids to form carboxamide derivatives.

The coupling reaction and purification was performed according to procedure A (benzisoxazoles), procedures B, E, or F (benzisothiazoles), or procedures C, D, E, or F (indazoles). The free base was dissolved in methanol (3.5 mL/mmol starting acid) and treated with 1N hydrochloric acid in ether (3.5 mL/mmol starting acid). The resulting suspension was diluted with ether (7 mL/mmol starting acid) and was maintained at room temperature for 2 h. The solids were collected by filtration, rinsed with ether, and dried, thus providing the hydrochloride salt in 40-60% yield.

The following compounds were prepared using this method:

71) N-[(3S)-1-Azabicyclo[2.2.2]oct-3-yl]-6-methoxy-1,2-benzisoxazole-3-carboxamide hydrochloride, $^1$H NMR (CD$_3$OD) δ 7.93 (d, J=8.7, 1H), 7.23 (s, 1H), 7.05 (d, J=8.7, 1H), 4.47 (m, 1H), 3.91 (s, 3H), 3.82-3.69 (m, 1H), 3.35-3.25 (m, 5H), 2.32 (m, 1H), 2.16 (m, 1H), 2.04 (m, 2H), 1.86 (m, 2H); LC/MS (EI) $t_R$ 2.75, m/z 302 ($M^+$+1);

74) N-[3S)-1-Azabicyclo[2.2.2]oct-3-yl]-1-ethyl-6-(1,3-oxazol-2-yl)-1H-indazole-3-carboxamide hydrochloride, LC/MS (EI) $t_R$ 3.07, m/z 366 ($M^+$+1);

51) N-[(3R)-1-Azabicyclo[2.2.2]oct-3-yl]-6-methoxy-1,2-benzisothiazole-3-carboxamide hydrochloride. LC/MS (EI) $t_R$ 14.4, m/z 318 ($M^+$+1);

52) N-[(3S)-1-Azabicyclo[2.2.2]oct-3-yl]-6-methoxy-1,2-benzisothiazole-3-carboxamide hydrochloride. LC/MS (EI) $t_R$ 14.35, m/z 318 ($M^+$+1);

53) N-[(3S)-1-Azabicyclo[2.2.2]oct-3-yl]-7-methoxy-1,2-benzisothiazole-3-carboxamide hydrochloride. LC/MS (EI) $t_R$ 15.36, m/z 318 ($M^+$+1), Procedure H Procedure H provides a method for the coupling between brominated 3-aminoquinuclidinecarboxamides and Grignard reagents to form alkyl-substituted derivatives.

A 5 mL microwave reaction vessel was charged with bis (triphenylphosphine)palladium (II) chloride (0.030 mmol, 0.1 eq) and the bromide (0.30 mmol). The vessel was evacuated and back-filled with argon gas. In a separate reaction vessel, solution of the Grignard (1.2 mmol, 4 eq) was added to a 0.5 M solution of zinc chloride (1.2 mmol, 4 eq) in tetrahydrofuran at rt. The suspension was maintained for 30 min and the entire contents were transferred to the reaction vessel via cannula. The vessel was sealed and subjected to microwave irradiation at 100° C. for 600 sec with a pre-stir time of 60 s. The reaction was quenched with acetic acid (0.5 mL), diluted with methanol, and was transferred to a SCX column. The column was washed with methanol (50 mL) and the product was eluted with 2 M ammonia in methanol (50 mL) and concentrated. The residue was purified by chromatography [90/10/1 dichloromethane/methanol/ammonium hydroxide or 1/1 to 0/1 ethyl acetate/(70/30/1 ethyl acetate/methanol/ammonium hydroxide)]or by preparative HPLC, thus providing the product in 20-50% yield.

The following compound was prepared using this method:

22) N-[(3S)-1-Azabicyclo[2.2.2]oct-3-yl]-1-(difluoromethyl)-6-(1,3-thiazol-2-yl)-1H-indazole-3-carboxamide.
$^1$H NMR (CD$_3$OD) δ 8.46 (s, 1H); 8.40 (d, J=8.6, 1H); 8.05 (d, J=8.6, 1H); 7.98 (t, J=58.3, 1H); 7.97 (d, J=3.3, 1H); 7.73 (d, J=3.3, 1H); 4.57 (m, 1H); 3.86 (m, 1H); 3.60-3.20 (m, 5H); 2.43 (m, 1H); 2.26 (m, 1H); 2.16 (m, 2H); 1.95 (m, 1H); LC/MS (EI) t$_R$ 4.04, m/z 404 (M$^+$+1).

Procedure I

Procedure I provides a method for the coupling between aniline or phenol bearing aminoquinuclidinecarboxamides and alkylating agents to form secondary aniline- or ether-substituted derivatives.

To a solution of N-[(3S)-1-azabicyclo[2.2.2]oct-3-yl]-6-hydroxy-1,2-benzisothiazole-3-carboxamide (0.400 mol) in N,N-dimethylformamide (6 mL) was added potassium carbonate (2.00 mol) and cyclopropylmethyl bromide (0.47 mmol). The reaction was maintained for 16 h and the solvent was removed in vacuo. The residue was extracted with 10/1 dichloromethane/methanol (3×) and the combined extracts were concentrated. The residue was purified by preparative HPLC using an 8 min gradient of 95/5 to 20/80 water (0.1% formic acid)/acetonitrile (0.1% formic acid), thus providing the product in 32% yield.

The following compounds were prepared using this method:

N-[(3S)-1-Azabicyclo[2.2.2]oct-3-yl]-6-(cyclopropylmethoxy)-1,2-benzisothiazole-3-carboxamide hydroformate;

13) (3S)-3-{[(5-Hydroxy-1,2-benzisothiazol-3-yl)carbonyl]amino}-1-methyl-1-azoniabicyclo[2.2.2]octane iodide or formate. LC/MS (EI) t$_R$ 2.55, m/z 318 (M$^+$+1);

N-[(3S)-1-Azabicyclo[2.2.2]oct-3-yl]-5-methoxy-1,2-benzisothiazole-3-carboxamide hydroformate.

The following compound may be prepared using this method:

1) (3S)-3-({[6-(Cyclopropylmethoxy)-1,2-benzisothiazol-3-yl]carbonyl}amino)-1-(cyclopropylmethyl)-1-azoniabicyclo[2.2.2]octane bromide or formate. LC/MS (EI) t$_R$ 5.76, m/z 412 (M$^+$+1).

Procedure J

Procedure J provides a method for the coupling between brominated 3-aminoquinuclidine benzisothiazoles and cyclic amines to form aniline derivatives.

Pyrrolidine (0.361 mmol), N-[(3S)-1-azabicyclo[2.2.2]oct-3-yl]-6-bromo-1,2-benzisothiazole-3-carboxamide (0.259 mmol), palladium acetate (0.021 mmol), 2-dicyclohexylphosphino-2',4',6'-tri-i-propyl-1,1'-biphenyl (0.049 mmol), and cesium carbonate (0.586 mmol) were combined in a microwave vessel. The vessel was evacuated and back-filled under an atmosphere of argon. Tetrahydrofuran (3.7 mL) was added and the vessel was sealed. The reaction was subjected to microwave irradiation at 135° C. for 30 min. The reaction mixture was filtered through Celite and the residue was purified by chromatography [100/0 to 80/20 ethyl acetate/(50/50/2 ethyl acetate/methanol/dimethylethylamine)]or preparative HPLC to provide the product in 34% yield.

The following compounds were prepared using this method:

2) N-[(3S)-1-Azabicyclo[2.2.2]oct-3-yl]-6-(3-methoxypyrrolidin-1-yl)-1,2-benzisothiazole-3-carboxamide, $^1$H NMR (CD$_3$OD) δ 7.91 (d, J=8.9, 1H); 7.77 (s, 1H); 7.09 (d, J=8.9, 1H); 4.3-4.1 (m, 2H); 3.7-3.3 (m, 8H); 3.1-2.8 (m, 5H); 2.20 (m, 2H); 2.09 (m,1H); 1.98 (m, 1H); 1.83 (m, 2H); 1.60 (m, 1H); LC/MS (EI) t$_R$ 3.7, m/z 387 (M++1);

64) N-[(3S)-1-Azabicyclo[2.2.2]oct-3-yl]-6-pyrrolidin-1-yl-1,2-benzisothiazole-3-carboxamide, LC/MS (EI) t$_R$ 4.13, m/z 357.2 (M++1);

66) N-[(3S)-1-Azabicyclo[2.2.2]oct-3-yl]-6-(1H-pyrrol-1-yl)-1,2-benzisothiazole-3-carboxamide, LC/MS (EI) t$_R$ 4.04, m/z 353.1 (M++1);

68) N-[(3S)-1-Azabicyclo[2.2.2]oct-3-yl]-6-[3-(cyclopropylmethoxy)pyrrolidin-1-yl]-1,2-benzisothiazole-3-carboxamide, LC/MS (EI) t$_R$ 4.31, m/z 427.2 (M++1);

69) N-[(3S)-1-Azabicyclo[2.2.2]oct-3-yl]-6-(3-methoxypyrrolidin-1-yl)-1,2-benzisoxazole-3-carboxamide, LC/MS (EI) t$_R$ 3.57, m/z 371.2 (M++1);

70) N-[(3S)-1-Azabicyclo[2.2.2]oct-3-yl]-7-(3-methoxypyrrolidin-1-yl)-1,2-benzisothiazole-3-carboxamide, LC/MS (EI) t$_R$ 3.83, m/z 387.2 (M++1);

72) N-[(3R)-1-Azabicyclo[2.2.2]oct-3-yl]-6-(3-methoxypyrrolidin-1-yl)-1,2-benzisothiazole-3-carboxamide, LC/MS (EI) t$_R$ 3.8, m/z 387.2 (M++1);

75) N-[(3S)-1-Azabicyclo[2.2.2]oct-3-yl]-6-[(3R)-3-methoxypyrrolidin-1-yl]-1,2-benzisothiazole-3-carboxamide, LC/MS (EI) t$_R$ 3.74, m/z 387.2 (M++1);

76) N-[(3S)-1-Azabicyclo[2.2.2]oct-3-yl]-6-[(3S)-3-methoxypyrrolidin-1-yl]-1,2-benzisothiazole-3-carboxamide, LC/MS (EI) t$_R$ 3.77, m/z 387.2 (M++1);

79) N-[(3S)-1-Azabicyclo[2.2.2]oct-3-yl]-6-[3-(difluoromethoxy)pyrrolidin-1-yl]-1,2-benzisothiazole-3-carboxamide, LC/MS (EI) t$_R$ 4.22, m/z 423.2 (M++1);

108) N-[(3S)-1-Azabicyclo[2.2.2]oct-3-yl]-6-[(3R)-3-methoxypyrrolidin-1-yl]-1,2-benzisoxazole-3-carboxamide, LC/MS (EI) t$_R$ 4.5, m/z 371.1 (M++1);

109) N-[(3S)-1-Azabicyclo[2.2.2]oct-3-yl]-6-[(3S)-3-methoxypyrrolidin-1-yl]-1,2-benzisoxazole-3-carboxamide, LC/MS (EI) t$_R$ 4.5, m/z 371.1 (M++1);

110) N-[(3R)-1-Azabicyclo[2.2.2]oct-3-yl]-7-[(3R)-3-methoxypyrrolidin-1-yl]-1,2-benzisothiazole-3-carboxamide hydroformate, LC/MS (EI) t$_R$ 3.92, m/z 387.1 (M++1);

111) N-[(3R)-1-Azabicyclo[2.2.2]oct-3-yl]-7-[(3S)-3-methoxypyrrolidin-1-yl]-1,2-benzisothiazole-3-carboxamide, LC/MS (EI) t$_R$ 3.91, m/z 387.1 (M++1);

112) N-[(3S)-1-Azabicyclo[2.2.2]oct-3-yl]-7-[(3R)-3-methoxypyrrolidin-1-yl]-1,2-benzisothiazole-3-carboxamide hydroformate, LC/MS (EI) t$_R$ 3.91, m/z 387.1 (M++1);

113) N-[(3S)-1-Azabicyclo[2.2.2]oct-3-yl]-7-[(3S)-3-methoxypyrrolidin-1-yl]-1,2-benzisothiazole-3-carboxamide hydroformate, LC/MS (EI) t$_R$ 3.94, m/z 387.1 (M++1).

The following compound was prepared from 3-[(2-trimethylsilylethoxy)methoxy]pyrrolidine using this method followed by treatment with 6 N hydrochloric acid, preparative HPLC purification, and isolation using SCX ion exchange:

78) N-[(3S)-1-Azabicyclo[2.2.2]oct-3-yl]-6-(3-hydroxypyrrolidin-1-yl)-1,2-benzisothiazole-3-carboxamide, LC/MS (EI) t$_R$ 4.44, m/z 373.1 (M$^+$+1).

Procedure K

Procedure K provides a method for the coupling between brominated 3-aminoquinuclidine indazoles and cyclic amines to form aniline derivatives.

2-Dicyclohexylphosphino-2',4',6'-tri-isopropyl-1,1'-biphenyl (0.0450 mmol), palladium(II) acetate (0.0150 mmol), cesium carbonate (2.25 mmol) and 3-(cyclopropylmethoxy)pyrrolidine (2.25 mmol) were combined in a vial. A solution of N-[(3S)-1-azabicyclo[2.2.2]oct-3-yl]-6-bromo-2-[2-(trimethylsilyl)ethoxy]methyl-1H-indazole-3-carboxamide (0.751 mmol) in toluene (6.36 mL) was added and the mixture was heated at 80° C. for 3 d. The reaction mixture was filtered through Celite, loaded onto a RediSep column (silica gel), and eluted using a gradient of 100/0 to 80/20 ethyl acetate/(50/50/2 ethyl acetate/methanol/dimethylethylamine). The residue was transferred to a SCX column (10 g) and the column was washed with methanol (5 volumes), 2.0 M ammonia in methanol (most of the SEM was removed by this process), and the ammonia eluent was concentrated. The residue was purified by preparative HPLC [90/10 to 50/50 water (0.1% formic acid)/acetonitrile (0.1% formic acid) over 10 min.] to give the desired product in 7% yield.

The following acid was prepared using this method:

58) N-[(3S)-1-Azabicyclo[2.2.2]oct-3-yl]-6-[3-(cyclopropylmethoxy)pyrrolidin-1-yl]-1H-indazole-3-carboxamide hydroformate, $^1$H NMR (CD$_3$OD) δ 8.44 (br s, 1H); 7.95 (d, J=9.0, 1H); 6.75 (d, J=9.0, 1H); 6.46 (s, 1H); 4.50 (m, 1H); 4.30 (m, 1H); 3.81 (m, 1H); 3.60-3.20 (m, 9H); 3.36 (d, J=6.9, 2H); 2.37 (m, 1H); 2.26 (m, 1H); 2.17 (m, 2H); 2.09 (m, 2H); 1.92 (m, 1H); 1.05 (m, 1H); 0.52 (m, 2H); 0.22 (m, 2H); LC/MS (EI) $t_R$ 4.48, m/z 410.2 (M$^+$+1);

61) N-[(3R)-1-Azabicyclo[2.2.2]oct-3-yl]-6-[3-(cyclopropylmethoxy)pyrrolidin-1-yl]-1H-indazole-3-carboxamide hydroformate, LC/MS (EI) $t_R$ 4.49, m/z 410.2 (M$^+$+1);

62) N-[(3R)-1-Azabicyclo[2.2.2]oct-3-yl]-6-(3-methoxy-pyrrolidin-1-yl)-1H-indazole-3-carboxamide hydroformate, LC/MS (EI) $t_R$ 4.1, m/z 370.3 (M$^+$+1).

Procedure L

Procedure L provides a method for the coupling between brominated aminoquinuclidinecarboxamides and cyclic amines to form aniline derivatives.

A mixture of 3-methoxypyrrolidine hydrochloride (6.27 mmol), N-[(3S)-1-azabicyclo[2.2.2]oct-3-yl]-6-bromo-1,2-benzisothiazole-3-carboxamide (4.42 mmol), 2-dicyclo-hexylphosphino-2',4',6'-tri-i-propyl-1,1'-biphenyl (0.845 mmol), palladium acetate (0.363 mmol), and cesium carbonate (9.97 mmol) was evacuated and back-filled with an atmosphere of argon. Tetrahydrofuran (60 mL) was added and the reaction was heated at reflux for 67 h. The reaction mixture was allowed to cool to rt and was filtered through Celite (MeOH) and concentrated. The residue was partitioned between 9/1 dichloromethane/methanol (100 mL) and sat sodium bicarbonate (40 mL) and the layers were separated. The aq layer was extracted with 9/1 dichloromethane/methanol (3×50 mL) and the combined organic layers were washed with brine and dried (sodium sulfate). The residue was purified by chromatography (70/30/1 ethyl acetate/methanol/ammonium hydroxide) to give the free base (84%) as a yellow foam. The mono-hydrochloride salt was prepared from methanolic hydrogen chloride [acetyl chloride (0.95 eq) in methanol (5 mL)] and was recrystallized from methanol/ethyl acetate.

The following compound was prepared using this procedure:

49) N-[(3S)-1-Azabicyclo[2.2.2]oct-3-yl]-6-(3-methoxypyrrolidin-1-yl)-1,2-benzisothiazole-3-carboxamide hydrochloride. $^1$H NMR (CD$_3$OD) δ 8.48 (d, J=9.1, 1H), 7.02 (d, J=1.9, 1H), 6.91 (dd, J=9.2, 2.1, 1H), 4.52-4.48 (m, 1H), 4.20-4.17 (m, 1H), 3.87-3.78 (m, 1H), 3.58 (dd, J=11.0, 4.7, 1H), 3.50-3.42 (m, 3H), 3.38 (s, 3H), 3.36-3.34 (m, 3H), 2.40-2.37 (m, 1H), 2.26-2.08 (m, 3H), 1.95-1.87 (m, 1H); LC/MS (EI) $t_R$ 3.47, m/z 387 (M$^+$+1).

Procedure M

Procedure M provides a method for the coupling between brominated aminoquinuclidinecarboxamides and benzophenone imine to form aniline derivatives.

The mixture of bromide (6.30 mmol), palladium acetate (1.00 mmol), and 9,9-dimethyl-4,5-bis(diphenylphosphino)xanthene (Xantphos) (0.700 mmol) was evacuated and back-filled with argon. The solids were diluted with tetrahydrofuran (150 mL) and treated with cesium carbonate (7.00 mmol) and benzophenone imine (6.80 mmol). The reaction mixture was heated at reflux for 16 h. The reaction mixture was concentrated and redissolved in a mixture of tetrahydrofuran (90 mL) and 3 N hydrochloric acid (30 mL). The reaction mixture was maintained for 2 h and was concentrated. The residue was purified by chromatography using a mixture of 70/30/1 ethyl acetate/methanol//ammonium hydroxide, thus providing the aniline in 79% yield. The aniline was used directly in subsequent reactions.

The following compounds were prepared using this method:

6-Amino-N-[(3S)-1-azabicyclo[2.2.2]oct-3-yl]-1-(methyl)-1H-indazole-3-carboxamide;

6-Amino-N-[(3S)-1-azabicyclo[2.2.2]oct-3-yl]-1-(difluoromethyl)-1H-indazole-3-carboxamide;

6-Amino-N-[(3S)-1-azabicyclo[2.2.2]oct-3-yl]-1-cyclopropyl-1H-indazole-3-carboxamide;

Procedure N

Procedure N provides a method for the coupling between amino aminoquinuclidinecarboxamides and acylating agents to form carboxamide derivatives.

To a solution of the aniline (0.42 mmol) in pyridine (2 mL) and N,N-dimethylformamide (2 mL) was added the acid chloride (0.55 mmol). The mixture was maintained at ambient temperature for 16 h and was concentrated in vacuo. The residue was purified by preparative HPLC, thus providing the product in 30-80% yield.

The following compounds were prepared using this method:

23) N-[(3S)-1-Azabicyclo[2.2.2]oct-3-yl]-6-[(cyclopropylcarbonyl)amino]-1-methyl-1H-indazole-3-carboxamide hydroformate, $^1$H NMR (CD$_3$OD) δ 8.40 (br s, 1H); 8.18 (s, 1H); 8.07 (d, J=8.7, 1H); 7.20 (d, J=8.7, 1H); 4.50 (m, 1H); 4.09 (s, 3H); 3.81 (m, 1H); 3.60-3.20 (m, 5H); 2.37 (m, 1H); 2.26 (m, 1H); 2.11 (m, 2H); 1.92 (m, 1H); 1.81 (m, 1H); 0.99 (m, 2H); 0.91 (m, 2H); LC/MS (EI) $t_R$ 3.15, m/z 368 (M$^+$+1);

24) N-[(3S)-1-Azabicyclo[2.2.2]oct-3-yl]-6-[(cyclopropylcarbonyl)amino]-1-(difluoromethyl)-1H-indazole-3-carboxamide hydroformate. LC/MS (EI) $t_R$ 3.79, m/z 404 (M$^+$+1);

38) N-[(3S)-1-Azabicyclo[2.2.2]oct-3-yl]-1-cyclopropyl-6-[(cyclopropylcarbonyl)amino]-1H-indazole-3-carboxamide. LC/MS (EI) $t_R$ 3.65, m/z 394 (M$^+$+1).

Procedure O

Procedure O provides a method for the coupling between amino aminoquinuclidinecarboxamides and isocyanates to form urea derivatives.

To the aniline (0.40 mmol) in a mixture of pyridine (2 mL) and N,N-dimethylformamide (1 mL) was added the isocyanate (0.53 mmol). The reaction mixture was maintained at ambient temperature for 16 h and was concentrated in vacuo. The residue was purified by preparative HPLC, thus providing the product in 50-80% yield.

The following compounds were prepared using this method:

18) N-[(3S)-1-Azabicyclo[2.2.2]oct-3-yl]-1-methyl-6-{[(propylamino)carbonyl]amino}-1H-indazole-3-carboxamide hydroformate, $^1$H NMR (CD$_3$OD) δ 8.50 (br s, 1H); 8.00 (d, J=8.7, 1H); 7.92 (s, 1H); 7.01 (d, J=8.7, 1H); 4.50 (m, 1H); 4.06 (s, 3H); 3.81 (m, 1H); 3.60-3.30 (m, 5H); 3.20 (t, J=7.1, 2H); 2.37 (m, 1H); 2.26 (m, 1H); 2.11 (m, 2H); 1.92 (m, 1H); 1.58 (m, J=7.1, 2H); 0.98 (t, J=7.3, 2H); LC/MS (EI) $t_R$ 3.36, m/z 385 (M$^+$+1);

25) N-[(3S)-1-Azabicyclo[2.2.2]oct-3-yl]-1-(difluoromethyl)-6-6-{[(propylamino)carbonyl]amino}-1H-indazole-3-carboxamide hydroformate. LC/MS (EI) $t_R$ 3.81, m/z 421 (M$^+$+1);

39) N-[(3S)-1-Azabicyclo[2.2.2]oct-3-yl]-1-cyclopropyl-6-{[(propylamino)carbonyl]amino}-1H-indazole-3-carboxamide. LC/MS (EI) $t_R$ 3.71, m/z 411 (M$^+$+1).

Procedure P

Procedure P provides a method for the demethylation of methoxy-substituted quinuclidinecarboxamides to form phenol derivatives.

Boron tribromide (20.0 mmol) to a solution of N-[(3S)-1-azabicyclo[2.2.2]oct-3-yl]-6-methoxy-1,2-benzisothiazole-3-carboxamide (3.80 mmol) in dichloromethane (100 mL) at 0° C. The reaction mixture was allowed to warm to rt and was maintained for 3 d. The reaction mixture was quenched with a saturated potassium carbonate solution (50 mL) and the layers were separated. The aqueous layer was further extracted with (10/1) dichloromethane/methanol (50 mL) and the organic layers were combined and concentrated. The residue was purified by chromatography [(70/30/1) ethyl acetate/methanol/ammonium hydroxide] to provide the product in 70% yield.

The following compounds were prepared using this procedure:

9) N-[(3S)-1-Azabicyclo[2.2.2]oct-3-yl]-4-hydroxy-1H-indazole-3-carboxamide hydroformate. $^1$H NMR (CD$_3$OD) δ 8.39 (s, 1H), 7.28 (t, J=8.3, 1H), 7.00 (d, J=8.4, 1H), 6.54 (d, J=7.6, 1H), 4.57 (m, 1H), 3.83 (t, J=11.4, 1H), 3.52-3.31 (m, 5H), 2.42-2.39 (m, 1H), 2.27 (m, 1H), 2.12-2.07 (m, 2H), 1.98-1.90 (m, 1H); LC/MS (EI) $t_R$ 3.18, m/z 287 (M$^+$+1);

10) N-[(3S)-1-Azabicyclo[2.2.2]oct-3-yl]-5-bromo-4-hydroxy-1H-indazole-3-carboxamide hydroformate. LC/MS (EI) $t_R$ 3.9, m/z 365/367 (M$^+$+1);

11) N-[(3S)-1-Azabicyclo[2.2.2]oct-3-yl]-5,7-dibromo-4-hydroxy-1H-indazole-3-carboxamide hydroformate. LC/MS (EI) $t_R$ 4.26, m/z 443/445/447 (M$^+$+1);

16) N-[(3S)-1-Azabicyclo[2.2.2]oct-3-yl]-7-hydroxy-1H-indazole-3-carboxamide hydroformate. LC/MS (EI) $t_R$ 2.48, m/z 287 (M$^+$+1);

50) N-[(3S)-1-Azabicyclo[2.2.2]oct-3-yl]-6-hydroxy-1,2-benzisothiazole-3-carboxamide. LC/MS (EI) $t_R$ 2.58, m/z 304 (M$^+$+1).

Procedure Q

Procedure Q provides a method for the preparation of cyclic amide derivatives from the corresponding brominated quinuclidine derivatives.

Palladium (II) acetate (0.09 mmol) was added to a solution of 2,2'-bis(diphenylphosphino)-1,1'-binaphthyl (0.14 mmol) in toluene (10 mL) and the reaction mixture was maintained until the contents completely dissolved. The resultant yellow solution was transferred to a mixture of the bromide (0.33 mmol), cesium carbonate (0.60 mmol) and the amide (1.00 mmol) under an atmosphere of nitrogen gas and the reaction mixture was heated at 100° C. for 16 h. The reaction mixture was filtered through Celite and concentrated. The residue was purified by HPLC, thus providing the product in 72% yield.

The following compounds were prepared using this method:

15) N-[(3S)-1-Azabicyclo[2.2.2]oct-3-yl]-1-ethyl-6-(2-oxopyrrolidin-1-yl)-1H-indazole-3-carboxamide hydroformate, $^1$H NMR (CD$_3$OD) δ 8.40 (br s, 1H); 8.15 (d, J=8.9, 1H); 7.88 (s, 1H); 7.54 (d, J=8.9, 1H); 4.55 (m, 1H); 4.49 (q, J=7.2, 2H); 3.99 (t, J=7.0, 2H); 3.81 (m, 1H); 3.60-3.30 (m, 5H); 2.63 (t, J=8.1, 2H); 2.38 (m, 1H); 2.26 (m, 1H); 2.19 (m, 2H); 2.10 (m, 2H); 1.92 (m, 1H); 1.51 (t, J=7.2, 3H); LC/MS (EI) $t_R$ 2.59, m/z 382 (M$^+$+1);

65) N-[(3S)-1-Azabicyclo[2.2.2]oct-3-yl]-6-(3-methyl-2-oxopyrrolidin-1-yl)-1,2-benzisothiazole-3-carboxamide, LC/MS (EI) $t_R$ 2.93, m/z 385.2 (M$^+$+1).

The following compound was prepared using this procedure, followed by removal of the protecting groups using 6 N hydrochloric acid:

41) N-[(3S)-1-Azabicyclo[2.2.2]oct-3-yl]-6-[(4S)-4-hydroxy-2-oxopyrrolidin-1-yl]-1H-indazole-3-carboxamide hydroformate. LC/MS (EI) $t_R$ 1.39, m/z 370 (M$^+$+1);

Procedure R

Procedure R provides a method for the coupling between aminoquinuclidinecarboxamides and alcohols via Mitsunobu conditions to form N(1)-alkylated derivatives.

Diisopropyl azodicarboxylate (0.212 mmol) was added dropwise to a solution of N-[(3S)-1-azabicyclo[2.2.2]oct-3-yl]-6-(1,3-oxazol-2-yl)-1H-indazole-3-carboxamide (0.141 mmol), cyclopropyl carbinol (0.283 mmol), triphenylphosphine (0.283 mmol), and N,N-dimethylformamide (1.00 mL). The reaction mixture was maintained for 16 h at rt and was loaded onto a column of silica gel. The mixture was purified by chromatography {95/5 to 85/15 ethyl acetate/[(50/50/2) ethyl acetate/methanol/dimethylethylamine]} to provide the product (20%) as a solid. The product contained about 7% of the 2-cyclopropylmethyl isomer.

The following compounds were prepared using this procedure:

4) N-[(3S)-1-Azabicyclo[2.2.2]oct-3-yl]-1-propyl-6-(1,3-thiazol-2-yl)-1H-indazole-3-carboxamide, $^1$H NMR (CD$_3$OD) δ 8.44 (br s,1H); 8.27 (d, J=8.6, 1H); 8.25 (s, 1H); 7.94 (d, J=3.3, 1H); 7.85 (d, J=8.5, 1H); 7.68 (d, J=3.3, 1H); 4.55 (m, 1H); 4.53 (t, J=7.0, 2H); 3.83 (m, 1H); 3.60-3.25 (m, 5H); 2.40 (m, 1H); 2.25 (m, 1H); 2.12 (m, 2H); 2.08 (m, 2H); 2.00 (m, 1H); LC/MS (EI) $t_R$ 4.02, m/z 396 (M++1);

5) N-[(3S)-1-Azabicyclo[2.2.2]oct-3-yl]-1-isopropyl-6-(1,3-thiazol-2-yl)-1H-indazole-3-carboxamide. LC/MS (EI) $t_R$ 3.9, m/z 396 (M++1);

30) N-[(3S)-1-Azabicyclo[2.2.2]oct-3-yl]-1-ethyl-6-(1,3-oxazol-2-yl)-1H-indazole-3-carboxamide. LC/MS (EI) $t_R$ 3.61, m/z 366 (M++1);

31) N-[(3S)-1-Azabicyclo[2.2.2]oct-3-yl]-1-(cyclopropylmethyl)-6-(1,3-oxazol-2-yl) -1H-indazole-3-carboxamide. LC/MS (EI) $t_R$ 3.88, m/z 392 (M++1);

32) N-[(3S)-1-Azabicyclo[2.2.2]oct-3-yl]-6-(1,3-oxazol-2-yl)-1-propyl-1H-indazole-3-carboxamide. LC/MS (EI) $t_R$ 3.79, m/z 380 (M++1);

33) N-[(3S)-1-Azabicyclo[2.2.2]oct-3-yl]-1-ethyl-N-methyl-6-(1,3-oxazol-2-yl)-1H-indazole-3-carboxamide. LC/MS (EI) $t_R$ 3.79, m/z 380 (M$^+$+1).

Procedure S

Procedure S provides a method for the formation of ether derivatives from the corresponding phenols using Mitsunobu conditions.

Diisopropyl azodicarboxylate (0.618 mmol) was added dropwise to a solution of N-[(3S)-1-azabicyclo[2.2.2]oct-3-yl]-6-hydroxy-1,2-benzisothiazole-3-carboxamide (0.594 mmol), 3-furanmethanol (0.594 mmol), and triphenylphosphine (0.594 mmol) in N,N-dimethylformamide (3.40 mL). The reaction mixture was maintained for 16 h and was concentrated. The residue was purified by chromatography { 100/0 to 90/10 ethyl acetate/[(70/30/2) ethyl acetate/methanol/dimethylethylamine]} to provide the product in 26% yield.

The following compound was prepared using this procedure:

14) N-[(3S)-1-Azabicyclo[2.2.2]oct-3-yl]-6-(3-furylmethoxy)-1,2-benzisothiazole-3-carboxamide hydroformate. $^1$H NMR (CD$_3$OD) δ 8.50-8.41 (m, 1H), 7.86-7.80 (m, 1H), 7.70-7.69 (m, 1H), 7.27-7.22 (m, 1H), 7.01-6.93 (m, 1H), 6.64-6.59 (m, 1H), 4.52 (m, 1H), 4.30 (m, 2H), 3.98-3.89 (m, 1H), 3.56-3.38 (m, 5H), 2.41-2.39 (m, 1H), 2.29 (m, 2H), 2.15-2.13 (m, 1H), 2.00 (m, 1H); LC/MS (EI) $t_R$ 3.58, m/z 384 (M$^+$+1).

Procedure T

Procedure T provides a method for the preparation of phenol-substituted quinuclidinecarboxamides from bromide derivatives.

Potassium acetate (0.600 mmol), palladium acetate (0.060 mmol), bis(pinacolato)diboron (0.800 mmol), and 2-dicyclohexylphosphino-2',4',6'-tri-i-propyl-1,1'-biphenyl (0.200 mmol) were added to a suspension of N-[(3S)-1-azabicyclo[2.2.2]oct-3-yl]-5-bromo-1,2-benzisothiazole-3-carboxamide (0.500 mmol) in toluene (8 mL). The reaction mixture was subjected to microwave irradiation (150° C.) for 5 min. The reaction mixture was allowed cool to rt, was filtered through Celite (methanol), and the filtrate was concentrated. The residue was purified by preparative HPLC to provide the product in 60% yield.

Hydrogen peroxide (0.500 mmol) was added to a solution of N-[(3S)-1-azabicyclo[2.2.2]oct-3-yl]-5-(4,4,5,5-tetramethyl-1,3,2-dioxaborolan-2-yl)-1,2-benzisothiazole-3-carboxamide (0.200 mmol) in acetone (3 mL). The reaction mixture was maintained for 2 h at rt and was diluted with water (2 mL). The product was extracted with (9/1) dichloromethane/methanol and the extract was concentrated to provide the product in 70% yield. The phenol was used directly in subsequent reactions.

The following compounds were prepared using this procedure:

12) N-[(3S)-1-Azabicyclo[2.2.2]oct-3-yl]-5-hydroxy-1,2-benzisothiazole-3-carboxamide hydroformate. $^1$H NMR (CD$_3$OD) δ 8.55 (d, 1H, J=9), 7.36 (d, 1H, J=2), 7.05 (dd, 1H, J=2.9), 4.51 (m, 1H), 3.83 (m, 1H), 3.38 (m, 5H), 2.40 (m, 1H), 2.38 (m, 1H), 2.12 (m, 2H), 1.94 (m, 1H); LC/MS (EI) $t_R$ 2.58, m/z 304 (M$^+$+1);

(3-[(3S)-1-Azabicyclo[2.2.2]oct-3-ylamino]carbonyl-1,2-benzisothiazol-5-yl)boronic acid;

(3-[(3S)-1-Azabicyclo[2.2.2]oct-3-ylamino]carbonyl-1,2-benzisothiazol-6-yl)boronic acid.

Procedure U

Procedure U provides a method for the coupling between 3-aminoquinuclidine benzisothiazole boronic acids to form aromatic aniline derivatives.

(3-[(3S)-1-Azabicyclo[2.2.2]oct-3-ylamino]carbonyl-1,2-benzisothiazol-6-yl)boronic acid (0.604 mmol), 1H-imidazole (1.8 mmol), cupric acetate (1.21 mmol), triethylamine (3.0 mmol), pyridine (4.8 mmol) and tetrahydrofuran (8.5 mL) were combined in a microwave vessel. The reaction mixture was subjected to microwave irradiation at 140° C. for 600 s. The reaction mixture was concentrated and residue was purified by chromatography [95/5 to 85/15 ethyl acetate/(1/1/0.1 ethyl acetate/methanol/dimethylethylamine)] to provide the pre-purified product as a yellow oil. The residue was further purified by preparative HPLC and the fractions containing the desired product were pooled and loaded onto a 5 g SCX column. The column was washed with methanol (120 mL), 2.0 M ammonia in methanol, and the ammonia eluent was concentrated to provide the product in 14% yield a white solid.

The following compounds were prepared using this method:

80) N-[(3S)-1-Azabicyclo[2.2.2]oct-3-yl]-6-(1H-imidazol-1-yl)-1,2-benzisothiazole-3-carboxamide, $^1$H NMR (CD$_3$OD) δ 8.87 (d, J=8.9, 1H); 8.35 (m, 2H); 7.81 (d, J=8.9, 1H); 7.75 (s, 1H); 7.22 (s, 1H); 4.20 (m, 1H); 3.35 (m, 1H); 3.20-2.75 (m, 5H); 2.09 (m, 1H); 1.95 (m, 1H); 1.82 (m, 2H); 1.56 (m, 1H); LC/MS (EI) $t_R$ 1.7, m/z 354.1 (M$^+$+1)

81) N-[(3S)-1-Azabicyclo[2.2.2]oct-3-yl]-6-(1H-pyrazol-1-yl)-1,2-benzisothiazole-3-carboxamide, LC/MS (EI) $t_R$ 3.27, m/z 354.1 (M$^+$+1);

82) N-[(3S)-1-Azabicyclo[2.2.2]oct-3-yl]-6-(3-methyl-1H-pyrazol-1-yl)-1,2-benzisothiazole-3-carboxamide, LC/MS (EI) $t_R$ 3.85, m/z 368.1 (M$^+$+1);

83) N-[(3S)-1-Azabicyclo[2.2.2]oct-3-yl]-6-(5-methyl-1H-pyrazol-1-yl)-1,2-benzisothiazole-3-carboxamide, LC/MS (EI) $t_R$ 3.47, m/z 368.1 (M$^+$+1).

Procedure V

Procedure V provides a method for the coupling between indazole quinuclidinecarboxamides and boronic acids to form N(1)-alkylated and arylated carboxamide derivatives.

A mixture of N-[(3S)-1-azabicyclo[2.2.2]oct-3-yl]-6-(1,3-thiazol-2-yl)-1H-indazole-3-carboxamide (0.280 mmol), cyclopropylboronic acid (0.840 mmol), and copper (II) acetate (5.60 mmol), was diluted with triethylamine (1.40 mmol), pyridine (2.2 mmol), and tetrahydrofuran (3.00 mL). The reaction mixture was subjected to microwave irradiation at 140° C. for 600 s. The reaction mixture was filtered and transferred to a SCX column. The column was washed with methanol (5 volumes) and the product was then eluted using 2.0 M ammonia in methanol, thus providing a light yellow solid. The residue was purified by chromatography {90/10 to 80/20 ethyl acetate/[(50/50/2) ethyl acetate/methanol/dimethylethylamine]} to provide the product in 22% yield. The final product contained about 3% of the regioisomer.

The following compounds were prepared using this method:

26) N-[(3S)-1-Azabicyclo[2.2.2]oct-3-yl]-1-cyclopropyl-6-(1,3-thiazol-2-yl)-1H-indazole-3-carboxamide, $^1$H NMR (CD$_3$OD) δ 8.28 (s, 1H); 8.21 (d, J=8.6, 1H); 7.91 (d, J=3.3, 1H); 7.80 (d, J=8.6, 1H); 7.65 (d, J=3.3, 1H); 4.20 (m, 1H); 3.82 (m, 1H); 3.35 (m,1H); 3.20-2.80 (m, 5H); 2.07 (m, 1H); 1.95 (m, 1H); 1.81 (m, 2H); 1.57 (m, 1H); 1.25 (m, 4H); LC/MS (EI) $t_R$ 3.9, m/z 394 (M$^+$+1);

27) N-[(3S)-1-Azabicyclo[2.2.2]oct-3-yl]-6-(1,3-thiazol-2-yl)-1-(3-thienyl)-1H-indazole-3-carboxamide LC/MS (EI) $t_R$ 4.28, m/z 436 (M$^+$+1);

N-[(3S)-1-Azabicyclo[2.2.2]oct-3-yl]-6-bromo-1-cyclopropyl-1H-indazole-3-carboxamide.

Procedure W

Procedure W provides a method for the coupling between bromo aminoquinuclidine benzisothiazoles and cyclic ureas to form urea derivatives.

A mixture of 1-propylimidazolidin-2-one (19.0 mmol), N-[(3S)-1-azabicyclo[2.2.2]oct-3-yl]-6-bromo-1,2-benzisothiazole-3-carboxamide (10.0 mmol), palladium(II) acetate (1.00 mmol), and di-tert-butyl (2',4',6'-triisopropylbiphenyl-2-yl)phosphine (2.00 mmol) was diluted with toluene (100 mL) and tetrahydrofuran (50 mL). The reaction mixture was heated at 100° C. for 16 h and the reaction mixture was filtered through Celite (methanol) and concentrated. The residue was transferred to a SCX column and was washed with methanol (100 mL). The crude product was eluted with 7 M ammonia in methanol (100 mL) and the combined product fractions were concentrated. The residue was purified by chromatography [(70/35/1) ethyl acetate/methanol/ammonium hydroxide] to provide the product in 90% yield. The mono-hydrochloride salt was prepared from methanolic hydrogen chloride [acetyl chloride (0.95 eq) in methanol (5 mL)] and was recrystallized from methanol/ethyl acetate.

Alternative method: A mixture of 1-ethylimidazolidin-2-one (41.2 mg, 0.000361 mol), N-[(3S)-1-azabicyclo[2.2.2]

oct-3-yl]-6-bromo-1,2-benzisothiazole-3-carboxamide (95.0 mg, 0.000259 mol), palladium(II) acetate (4.8 mg, 0.000021 mol), 2-dicyclohexylphosphino-2 ',4',6'-tri-i-propyl-1,1'-biphenyl (23.2 mg, 0.0000488 mol), and cesium carbonate (191 mg, 0.000586 mol) in a microwave tube was evacuated and back-filled under an atmosphere of argon. Tetrahydrofuran (3.7 mL, 0.045 mol) was added, the vessel was sealed, and the reaction mixture was subjected to microwave irradiation at 135° C. for 30 min. The reaction mixture was filtered through Celite and was concentrated. The residue was purified by chromatography [100/0 to 80/20 ethyl acetate/(50/50/2 ethyl acetate/methanol/dimethylethylamine)] to provide the product in 24% yield.

The following compounds were prepared using this method:

67) N-[(3S)-1-Azabicyclo[2.2.2]oct-3-yl]-6-(3-ethyl-2-oxoimidazolidin-1-yl)-1,2-benzisothiazole-3-carboxamide, $^1$H NMR (CD$_3$OD) δ 8.64 (d, J=9.1, 1H); 8.16 (d, J=1.8, 1H); 7.93 (dd, J=1.9/9.1, 1H); 4.20 (m, 1H); 3.98 (m, 2H); 3.61 (m, 2H); 3.60-3.35 (m, 1H); 3.37 (q, J=7.3, 2H); 3.1-2.75 (m, 5H); 2.08 (m, 1H); 1.92 (m, 1H); 1.81 (m, 2H); 1.55 (m, 1H); 1.20 (t, J=7.3, 3H); LC/MS (EI) $t_R$ 3.25, m/z 400.2 (M$^+$+1);

131) N-[(3R)-1-Azabicyclo[2.2.2]oct-3-yl]-6-(2-oxo-3-propylimidazolidin-1-yl)-1,2-benzisothiazole-3-carboxamide, LC/MS (EI) $t_R$ 3.76, m/z 414.2 (M$^+$+1);

54) N-[(3S)-1-Azabicyclo[2.2.2]oct-3-yl]-6-(2- oxo-3-propylimidazolidin-1-yl)-1,2-benzisothiazole-3-carboxamide hydrochloride. LC/MS (EI) $t_R$ 3.68, m/z 414 (M$^+$+1).

Procedure X

Procedure X provides a method for the coupling between bromo aminoquinuclidine indazoles and cyclic ureas to form urea derivatives.

A mixture of 1-propylimidazolidin-2-one (0.5684 mmol), N-[(3S)-1-azabicyclo[2.2.2]oct-3-yl]-6-bromo-2-[2-(trimethylsilyl)ethoxy] methyl-1H-indazole-3-carboxamide (0.409 mmol), palladium acetate (0.034 mmol), 2-dicyclohexylphosphino-2',4',6'-tri-i-propyl-1,1'-biphenyl (0.0768 mmol), and cesium carbonate (0.924 mmol) in a microwave tube was evacuated and back-filled under an atmosphere of argon. Tetrahydrofuran (5.8 mL) was added and the vessel was sealed. The reaction mixture was subjected to microwave irradiation at 135° C. for 30 min. The reaction mixture was filtered through Celite and concentrated. The residue was purified by chromatography [100/0 to 80/20 ethyl acetate/ (50/50/2 ethyl acetate/methanol/dimethylethylamine)] to yield the purified SEM protected product. The residue was dissolved in tetrahydrofuran (5 mL) and 6 N hydrochloric acid (5 mL) and the reaction mixture was subjected to microwave irradiation at 140° C. for 600 s. The reaction mixture was transferred to a SCX column (10g) and the column was flushed with methanol (120 mL) and 2.0 M ammonia in methanol (60 mL) and the ammonia eluent was concentrated. The residue was purified by preparative HPLC and the fractions containing the desired product were pooled and transferred to a SCX column (10 g). The column was flushed with methanol (120 mL) and 2.0 M ammonia in methanol (60 mL) and the ammonia eluent was concentrated to provide the product in 28% yield.

The following compounds were prepared using this method:

77) N-[(3S)-1-Azabicyclo[2.2.2]oct-3-yl]-6-(2-oxo-3-propylimidazolidin-1-yl)-1H-indazole-3-carboxamide, $^1$H NMR (CD$_3$OD) δ 8.09 (d, J=9.0, 1H); 7.72 (s, 1H); 7.51 (d, J=9.0, 1H); 4.18 (m, 1H); 3.90 (m, 2H); 3.51 (m, 2H); 3.35 (m, 1H); 3.23 (t, J=7.2, 2H); 3.15-2.75 (m, 5H); 2.05 (m, 1H); 1.95 (m,1H); 1.79 (m, 2H); 1.60 (m, 1H); 1.59 (m, J=7.3, 2H); 0.95 (t, J=7.3, 3H); LC/MS (H) $t_R$ 3.03, m/z 397.2 (M$^+$+1);

63) N-[(3R)-1-Azabicyclo[2.2.2]oct-3-yl]-6-(2-oxo-3-propylimidazolidin-1-yl)-1H-indazole-3-carboxamide, LC/MS (EI) $t_R$ 4.14, m/z 397.3 (M$^+$+1).

Procedure Y

Procedure Y provides a method for the oxidation of quinuclidinecarboxamides to form N-oxide derivatives.

m-Chloroperbenzoic acid (0.266 mmol) was added in portions to a −78° C. suspension of the quinuclidine amide (0.21 mmol) in dichloromethane (3 mL) and the reaction mixture was allowed to warm to rt and was maintained for 16 h. The reaction mixture was diluted with methanol and loaded onto an SCX column. The column was washed with methanol (50 mL), 2 M ammonia in methanol (60 mL) and the ammonia wash was concentrated. The crude product was purified by preparative HPLC thus providing 26.5 mg (38%) of the product.

The following compounds were prepared using this method:

55) N-[(3S)-1-Oxido-1-azabicyclo[2.2.2]oct-3-yl]-5-(trifluoromethoxy)-1H-indazole-3-carboxamide, $^1$H NMR (CD$_3$OD) δ 8.31 (br m, 1H), 8.08 (s, 1H), 7.69 (d, J=9.1, 1H), 7.36 (dd, J=9.0, 1.3, 1H), 4.72-4.69 (m, 1H), 4.13-4.04 (m, 1H), 3.80-3.63 (m, 5H), 2.45-2.35 (m, 3H), 2.28-2.25 (m, 1H), 2.15-2.11 (m, 1H); LC/MS (EI) $t_R$ 3.99, m/z 371 (M$^+$+1);

56) 6-Methoxy-N-[(3S)-1-oxido-1-azabicyclo[2.2.2]oct-3-yl]-1,2-benzisothiazole-3-carboxamide, LC/MS (EI) $t_R$ 3.65, m/z 334 (M$^+$+1).

Procedure Z

Procedure Z provides a method for the conversion of aminoquinuclidinecarboxamide nitriles to dihydroimidazole derivatives using diamines.

Hydrogen sulfide was bubbled through a solution of 6-cyano-N-(quinuclidin-3-yl)-1H-indazole-3-carboxamide (90 mg, 0.31 mmol) in ethanol (6 mL) in a pressure tube at 0° C. for 30 min. The vessel was sealed and the reaction mixture was heated at 80° C. for 16 h and was concentrated. The residue was diluted with ethylenediamine (4 mL) and was heated at 100° C. for 16 h. The reaction mixture was concentrated to provide 110 mg (94%) of the dihydroimidazole as a brown solid.

The following compound was prepared using this method:

89) N-[(3R)-1-Azabicyclo[2.2.2]oct-3-yl]-6-(4,5-dihydro-1H-imidazol-2-yl)-1H-indazole-3-carboxamide, $^1$H NMR (CD$_3$OD) δ 8.27 (d, J=8.5, 1H), 8.08 (s, 1H), 7.66 (d, J=8.5, 1H), 4.22 (m, 1H), 3.87 (s, 3H), 3.69 (s, 1H), 3.37 (m, 6H), 2.91 (m, 8H), 2.08 (m, 2H), 1.82 (m, 2H), 1.55 (m, 1H); LC/MS (EI) $t_R$ 1.63, m/z 339.2 (M$^+$+1).

Procedure AA

Procedure AA provides a method for the reaction of 3-aminoquinuclidine carboxamides with electrophiles to form quaternary ammonium salt derivatives.

N-[(3S)-1-Azabicyclo[2.2.2]oct-3-yl]-1H-indazole-3-carboxamide (3.26 mmol) was dissolved in dichloromethane (50.0 mL) and the reaction mixture was maintained at rt for 3 d. After a few minutes the mixture became cloudy and after 1 h a white precipitate was evident. The precipitated solid was collected by filtration, washed with dichloromethane and ethyl acetate, and was dried to provide the product in 92% yield as a colorless solid. Analysis by analytical LC/MS showed the product was contaminated with a small amount of starting material (ca. 5%).

To a solution of (3S)-1-(chloromethyl)-3-[(1H-indazol-3-ylcarbonyl)amino]-1-azoniabicyclo[2.2.2]octane chloride (0.999 mmol) in methanol (10.0 mL) was added MP-diisopropylethylamine (415 mmol/g loading; 41.5 mol) and MP-carbonate (3.5 mmol/g loading; 0.050 mmol). The reaction mixture was shaken for 24 h and the solid support reagents were removed by filtration. The solvent was evaporated to ca. 3 mL and ethyl acetate (15 mL) was added. The precipitated solid was collected to provide the product in 94% yield.

The following compound was prepared using this method:

165) (3S)-1-(Chloromethyl)-3-[(1H-indazol-3-ylcarbonyl)amino]-1-azoniabicyclo[2.2.2]octane chloride, $^1$H NMR (CD$_3$OD) δ 8.19 (d, J=8.2, 1H); 7.60 (d, J=8.5, 1H); 7.43 (t, J=8.5, 1H); 7.26 (t, J=8.2, 1H); 5.23 (s, 2H); 4.63 (m, 1H); 4.10 (m, 1H); 3.55-3.85 (m, 5H); 2.48 (m, 1H); 2.41 (m, 1H); 2.23 (m, 2H); 2.09 (m, 1H); LC/MS (EI) t$_R$ 2.38, m/z 321/319 (M$^+$+1).

Procedure AB

Procedure AB provides a method for the hydrolysis of 3-aminoquinuclidine nitriles to the carboxylic acids and subsequent coupling with amines to form amide derivatives.

Potassium hydroxide (7.0 mmol) was added to a solution of N-[(3S)-1-azabicyclo[2.2.2]oct-3-yl]-6-cyano-1H-indazole-3-carboxamide (2.3 mmol) in 1,2-ethanediol (6 mL) and the reaction mixture was heated at 140° C. for 7 h. The reaction was allowed to cool to rt and was treated with 6 mL of 1 M hydrochloric acid. The precipitate formed was isolated by filtration and dried under vacuum to provide the product in 45% yield as the HCl salt.

Into a vial was added 3-[(3S)-1-azabicyclo[2.2.2]oct-3-ylamino]carbonyl-1H-indazole-6-carboxylic acid hydrochloride (0.3 mmol), TBTU (0.4 mmol) and dimethylamine (0.432 mmol). N,N-Dimethylformamide (2 mL) and N,N-diisopropylethylamine (0.249 mL, 1.43 mmol) were added and the reaction mixture was maintained for 16 h at rt. The reaction mixture was loaded onto a SCX column (10 g) and flushed with methanol (200 mL). The partially purified product was then eluted using 7.0 M ammonia in methanol (60 mL). The residue was purified by preparative HPLC and the product fractions were pooled and loaded onto a SCX column (10 g). The column was flushed with methanol (200 mL) followed by 7.0 M ammonia in methanol (60 mL). The ammonia layer was evaporated to provide the amide in 30% yield.

The following compounds were prepared using this method:

185) 3-[(3S)-1-Azabicyclo[2.2.2]oct-3-ylamino]carbonyl-1H-indazole-6-carboxylic acid hydrochloride, LC/MS (EI) t$_R$ 1.50, m/z 315 (M$^+$+1);

186) N(3)-[(3S)-1-Azabicyclo[2.2.2]oct-3-yl]-N(6),N(6)-dimethyl-1H-indazole-3,6-dicarboxamide, $^1$H NMR (CD$_3$OD) δ 8.22 (s, 1H), 7.74 (s, 1H), 7.25 (s, 1H), 4.78 (s, 6H), 4.58 (m, 1H), 3.67 (m, 1H), 3.33 (m, 6H), 2.39 (m, 1H), 2.38 (m, 1H), 2.11 (m, 2H), 1.22 (m, 1H); LC/MS (EI) t$_R$ 2.50, m/z 342 (M$^+$+1);

187) N-[(3S)-1-Azabicyclo[2.2.2]oct-3-yl]-6-[(4-methylpiperazin-1-yl)carbonyl]-1H-indazole-3-carboxamide, LC/MS (EI) t$_R$ 2.40, m/z 397 (M$^+$+1);

188) N-[(3S)-1-Azabicyclo[2.2.2]oct-3-yl]-6-[(3R)-3-methoxypyrrolidin-1-yl]carbonyl-1H-indazole-3-carboxamide, LC/MS (EI) t$_R$ 2.50, m/z 398 (M$^+$+1).

Procedure AC

Procedure AC provides a method for the production of ether derivatives of 7-azabenzisothiazoles from the corresponding chloride.

Sodium methoxide (30.0 mmol) was added to a solution of N-[(3S)-1-azabicyclo[2.2.2]oct-3-yl]-6-chloroisothiazolo[5,4-b]pyridine-3-carboxamide (0.3 mmol) in methanol (2 mL) and the reaction mixture was heated at reflux for 16 h. The reaction mixture was allowed to cool to rt, quenched with methanol, and concentrated. The residue was purified by preparative HPLC and the product fractions were pooled and loaded onto a SCX column (10g). The column was flushed with methanol (200 mL) followed by 7.0 M ammonia in methanol (60 mL). The ammonia layer was evaporated to provide the product in 30% yield.

The following compound was prepared using this method:

189) N-[(3S)-1-Azabicyclo[2.2.2]oct-3-yl]-6-methoxyisothiazolo[5,4-b]pyridine-3-carboxamide, LC/MS (EI) t$_R$ 3.25, m/z 319 (M$^+$+1).

Binding Example: [$^3$H] MLA Binding

Materials:

Rat Brain: Pel-Freez Biologicals, CAT No. 56004-2

Protease inhibitor cocktail tablet: Roche, CAT No. 1697498

Membrane Preparation

Rat brains in 20 vol (w/v) of ice-cold 0.32 M sucrose with protease inhibitors (one tablet per 50 ml,) were homogenized with a polytron for 10 sec at setting 11, then centrifuged 10 mM at 1000 g, 4° C. The supernatant was centrifuged again for 20 mM at 20,000 g, 4° C. The pellets were resuspended in binding buffer (200 mM TRIS-HCl, 20 mM HEPES, pH 7.5, 144 mM NaCl, 1.5 mM KCl, 1 mM MgSO$_4$, 2 mM CaCl$_2$, 0.1% (w/v) BSA) and stored membrane prep at −80° C.

For saturation assay, the 200 μl assay mixture in binding buffer contains 200 μg of membrane protein, 0.2 to 44 nM of [$^3$H] MLA. The nonspecific binding was defined using 1 μM MLA. Competition assay was carried out with 2 nM [$^3$H] MLA and a desirable range of compounds. The assay mixture was incubated at 22° C. for 2 hours, then harvested with GF/B filter presoaked with 0.3% PEI in binding buffer using Tomtec harvester. The filter was washed three times with binding buffer and the radioactivity was counted with Trilux.

Binding affinities for the preferred compounds of the invention are 2 nM to 25 μM, especially 2 nM to 2.5 μM.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim:

1. A compound according to Formulas I, II, III, or IV:

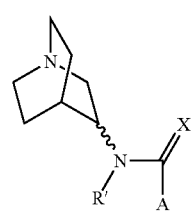

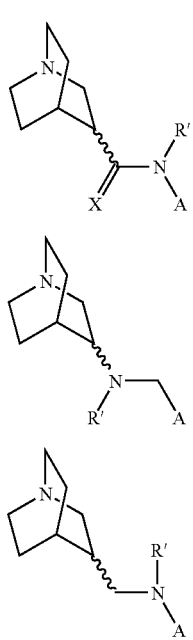

(II)

(III)

(IV)

wherein
A is

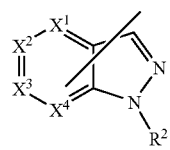
(a)

X is O or S;

X¹ to X⁴ are each, independently, N, CH, CR¹, or C—, wherein C— represents the point of attachment of group A to the remainder of the structure of formulas (I), (II), (III) or (IV);

R' is H, alkyl having 1 to 4 carbon atoms, halogenated alkyl having 1 to 4 carbon atoms, cycloalkyl having 3 to 7 carbon atoms, or cycloalkylalkyl having 4 to 7 carbon atoms;

R¹ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—$(C_{1-6}$-alkyl-O$)_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —$C_{1-6}$-alkyl-$NR^6R^7$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, —CO—$R^{10}$, or combinations thereof, cycloalkylalkyl having 4 to 7 carbon atoms, cycloalkenylalkyl having 6 to 9 carbon atoms, alkoxy having 1 to 4 carbon atoms, cycloalkoxy having 3 to 7 carbon atoms, cycloalkylalkoxy having 4 to 7 carbon atoms, alkylthio having 1 to 4 carbon atoms, fluorinated alkoxy having 1 to 4 carbon atoms, hydroxyalkyl having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl—O—, Het-$C_{1-6}$-alkyl-O—, Het-CO-Het-, Het-$C_{1-6}$-alkyl-$NR^2$—, or Ar—$C_{1-6}$-alkyl-Het-O—; or R¹ is of one of the following formulas

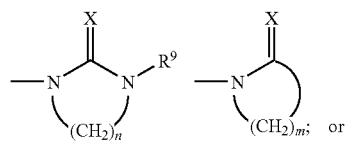

two R¹ can together form a 5-membered fused ring structure containing at least one N atom;

R² is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl-, Ar—$C_{1-4}$-alkyl-NH—CO—, or Het-NH—CO—;

R⁶ and R⁷ are each, independently, H, alkyl having 1 to 4 carbon atoms, alkoxyalkyl having 2 to 8 carbon atoms, cycloalkyl having 3 to 7 carbon atoms, or cycloalkylalkyl having 4 to 7 carbon atoms, or R⁶ and R⁷ together are an alkylene group containing 4-6 carbon atoms which forms a ring with the N atom;

R⁸ is H, alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 1 to 4 carbon atoms, fluorinated hydroxyalkyl having 1 to 4 carbon atoms, monoalkylamino having 1 to 4 carbon atoms, dialkylamino wherein each alkyl group independently has 1 to 4 carbon atoms, Ar, or Het;

R⁹ is alkyl having 1 to 4 carbon atoms, Ar, Ar-alkyl wherein the alkyl portion has 1 to 4 carbon atoms, or Het;

R¹⁰ is alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, $NR^6R^7$, $NR^2R^8$, Ar, or Het;

Ar is an aryl group having 6 to 10 carbon atoms which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, aryloxy wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, arylthio wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, or acyloxy, or combinations thereof, cycloalkyloxy wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, sulfo, sulfonylamino, acylamido, acyloxy or combinations thereof;

Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms which is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, alkyl having 1 to 8 C atoms, alkoxy having 1 to 8 C atoms, cycloalkyl having 3 to 7 carbon atoms, cycloalkylalkyl having 4 to 7 carbon atoms, halogenated alkoxy having 1 to 8 C atoms, cycloalkoxy having 3 to 7 carbon atoms, cycloalkylalkoxy having 4 to 7 carbon atoms, alkoxyalkyl having 2 to 8 carbon atoms, alkyl(halogenated alkyl)amino wherein each alkyl group has 1 to 8 C atoms, di(halogenated alkyl)amino wherein each alkyl group has 1 to 8 C atoms, (halogenated alkyl)amino having 1 to 8 C atoms, cyano, halogenated alkyl having 1 to 8 carbon atoms, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, $-CXR^{11}$, piperidinylethyl or combinations thereof;

Carbo is a partially unsaturated carbocyclic group having 5 to 14 carbon atoms, which is unsubstituted or substituted one or more times by halogen, alkyl having 1 to 8 C atoms, alkoxy having 1 to 8 C atoms, hydroxy, nitro, cyano, oxo, or combinations thereof; and $R^{11}$ is alkyl having 1 to 4 carbon atoms, halogenated alkyl having 1 to 4 carbon atoms, alkenyl having 3 to 6 carbon atoms, alkynyl having 3 to 6 carbon atoms, wherein the alkyl, halogenated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, or Ar;

and pharmaceutically acceptable salts or N-oxides thereof, or pharmaceutically acceptable salts of N-oxides thereof, wherein said compound can also be in the form of a polymorph, wherein if said compound exhibits chirality it can be in the form of a mixture of enantiomers or a mixture of diastereomers, or can be in the form of a single enantiomer or a single diastereomer, and wherein at least one $R^1$ group is Het or OHet in which the Het group is selected from, in each case substituted or unsubstituted, azabicyclooctyl, oxa-azabicycloheptyl, diazabicycloheptyl, diazabicyclononyl, diazabicyclooctyl, pyrazolyl, dihydroimidazolyl, 1,4-diazepanyl, hexahydropyrrolopyrazinyl, and octahydropyrrolopyridinyl.

2. A compound according to claim 1, wherein at least one $R^1$ group is 1-azabicyclo[2.2.2]oct-3-yloxy, 2-oxa-5-azabicyclo[2.2.1]heptyl, diazabicycloheptyl, 5-methyl-2,5-diazabicyclo[2.2.2]oct-2-yl, 8-methyl-3,8-diazabicyclo[3.2.1]oct-3-yl), pyrazolyl, dihydroimidazolyl, 1,4-diazepan-1-yl, 4-methyl-1,4-diazepan-1-yl, hexahydropyrrolo[1,2-a]pyrazin-2(1H)-yl), or 1-(cyclopropylcarbonyl)-octahydro-6H-pyrrolo[3,4-b]pyridin-6-yl).

3. A compound according to claim 1, wherein

Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms which is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, alkyl having 1 to 8 C atoms, alkoxy having 1 to 8 C atoms, cycloalkyl having 3 to 7 carbon atoms, halogenated alkoxy having 1 to 8 C atoms, cycloalkoxy having 3 to 7 carbon atoms, cycloalkylalkoxy having 4 to 7 carbon atoms, alkoxyalkyl having 2 to 8 carbon atoms, alkyl (halogenated alkyl)amino wherein each alkyl group has 1 to 8 C atoms, di(halogenated alkyl)amino wherein each alkyl group has 1 to 8 C atoms, (halogenated alkyl) amino having 1 to 8 C atoms, cyano, halogenated alkyl having 1 to 8 carbon atoms, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, —$CXR^{11}$, piperidinylethyl or combinations thereof;

$R^2$ is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl-, or Ar—$C_{1-4}$-alkyl-NH—CO—; and at least one $R^1$ group is substituted or unsubstituted diazabicycloheptyl or oxaazabicycloheptyl.

4. A compound according to claim 3, wherein at least one $R^1$ group is 2,5-diazabicyclo[2.2.1]hept-2-yl, methyl-2,5-diazabicyclo[2.2.1]hept-2-yl, trifluoroethyl-2,5-diazabicyclo[2.2.1]hept-2-yl, or 2-oxa-5-azabicyclo[2.2.1]hept-5yl.

5. A compound according to Formulas I, II, III, or IV:

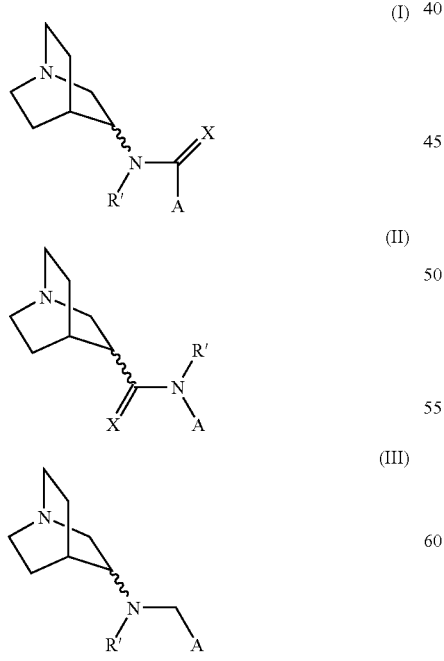

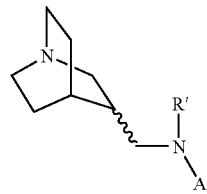

wherein
A is

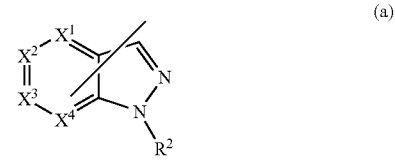

X is O or S;

$X^1$ to $X^4$ are each, independently, N, CH, $CR^1$, or C—, wherein C— represents the point of attachment of group A to the remainder of the structure of formulas (I), (II), (III) or (IV);

R' is H, alkyl having 1 to 4 carbon atoms, halogenated alkyl having 1 to 4 carbon atoms, cycloalkyl having 3 to 7 carbon atoms, or cycloalkylalkyl having 4 to 7 carbon atoms;

$R^1$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—($C_{1-6}$-alkyl-O)$_{1-2}$—$C_{1-6}$-alkyl, $NR^2$-$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, —CO—$R^{10}$, or combinations thereof, cycloalkylalkyl having 4 to 7 carbon atoms, cycloalkenylalkyl having 6 to 9 carbon atoms, alkoxy having 1 to 4 carbon atoms, cycloalkoxy having 3 to 7 carbon atoms, cycloalkylalkoxy having 4 to 7 carbon atoms, alkylthio having 1 to 4 carbon atoms, fluorinated alkoxy having 1 to 4 carbon atoms, hydroxyalkyl having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^1$ is of one of the following formulas

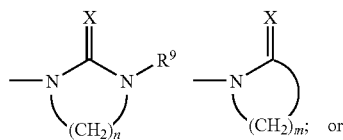

two $R^1$ can together form a 5-membered fused ring structure containing at least one N atom;

$R^2$ is alkyl having 2 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-SO$_2$—, $C_{1-4}$-alkyl-O—$C_{1-4}$-alkyl-, or Ar—$C_{1-4}$-alkyl-NH—CO—;

$R^6$ and $R^7$ are each, independently, H, alkyl having 1 to 4 carbon atoms, alkoxyalkyl having 2 to 8 carbon atoms, cycloalkyl having 3 to 7 carbon atoms, or cycloalkylalkyl having 4 to 7 carbon atoms, or $R^6$ and $R^7$ together are an alkylene group containing 4-6 carbon atoms which forms a ring with the N atom;

$R^8$ is H, alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 1 to 4 carbon atoms, fluorinated hydroxyalkyl having 1 to 4 carbon atoms, monoalkylamino having 1 to 4 carbon atoms, dialkylamino wherein each alkyl group independently has 1 to 4 carbon atoms, Ar, or Het;

$R^9$ is alkyl having 1 to 4 carbon atoms, Ar, Ar-alkyl wherein the alkyl portion has 1 to 4 carbon atoms, or Het;

$R^{10}$ is alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, $NR^6R^7$, $NR^2R^8$, Ar, or Het;

Ar is an aryl group having 6 to 10 carbon atoms which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, aryloxy wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, arylthio wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, cycloalkyloxy wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, sulfo, sulfonylamino, acylamido, acyloxy or combinations thereof;

Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms which is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, alkyl having 1 to 8 C atoms, alkoxy having 1 to 8 C atoms, cycloalkyl having 3 to 7 carbon atoms, cycloalkylalkyl having 4 to 7 carbon atoms, halogenated alkoxy having 1 to 8 C atoms, cycloalkoxy having 3 to 7 carbon atoms, cycloalkylalkoxy having 4 to 7 carbon atoms, alkoxyalkyl having 2 to 8 carbon atoms, alkyl(halogenated alkyl)amino wherein each alkyl group has 1 to 8 C atoms, di(halogenated alkyl)amino wherein each alkyl group has 1 to 8 C atoms, (halogenated alkyl)amino having 1 to 8 C atoms, cyano, halogenated alkyl having 1 to 8 carbon atoms, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, —$CXR^{11}$, piperidinylethyl or combinations thereof;

Carbo is a partially unsaturated carbocyclic group having 5 to 14 carbon atoms, which is unsubstituted or substituted one or more times by halogen, alkyl having 1 to 8 C atoms, alkoxy having 1 to 8 C atoms, hydroxy, nitro, cyano, oxo, or combinations thereof; and $R^{11}$ is alkyl having 1 to 4 carbon atoms, halogenated alkyl having 1 to 4 carbon atoms, alkenyl having 3 to 6 carbon atoms, alkynyl having 3 to 6 carbon atoms, wherein the alkyl, halogenated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, or Ar;

and pharmaceutically acceptable salts or N-oxides thereof, or pharmaceutically acceptable salts of N-oxides thereof, wherein said compound can also be in the form of a polymorph, wherein if said compound exhibits chirality it can be in the form of a mixture of enantiomers or a mixture of diastereomers, or can be in the form of a single enantiomer or a single diastereomer, and with the proviso that:

A has at least one $R^1$ substituent that is Het other than thiazolyl.

6. A compound according to claim 5, wherein

Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms which is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, alkyl having 1 to 8 C atoms, alkoxy having 1 to 8 C atoms, cycloalkyl having 3 to 7 carbon atoms, halogenated alkoxy having 1 to 8 C atoms, cycloalkoxy having 3 to 7 carbon atoms, cycloalkylalkoxy having 4 to 7 carbon atoms, alkoxyalkyl having 2 to 8 carbon atoms, alkyl(halogenated alkyl)amino wherein each alkyl group has 1 to 8 C atoms, di(halogenated alkyl)amino wherein each alkyl group has 1 to 8 C atoms, (halogenated alkyl) amino having 1 to 8 C atoms, cyano, halogenated alkyl having 1 to 8 carbon atoms, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, —$CXR^{11}$, piperidinylethyl or combinations thereof.

7. A compound according to claim 5, wherein said compound is of Formula I.

8. A compound according to claim 5, wherein said compound is of Formula II.

9. A compound according to claim 5, wherein said compound is of Formula III.

10. A compound according to claim 5, wherein said compound is of Formula IV.

11. A compound according to claim 5, wherein A is attached to the remainder of the compound via its 3, 4 or 7 position.

12. A compound according to claim 11, wherein A is attached to the remainder of the compound via its 3 position.

13. A compound according to Formulas I, II, III, or IV:

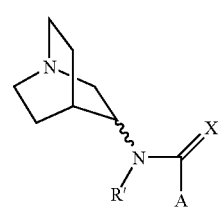

(I)

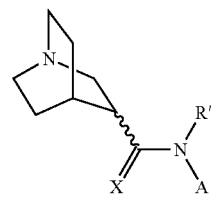

(II)

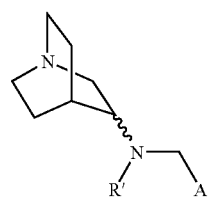

(III)

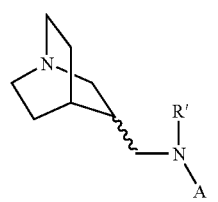

(IV)

wherein
A is

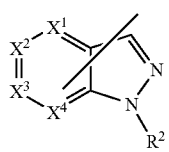

(a)

X is O or S;

$X^1$ to $X^4$ are each, independently, N, CH, $CR^1$, or C—, wherein C— represents the point of attachment of group A to the remainder of the structure of formulas (I), (II), (III) or (IV);

R' is H, alkyl having 1 to 4 carbon atoms, halogenated alkyl having 1 to 4 carbon atoms, cycloalkyl having 3 to 7 carbon atoms, or cycloalkylalkyl having 4 to 7 carbon atoms;

$R^1$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, NR$^2$SO$_2$R$^{10}$, NR$^2$CONR$^6$R$^7$, NR$^2$CSNR$^6$R$^7$, NR$^2$R$^9$, SO$_2$ R$_{10}$, SOR$^{10}$, —O—(C$_{1-6}$-alkyl-O)$_{1-2}$—C$_{1-6}$-alkyl, NR$^2$—C$_{1-6}$-alkyl-NR$^6$R$^7$, NR$^2$—C$_{1-6}$-alkyl-CONR$^6$R$^7$, NR$^2$—CO—C$_{1-6}$-alkyl-Ar, NR$^2$-C$_{1-6}$-alkyl-CO—O—R$^2$, NR$^2$—C$_{1-6}$-alkyl-NR$^2$(CO—O—R$^2$), —C$_{1-6}$-alkyl-NR$^2$, —O—C$_{1-6}$-alkyl-NR$^6$R$^7$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms which is unsubstituted or substituted by HCO—, C$_{1-6}$-alkoxy, NR$^6$R$^7$, CO—NR$^6$R$^7$, C$_{2-6}$-alkoxycarbonyl, —CO—R$^{10}$, or combinations thereof, cycloalkylalkyl having 4 to 7 carbon atoms, cycloalkenylalkyl having 6 to 9 carbon atoms, alkoxy having 1 to 4 carbon atoms, cycloalkoxy having 3 to 7 carbon atoms, cycloalkylalkoxy having 4 to 7 carbon atoms, alkylthio having 1 to 4 carbon atoms, fluorinated alkoxy having 1 to 4 carbon atoms, hydroxyalkyl having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—C$_{1-6}$-alkyl-O—, Het-C$_{1-6}$-alkyl-O—, Het-CO-Het-, Het-C$_{1-6}$-alkyl-NR$^2$—, or Ar—C$_{1-6}$-alkyl-Het-O—; or R$^1$ is of one of the following formulas

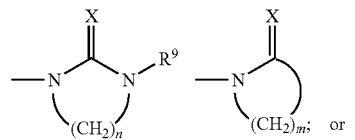

two R$^1$ can together form a 5-membered fused ring structure containing at least one N atom;

R$^2$ is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated C$_{1-4}$-alkyl-CO—, C$_{3-7}$-cycloalkyl-CO—, C$_{1-4}$-alkyl-NH—CO—, C$_{3-7}$-cycloalkyl-NH—CO—, Het, Ar—C$_{1-4}$-alkyl-, Ar—C$_{1-4}$-alkyl-CO—, Ar—C$_{1-4}$-alkyl-SO$_2$—, C$_{1-4}$-alkyl-O—C$_{1-4}$-alkyl-, Ar—C$_{1-4}$-alkyl-NH—CO—, or Het-NH—CO—;

R$^6$ and R$^7$ are each, independently, H, alkyl having 1 to 4 carbon atoms, alkoxyalkyl having 2 to 8 carbon atoms, cycloalkyl having 3 to 7 carbon atoms, or cycloalkylalkyl having 4 to 7 carbon atoms, or R$^6$ and R$^7$ together are an alkylene group containing 4-6 carbon atoms which forms a ring with the N atom;

R$^8$ is H, alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 1 to 4 carbon atoms, fluorinated hydroxyalkyl having 1 to 4 carbon atoms, monoalkylamino having 1 to 4 carbon atoms, dialkylamino wherein each alkyl group independently has 1 to 4 carbon atoms, Ar, or Het;

R$^9$ is alkyl having 1 to 4 carbon atoms, Ar, Ar-alkyl wherein the alkyl portion has 1 to 4 carbon atoms, or Het;

R$^{10}$ is alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, NR$^6$R$^7$, NR$^2$R$^8$, Ar, or Het;

Ar is an aryl group having 6 to 10 carbon atoms which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, aryloxy wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, arylthio wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, cycloalkyloxy wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, sulfo, sulfonylamino, acylamido, acyloxy or combinations thereof;

Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms which is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, alkyl having 1 to 8 C atoms, alkoxy having 1 to 8 C atoms, cycloalkyl having 3 to 7 carbon atoms, cycloalkylalkyl having 4 to 7 carbon atoms, halogenated alkoxy having 1 to 8 C atoms, cycloalkoxy having 3 to 7 carbon atoms, cycloalkylalkoxy having 4 to 7 carbon atoms, alkoxyalkyl having 2 to 8 carbon atoms, alkyl(halogenated alkyl)amino wherein each alkyl group has 1 to 8 C atoms, di(halogenated alkyl)amino wherein each alkyl group has 1 to 8 C atoms, (halogenated alkyl)amino having 1 to 8 C atoms, cyano, halogenated alkyl having 1 to 8 carbon atoms, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, —$CXR^{11}$, piperidinylethyl or combinations thereof;

Carbo is a partially unsaturated carbocyclic group having 5 to 14 carbon atoms, which is unsubstituted or substituted one or more times by halogen, alkyl having 1 to 8 C atoms, alkoxy having 1 to 8 C atoms, hydroxy, nitro, cyano, oxo, or combinations thereof; and $R^{11}$ is alkyl having 1 to 4 carbon atoms, halogenated alkyl having 1 to 4 carbon atoms, alkenyl having 3 to 6 carbon atoms, alkynyl having 3 to 6 carbon atoms, wherein the alkyl, halogenated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, or Ar;

and pharmaceutically acceptable salts or N-oxides thereof, or or pharmaceutically acceptable salts of N-oxides thereof, wherein said compound can also be in the form of a polymorph, wherein if said compound exhibits chirality it can be in the form of a mixture of enantiomers or a mixture of diastereomers, or can be in the form of a single enantiomer or a single diastereomer, and wherein said compound possess at least one Het group which is fully saturated, partially saturated or fully unsaturated, having 5 to 10 ring atoms in which at least 1 ring atom is a N, O or S atom, and which is substituted, wherein at least one of the substituents is halogenated alkoxy having 1 to 8 C atoms, cycloalkoxy having 3 to 7 carbon atoms, cycloalkylalkoxy having 4 to 7 carbon atoms, cycloalkylalkyl having 4 to 7 carbon atoms, halogenated alkyl having 2 to 8 carbon atoms, alkoxyalkyl having 2 to 8 carbon atoms, alkyl(halogenated alkyl)amino wherein each alkyl group has 1 to 8 C atoms, di(halogenated alkyl)amino wherein each alkyl group has 1 to 8 C atoms, or (halogenated alkyl)amino having 1 to 8 C atoms.

14. A compound according to claim 13, wherein said compound possess at least one Het group which is fully saturated, partially saturated or fully unsaturated, having 5 to 10 ring atoms in which at least 1 ring atom is a N, O or S atom, and which is substituted, wherein at least one of the substituents is halogenated alkoxy having 1 to 8 C atoms, cycloalkoxy having 3 to 7 carbon atoms, cycloalkylalkoxy having 4 to 7 carbon atoms, halogenated alkyl having 2 to 8 carbon atoms, alkoxyalkyl having 2 to 8 carbon atoms, alkyl(halogenated alkyl)amino wherein each alkyl group has 1 to 8 C atoms, di(halogenated alkyl)amino wherein each alkyl group has 1 to 8 C atoms, or (halogenated alkyl)amino having 1 to 8 C atoms.

15. A compound according to claim 13, wherein $R^2$ is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl-, or Ar—$C_{1-4}$-alkyl-NH—CO—.

16. A compound according to Formulas I, II, III, or IV:

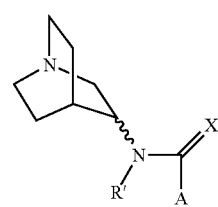

(I)

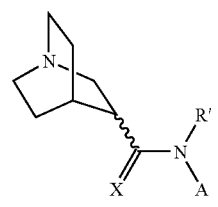

(II)

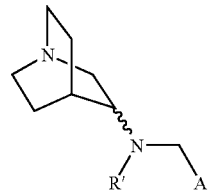

(III)

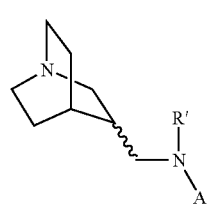

(IV)

wherein
A is

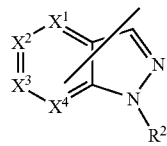

(a)

X is O or S;
X¹ to X⁴ are each, independently, N, CH, CR¹, or C—, wherein C— represents the point of attachment of group A to the remainder of the structure of formulas (I), (II), (III) or (IV);
R' is H, alkyl having 1 to 4 carbon atoms, halogenated alkyl having 1 to 4 carbon atoms, cycloalkyl having 3 to 7 carbon atoms, or cycloalkylalkyl having 4 to 7 carbon atoms;
$R^1$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$ $SOR^{10}$, —O—($C_{1-6}$-alkyl-O)$_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, —CO—$R^{10}$, or combinations thereof, cycloalkylalkyl having 4 to 7 carbon atoms, cycloalkenylalkyl having 6 to 9 carbon atoms, alkoxy having 1 to 4 carbon atoms, cycloalkoxy having 3 to 7 carbon atoms, cycloalkylalkoxy having 4 to 7 carbon atoms, alkylthio having 1 to 4 carbon atoms, fluorinated alkoxy having 1 to 4 carbon atoms, hydroxyalkyl having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or
$R^1$ is of one of the following formulas

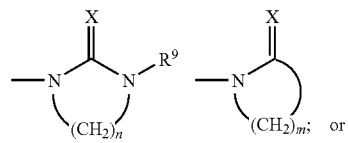

two $R^1$ can together form a 5-membered fused ring structure containing at least one N atom;

$R^2$ is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl-, Ar—$C_{1-4}$-alkyl-NH—CO—, or Het-NH—CO—;
$R^6$ and $R^7$ are each, independently, H, alkyl having 1 to 4 carbon atoms, alkoxyalkyl having 2 to 8 carbon atoms, cycloalkyl having 3 to 7 carbon atoms, or cycloalkylalkyl having 4 to 7 carbon atoms, or $R^6$ and $R^7$ together are an alkylene group containing 4-6 carbon atoms which forms a ring with the N atom;
$R^8$ is H, alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 1 to 4 carbon atoms, fluorinated hydroxyalkyl having 1 to 4 carbon atoms, monoalkylamino having 1 to 4 carbon atoms, dialkylamino wherein each alkyl group independently has 1 to 4 carbon atoms, Ar, or Het;
$R^9$ is alkyl having 1 to 4 carbon atoms, Ar, Ar-alkyl wherein the alkyl portion has 1 to 4 carbon atoms, or Het;
$R^{10}$ is alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, $NR^6R^7$, $NR^2R^8$, Ar, or Het;
Ar is an aryl group having 6 to 10 carbon atoms which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, aryloxy wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, arylthio wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, cycloalkyloxy wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, sulfo, sulfonylamino, acylamido, acyloxy or combinations thereof;

Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms which is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, alkyl having 1 to 8 C atoms, alkoxy having 1 to 8 C atoms, cycloalkyl having 3 to 7 carbon atoms, cycloalkylalkyl having 4 to 7 carbon atoms, halogenated alkoxy having 1 to 8 C atoms, cycloalkoxy having 3 to 7 carbon atoms, cycloalkylalkoxy having 4 to 7 carbon atoms, alkoxyalkyl having 2 to 8 carbon atoms, alkyl(halogenated alkyl)amino wherein each alkyl group has 1 to 8 C atoms, di(halogenated alkyl)amino wherein each alkyl group has 1 to 8 C atoms, (halogenated alkyl)amino having 1 to 8 C atoms, cyano, halogenated alkyl having 1 to 8 carbon atoms, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, $—CXR^{11}$, piperidinylethyl or combinations thereof;

Carbo is a partially unsaturated carbocyclic group having 5 to 14 carbon atoms, which is unsubstituted or substituted one or more times by halogen, alkyl having 1 to 8 C atoms, alkoxy having 1 to 8 C atoms, hydroxy, nitro, cyano, oxo, or combinations thereof; and $R^{11}$ is alkyl having 1 to 4 carbon atoms, halogenated alkyl having 1 to 4 carbon atoms, alkenyl having 3 to 6 carbon atoms, alkynyl having 3 to 6 carbon atoms, wherein the alkyl, halogenated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, or Ar;

and pharmaceutically acceptable salts or N-oxides thereof, or pharmaceutically acceptable salts of N-oxides thereof, wherein said compound can also be in the form of a polymorph, wherein if said compound exhibits chirality it can be in the form of a mixture of enantiomers or a mixture of diastereomers, or can be in the form of a single enantiomer or a single diastereomer, and wherein at least one of $X^1$, $X^2$, $X^3$, and $X^4$ is N.

17. A compound according to claim 16, wherein

Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms which is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, alkyl having 1 to 8 C atoms, alkoxy having 1 to 8 C atoms, cycloalkyl having 3 to 7 carbon atoms, halogenated alkoxy having 1 to 8 C atoms, cycloalkoxy having 3 to 7 carbon atoms, cycloalkylalkoxy having 4 to 7 carbon atoms, alkoxyalkyl having 2 to 8 carbon atoms, alkyl (halogenated alkyl)amino wherein each alkyl group has 1 to 8 C atoms, di(halogenated alkyl)amino wherein each alkyl group has 1 to 8 C atoms, (halogenated alkyl) amino having 1 to 8 C atoms, cyano, halogenated alkyl having 1 to 8 carbon atoms, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, $—CXR^{11}$, piperidinylethyl or combinations thereof; and $R^2$ is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl-, or Ar—$C_{1-4}$-alkyl-NH—CO—.

18. A compound according to claim 16, wherein at least one of $X^1$, $X^2$, $X^3$, and $X^4$ is N, and 1 or 2 of the remaining $X^1$-$X^4$ are $CR^1$.

19. A compound according to claim 1, wherein A is attached to the remainder of the compound via its 3, 4 or 7 position.

20. A compound according to claim 19, wherein said compound is of Formula I.

21. A compound according to claim 19, wherein said compound is of Formula II.

22. A compound according to claim 19, wherein said compound is of Formula III.

23. A compound according to claim 19, wherein said compound is of Formula IV.

24. A compound according to Formulas I, II, III, or IV:

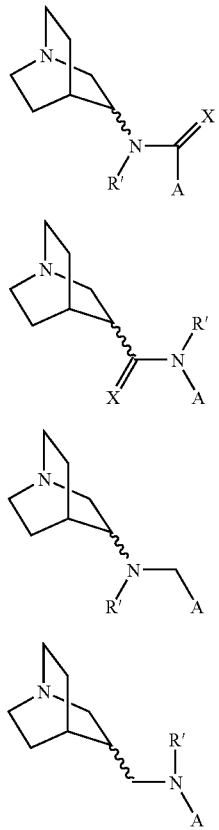

(I)

(II)

(III)

(IV)

wherein
A is

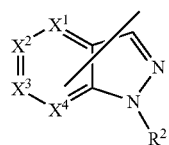

(a)

X is O or S;

X1 to X4 are each, independently, N, CH, CR1, or C—, wherein C— represents the point of attachment of group A to the remainder of the structure of formulas (I), (II), (III) or (IV);

R' is H, alkyl having 1 to 4 carbon atoms, halogenated alkyl having 1 to 4 carbon atoms, cycloalkyl having 3 to 7 carbon atoms, or cycloalkylalkyl having 4 to 7 carbon atoms;

$R^1$ is H, F, Cl, Br, I, OH, CN, nitro, $NH_2$, COH, $NR^6R^7$, carboxy, $CONR^6R^7$, $NR^2COR^8$, $NR^2COOR^8$, $NR^2CSR^8$, $NR^2CONR^2R^9$, $NR^2CSNR^2R^9$, $NR^2SO_2R^{10}$, $NR^2CONR^6R^7$, $NR^2CSNR^6R^7$, $NR^2R^9$, $SO_2R^{10}$, $SOR^{10}$, —O—$(C_{1-6}$-alkyl-O$)_{1-2}$—$C_{1-6}$-alkyl, $NR^2$—$C_{1-6}$-alkyl-$NR^6R^7$, $NR^2$—$C_{1-6}$-alkyl-$CONR^6R^7$, $NR^2$—CO—$C_{1-6}$-alkyl-Ar, $NR^2$—$C_{1-6}$-alkyl-CO—O—$R^2$, $NR^2$—$C_{1-6}$-alkyl-$NR^2$(CO—O—$R^2$), —$C_{1-6}$-alkyl-$NR^2$, —O—$C_{1-6}$-alkyl-$NR^6R^7$, alkyl having 1 to 4 carbon atoms, fluorinated alkyl having 1 to 4 carbon atoms, alkenyl having 2 to 6 carbon atoms, alkynyl having 2 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms which is unsubstituted or substituted by HCO—, $C_{1-6}$-alkoxy, $NR^6R^7$, CO—$NR^6R^7$, $C_{2-6}$-alkoxycarbonyl, —CO—$R^{10}$, or combinations thereof, cycloalkylalkyl having 4 to 7 carbon atoms, cycloalkenylalkyl having 6 to 9 carbon atoms, alkoxy having 1 to 4 carbon atoms, cycloalkoxy having 3 to 7 carbon atoms, cycloalkylalkoxy having 4 to 7 carbon atoms, alkylthio having 1 to 4 carbon atoms, fluorinated alkoxy having 1 to 4 carbon atoms, hydroxyalkyl having 1 to 4 carbon atoms, fluorinated hydroxyalkyl having 1 to 4 carbon atoms, hydroxyalkoxy having 2 to 4 carbon atoms, fluorinated hydroxyalkoxy having 2 to 4 carbon atoms, monoalkylamino having 1 to 4 carbon atoms, dialkylamino wherein each alkyl group independently has 1 to 4 carbon atoms, alkoxycarbonyl having 2 to 6 carbon atoms, Ar, Het, OAr, OHet, Carbo-O, Ar—$C_{1-6}$-alkyl-O—, Het-$C_{1-6}$-alkyl-O—, Het-CO-Het-, Het-$C_{1-6}$-alkyl-$NR^2$—, or Ar—$C_{1-6}$-alkyl-Het-O—; or $R^1$ is of one of the following formulas

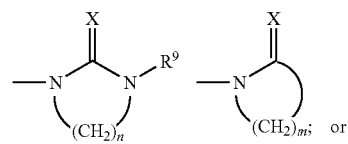

two $R^1$ can together form a 5-membered fused ring structure containing at least one N atom;

$R^2$ is H, alkyl having 1 to 4 carbon atoms, fluorinated alkyl having 1 to 4 carbon atoms, cycloalkyl having 3 to 7 carbon atoms, cycloalkylalkyl having 4 to 7 carbon atoms, fluorinated $C_{1-4}$-alkyl-CO—, $C_{3-7}$-cycloalkyl-CO—, $C_{1-4}$-alkyl-NH—CO—, $C_{3-7}$-cycloalkyl-NH—CO—, Het, Ar—$C_{1-4}$-alkyl-, Ar—$C_{1-4}$-alkyl-CO—, Ar—$C_{1-4}$-alkyl-$SO_2$—, $C_{1-4}$-alkyl-O—$C_{1-4}$-alkyl-, Ar—$C_{1-4}$-alkyl-NH—CO—, or Het-NH—CO—;

$R^6$ and $R^7$ are each, independently, H, alkyl having 1 to 4 carbon atoms, alkoxyalkyl having 2 to 8 carbon atoms, cycloalkyl having 3 to 7 carbon atoms, or cycloalkylalkyl having 4 to 7 carbon atoms, or $R^6$ and $R^7$ together are an alkylene group containing 4-6 carbon atoms which forms a ring with the N atom;

$R^8$ is H, alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 1 to 4 carbon atoms, fluorinated hydroxyalkyl having 1 to 4 carbon atoms, monoalkylamino having 1 to 4 carbon atoms, dialkylamino wherein each alkyl group independently has 1 to 4 carbon atoms, Ar, or Het;

$R^9$ is alkyl having 1 to 4 carbon atoms, Ar, Ar-alkyl wherein the alkyl portion has 1 to 4 carbon atoms, or Het;

$R^{10}$ is alkyl having 1 to 4 carbon atoms, fluorinated alkyl having 1 to 4 carbon atoms, alkenyl having 3 to 6 carbon atoms, alkynyl having 3 to 6 carbon atoms, wherein the alkyl, fluorinated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, $NR^6R^7$, $NR^2R^8$, Ar, or Het;

Ar is an aryl group having 6 to 10 carbon atoms which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, aryloxy wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, arylthio wherein the aryl portion has 6 to 10 carbon atoms and is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, cycloalkyloxy wherein the cycloalkyl group has 3 to 7 C atoms and is optionally substituted by alkyl having 1 to 4 carbon atoms, alkoxy having 1 to 4 carbon atoms, hydroxyl, amino, monoalkylamino having 1 to 4 carbon atoms, dialklyamino in which each alkyl group has 1 to 4 carbon atoms, or combinations thereof, sulfo, sulfonylamino, acylamido, acyloxy or combinations thereof;

Het is a heterocyclic group, which is fully saturated, partially saturated or fully unsaturated, having 5 to 10 ring atoms in which at least 1 ring atom is a N, O or S atom, which is unsubstituted or substituted one or more times by halogen, aryl having 6 to 10 carbon atoms which is optionally substituted by halogen, alkyl having 1 to 8 carbon atoms, hydroxy, alkoxy having 1 to 8 carbon atoms, nitro, methylenedioxy, ethylenedioxy, amino, alkylamino having 1 to 8 carbon atoms, dialkylamino in which each alkyl group has 1 to 8 carbon atoms, hydroxyalkyl having 1 to 8 carbon atoms, hydroxyalkoxy having 1 to 8 carbon atoms, carboxy, cyano, acyl, alkoxycarbonyl wherein the alkoxy group has 1 to 8 carbon atoms, alkylthio, alkylsulphinyl having 1 to 8 carbon atoms, alkylsulphonyl having 1 to 8 carbon atoms, phenoxy, acyloxy, or combinations thereof, alkyl having 1 to 8 C atoms, alkoxy having 1 to 8 C atoms, cycloalkyl having 3 to 7 carbon atoms, cycloalkylalkyl having 4 to 7 carbon atoms, halogenated alkoxy having 1 to 8 C atoms, cycloalkoxy having 3 to 7 carbon atoms, cycloalkylalkoxy having 4 to 7 carbon atoms, alkoxyalkyl having 2 to 8 carbon atoms, alkyl(halogenated alkyl)amino wherein each alkyl group has 1 to 8 C atoms, di(halogenated alkyl)amino wherein each alkyl group has 1 to 8 C atoms, (halogenated alkyl)amino having 1 to 8 C atoms, cyano, halogenated alkyl having 1 to 8 carbon atoms, nitro, oxo, OH, alkoxycarbonylalkyl having 3 to 8 carbon atoms, amino, monoalkylamino having 1 to 8 C atoms, dialkylamino wherein each alkyl group has 1 to 8 C atoms, $SO_2R^{11}$, $-CXR^{11}$, piperidinylethyl or combinations thereof;

Carbo is a partially unsaturated carbocyclic group having 5 to 14 carbon atoms, which is unsubstituted or substituted one or more times by halogen, alkyl having 1 to 8 C atoms, alkoxy having 1 to 8 C atoms, hydroxy, nitro, cyano, oxo, or combinations thereof; and $R^{11}$ is alkyl having 1 to 4 carbon atoms, halogenated alkyl having 1 to 4 carbon atoms, alkenyl having 3 to 6 carbon atoms, alkynyl having 3 to 6 carbon atoms, wherein the alkyl, halogenated alkyl, alkenyl, or alkynyl groups are in each case unsubstituted or substituted by Ar or Het, cycloalkyl having 3 to 7 carbon atoms, cycloalkenyl having 5 to 8 carbon atoms, cycloalkylalkyl having 4 to 7 carbon atoms, cycloalkenylalkyl having 6 to 9 carbon atoms, hydroxyalkyl having 2 to 4 carbon atoms, fluorinated hydroxyalkyl having 2 to 4 carbon atoms, monoalkylamino having 1 to 4 carbon atoms, dialkylamino wherein each alkyl group independently has 1 to 4 carbon atoms, or Ar;

and pharmaceutically acceptable salts, or N-oxides thereof, or pharmaceutically acceptable salts of N-oxides thereof, wherein said compound can also be in the form of a polymorph, and wherein if said compound exhibits chirality it can be in the form of a mixture of enantiomers or a mixture of diastereomers, or can be in the form of a single enantiomer or a single diastereomer;

with the proviso that the 1-azabicyclo group is in the form of a quaternary ammonium salt of the subformula:

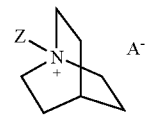

wherein Z is alkyl having 1 to 4 carbon atoms, halogenated alkyl having 1 to 4 carbon atoms, cycloalkylalkyl having 4 to 7 carbon atoms, or arylalkyl having 7 to 16 carbon atoms, and anion A is iodide, bromide, chloride, triflate, tosylate, or mesylate.

25. A compound according to claim 24, wherein $X^1$ to $X^4$ are each CH, $CR^1$, or C—.

26. A compound according to claim 1, wherein X is O.

27. A compound according to claim 1, wherein R' is H, cyclopropylmethyl, or $CH_3$.

28. A compound selected from:

3) N-[(3S)-1-Azabicyclo[2.2.2]oct-3-yl]-5,6-dimethoxy-1H-indazole-3-carboxamide hydroformate, 4) N-[(3S)-1-Azabicyclo[2.2.2]oct-3-yl]-1-propyl-6-(1,3-thiazol-2-yl)-1H-indazole-3-carboxamide, 5) N-[(3S)-1-Azabicyclo[2.2.2]oct-3-yl]-1-isopropyl-6-(1,3-thiazol-2-yl)-1H-indazole-3-carboxamide, 6) N-[(3S)-1-Azabicyclo[2.2.2]oct-3-yl]-6-(tetrahydrofuran-3-yloxy)-1H-indazole-3-carboxamide hydroformate, 7) N-[(3S)-1-Azabicyclo[2.2.2]oct-3-yl]-6-(tetrahydro-2H-pyran-4-yloxy)-1H-indazole-3-carboxamide hydroformate, 8) N-[(3S)-1-Azabicyclo[2.2.2]oct-3-yl]-6-[(1-methylpyrrolidin-3-yl)oxy]-1H-indazole-3-carboxamide hydroformate, 9) N-[(3S)-1-Azabicyclo[2.2.2]oct-3-yl]-4-hydroxy-1H-indazole-3-carboxamide hydroformate, 10) N-[(3S)-1-Azabicyclo[2.2.2]oct-3-yl]-5-bromo-4-hydroxy-1H-indazole-3-carboxamide hydroformate, 11) N-[(3S)-1-Azabicyclo[2.2.2]oct-3-yl]-5,7-dibromo-4-hydroxy-1H-indazole-3-carboxamide hydroformate, 15) N-[(3S)-1-Azabicyclo[2.2.2]oct-3-yl]-1-ethyl-6-(2-oxopyrrolidin-1-yl)-1H-indazole-3-carboxamide hydroformate, 16) N-[(3S)-1-Azabicyclo[2.2.2]oct-3-yl]-7-hydroxy-1H-indazole-3-carboxamide hydroformate, 17) N-[(3R)-1-Azabicyclo[2.2.2]oct-3-yl]-6-methoxy-N-methyl-1H-indazole-3-carboxamide hydroformate, 18) N-[(3S)-1-Azabicyclo[2.2.2]oct-3-yl]-1-methyl-6-{[(propylamino)carbonyl]amino}-1H-indazole-3-carboxamide hydroformate, 19) N-[(3S)-1-Azabicyclo[2.2.2]oct-3-yl]-1-ethyl-6-methoxy-1H-indazole-3-carboxamide, 20) N-[(3R)-1-Azabicyclo[2.2.2]oct-3-yl]-1-ethyl-6-methoxy-1H-indazole-3-carboxamide, 21) N-[(3S)-1-Azabicyclo[2.2.2]oct-3-yl]-1-(difluoromethyl)-6-methoxy-1H-indazole-3-carboxamide, 22) N-[(3S)-1-Azabicyclo[2.2.2]oct-3-yl]-1-(difluoromethyl)-6-(1,3-thiazol-2-yl)-1H-indazole-3-carboxamide, 23) N-[(3S)-1-Azabicyclo[2.2.2]oct-3-yl]-6-[(cyclopropylcarbonyl)amino]-1-methyl-1H-indazole-3-carboxamide hydroformate, 24) N-[(3S)-1-Azabicyclo[2.2.2]oct-3-yl]-6-[(cyclopropylcarbonyl)amino]-1-(difluoromethyl)-1H-indazole-3-carboxamide hydroformate, 25) N-[(3S)-1-Azabicyclo[2.2.2]oct-3-yl]-1-(difluoromethyl)-6-{[(propylamino)carbonyl]amino}-1H-indazole-3-carboxamide hydroformate, 26) N-[(3S)-1-Azabicyclo[2.2.2]oct-3-yl]-1-cyclopropyl-6-(1,3-thiazol-2yl)-1H-indazole-3-carboxamide, 27) N-[(3S)-1-Azabicyclo[2.2.2]oct-3-yl]-6-(1,3-thiazol-2-yl)-1-(3-thienyl)-1H-indazole-3-carboxamide, 28) N-[(3S)-1-Azabicyclo[2.2.2]oct-3-yl]-N-methyl-6-(1,3-oxazol-2-yl)-1H-indazole-3-carboxamide, 29) N-[(3S)-1-Azabicyclo[2.2.2]oct-3-yl]-N-methyl-6-(1,3-thiazol-2-yl)-1H-indazole-3-carboxamide, 30) N-[(3S)-1-Azabicyclo[2.2.2]oct-3-yl]-1-ethyl-6-(1,3-oxazol-2-yl)-1H-indazole-3-carboxamide, 31) N-[(3S)-1-Azabicyclo[2.2.2]oct-3-yl]-1-(cyclopropylmethyl)-6-(1,3-oxazol-2-yl)-1H-indazole-3-carboxamide, 32) N-[(3S)-1-Azabicyclo[2.2.2]oct-3-yl]-6-(1,3-oxazol-2-yl)-1-propyl-1H-indazole-3-carboxamide, 33) N-[(3S)-1-Azabicyclo[2.2.2]oct-3-yl]-1-ethyl-N-methyl-6-(1,3-oxazol-2-yl)-1H-indazole-3-carboxamide, 34) N-[(3S)-1-Azabicyclo[2.2.2]oct-3-yl]-N-methyl-6-(tetrahydro-2H-pyran-4-yl)-1H-indazole-3-carboxamide, 35) N-[(3S)-1-Azabicyclo[2.2.2]oct-3-yl]-N-methyl-5-(tetrahydro-2H-pyran-4-yl)-1H-indazole-3-carboxamide, 36) N-[(3S)-1-Azabicyclo[2.2.2]oct-3-yl]-5-(difluoromethoxy)-N-methyl-1H-indazole-3-carboxamide, 37) N-[(3S)-1-Azabicyclo[2.2.2]oct-3-yl]-6-(difluoromethoxy)-N-methyl-1H-indazole-3-carboxamide, 38) N-[(3S)-1-Azabicyclo[2.2.2]oct-3-yl]-1-cyclopropyl-6-[(cyclopropylcarbonyl)amino]-1H-indazole-3-carboxamide, 39) N-[(3S)-1-Azabicyclo[2.2.2]oct-3-yl]-1-cyclopropyl-6-{[(propylamino)carbonyl]amino}-1H-indazole-3-carboxamide, 40) N-[(3S)-1-Azabicyclo[2.2.2]oct-3-yl]-5-methoxy-N-methyl-1H-indazole-3-carboxamide, 41) N-[(3S)-1-Azabicyclo[2.2.2]oct-3-yl]-6-[(4S)-4-hydroxy-2-oxopyrrolidin-1-yl]-1H-indazole-3-carboxamide hydroformate, 42) N-[(3R)-1-Azabicyclo[2.2.2]oct-3-yl]-5-methoxy-N-methyl-1H-indazole-3-carboxamide hydroformate, 43) N-[(3R)-1-Azabicyclo[2.2.2]oct-3-yl]-5-(difluoromethoxy)-N-methyl-1H-indazole-3-carboxamide hydroformate, 44) N-[(3R)-1-Azabicyclo[2.2.2]oct-3-yl]-6-(difluoromethoxy)-N-methyl-1H-indazole-3-carboxamide hydroformate, 45) N-[(3R)-1-Azabicyclo[2.2.2]oct-3-yl]-N-methyl-6-(tetrahydro-2H-pyran-4-yl)-1H-indazole-3-carboxamide hydroformate, 46) N-[(3R)-1-Azabicyclo[2.2.2]oct-3-yl]-N-methyl-5-(tetrahydro-2H-pyran-4-yl)-1H-indazole-3-carboxamide hydroformate, 47) N-[(3R)-1-Azabicyclo[2.2.2]oct-3-yl]-N-methyl-6-(1,3-thiazol-2-yl)-1H-indazole-3-carboxamide hydroformate, 55) N-[(3S)-1-Oxido-1-azabicyclo[2.2.2]oct-3-yl]-5-(trifluoromethoxy)-1H-indazole-3-carboxamide, 58) N-[(3S)-1-Azabicyclo[2.2.2]oct-3-yl]-6-[3-(cyclopropylmethoxy)pyrrolidin-1-yl]-1H-indazole-3-carboxamide hydroformate, 61) N-[(3R)-1-Azabicyclo[2.2.2]oct-3-yl]-6-[3-(cyclopropylmethoxy)pyrrolidin-1-yl]-1H-indazole-3-carboxamide hydroformate, 62) N-[(3R)-1-Azabicyclo[2.2.2]oct-3-yl]-6-(3-methoxypyrrolidin-1-yl)-1H-indazole-3-carboxamide hydroformate, 63) N-[(3R)-1-Azabicyclo[2.2.2]oct-3-yl]-6-(2-oxo-3-propylimidazolidin-1-yl)-1H-indazole-3-carboxamide hydroformate, 73) N-[(3R)-1-Azabicyclo[2.2.2]oct-3-yl]-1-ethyl-6-(1,3-oxazol-2-yl)-1H-indazole-3-carboxamide hydroformate, 74) N-[(3S)-1-Azabicyclo[2.2.2]oct-3-yl]-1-ethyl-6-(1,3-oxazol-2-yl)-1H-indazole-3-carboxamide hydrochloride, 77) N-[(3S)-1-Azabicyclo[2.2.2]oct-3-yl]-6-(2-oxo-3-propylimidazolidin-1-yl)-1H-indazole-3-carboxamide,
89) N-[(3R)-1-Azabicyclo[2.2.2]oct-3-yl]-6-(4,5-dihydro-1H-imidazol-2-yl)-1H-indazole-3-carboxamide,
161) N,N'-di-(3S)-1-Azabicyclo[2.2.2]oct-3-yl-1H-indazole-1,3-dicarboxamide,
162) N-[(3R)-1-Azabicyclo[2.2.2]oct-3-yl]-6-(1-methyl-4,5-dihydro-1H-imidazol-2-yl)-1H-indazole-3-carboxamide,
163) N-[(3S)-1-Azabicyclo[2.2.2]oct-3-yl]-6-(1-methyl-4,5-dihydro-1H-imidazol-2-yl)-1H-indazole-3-carboxamide,
164) N-[(3S)-1-Azabicyclo[2.2.2]oct-3-yl]-5-[(3S)-3-(cyclopropylmethoxy)pyrrolidin-1-yl]-1H-indazole-3-carboxamide,
165) (3S)-1-(Chloromethyl)-3-[(1H-indazol-3-ylcarbonyl)amino]-1-azoniabicyclo[2.2.2]octane chloride,
166) N-[(3S)-1-Azabicyclo[2.2.2]oct-3-yl]-5-[(3S)-3-methoxypyrrolidin-1-yl]-1H-indazole-3-carboxamide dihydroformate,
184) N-[(3S)-1-Azabicyclo[2.2.2]oct-3-yl]-6-cyano-1H-indazole-3-carboxamide,
185) 3-[(3S)-1-Azabicyclo[2.2.2]oct-3-ylamino]carbonyl-1H-indazole-6-carboxylic acid hydrochloride,
186) N(3)-[(3S)-1-Azabicyclo[2.2.2]oct-3-yl]-N(6),N(6)-dimethyl-1H-indazole-3,6-dicarboxamide,
187) N-[(3S)-1-Azabicyclo[2.2.2]oct-3-yl]-6-[(4-methylpiperazin-1-yl)carbonyl]-1H-indazole-3-carboxamide,
188) N-[(3S)-1-Azabicyclo[2.2.2]oct-3-yl]-6-[(3R)-3-methoxypyrrolidin-1-yl]carbonyl-1H-indazole-3-carboxamide, and
190) N-[(3R)-1-Azabicyclo[2.2.2]oct-3-yl]-5-(tetrahydro-2H-pyran-4-yloxy)-1H-indazole-3-carboxamide,
wherein salts listed above can also be in free base form or in the form of another pharmaceutically acceptable salt, and free base forms listed above can also be in the form of a pharmaceutically acceptable salt,
wherein a compound listed above, in either a free base form or in the form of a pharmaceutically acceptable salt, can also be in the form of an N-oxide,
wherein a compound listed above, in a free base form or N-oxide thereof, or in the form of a pharmaceutically acceptable salt, can also be in the form of a polymorph, and
wherein if the compound exhibits chirality it can be in the form of a mixture of enantiomers or a mixture of diastereomers, or can be in the form of a single enantiomer or a single diastereomer.

29. A compound according to claim 28, wherein said compound is selected from:
3) N-[(3S)-1-Azabicyclo[2.2.2]oct-3-yl]-5,6-dimethoxy-1H-indazole-3-carboxamide hydroformate,
4) N-[(3S)-1-Azabicyclo[2.2.2]oct-3-yl]-1-propyl-6-(1,3-thiazol-2-yl)-1H-indazole-3-carboxamide,
5) N-[(3S)-1-Azabicyclo[2.2.2]oct-3-yl]-1-isopropyl-6-(1,3-thiazol-2-yl)-1H-indazole-3-carboxamide,
6) N-[(3S)-1-Azabicyclo[2.2.2]oct-3-yl]-6-(tetrahydrofuran-3-yloxy)-1H-indazole-3-carboxamide hydroformate,
7) N-[(3S)-1-Azabicyclo[2.2.2]oct-3-yl]-6-(tetrahydro-2H-pyran-4-yloxy)-1H-indazole-3-carboxamide hydroformate,
8) N-[(3S)-1-Azabicyclo[2.2.2]oct-3-yl]-6-[(1-methylpyrrolidin-3-yl)oxy]-1H-indazole-3-carboxamide hydroformate,
9) N-[(3S)-1-Azabicyclo[2.2.2]oct-3-yl]-4-hydroxy-1H-indazole-3-carboxamide hydroformate,
10) N-[(3S)-1-Azabicyclo[2.2.2]oct-3-yl]-5-bromo-4-hydroxy-1H-indazole-3-carboxamide hydroformate,
11) N-[(3S)-1-Azabicyclo[2.2.2]oct-3-yl]-5,7-dibromo-4-hydroxy-1H-indazole-3-carboxamide hydroformate,
15) N-[(3S)-1-Azabicyclo[2.2.2]oct-3-yl]-1-ethyl-6-(2-oxopyrrolidin-1-yl)-1H-indazole-3-carboxamide hydroformate,
16) N-[(3S)-1-Azabicyclo[2.2.2]oct-3-yl]-7-hydroxy-1H-indazole-3-carboxamide hydroformate,
17) N-[(3R)-1-Azabicyclo[2.2.2]oct-3-yl]-6-methoxy-N-methyl-1H-indazole-3-carboxamide hydroformate,
18) N-[(3S)-1-Azabicyclo[2.2.2]oct-3-yl]-1-methyl-6-{[(propylamino)carbonyl]amino}-1H-indazole-3-carboxamide hydroformate,
19) N-[(3S)-1-Azabicyclo[2.2.2]oct-3-yl]-1-ethyl-6-methoxy-1H-indazole-3-carboxamide,
20) N-[(3R)-1-Azabicyclo[2.2.2]oct-3-yl]-1-ethyl-6-methoxy-1H-indazole-3-carboxamide,
21) N-[(3S)-1-Azabicyclo[2.2.2]oct-3-yl]-1-(difluoromethyl)-6-methoxy-1H-indazole-3-carboxamide,
22) N-[(3S)-1-Azabicyclo[2.2.2]oct-3-yl]-1-(difluoromethyl)-6-(1,3-thiazol-2-yl)-1H-indazole-3-carboxamide,
23) N-[(3S)-1-Azabicyclo[2.2.2]oct-3-yl]-6-[(cyclopropylcarbonyl)amino]-1-methyl-1-methyl-1H-indazole-3-carboxamide hydroformate,
24) N-[(3S)-1-Azabicyclo[2.2.2]oct-3-yl]-6-[(cyclopropylcarbonyl)amino]-1-(difluoromethyl)-1H-indazole-3-carboxamide hydroformate,
25) N-[(3S)-1-Azabicyclo[2.2.2]oct-3-yl]-1-(difluoromethyl)-6-{[(propylamino)carbonyl]amino}-1H-indazole-3-carboxamide hydroformate,
26) N-[(3S)-1-Azabicyclo[2.2.2]oct-3-yl]-1-cyclopropyl-6-(1,3-thiazol-2-yl)-1H-indazole-3-carboxamide,
27) N-[(3S)-1-Azabicyclo[2.2.2]oct-3-yl]-6-(1,3-thiazol-2-yl)-1-(3-thienyl)-1H-indazole-3-carboxamide,
28) N-[(3S)-1-Azabicyclo[2.2.2]oct-3-yl]-N-methyl-6-(1,3-oxazol-2-yl)-1H-indazole-3-carboxamide,
29) N-[(3S)-1-Azabicyclo[2.2.2]oct-3-yl]-N-methyl-6-(1,3-thiazol-2-yl)-1H-indazole-3-carboxamide,
30) N-[(3S)-1-Azabicyclo[2.2.2]oct-3-yl]-1-ethyl-6-(1,3-oxazol-2-yl)-1H-indazole-3-carboxamide,
31) N-[(3S)-1-Azabicyclo[2.2.2]oct-3-yl]-1-(cyclopropylmethyl)-6-(1,3-oxazol-2-yl)-1H-indazole-3-carboxamide,
32) N-[(3S)-1-Azabicyclo[2.2.2]oct-3-yl]-6-(1,3-oxazol-2-yl)-1-propyl-1H-indazole-3-carboxamide,
33) N-[(3S)-1-Azabicyclo[2.2.2]oct-3-yl]-1-ethyl-N-methyl-6-(1,3-oxazol-2-yl)-1H-indazole-3-carboxamide,
34) N-[(3S)-1-Azabicyclo[2.2.2]oct-3-yl]-N-methyl-6-(tetrahydro-2H-pyran-4-yl)-1H-indazole-3-carboxamide,
35) N-[(3S)-1-Azabicyclo[2.2.2]oct-3-yl]-N-methyl-5-(tetrahydro-2H-pyran-4-yl)-1H-indazole-3-carboxamide,
36) N-[(3S)-1-Azabicyclo[2.2.2]oct-3-yl]-5-(difluoromethoxy)-N-methyl-1H-indazole-3-carboxamide,
37) N-[(3S)-1-Azabicyclo[2.2.2]oct-3-yl]-6-(difluoromethoxy)-N-methyl-1H-indazole-3-carboxamide,
38) N-[(3S)-1-Azabicyclo[2.2.2]oct-3-yl]-1-cyclopropyl-6-[(cyclopropylcarbonyl)amino]-1H-indazole-3-carboxamide,
39) N-[(3S)-1-Azabicyclo[2.2.2]oct-3-yl]-1-cyclopropyl-6-{[(propylamino)carbonyl]amino}-1H-indazole-3-carboxamide, 40) N-[(3S)-1-Azabicyclo[2.2.2]oct-3-yl]-5-methoxy-N-methyl-1H-indazole-3-carboxamide,
41) N-[(3S)-1-Azabicyclo[2.2.2]oct-3-yl]-6-[(4S)-4-hydroxy-2-oxopyrrolidin-1-yl]-1H-indazole-3-carboxamide hydroformate,
42) N-[(3R)-1-Azabicyclo[2.2.2]oct-3-yl]-5-methoxy-N-methyl-1H-indazole-3-carboxamide hydroformate,
43) N-[(3R)-1-Azabicyclo[2.2.2]oct-3-yl]-5-(difluoromethoxy)-N-methyl-1H-indazole-3-carboxamide hydroformate,
44) N-[(3R)-1-Azabicyclo[2.2.2]oct-3-yl]-6-(difluoromethoxy)-N-methyl-1H-indazole-3-carboxamide hydroformate,
45) N-[(3R)-1-Azabicyclo[2.2.2]oct-3-yl]-N-methyl-6-(tetrahydro-2H-pyran-4-yl)-1H-indazole-3-carboxamide hydroformate,
46) N-[(3R)-1-Azabicyclo[2.2.2]oct-3-yl]-N-methyl-5-(tetrahydro-2H-pyran-4-yl)-1H-indazole-3-carboxamide hydroformate,
47) N-[(3R)-1-Azabicyclo[2.2.2]oct-3-yl]-N-methyl-6-(1,3-thiazol-2-yl)-1H-indazole-3-carboxamide hydroformate, and
55) N-[(3S)-1-Oxido-1-azabicyclo[2.2.2]oct-3-yl]-5-(trifluoromethoxy)-1H-indazole-3-carboxamide,
wherein salts listed above can also be in free base form or in the form of another pharmaceutically acceptable salt, and free base forms listed above can also be in the form of a pharmaceutically acceptable salt,
wherein a compound listed above, in either a free base form or in the form of a pharmaceutically acceptable salt, can also be in the form of an N-oxide,
wherein a compound listed above, in a free base form or N-oxide thereof, or in the form of a pharmaceutically acceptable salt, can also be in the form of a polymorph, and
wherein if the compound exhibits chirality it can be in the form of a mixture of enantiomers or a mixture of diastereomers, or can be in the form of a single enantiomer or a single diastereomer.

30. A compound according to claim 28, wherein said compound is selected from:
3) N-[(3S)-1-Azabicyclo[2.2.2]oct-3-yl]-5,6-dimethoxy-1H-indazole-3-carboxamide hydroformate,
4) N-[(3S)-1-Azabicyclo[2.2.2]oct-3-yl]-1-propyl-6-(1,3-thiazol-2-yl)-1H-indazole-3-carboxamide,
5) N-[(3S)-1-Azabicyclo[2.2.2]oct-3-yl]-1-isopropyl-6-(1,3-thiazol-2-yl)-1H-indazole-3-carboxamide,
6) N-[(3S)-1-Azabicyclo[2.2.2]oct-3-yl]-6-(tetrahydrofuran-3-yloxy)-1H-indazole-3-carboxamide hydroformate,
7) N-[(3S)-1-Azabicyclo[2.2.2]oct-3-yl]-6-(tetrahydro-2H-pyran-4-yloxy)-1H-indazole-3-carboxamide hydroformate,
8) N-[(3S)-1-Azabicyclo[2.2.2]oct-3-yl]-6-[(1-methylpyrrolidin-3-yl)oxy]-1H-indazole-3-carboxamide hydroformate,
9) N-[(3S)-1-Azabicyclo[2.2.2]oct-3-yl]-4-hydroxy-1H-indazole-3-carboxamide hydroformate,
10) N-[(3S)-1-Azabicyclo[2.2.2]oct-3-yl]-5-bromo-4-hydroxy-1H-indazole-3-carboxamide hydroformate,
11) N-[(3S)-1-Azabicyclo[2.2.2]oct-3-yl]-5,7-dibromo-4-hydroxy-1H-indazole-3-carboxamide hydroformate,
15) N-[(3S)-1-Azabicyclo[2.2.2]oct-3-yl]-1-ethyl-6-(2-oxopyrrolidin-1-yl)-1H-indazole-3-carboxamide hydroformate,
16) N-[(3S)-1-Azabicyclo[2.2.2]oct-3-yl]-7-hydroxy-1H-indazole-3-carboxamide hydroformate,
17) N-[(3R)-1-Azabicyclo[2.2.2]oct-3-yl]-6-methoxy-N-methyl-1H-indazole-3-carboxamide hydroformate,
18) N-[(3S)-1-Azabicyclo[2.2.2]oct-3-yl]-1-methyl-6-{[(propylamino)carbonyl]amino}-1H-indazole-3-carboxamide hydroformate,
19) N-[(3S)-1-Azabicyclo[2.2.2]oct-3-yl]-1-ethyl-6-methoxy-1H-indazole-3-carboxamide,
20) N-[(3R)-1-Azabicyclo[2.2.2]oct-3-yl]-1-ethyl-6-methoxy-1H-indazole-3-carboxamide,
21) N-[(3S)-1-Azabicyclo[2.2.2]oct-3-yl]-1-(difluoromethyl)-6-methoxy-1H-indazole-3-carboxamide,
22) N-[(3S)-1-Azabicyclo[2.2.2]oct-3-yl]-1-(difluoromethyl)-6-(1,3-thiazol-2-yl)-1H-indazole-3-carboxamide,
23) N-[(3S)-1-Azabicyclo[2.2.2]oct-3-yl]-6-[(cyclopropylcarbonyl)amino]-1-methyl-1H-indazole-3-carboxamide hydroformate,
24) N-[(3S)-1-Azabicyclo[2.2.2]oct-3-yl]-6-[(cyclopropylcarbonyl)amino]-1-(difluoromethyl)-1H-indazole-3-carboxamide hydroformate,
25) N-[(3S)-1-Azabicyclo[2.2.2]oct-3-yl]-1-(difluoromethyl)-6-{[(propylamino)carbonyl]amino}-1H-indazole-3-carboxamide hydroformate,
26) N-[(3S)-1-Azabicyclo[2.2.2]oct-3-yl]-1-cyclopropyl-6-(1,3-thiazol-2-yl)-1H-indazole-3-carboxamide,
27) N-[(3S)-1-Azabicyclo[2.2.2]oct-3-yl]-6-(1,3-thiazol-2-yl)-1-(3-thienyl)-1H-indazole-3-carboxamide,
28) N-[(3S)-1-Azabicyclo[2.2.2]oct-3-yl]-N-methyl-6-(1,3-oxazol-2-yl)-1H-indazole-3-carboxamide,
29) N-[(3S)-1-Azabicyclo[2.2.2]oct-3-yl]-N-methyl-6-(1,3-thiazol-2-yl)-1H-indazole-3-carboxamide,
30) N-[(3S)-1-Azabicyclo[2.2.2]oct-3-yl]-1-ethyl-6-(1,3-oxazol-2-yl)-1H-indazole-3-carboxamide,
31) N-[(3S)-1-Azabicyclo[2.2.2]oct-3-yl]-1-(cyclopropylmethyl)-6-(1,3-oxazol-2-yl)-1H-indazole-3-carboxamide,
32) N-[(3S)-1-Azabicyclo[2.2.2]oct-3-yl]-6-(1,3-oxazol-2-yl)-1-propyl-1H-indazole-3-carboxamide,
33) N-[(3S)-1-Azabicyclo[2.2.2]oct-3-yl]-1-ethyl-N-methyl-6-(1,3-oxazol-2-yl)-1H-indazole-3-carboxamide,
34) N-[(3S)-1-Azabicyclo[2.2.2]oct-3-yl]-N-methyl-6-(tetrahydro-2H-pyran-4-yl)-1H-indazole-3-carboxamide,
35) N-[(3S)-1-Azabicyclo[2.2.2]oct-3-yl]-N-methyl-5-(tetrahydro-2H-pyran-4-yl)-1H-indazole-3-carboxamide,
36) N-[(3S)-1-Azabicyclo[2.2.2]oct-3-yl]-5-(difluoromethoxy)-N-methyl-1H-indazol-3-carboxamide,
37) N-[(3S)-1-Azabicyclo[2.2.2]oct-3-yl]-6-(difluoromethoxy)-N-methyl-1H-indazole-3-carboxamide,
38) N-[(3S)-1-Azabicyclo[2.2.2]oct-3-yl]-1-cyclopropyl-6-[(cyclopropylcarbonyl)amino]-1H-indazole-3-carboxamide,
39) N-[(3S)-1-Azabicyclo[2.2.2]oct-3-yl]-1-cyclopropyl-6-{[(propylamino)carbonyl]amino}-1H-indazole-3-carboxamide,
40) N-[(3S)-1-Azabicyclo[2.2.2]oct-3-yl]-5-methoxy-N-methyl-1H-indazole-3-carboxamide,
41) N-[(3S)-1-Azabicyclo[2.2.2]oct-3-yl]-6-[(4S)-4-hydroxy-2-oxopyrrolidin-1-yl]-1H-indazole-3-carboxamide hydroformate,
42) N-[(3R)-1-Azabicyclo[2.2.2]oct-3-yl]-5-methoxy-N-methyl-1H-indazole-3-carboxamide hydroformate,
43) N-[(3R)-1-Azabicyclo[2.2.2]oct-3-yl]-5-(difluoromethoxy)-N-methyl-1H-indazole-3-carboxamide hydroformate, 44) N-[(3R)-1-Azabicyclo[2.2.2]oct-3-yl]-6-(difluoromethoxy)-N-methyl-1H-indazole-3-carboxamide hydroformate, 45) N-[(3R)-1-Azabicyclo[2.2.2]oct-3-yl]-N-methyl-6-(tetrahydro-2H-pyran-4-yl)-1H-indazole-3-carboxamide hydroformate, 46) N-[(3R)-1-Azabicyclo[2.2.2]oct-3-yl]-N-methyl-5-(tetrahydro-2H-pyran-4-yl)-1H-indazole-3-carboxamide hydroformate, and 47) N-[(3R)-1-Azabicyclo[2.2.2]oct-3-yl]-N-methyl-6-(1,3-thiazol-2-yl)-1H-indazole-3-carboxamide hydroformate, wherein salts listed above can also be in free base form or in the form of another pharmaceutically acceptable salt, and free base forms listed above can also be in the form of a pharmaceutically acceptable salt, wherein a compound listed above, in either a free base form or in the form of a pharmaceutically acceptable salt, can also be in the form of an N-oxide, wherein a compound listed above, in a free base form or N-oxide thereof, or in the form of a pharmaceutically acceptable salt, can also be in the form of a polymorph, and wherein if the compound exhibits chirality it can be in the form of a mixture of enantiomers or a mixture of diastereomers, or can be in the form of a single enantiomer or a single diastereomer.

31. A compound according to claim 28, wherein said compound is selected from:

58) N-[(3S)-1-Azabicyclo[2.2.2]oct-3-yl]-6-[3-(cyclopropylmethoxy)pyrrolidin-1-yl]-1H-indazole-3-carboxamide hydroformate, 61) N-[(3R)-1-Azabicyclo[2.2.2]oct-3-yl]-6-[3-(cyclopropylmethoxy)pyrrolidin-1-yl]-1H-indazole-3-carboxamide hydroformate, 62) N-[(3R)-1-Azabicyclo[2.2.2]oct-3-yl]-6-(3-methoxypyrrolidin-1-yl)-1H-indazole-3-carboxamide hydroformate, 63) N-[(3R)-1-Azabicyclo[2.2.2]oct-3-yl]-6-(2-oxo-3-propylimidazolidin-1-yl)-1H-indazole-3-carboxamide hydroformate, 73) N-[(3R)-1-Azabicyclo[2.2.2]oct-3-yl]-1-ethyl-6-(1,3-oxazol-2-yl)-1H-indazole-3-carboxamide hydroformate, 74) N-[(3S)-1-Azabicyclo[2.2.2]oct-3-yl]-1-ethyl-6-(1,3-oxazol-2-yl)-1H-indazole-3-carboxamide hydrochloride, 77) N-[(3S)-1-Azabicyclo[2.2.2]oct-3-yl]-6-(2-oxo-3-propylimidazolidin-1-yl)-1H-indazole-3-carboxamide, and 89) N-[(3R)-1-Azabicyclo[2.2.2]oct-3-yl]-6-(4,5-dihydro-1H-imidazol-2-yl)-1H-indazole-3-carboxamide, wherein salts listed above can also be in free base form or in the form of another pharmaceutically acceptable salt, and free base forms listed above can also be in the form of a pharmaceutically acceptable salt, wherein a compound listed above, in either a free base form or in the form of a pharmaceutically acceptable salt, can also be in the form of an N-oxide, wherein a compound listed above, in a free base form or N-oxide thereof, or in the form of a pharmaceutically acceptable salt, can also be in the form of a polymorph, and wherein if the compound exhibits chirality it can be in the form of a mixture of enantiomers or a mixture of diastereomers, or can be in the form of a single enantiomer or a single diastereomer.

32. A compound according to claim 28, wherein said compound is selected from:

161) N,N'-di-(3S)-1-Azabicyclo[2.2.2]oct-3-yl-1H-indazole-1,3-dicarboxamide,

162) N-[(3R)-1-Azabicyclo[2.2.2]oct-3-yl]-6-(1-methyl-4,5-dihydro-1H-imidazol-2-yl)-1H-indazole-3-carboxamide, 163) N-[(3S)-1-Azabicyclo[2.2.2]oct-3-yl]-6-(1-methyl-4,5-dihydro-1H-imidazol-2-yl)-1H-indazole-3-carboxamide, 164) N-[(3S)-1-Azabicyclo[2.2.2]oct-3-yl]-5-[(3S)-3-(cyclopropylmethoxy)pyrrolidin-1-yl]-1H-indazole-3-carboxamide, 165) (3S)-1-(Chloromethyl)-3-[(1H-indazol-3-ylcarbonyl)amino]-1-azoniabicyclo[2.2.2]octane chloride, 166) N-[(3S)-1-Azabicyclo[2.2.2]oct-3-yl]-5-[(3S)-3-methoxypyrrolidin-1-yl]-1H-indazole-3-carboxamide dihydroformate, 184) N-[(3S)-1-Azabicyclo[2.2.2]oct-3-yl]-6-cyano-1H-indazole-3-carboxamide, 185) 3-[(3S)-1-Azabicyclo[2.2.2]oct-3-ylamino]carbonyl-1H-indazole-6-carboxylic acid hydrochloride, 186) N(3)-[(3S)-1-Azabicyclo[2.2.2]oct-3-yl]-N(6),N(6)-dimethyl-1H-indazole-3,6-dicarboxamide, 187) N-[(3S)-1-Azabicyclo[2.2.2]oct-3-yl]-6-[(4-methylpiperazin-1-yl)carbonyl]-1H-indazole-3-carboxamide, and 188) N-[(3S)-1-Azabicyclo[2.2.2]oct-3-yl]-6-[(3R)-3-methoxypyrrolidin-1-yl]carbonyl-1H-indazole-3-carboxamide, wherein salts listed above can also be in free base form or in the form of another pharmaceutically acceptable salt, and free base forms listed above can also be in the form of a pharmaceutically acceptable salt, wherein a compound listed above, in either a free base form or in the form of a pharmaceutically acceptable salt, can also be in the form of an N-oxide, wherein a compound listed above, in a free base form or N-oxide thereof, or in the form of a pharmaceutically acceptable salt, can also be in the form of a polymorph, and wherein if the compound exhibits chirality it can be in the form of a mixture of enantiomers or a mixture of diastereomers, or can be in the form of a single enantiomer or a single diastereomer.

33. A pharmaceutical composition comprising a compound according to claim 1 and a pharmaceutically acceptable carrier.

34. A pharmaceutical composition according to claim 33, wherein said composition further comprises at least one additional pharmaceutical agent selected from other α-7 agonists, PDE4 inhibitors, calcium channel blockers, muscarinic m1 modulators, muscarinic m2 modulators, adenosine receptor modulators, ampakines, NMDA-R modulators, mGluR modulators, dopamine modulators, serotonin modulators, canabinoid modulators, and cholinesterase inhibitors.

35. A pharmaceutical composition comprising a compound according to claim 5 and a pharmaceutically acceptable carrier.

36. A pharmaceutical composition comprising a compound according to claim 13 and a pharmaceutically acceptable carrier.

37. A pharmaceutical composition comprising a compound according to claim 16 and a pharmaceutically acceptable carrier.

38. A pharmaceutical composition comprising a compound according to claim 24 and a pharmaceutically acceptable carrier.

39. A pharmaceutical composition comprising a compound according to claim 28 and a pharmaceutically acceptable carrier.

* * * * *